US012741970B2

(12) United States Patent
Vidal et al.

(10) Patent No.: US 12,741,970 B2
(45) Date of Patent: Sep. 22, 2026

(54) PYRAZOLO[3,4-d]PYRIMIDIN-6-yl-SULFONAMIDE DERIVATIVES FOR THE INHIBITION OF SGK-1

(71) Applicant: THRYV THERAPEUTICS INC., Montreal (CA)

(72) Inventors: Marc Vidal, Laval (CA); Maroua Khalifa, Laval (CA); Martin Maguire, Plattsburgh, NY (US)

(73) Assignee: THRYV THERAPEUTICS INC., Montreal (CA)

( * ) Notice: Subject to any disclaimer, the term of this patent is extended or adjusted under 35 U.S.C. 154(b) by 516 days.

(21) Appl. No.: 18/272,162

(22) PCT Filed: Jan. 12, 2022

(86) PCT No.: PCT/CA2022/050038
§ 371 (c)(1),
(2) Date: Jul. 13, 2023

(87) PCT Pub. No.: WO2022/150911
PCT Pub. Date: Jul. 21, 2022

(65) Prior Publication Data

US 2024/0309005 A1 Sep. 19, 2024

Related U.S. Application Data

(60) Provisional application No. 63/262,040, filed on Oct. 4, 2021, provisional application No. 63/136,782, filed on Jan. 13, 2021.

(51) Int. Cl.

| | |
|---|---|
| ***C07D 487/04*** | (2006.01) |
| ***A61K 31/519*** | (2006.01) |
| ***A61K 31/55*** | (2006.01) |
| ***A61P 9/00*** | (2006.01) |
| *A61P 9/04* | (2006.01) |
| *A61P 9/06* | (2006.01) |
| *A61P 9/10* | (2006.01) |
| *A61P 25/08* | (2006.01) |
| *A61P 25/16* | (2006.01) |
| *A61P 25/28* | (2006.01) |
| *A61P 35/00* | (2006.01) |

(52) U.S. Cl.
CPC .......... *C07D 487/04* (2013.01); *A61K 31/519* (2013.01); *A61K 31/55* (2013.01); *A61P 9/00* (2018.01)

(58) Field of Classification Search
CPC .................................................... C07D 487/04
See application file for complete search history.

(56) References Cited

FOREIGN PATENT DOCUMENTS

| | | | | |
|---|---|---|---|---|
| CN | 105189502 A | | 12/2015 | |
| EP | 4 147 700 | | 3/2023 | |
| JP | 2016-514116 A | | 5/2016 | |
| WO | WO-2014140065 A1 | * | 9/2014 | ................ A61P 3/10 |
| WO | 2015048531 A1 | | 4/2015 | |
| WO | WO-2022/150911 A1 | | 7/2022 | |

OTHER PUBLICATIONS

Biomimetic Technologies, CH 1.2.1 Amino Acids, 2015, Abstract (Year: 2015).*

Halland, N. et al., "Rational design of highly potent, selective, and bioavailable SGK1 protein kinase inhibitors for the treatment of osteoarthritis", J. Med. Chem., 2022 65:1567-1584 (Published: Dec. 21, 2021).

Tovell, H. et al., "Design and characterization of SGK3 PROTAC1, an isoform specific SGK3 kinase PROTAC degrader", ACS Chem. Biol. 2024-2034 (2109).

International Search Report and Written Opinion from corresponding International Patent Application No. PCT/CA2022/050038, mailed Apr. 12, 2022.

Chinese Office Action on Application No. 202280012928.4 dated Jun. 3, 2025.

Notice of Reasons for Rejection on Japanese Patent Application No. 2023-541702 dated Mar. 10, 2026 (6 pages).

International Search Report and Written Opinion for PCT/CA2023/0509307 dated Sep. 27, 2023.

* cited by examiner

*Primary Examiner* — Bruck Kifle
*Assistant Examiner* — Kevin S Martin
(74) *Attorney, Agent, or Firm* — Foley & Lardner LLP

(57) ABSTRACT

Compounds of Formula I: Formula I and pharmaceutically acceptable salts thereof are provided for as inhibitors of SGK-1 for example for the treatment of conditions such as Long QT syndrome, heart failure, arrhythmia, ischemic injury, ischemic infarction, cardiac fibrosis, vascular proliferation, restenosis, dilated cardiomyopathy, stent failure, prostate cancer, epilepsy, colorectal cancer, breast cancer, Parkinson's disease and Lafora disease.

Formula I

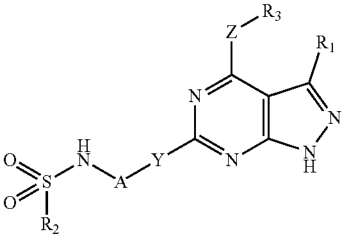

20 Claims, No Drawings

PYRAZOLO[3,4-d]PYRIMIDIN-6-yl-SULFONAMIDE DERIVATIVES FOR THE INHIBITION OF SGK-1

TECHNICAL FIELD

The technical field relates to pyrazolo[3,4-d]pyrimidin-6-yl-sulfonamide derivatives and pharmaceutical compositions that inhibit SGK-1, and more particularly relates to pyrazolo[3,4-d]pyrimidin-6-yl-sulfonamide derivatives and pharmaceutical compositions for the treatment of heart conditions treatable by SGK-1 inhibition such as Long QT syndrome.

BACKGROUND

Long QT syndrome (LQTS) is a condition of the heart's electrical system, in which repolarization of the heart after a heartbeat is affected. LQTS results in an increased risk of an irregular heartbeat which can result in fainting, drowning or even sudden death. Several genetic causes for LQTS have been identified, and a majority of mutations are seen in genes encoding for three main cardiac ion channels (KCNQ1, KCNH2 and SCN5a).

There are several existing treatment options for LQTS, such as the use of beta-blockers that slow the heart rate by reducing the effect of adrenaline on the heart, surgery on the nerves that regulate the heartbeat, and/or the use of an implantable cardioverter defibrillator. However, none of the existing treatment options address the underlying mechanistic problem.

Serine/threonine-protein kinase (SGK-1) (also known as serum/glucocorticoid-regulated kinase 1) is a protein kinase that plays a role in a cell's response to stress. SGK-1 activates certain potassium, sodium, and chloride channels. For instance, SGK-1 is known to regulate the myo-inositol transporter during osmotic stress. The use of SGK-1 inhibitors has been reported in WO 2015048531 for the treatment of LQTS. However, several challenges remain in the development of an SGK-1 inhibitor for the treatment of heart conditions such as LQTS.

SUMMARY

In one aspect, a compound of Formula I is provided:

Formula I

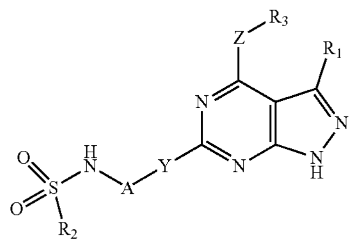

or a pharmaceutically acceptable salt thereof, wherein:

Z is selected from the group consisting of a direct bond, O, S, $CH(R_9)$ and $N(R_{10})$;

$R_1$ is selected from the group consisting of H, —$N(R_{11})R_{12}$, —$N(R_{13})$—C(O)—$R_{14}$, —$NR_{13}$—$S(O)_2$—$R_{15}$, —$NR_{13}$—C(O)—NH—$R_{16}$, —$(C_1$-$C_4)$-alkyl, —$(C_1$-$C_4)$-alkyl-$OR_{17}$ and —$(C_1$-$C_4)$-alkyl-$N(R_{18})R_{19}$;

$R_3$ is selected from the group consisting of H, $(C_1$-$C_8)$-alkyl, $R_{30}$ and $(C_1$-$C_4)$-alkyl-$R_{30}$, wherein $(C_1$-$C_8)$-alkyl is unsubstituted or substituted by one or more identical or different substituents $R_{31}$;

$R_{30}$ is a 3-membered to 12-membered, monocyclic or bicyclic, saturated, partially unsaturated or aromatic, cyclic group which comprises 0, 1, 2 or 3 identical or different ring heteroatoms selected from the group consisting of nitrogen, oxygen and sulfur, which is unsubstituted or substituted by one or more identical or different substituents $R_{32}$;

$R_{31}$ is selected from the group consisting of halogen, —OH, —$CF_3$, —O—$(C_1$-$C_4)$-alkyl, —$N(R_{33})$—$R_{34}$ and —CN;

$R_{32}$ is selected from the group consisting of halogen, $(C_1$-$C_4)$-alkyl, $(C_3$-$C_7)$-cycloalkyl, —$(C_1$-$C_4)$-alkyl-$(C_3$-$C_7)$-cycloalkyl, —$(C_1$-$C_4)$-alkyl-O—$R_{37}$, —$(C_1$-$C_4)$-alkyl-$N(R_{38})$—$R_{39}$, —$(C_1$-$C_4)$-alkyl-CN, —C(O)—$(C_1$-$C_4)$-alkyl, —CN, —OH, =O, —O—$(C_1$-$C_4)$-alkyl, —$N(R_{40})$—$R_{41}$, —C(O)—O—$(C_1$-$C_4)$-alkyl and —C(O)—$N(R_{42})$—$R_{43}$;

A is a direct bond or —$CH_2$—;

Y is selected from the group consisting of carbocyclylene and heterocyclylene, which is unsubstituted or substituted by one or more identical or different substituents $R_5$;

$R_5$ is selected from the group consisting of halogen, $(C_1$-$C_4)$-alkyl, —O—$(C_1$-$C_4)$-alkyl and —CN;

when Y is not 1,4-phenylene, or when Y is 1,4-phenylene and $R_1$ is —$(C_1$-$C_4)$-alkyl-$N(R_{18})R_{19}$: $R_2$ is selected from the group consisting of from the group consisting of $(C_1$-$C_4)$-alkyl, $(C_3$-$C_7)$-cycloalkyl, $(C_2$-$C_4)$-alkenyl, $(C_2$-$C_4)$-alkynyl, phenyl and a 5-membered or 6-membered monocyclic, saturated, partially unsaturated or aromatic, heterocyclic group which comprises 1, 2 or 3 identical or different ring heteroatoms selected from the group consisting of nitrogen, oxygen and sulfur, and is bonded via a ring carbon atom or a ring nitrogen atom, wherein $R_2$ is unsubstituted or substituted by one or more identical or different substituents $R_{20}$;

when Y is 1,4-phenylene and $R_1$ is H, —$N(R_{11})$ $R_{12}$, —$N(R_{13})$—C(O)—$R_{14}$, —$NR_{13}$—$S(O)_2$—$R_{15}$, —$NR_{13}$—C(O)—NH—$R_{16}$, —$(C_1$-$C_4)$-alkyl or —$(C_1$-$C_4)$-alkyl-$OR_{17}$: $R_2$ is selected from the group consisting of $(C_1$-$C_4)$-alkyl, $(C_3$-$C_7)$-cycloalkyl, $(C_2$-$C_4)$-alkenyl, $(C_2$-$C_4)$-alkynyl and a 5-membered or 6-membered monocyclic, saturated or partially unsaturated, heterocyclic group which comprises 1, 2 or 3 identical or different ring heteroatoms selected from the group consisting of nitrogen, oxygen and sulfur, and is bonded via a ring carbon atom or a ring nitrogen atom, wherein $R_2$ is unsubstituted or substituted by one or more identical or different substituents $R_{20}$;

$R_{20}$ is selected from the group consisting of halogen, —$CF_3$, $(C_1$-$C_4)$-alkyl, —$OR_{21}$, —$N(R_{22})$ $R_{23}$, $(C_1$-$C_4)$-alkyl-$OR_{24}$, $(C_1$-$C_4)$-alkyl-$N(R_{25})R_{26}$ and —CN;

$R_9$, $R_{10}$, $R_{11}$, $R_{12}$, $R_{13}$, $R_{14}$, $R_{15}$, $R_{16}$, $R_{17}$, $R_{18}$, $R_{19}$, $R_{21}$, $R_{22}$, $R_{23}$, $R_{24}$, $R_{25}$, $R_{26}$, $R_{37}$, $R_{38}$, $R_{39}$, $R_{40}$, $R_{41}$, $R_{42}$ and $R_{43}$ are independently of one another selected from the group consisting of H and $(C_1$-$C_4)$-alkyl;

$R_{33}$ and $R_{34}$ are independently of one another selected from the group consisting of H, —CH=O, $(C_1$-$C_4)$-alkyl and $(C_3$-$C_7)$-cycloalkyl, wherein $(C_1$-$C_4)$-alkyl and $(C_3$-$C_7)$-cycloalkyl are unsubstituted or substituted by one or more identical or different substituents $R_{50}$; and $R_{50}$ is selected from the group consisting of halogen, —OH, —O—($C_1$-$C_4$)-alkyl, —$CF_3$ and —CN.

In one aspect, a compound of Formula II is provided:

Formula II

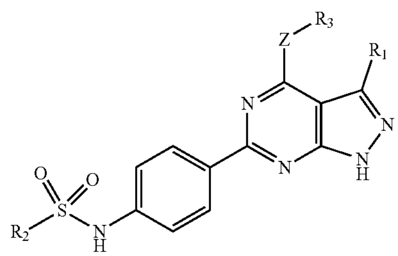

or a pharmaceutically acceptable salt thereof, wherein:

Z is selected from the group consisting of O, $CH_2$, S and NH;

$R_1$ is selected from the group consisting of H, and —($C_1$-$C_4$)-alkyl;

$R_3$ is selected from the group consisting of —$(CH_2)_p$—N($R_{33}$) $R_{34}$;

p is 1, 2, 3 or 4;

$R_2$ is selected from the group consisting of a 5-membered or 6-membered monocyclic, aromatic or heteroaromatic group which comprises 1, 2 or 3 identical or different ring heteroatoms selected from the group consisting of nitrogen, oxygen and sulfur, wherein $R_2$ is unsubstituted or substituted by one or more identical or different substituents $R_{20}$;

$R_{20}$ is selected from the group consisting of halogen, —$CF_3$, ($C_1$-$C_4$)-alkyl, —$OR_{21}$, —N($R_{22}$)$R_{23}$, ($C_1$-$C_4$)-alkyl-$OR_{24}$, ($C_1$-$C_4$)-alkyl-N($R_{25}$)$R_{26}$ and —CN;

$R_{21}$, $R_{22}$, $R_{23}$, $R_{24}$, $R_{25}$ and $R_{26}$, are independently of one another selected from the group consisting of H and ($C_1$-$C_4$)-alkyl;

$R_{33}$ and $R_{34}$ are independently of one another selected from the group consisting of —CH═O, ($C_1$-$C_4$)-alkyl and ($C_3$-$C_7$)-cycloalkyl, wherein ($C_1$-$C_4$)-alkyl and ($C_3$-$C_7$)-cycloalkyl are each unsubstituted or substituted by one or more identical or different substituents $R_{50}$; and $R_{50}$ is selected from the group consisting of halogen, —OH, —O—($C_1$-$C_4$)-alkyl, $CF_3$, and —CN.

In another aspect, a compound of Formula II is provided:

Formula II

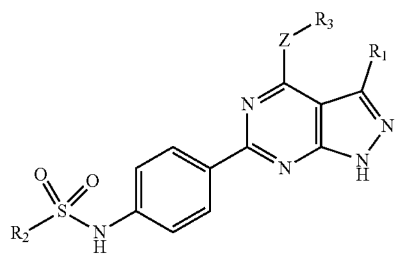

or a pharmaceutically acceptable salt thereof, wherein:

Z is selected from the group consisting of a direct bond, O, S, CH($R_9$) and N($R_{10}$);

$R_1$ is selected from the group consisting of H, —N($R_{11}$)$R_{12}$, —N($R_{13}$)—C(O)—$R_{14}$, —$NR_{13}$—$S(O)_2$—$R_{15}$, —$NR_{13}$—C(O)—NH—$R_{16}$, —($C_1$-$C_4$)-alkyl, —($C_1$-$C_4$)-alkyl-$OR_{17}$ and —($C_1$-$C_4$)-alkyl-N($R_{18}$)$R_{19}$;

$R_3$ is selected from the group consisting of H, ($C_1$-$C_8$)-alkyl, $R_{30}$ and ($C_1$-$C_4$)-alkyl-$R_{30}$, wherein ($C_1$-$C_5$)-alkyl is unsubstituted or substituted by one or more identical or different substituents $R_{31}$;

$R_{30}$ is a 3-membered to 12-membered, monocyclic or bicyclic, saturated, partially unsaturated or aromatic, cyclic group which comprises 0, 1, 2 or 3 identical or different ring heteroatoms selected from the group consisting of nitrogen, oxygen and sulfur, which is unsubstituted or substituted by one or more identical or different substituents $R_{32}$ $R_{31}$ is selected from the group consisting of halogen, —OH, —$CF_3$, —O—($C_1$-$C_4$)-alkyl, —N($R_{33}$)—$R_{34}$ and —CN;

$R_{32}$ is selected from the group consisting of halogen, ($C_1$-$C_4$)-alkyl, ($C_3$-$C_7$)-cycloalkyl, —($C_1$-$C_4$)-alkyl-($C_3$-$C_7$)-cycloalkyl, —($C_1$-$C_4$)-alkyl-O—$R_{37}$, —($C_1$-$C_4$)-alkyl-N($R_{38}$)—$R_{39}$, —($C_1$-$C_4$)-alkyl-CN, —C(O)—($C_1$-$C_4$)-alkyl, —CN, —OH, ═O, —O—($C_1$-$C_4$)-alkyl, —N($R_{40}$)—$R_{41}$, —C(O)—O—($C_1$-$C_4$)-alkyl and —C(O)—N($R_{42}$)—$R_{43}$;

$R_2$ is a 6-membered monocyclic, heteroaromatic group which comprises 1 or 2 nitrogen atoms, wherein $R_2$ is unsubstituted or substituted by one or more identical or different substituents $R_{20}$;

$R_{20}$ is selected from the group consisting of halogen, —$CF_3$, ($C_1$-$C_4$)-alkyl, —$OR_{21}$, —N($R_{22}$)$R_{23}$, ($C_1$-$C_4$)-alkyl-$OR_{24}$, ($C_1$-$C_4$)-alkyl-N($R_{25}$)$R_{26}$ and —CN;

$R_9$, $R_{10}$, $R_{11}$, $R_{12}$, $R_{13}$, $R_{14}$, $R_{15}$, $R_{16}$, $R_{17}$, $R_{18}$, $R_{19}$, $R_{21}$, $R_{22}$, $R_{23}$, $R_{24}$, $R_{25}$, $R_{26}$, $R_{37}$, $R_{38}$, $R_{39}$, $R_{40}$, $R_{41}$, $R_{42}$ and $R_{43}$ are independently of one another selected from the group consisting of H and ($C_1$-$C_4$)-alkyl;

$R_{33}$ and $R_{34}$ are independently of one another selected from the group consisting of H, —CH═O, ($C_1$-$C_4$)-alkyl and ($C_3$-$C_7$)-cycloalkyl wherein ($C_1$-$C_4$)-alkyl and ($C_3$-$C_7$)-cycloalkyl are unsubstituted or substituted by one or more identical or different substituents $R_{50}$; and $R_{50}$ is selected from the group consisting of halogen, —OH, —O—($C_1$-$C_4$)-alkyl, —$CF_3$ and —CN.

In yet another aspect, a compound of Formula II is provided:

Formula II

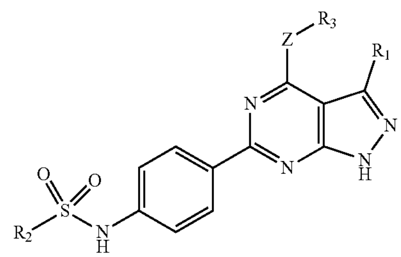

or a pharmaceutically acceptable salt thereof, wherein:

Z is selected from the group consisting of O, $CH_2$, S and NH;

$R_1$ is selected from the group consisting of H, and —($C_1$-$C_4$)-alkyl;

$R_3$ is selected from the group consisting of —$(CH_2)_p$—$N(R_{33})$ $R_{34}$;

p is 1, 2, 3 or 4;

$R_2$ is a 6-membered monocyclic, heteroaromatic group which comprises 1 or 2 nitrogen atoms, wherein $R_2$ is unsubstituted or substituted by one or more identical or different substituents $R_{20}$;

$R_{20}$ is selected from the group consisting of halogen, —$CF_3$, $(C_1$-$C_4)$-alkyl, —$OR_{21}$, —$N(R_{22})R_{23}$, $(C_1$-$C_4)$-alkyl-$OR_{24}$, $(C_1$-$C_4)$-alkyl-$N(R_{25})R_{26}$ and —CN;

$R_{21}$, $R_{22}$, $R_{23}$, $R_{24}$, $R_{25}$ and $R_{26}$, are independently of one another selected from the group consisting of H and $(C_1$-$C_4)$-alkyl;

$R_{33}$ and $R_{34}$ are independently of one another selected from the group consisting of —CH═O, $(C_1$-$C_4)$-alkyl and $(C_3$-$C_7)$-cycloalkyl, wherein $(C_1$-$C_4)$-alkyl and $(C_3$-$C_7)$-cycloalkyl are each unsubstituted or substituted by one or more identical or different substituents $R_{50}$; and $R_{50}$ is selected from the group consisting of halogen, —OH, —O—$(C_1$-$C_4)$-alkyl, $CF_3$, and —CN.

In another aspect, there is provided a compound of Formula III:

Formula III

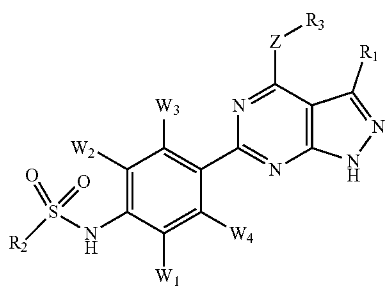

or a pharmaceutically acceptable salt thereof, wherein:

Z is selected from the group consisting of O, $CH_2$, S and NH;

$R_1$ is selected from the group consisting of H, and —$(C_1$-$C_4)$-alkyl;

$R_3$ is selected from the group consisting of —$(CH_2)_p$—$N(R_{33})R_{34}$, wherein zero, one or two hydrogen atoms of the group —$(CH_2)_p$— are independently replaced with F;

p is 1, 2, 3 or 4;

$R_2$ is selected from the group consisting of a 5-membered or 6-membered monocyclic, aromatic or heteroaromatic group which comprises 1, 2 or 3 identical or different ring heteroatoms selected from the group consisting of nitrogen, oxygen and sulfur, wherein $R_2$ is unsubstituted or substituted by one or more identical or different substituents $R_{20}$;

$R_{20}$ is selected from the group consisting of halogen, —$CF_3$, $(C_1$-$C_4)$-alkyl, —$OR_{21}$, —$N(R_{22})R_{23}$, $(C_1$-$C_4)$-alkyl-$OR_{24}$, $(C_1$-$C_4)$-alkyl-$N(R_{25})R_{26}$ and —CN;

$R_{21}$, $R_{22}$, $R_{23}$, $R_{24}$, $R_{25}$ and $R_{26}$, are independently of one another selected from the group consisting of H and $(C_1$-$C_4)$-alkyl;

$R_{33}$ and $R_{34}$ are independently of one another selected from the group consisting of —CH═O, $(C_1$-$C_4)$-alkyl and $(C_3$-$C_7)$-cycloalkyl, wherein $(C_1$-$C_4)$-alkyl and $(C_3$-$C_7)$-cycloalkyl are each unsubstituted or substituted by one or more identical or different substituents $R_{50}$;

$R_{50}$ is selected from the group consisting of halogen, —$OR_{27}$, —O—$(C_1$-$C_4)$-alkyl, $CF_3$, and —CN;

$R_{27}$ is selected from the group consisting of H, —C(═O)—$(C_1$-$C_4)$-alkyl, a natural amino acid bound by the α-carboxyl group, or $P(═O)(OH)_2$; and $W_1$, $W_2$, $W_3$, $W_4$ are independently of one another selected from the group consisting of H, halogen, —$OR_{21}$, —$CF_3$, $(C_1$-$C_4)$-alkyl, and —CN.

In another aspect, there is provided a compound of Formula III:

Formula III

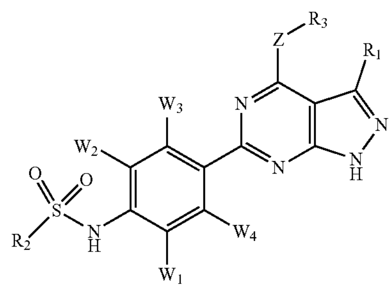

or a pharmaceutically acceptable salt thereof, wherein:

Z is selected from the group consisting of O and NH;

$R_1$ is selected from the group consisting of H and $(C_1$-$C_4)$-alkyl;

$R_3$ is —$(CH_2)_p$—$N(R_{33})$ $R_{34}$;

p is 2, 3 or 4;

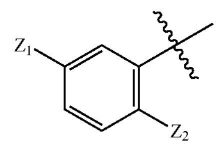

$R_2$ is $Z_1$ and $Z_2$ are independently from one another selected from the group consisting of Cl, F, —OMe and —CN;

$R_{33}$ and $R_{34}$ are independently of one another a $(C_1$-$C_4)$-alkyl; and $W_1$, $W_2$, $W_3$, $W_4$ are independently of one another selected from the group consisting of H, halogen, —$OR_{21}$, —$CF_3$, $(C_1$-$C_4)$-alkyl, and —CN, $R_{21}$, is selected from the group consisting of H and $(C_1$-$C_4)$-alkyl.

In another aspect, there is provided a compound of Formula III:

Formula III

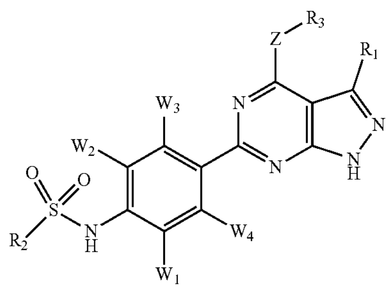

or a pharmaceutically acceptable salt thereof, wherein:

Z is selected from the group consisting of O, and NH;

$R_1$ is selected from the group consisting of H, and —($C_1$-$C_4$)-alkyl;

$R_3$ is a nitrogen-bearing heterocycle selected from the group consisting of

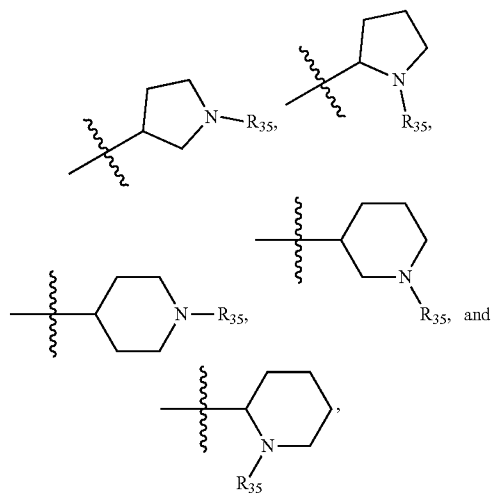

wherein zero, one or two hydrogens on any of the —$CH_2$-groups of the nitrogen-bearing heterocycle is replaced with halogen, —OH, —CN, —$CF_3$ or ($C_1$-$C_4$)-alkyl;

$R_{35}$ is H or ($C_1$-$C_4$)-alkyl which is unsubstituted or substituted by one or more identical or different substituents $R_{50}$; and $R_{50}$ is selected from the group consisting of halogen, —OH, —O—($C_1$-$C_4$)-alkyl, $CF_3$, and —CN;

$R_2$ is

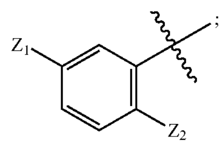

$Z_1$ and $Z_2$ are independently from one another selected from the group consisting of Cl, F, —OMe and —CN;

$W_1$ is F or OMe;

$W_2$ is H or F;

$W_3$ is H; and $W_4$ is H.

In another aspect, there is provided a compound of Formula III:

Formula III

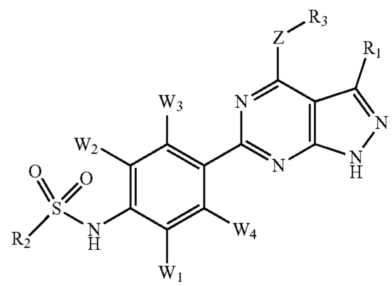

or a pharmaceutically acceptable salt thereof, wherein:

Z is selected from the group consisting of O, and NH;

$R_1$ is selected from the group consisting of H, and —($C_1$-$C_4$)-alkyl;

$R_3$ is a nitrogen-bearing heterocycle selected from the group consisting of

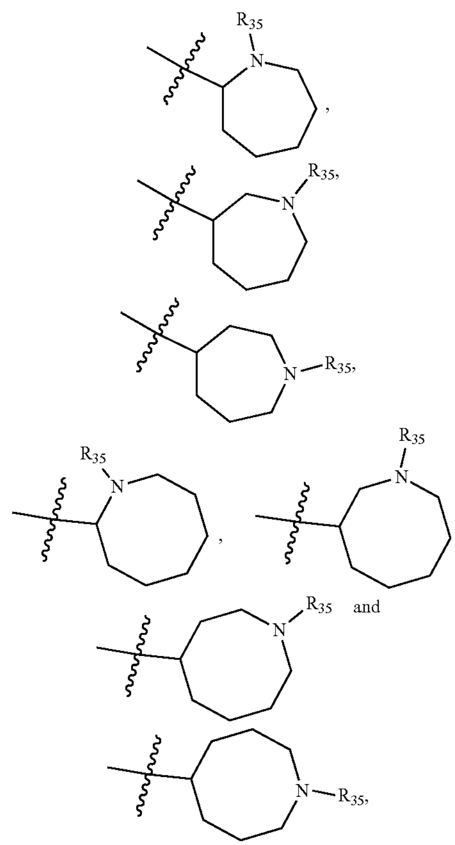

wherein zero, one or two hydrogens on any of the —$CH_2$— groups of the nitrogen-bearing heterocycle is replaced with halogen, —OH, —CN, —$CF_3$ or ($C_1$-$C_4$)-alkyl;

$R_{35}$ is H or ($C_1$-$C_4$)-alkyl which is unsubstituted or substituted by one or more identical or different substituents $R_{50}$; and $R_{50}$ is selected from the group consisting of halogen, —OH, —O—($C_1$-$C_4$)-alkyl, $CF_3$, and —CN;

$R_2$ is

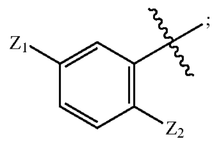

$Z_1$ and $Z_2$ are independently from one another selected from the group consisting of Cl, F, —OMe and —CN;

$W_1$, $W_2$, $W_3$, $W_4$ are independently of one another selected from the group consisting of H, halogen, —$OR_{21}$, —$CF_3$, ($C_1$-$C_4$)-alkyl, and —CN, $R_{21}$ is selected from the group consisting of H and ($C_1$-$C_4$)-alkyl.

In another aspect, there is provided a compound of Formula III:

Formula III

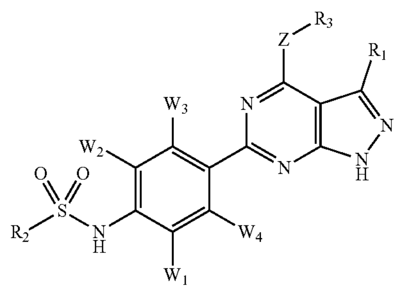

or a pharmaceutically acceptable salt thereof, wherein:

Z is selected from the group consisting of O and NH;

$R_1$ is ($C_1$-$C_4$)-alkyl;

$R_3$ is selected from the group consisting of: —$(CH_2)_p$—$N(R_{33})R_{34}$,

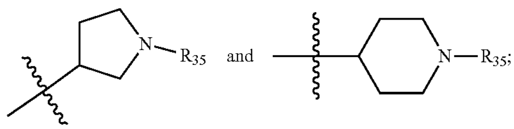

p is 2, 3 or 4;

$R_{33}$, $R_{34}$ and $R_{35}$ are independently from one another a ($C_1$-$C_4$)-alkyl which is unsubstituted or substituted by one or more identical or different substituents $R_{50}$;

$R_{50}$ is selected from the group consisting of halogen, —$OR_{27}$, —O—($C_1$-$C_4$)-alkyl, $CF_3$, and —CN;

$R_{27}$ is selected from the group consisting of H, —C(═O)—($C_1$-$C_4$)alkyl, a natural amino acid bound by the α-carboxyl group, or P(═O)$(OH)_2$;

$R_2$ is

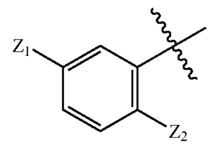

$Z_1$ and $Z_2$ are independently of one another selected from the group consisting of Cl, F, —OMe and —CN;

$W_1$ is F or OMe;

$W_2$ is H;

$W_3$ is H; and $W_4$ is H.

In yet another aspect, a compound of Formula IV is provided:

Formula IV

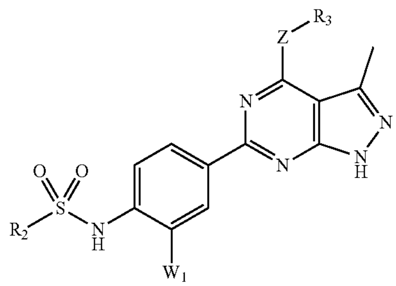

or a pharmaceutically acceptable salt thereof, wherein:

Z is selected from the group consisting of O and NH;

$R_3$ is selected from the group consisting of: —$(CH_2)_p$—$N(R_{33})R_{34}$,

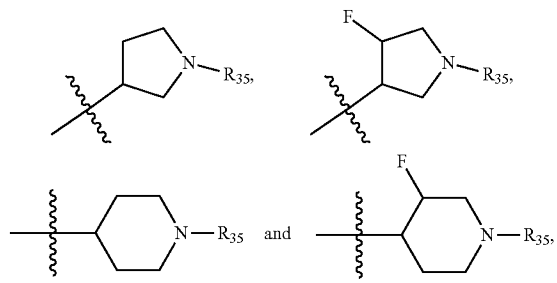

p is 2, 3 or 4;

$R_{33}$ and $R_{34}$ are independently from one another a ($C_1$-$C_4$)-alkyl which is unsubstituted or substituted by one or more identical or different substituents $R_{50}$;

$R_{35}$ is H or a ($C_1$-$C_4$)-alkyl which is unsubstituted or substituted by one or more identical or different substituents $R_{50}$;

$R_{50}$ is selected from the group consisting of halogen, —$OR_{27}$, —O—($C_1$-$C_4$)-alkyl, —$CF_3$, and —CN;

$R_{27}$ is selected from the group consisting of H, —C(═O)—($C_1$-$C_4$)alkyl, a natural amino acid bound by the α-carboxyl group, and P(═O)$(OH)_2$;

$R_2$ is

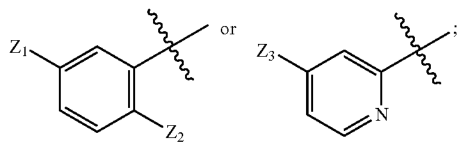

or

;

$Z_1$ and $Z_2$ are independently of one another selected from the group consisting of halogen, $(C_1\text{-}C_4)$alkyl, —OH, —O—$(C_1\text{-}C_4)$alkyl, —$CF_3$, and —CN;

$Z_3$ is selected from the group consisting of H, halogen, $(C_1\text{-}C_4)$alkyl, —OH, —O—$(C_1\text{-}C_4)$alkyl, —$CF_3$ and —CN; and $W_1$ is halogen.

In another aspect, a compound of Formula IV is provided:

Formula IV

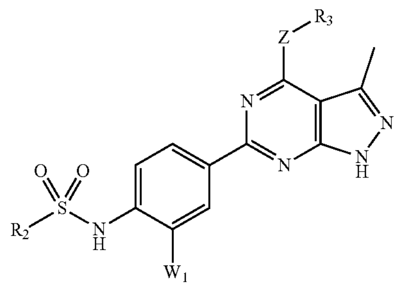

or a pharmaceutically acceptable salt thereof, wherein:

Z—$R_3$ is selected from the group consisting of:

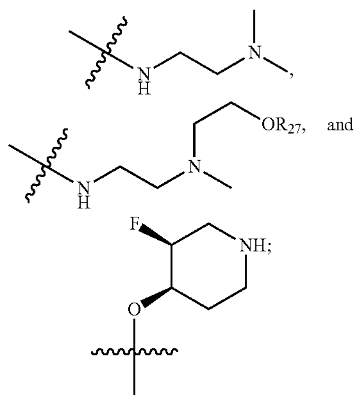

and $R_{27}$ is selected from the group consisting of: H,

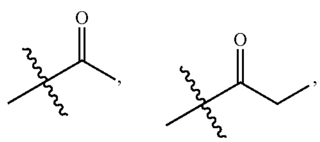

-continued

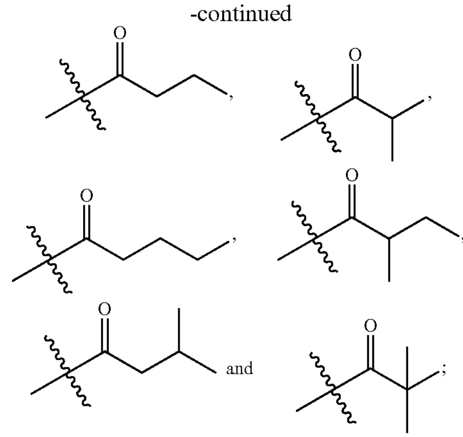

and $R_2$ is selected from the group consisting of

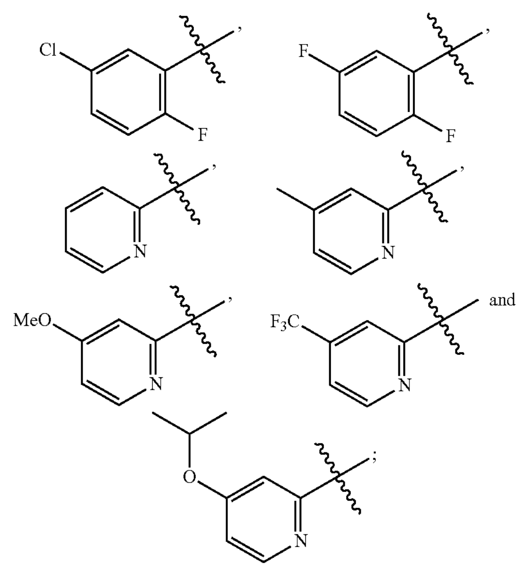

and and $W_1$ is selected from the group consisting of Cl and F.

In another aspect, a compound of Formula V is provided:

Formula V

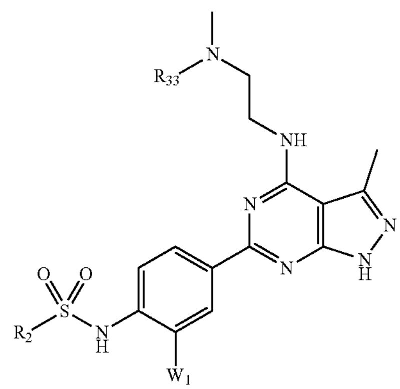

or a pharmaceutically acceptable salt thereof, wherein:

$R_2$ is

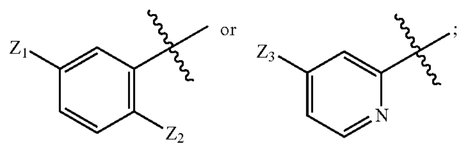

$Z_1$ and $Z_2$ are independently from one another selected from the group consisting of halogen, $(C_1\text{-}C_4)$alkyl, —OH, —O—$(C_1\text{-}C_4)$alkyl, —$CF_3$, and —CN;

$Z_3$ is selected from the group consisting of H, halogen, $(C_1\text{-}C_4)$alkyl, —OH, —O—$(C_1\text{-}C_4)$alkyl, —$CF_3$ and —CN;

$W_1$ is selected from the group consisting of H and halogen;

$R_{33}$ is —$CH_3$ or —$(CH_2)$—$(CH_2)$—$OR_{27}$; and $R_{27}$ is selected from the group consisting of H, —C(═O)—$(C_1\text{-}C_4)$alkyl, a natural amino acid bound by the α-carboxyl group, and —P(═O)$(OH)_2$.

In one aspect, a compound of Formula Vb is provided:

Formula Vb

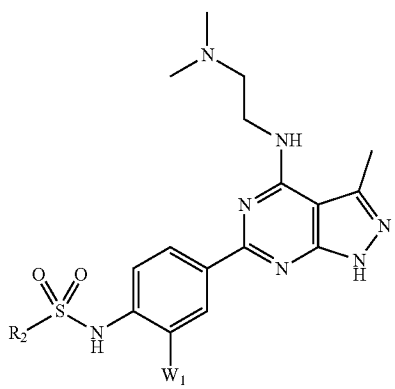

or a pharmaceutically acceptable salt thereof, wherein:

$R_2$ is

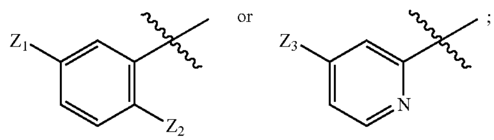

$Z_1$ and $Z_2$ are independently from one another selected from the group consisting of halogen, $(C_1\text{-}C_4)$alkyl, —OH, —O—$(C_1\text{-}C_4)$alkyl, —$CF_3$, and —CN;

$Z_3$ is selected from the group consisting of H, halogen, $(C_1\text{-}C_4)$alkyl, —OH, —O—$(C_1\text{-}C_4)$alkyl, —$CF_3$ and —CN; and $W_1$ is selected from the group consisting of H and halogen.

In another aspect, there is provided a compound of Formula VI:

Formula VI

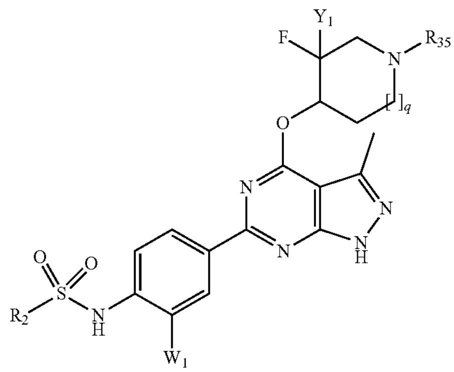

or a pharmaceutically acceptable salt thereof, wherein:

$Y_1$ is H or F;

q is 0 or 1;

$R_2$ is

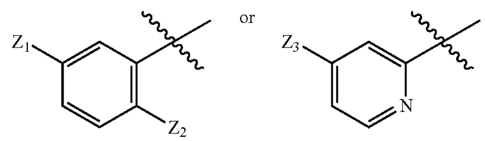

$Z_1$ and $Z_2$ are independently from one another selected from the group consisting of halogen, $(C_1\text{-}C_4)$alkyl, —OH, —O—$(C_1\text{-}C_4)$alkyl, —$CF_3$, and —CN;

$Z_3$ is selected from the group consisting of H, halogen, $(C_1\text{-}C_4)$alkyl, —OH, —O—$(C_1\text{-}C_4)$alkyl, —$CF_3$ and —CN;

$W_1$ is selected from the group consisting of H and halogen;

$R_{35}$ is H or a $(C_1\text{-}C_4)$-alkyl which is unsubstituted or substituted by one or more identical or different substituents $R_{50}$;

$R_{50}$ is selected from the group consisting of halogen, —$OR_{27}$, —O—$(C_1\text{-}C_4)$-alkyl, —$CF_3$, and —CN;

$R_{27}$ is selected from the group consisting of H, —C(═O)—$(C_1\text{-}C_4)$alkyl, a natural amino acid bound by the α-carboxyl group, and P(═O)$(OH)_2$.

In yet another aspect, a pharmaceutical composition is provided, comprising a compound as defined herein or a pharmaceutically acceptable salt thereof, and at least one pharmaceutically acceptable carrier or excipient.

In yet another aspect, there is provided the use of a compound as defined herein, or a pharmaceutically acceptable salt thereof, as an inhibitor of SGK-1. For example, the compounds as defined herein, or a pharmaceutically acceptable salt thereof, may be used for the treatment of prostate cancer or epilepsy. For example, the compounds as defined herein, or a pharmaceutically acceptable salt thereof, may be used for the treatment of a cardiovascular disease selected from the group consisting of Long QT syndrome, heart failure, arrhythmia, ischemic injury, ischemic infarction, cardiac fibrosis, vascular proliferation, restenosis, dilated cardiomyopathy, and stent failure. More particularly, the compounds as defined herein, or a pharmaceutically acceptable salt thereof, may be used for the treatment of Long QT syndrome.

In another aspect, there is provided the use of the compound as defined herein, or a pharmaceutically acceptable salt thereof, for the manufacture of a medicament that inhibits SGK-1 in a subject. For example, the medicament may be for the treatment of prostate cancer. For example, the medicament may be for the treatment of epilepsy. For example, the medicament may be for the treatment of a cardiovascular disease selected from the group consisting of Long QT syndrome, heart failure, arrhythmia, ischemic injury, ischemic infarction, cardiac fibrosis, vascular proliferation, restenosis, dilated cardiomyopathy, and stent failure. More particularly, the medicament may be used for the treatment of Long QT syndrome.

In another aspect, a method for the treatment of other conditions related to SGK-1 mediated mechanisms is provided. Such conditions can include, without limitations, at least one of prostate cancer, colorectal cancer, breast cancer (e.g., resistant breast cancer), Parkinson's disease and Lafora disease.

In another aspect, a method for the treatment of prostate cancer is provided. The method comprises administering to a subject a therapeutically effective amount of a compound as defined herein, or a pharmaceutically acceptable salt thereof. The method comprising administering to a subject a therapeutically effective amount of a compound as defined herein, or a pharmaceutically acceptable salt thereof.

In another aspect, a method for the treatment of a cardiovascular disease is provided. The method comprises administering to a subject a therapeutically effective amount of a compound as defined herein, or a pharmaceutically acceptable salt thereof. The cardiovascular disease is selected from the group consisting of Long QT syndrome, heart failure, arrhythmia, ischemic injury, ischemic infarction, cardiac fibrosis, vascular proliferation, restenosis, dilated cardiomyopathy, and stent failure.

In another aspect, a method for the treatment of Long QT syndrome is provided. The method comprises administering to a subject a therapeutically effective amount of a compound as defined herein, or a pharmaceutically acceptable salt thereof.

DETAILED DESCRIPTION

The present description relates to compounds of Formula I, or pharmaceutically acceptable salts thereof.

Formula I

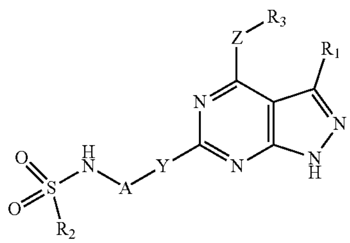

The compounds of Formula I and their pharmaceutically acceptable salts are pharmacologically active compounds that modulate protein kinase activity, specifically the activity of serum and glucocorticoid regulated kinase isoform 1 (SGK-1). The compounds of Formula I or their pharmaceutically acceptable salts can be suitable for the treatment of conditions in which SGK-1 activity is inappropriate. Non-limiting examples of such conditions can include Long QT syndrome, heart failure, arrhythmia, ischemic injury, ischemic infarction, cardiac fibrosis, vascular proliferation, restenosis, dilated cardiomyopathy, stent failure, prostate cancer and epilepsy. The compounds of Formula I and their pharmaceutically acceptable salts are described in more detail herein.

Definitions

Unless stated otherwise, the following terms and phrases as used herein are intended to have the following meanings. The fact that a particular term or phrase is not specifically defined should not be correlated to indefiniteness or lacking clarity, but rather terms herein are used within their ordinary meaning. When trade names are used herein, it is intended to independently include the tradename product and the active pharmaceutical ingredient(s) of the tradename product.

"Alkyl" is hydrocarbon containing primary, secondary or tertiary carbon atoms. For example, an alkyl group can have 1 to 20 carbon atoms (i.e, $C_1$-$C_{20}$ alkyl), 1 to 8 carbon atoms (i.e., $C_1$-$C_8$ alkyl), or 1 to 4 carbon atoms (i.e., $C_1$-$C_4$ alkyl). Examples of suitable alkyl groups include, but are not limited to, methyl (Me, $—CH_3$), ethyl (Et, $—CH_2CH_3$), 1-propyl (n-Pr, n-propyl, $—CH_2CH_2CH_3$), 2-propyl (i-Pr, i-propyl, $—CH(CH_3)_2$), 1-butyl (n-Bu, n-butyl, $—CH_2CH_2CH_2CH_3$), 2-methyl-1-propyl (i-Bu, i-butyl, $—CH_2CH(CH_3)_2$), 2-butyl (s-Bu, s-butyl, $—CH(CH_3)CH_2CH_3$), 2-methyl-2-propyl (t-Bu, t-butyl, $—C(CH_3)_3$), 1-pentyl (n-pentyl, $—CH_2CH_2CH_2CH_2CH_3$), 2-pentyl ($—CH(CH_3)CH_2CH_2CH_3$), 3-pentyl ($—CH(CH_2CH_3)_2$), 2-methyl-2-butyl ($—C(CH_3)_2CH_2CH_3$), 3-methyl-2-butyl ($—CH(CH_3)CH(CH_3)_2$), 3-methyl-1-butyl ($—CH_2CH_2CH(CH_3)_2$), 2-methyl-1-butyl ($—CH_2CH(CH_3)CH_2CH_3$), 1-hexyl ($—CH_2CH_2CH_2CH_2CH_2CH_3$), 2-hexyl ($—CH(CH_3)CH_2CH_2CH_2CH_3$), 3-hexyl ($—CH(CH_2CH_3)(CH_2CH_2CH_3)$), 2-methyl-2-pentyl ($—C(CH_3)_2CH_2CH_2CH_3$), 3-methyl-2-pentyl ($—CH(CH_3)CH(CH_3)CH_2CH_3$), 4-methyl-2-pentyl ($—CH(CH_3)CH_2CH(CH_3)_2$), 3-methyl-3-pentyl ($—C(CH_3)(CH_2CH_3)_2$), 2-methyl-3-pentyl ($—CH(CH_2CH_3)CH(CH_3)_2$), 2,3-dimethyl-2-butyl ($—C(CH_3)_2CH(CH_3)_2$), 3,3-dimethyl-2-butyl ($—CH(CH_3)C(CH_3)_3$, and octyl ($—(CH_2)CH_3$).

Alkoxy" means a group having the formula-O-alkyl, in which an alkyl group, as defined above, is attached to the parent molecule via an oxygen atom. The alkyl portion of an alkoxy group can have 1 to 20 carbon atoms (i.e., $C_1$-$C_{20}$ alkoxy), 1 to 12 carbon atoms (i.e., $C_1$-$C_{12}$ alkoxy), or 1 to 4 carbon atoms (i.e., $C_1$-$C_4$ alkoxy). Examples of suitable alkoxy groups include, but are not limited to, methoxy ($—O—CH_3$ or —OMe), ethoxy ($—OCH_2CH_3$ or -OEt), t-butoxy ($—O—C(CH_3)_3$ or -OtBu), and the like.

"Haloalkyl" is an alkyl group, as defined above, in which one or more hydrogen atoms of the alkyl group is replaced with a halogen atom. The alkyl portion of a haloalkyl group can have 1 to 20 carbon atoms (i.e., $C_1$-$C_{20}$ haloalkyl), 1 to 12 carbon atoms (i.e., $C_1$-$C_{12}$ haloalkyl), or 1 to 4 carbon atoms (i.e., $C_1$-$C_4$ haloalkyl). Examples of suitable haloalkyl groups include, but are not limited to, $—CF_3$, $—CHF_2$, $—CFH_2$, $—CH_2CF_3$, and the like.

"Cycloalkyl" means a mono or bicyclic carbocyclic ring functional group including, but not limited to, cyclopropyl, cyclobutyl, cyclopentyl, cyclohexyl, cycloheptyl, cyclooctyl, cyclononyl, bicyclo[2.2.1]heptanyl, bicyclo[3.2.1]octanyl, and bicyclo[5.2.0]nonanyl. The cycloalkyl can have 3 to 12 carbon atoms (i.e., $C_3$-$C_{12}$ cycloalkyl), 3 to 7 carbon atoms (i.e., $C_3$-$C_7$ cycloalkyl) or 3 to 6 carbon atoms (i.e., $C_3$-$C_6$ cycloalkyl). Unless otherwise indicated, the term "($C_3$-$C_7$)cycloalkyl" refers to a cycloalkyl group containing from 3 to 8 carbons. Thus, the term "($C_3$-$C_7$)cycloalkyl"

encompasses a monocyclic cycloalkyl group containing from 3 to 7 carbons and a bicyclic cycloalkyl group containing from 6 to 7 carbons.

"Alkenyl" is a hydrocarbon containing primary, secondary or tertiary carbon atoms with at least one site of unsaturation, i.e. a carbon-carbon, sp2 double bond. For example, an alkenyl group can have 2 to 20 carbon atoms (i.e., $C_2$-$C_{20}$ alkenyl), 2 to 12 carbon atoms (i.e., $C_2$-$C_{12}$ alkenyl), or 2 to 6 carbon atoms (i.e., $C_2$-$C_6$ alkenyl). Examples of suitable alkenyl groups include, but are not limited to, ethylene, vinyl ($—CH{=}CH_2$), allyl ($—CH_2CH{=}CH_2$), cyclopentenyl ($—C_5H_7$), and 5-hexenyl ($—CH_2CH_2CH_2CH_2CH{=}CH_2$).

"Alkynyl" is a hydrocarbon containing primary, secondary or tertiary carbon atoms with at least one site of unsaturation, i.e. a carbon-carbon, sp triple bond. For example, an alkynyl group can have 2 to 20 carbon atoms (i.e., $C_2$-$C_{20}$ alkynyl), 2 to 12 carbon atoms (i.e., $C_2$-$C_{12}$ alkynyl), or 2 to 6 carbon atoms (i.e., $C_2$-$C_6$ alkynyl). Examples of suitable alkynyl groups include, but are not limited to, acetylenic ($—C{\equiv}CH$), propargyl ($—CH_2C{=}CH$), and the like.

"Alkylene" refers to a saturated, branched or straight hydrocarbon radical having two monovalent radical centers derived by the removal of two hydrogen atoms from the same or two different carbon atoms of a parent alkane. For example, an alkylene group can have 1 to 20 carbon atoms, 1 to 10 carbon atoms, or 1 to 6 carbon atoms. Typical alkylene radicals include, but are not limited to, methylene ($—CH_2—$), 1,1-ethylene ($—CH(CH_3)—$), 1,2-ethylene ($—CH_2CH_2—$), 1,1-propylene ($—CH(CH_2CH_3)—$), 1,2-propylene ($—CH_2CH(CH_3)—$), 1,3-propylene ($—CH_2CH_2CH_2—$), 1,4-butylene ($—CH_2CH_2CH_2CH_2—$), and the like.

"Alkenylene" refers to an unsaturated, branched or straight hydrocarbon radical having two monovalent radical centers derived by the removal of two hydrogen atoms from the same or two different carbon atoms of a parent alkene. For example, and alkenylene group can have 1 to 20 carbon atoms, 1 to 10 carbon atoms, or 1 to 6 carbon atoms. Typical alkenylene radicals include, but are not limited to, 1,2-ethylene ($—CH{=}CH—$).

"Alkynylene" refers to an unsaturated, branched or straight hydrocarbon radical having two monovalent radical centers derived by the removal of two hydrogen atoms from the same or two different carbon atoms of a parent alkyne. For example, an alkynylene group can have 1 to 20 carbon atoms, 1 to 10 carbon atoms, or 1 to 6 carbon atoms. Typical alkynylene radicals include, but are not limited to, acetylene ($—C{\equiv}C—$), propargyl ($—CH_2C{=}C—$), and 4-pentynyl ($—CH_2CH_2CH_2C{\equiv}C—$).

"Aryl" means a monovalent aromatic hydrocarbon radical derived by the removal of one hydrogen atom from a single carbon atom of a parent aromatic ring system. For example, an aryl group can have 6 to 20 carbon atoms, 6 to 14 carbon atoms, or 6 to 12 carbon atoms. Typical aryl groups include, but are not limited to, radicals derived from benzene (e.g., phenyl), substituted benzene, naphthalene, anthracene, biphenyl, and the like.

"Arylene" refers to an aryl as defined above having two monovalent radical centers derived by the removal of two hydrogen atoms from the same or two different carbon atoms of a parent aryl. Typical arylene radicals include, but are not limited to, phenylene, such as 1,4-phenylene.

"Arylalkyl" refers to an acyclic alkyl radical in which one of the hydrogen atoms bonded to a carbon atom, typically a terminal or sp3 carbon atom, is replaced with an aryl radical. Typical arylalkyl groups include, but are not limited to, benzyl, 2-phenylethan-1-yl, naphthylmethyl, 2-naphthylethan-1-yl, naphthobenzyl, 2-naphthophenylethan-1-yl and the like. The arylalkyl group can comprise 6 to 20 carbon atoms, e.g., the alkyl moiety is 1 to 6 carbon atoms and the aryl moiety is 6 to 14 carbon atoms.

"Arylalkenyl" refers to an acyclic alkenyl radical in which one of the hydrogen atoms bonded to a carbon atom, typically a terminal or sp3 carbon atom, but also an sp2 carbon atom, is replaced with an aryl radical. The aryl portion of the arylalkenyl can include, for example, any of the aryl groups disclosed herein, and the alkenyl portion of the arylalkenyl can include, for example, any of the alkenyl groups disclosed herein. The arylalkenyl group can comprise 6 to 20 carbon atoms, e.g., the alkenyl moiety is 1 to 6 carbon atoms and the aryl moiety is 6 to 14 carbon atoms.

"Arylalkynyl" refers to an acyclic alkynyl radical in which one of the hydrogen atoms bonded to a carbon atom, typically a terminal or sp3 carbon atom, but also an sp carbon atom, is replaced with an aryl radical. The aryl portion of the arylalkynyl can include, for example, any of the aryl groups disclosed herein, and the alkynyl portion of the arylalkynyl can include, for example, any of the alkynyl groups disclosed herein. The arylalkynyl group can comprise 6 to 20 carbon atoms, e.g., the alkynyl moiety is 1 to 6 carbon atoms and the aryl moiety is 6 to 14 carbon atoms.

As used herein, the "halogen" refers to F, Cl, Br, or I.

As used herein the term "haloalkyl" refers to an alkyl group, as defined herein, that is substituted with at least one halogen. Examples of branched or straight chained "haloalkyl" groups as used herein include, but are not limited to, methyl, ethyl, propyl, isopropyl, n-butyl, and t-butyl substituted independently with one or more halogens, for example, fluoro, chloro, bromo, and iodo. The term "haloalkyl" should be interpreted to include such substituents as perfluoroalkyl groups such as $—CF_3$.

The term "substituted" in reference to alkyl, aryl, arylalkyl, carbocyclyl, heterocyclyl, and other groups used herein, for example, "substituted alkyl", "substituted cycloalkyl", "substituted aryl", "substituted arylalkyl", "substituted heterocyclyl", and "substituted carbocyclyl" means a group, alkyl, alkylene, aryl, arylalkyl, heterocyclyl, carbocyclyl respectively, in which one or more hydrogen atoms are each independently replaced with a non-hydrogen substituent. Typical substituents include, but are not limited to, —X, —R, —O—, =O, —OR, —SR, —S—, $—NR_2$, $—N(+)R_3$, =NR, $—CX_3$, $—CRX_2$, $—CR_2X$, —CN, —OCN, —SCN, —N—C—O, —NCS, —NO, $—NO_2$, $=N_2$, $—N_3$, —NRC(=O)R, —NRC(=O)OR, —NRC(=O)NRR, —C(=O)NRR, —C(=O)OR, —OC(=O)NRR, —OC(=O)OR, —C(=O)R, $—S(=O)_2OR$, $—S(=O)_2R$, $—OS(=O)_2OR$, $—S(=O)_2NR$, —S(=O)R, $—NRS(=O)_2R$, $—NRS(=O)_2NRR$, $—NRS(=O)_2OR$, $—OP(=O)(OR)_2$, $—P(=O)(OR)_2$, —P(O)(OR)(O)R, —C(=O)R, —C(=S)R, —C(=O)OR, —C(=S)OR, —C(=O)SR, —C(=S)SR, —C(=O)NRR, —C(=S)NRR, —C(=NR)NRR, —NRC(=NR)NRR, where each X is independently a halogen: F, Cl, Br, or I; and each R is independently H, alkyl, cycloalkyl, aryl, arylalkyl, a heterocycle, or a protecting group or prodrug moiety. Divalent groups may also be similarly substituted.

Those skilled in the art will recognize that when moieties such as "alkyl", "aryl", "heterocyclyl", etc. are substituted with one or more substituents, they could alternatively be referred to as "alkylene", "arylene", "heterocyclylene", etc. moieties (i.e., indicating that at least one of the hydrogen atoms of the parent "alkyl", "aryl", "heterocyclyl" moieties has been replaced with the indicated substituent(s)). When moieties such as "alkyl", "aryl", "heterocyclyl", etc. are referred to herein as "substituted" or are shown diagrammatically to be substituted (or optionally substituted, e.g., when the number of substituents ranges from zero to a positive integer), then the terms "alkyl", "aryl", "heterocyclyl", etc. are understood to be interchangeable with "alkylene", "arylene", "heterocyclylene", etc.

"Heteroalkyl" refers to an alkyl group where one or more carbon atoms have been replaced with a heteroatom, such as, O, N, or S. For example, if the carbon atom of the alkyl group which is attached to the parent molecule is replaced with a heteroatom (e.g., O, N, or S) the resulting heteroalkyl groups are, respectively, an alkoxy group (e.g., $—OCH_3$, etc.), an amine (e.g., $—NHCH_3$, $—N(CH_3)_2$, and the like), or a thioalkyl group (e.g., $—SCH_3$). If a non-terminal carbon atom of the alkyl group which is not attached to the parent molecule is replaced with a heteroatom (e.g., O, N, or S) and the resulting heteroalkyl groups are, respectively, an alkyl ether (e.g., $—CH_2CH_2—O—CH_3$, etc.), an alkyl amine (e.g., $—CH_2NHCH_3$, $—CH_2N(CH_3)_2$, and the like), or a thioalkyl ether (e.g., $—CH_2—S—CH_3$). If a terminal carbon atom of the alkyl group is replaced with a heteroatom (e.g., O, N, or S), the resulting heteroalkyl groups are, respectively, a hydroxyalkyl group (e.g., $—CH_2CH_2—OH$), an aminoalkyl group (e.g., $—CH_2NH_2$), or an alkyl thiol group (e.g., $—CH_2CH_2—SH$). A heteroalkyl group can have, for example, 1 to 20 carbon atoms, 1 to 10 carbon atoms, or 1 to 6 carbon atoms. A $C_1$-$C_6$ heteroalkyl group means a heteroalkyl group having 1 to 6 carbon atoms.

"Heterocycle" or "heterocyclyl" as used herein includes by way of example and not limitation those heterocycles described in Paquette, Leo A.; *Principles of Modern Heterocyclic Chemistry* (W. A. Benjamin, New York, 1968), particularly Chapters 1, 3, 4, 6, 7, and 9; The Chemistry of Heterocyclic Compounds, A Series of Monographs" (John Wiley & Sons, New York, 1950 to present), in particular Volumes 13, 14, 16, 19, and 28; and *J. Am. Chem. Soc.* (1960) 82:5566. In one specific embodiment of the invention "heterocycle" includes a "carbocycle" as defined herein, wherein one or more (e.g. 1, 2, 3, or 4) carbon atoms have been replaced with a heteroatom (e.g. O, N, P or S). The terms "heterocycle" or "heterocyclyl" includes saturated rings, partially unsaturated rings, and aromatic rings (i.e., heteroaromatic rings). Heterocycles includes aromatic and non-aromatic mono-, bi-, and poly-cyclic rings, whether fused, bridged, or spiro. As used herein, the term "heterocycle" encompasses, but is not limited to "heteroaryl."

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, azetidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, ß-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl and isatinoyl.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

"Heterocyclylene" refers to a heterocyclyl, as defined herein, derived by replacing a hydrogen atom from a carbon atom or heteroatom of a heterocyclyl, with an open valence. Similarly, "heteroarylene" refers to an aromatic heterocyclylene.

"Heterocyclylalkyl" refers to an acyclic alkyl radical in which one of the hydrogen atoms bonded to a carbon atom, typically a terminal or sp3 carbon atom, is replaced with a heterocyclyl radical (i.e., a heterocyclyl-alkylene-moiety). Typical heterocyclyl alkyl groups include, but are not limited to heterocyclyl-$CH_2$—, 2-(heterocyclyl)ethan-1-yl, and the like, wherein the "heterocyclyl" portion includes any of the heterocyclyl groups described above, including those described in *Principles of Modern Heterocyclic Chemistry*. One skilled in the art will also understand that the heterocyclyl group can be attached to the alkyl portion of the heterocyclyl alkyl by means of a carbon-carbon bond or a carbon-heteroatom bond, with the proviso that the resulting group is chemically stable. The heterocyclyl alkyl group comprises 2 to 20 carbon atoms, e.g., the alkyl portion of the arylalkyl group comprises 1 to 6 carbon atoms and the heterocyclyl moiety comprises 1 to 14 carbon atoms. Examples of heterocyclylalkyls include by way of example and not limitation 5-membered sulfur, oxygen, and/or nitrogen containing heterocycles such as thiazolylmethyl, 2-thiazolylethan-1-yl, imidazolylmethyl, oxazolylmethyl, thiadiazolylmethyl, and the like, 6-membered sulfur, oxygen, and/or nitrogen containing heterocycles such as piperidinylmethyl, piperazinylmethyl, morpholinylmethyl, pyridinylmethyl, pyridizylmethyl, pyrimidylmethyl, pyrazinylmethyl, and the like.

"Heterocyclylalkenyl" refers to an acyclic alkenyl radical in which one of the hydrogen atoms bonded to a carbon atom, typically a terminal or sp3 carbon atom, but also a sp2 carbon atom, is replaced with a heterocyclyl radical (i.e., a heterocyclyl-alkenylene-moiety). The heterocyclyl portion of the heterocyclyl alkenyl group includes any of the heterocyclyl groups described herein, including those described in *Principles of Modern Heterocyclic Chemistry*, and the alkenyl portion of the heterocyclyl alkenyl group includes any of the alkenyl groups disclosed herein. One skilled in the art will also understand that the heterocyclyl group can be attached to the alkenyl portion of the heterocyclyl alkenyl by means of a carbon-carbon bond or a carbon-heteroatom bond, with the proviso that the resulting group is chemically stable. The heterocyclyl alkenyl group comprises 2 to 20 carbon atoms, e.g., the alkenyl portion of the heterocyclyl alkenyl group comprises 1 to 6 carbon atoms and the heterocyclyl moiety comprises 1 to 14 carbon atoms.

"Heteroaryl" refers to a monovalent aromatic heterocyclyl having at least one heteroatom in the ring. Non-limiting examples of suitable heteroatoms which can be included in the aromatic ring include oxygen, sulfur, and nitrogen. Non-limiting examples of heteroaryl rings include all of those listed in the definition of "heterocyclyl", including pyridinyl, pyrrolyl, oxazolyl, indolyl, isoindolyl, purinyl, furanyl, thienyl, benzofuranyl, benzothiophenyl, carbazolyl, imidazolyl, thiazolyl, isoxazolyl, pyrazolyl, isothiazolyl, quinolyl, isoquinolyl, pyridazyl, pyrimidyl, pyrazyl, and the like.

"Carbocycle" or "carbocyclyl" refers to a saturated, partially unsaturated or aromatic ring having 3 to 7 carbon atoms as a monocycle, 7 to 12 carbon atoms as a bicycle, and up to about 20 carbon atoms as a polycycle. Monocyclic carbocycles have 3 to 6 ring atoms, still more typically 5 or 6 ring atoms. Bicyclic carbocycles have 7 to 12 ring atoms, e.g., arranged as a bicyclo (4,5), (5,5), (5,6) or (6,6) system, or 9 or 10 ring atoms arranged as a bicyclo (5,6) or (6,6) system. Carbocycles includes aromatic and non-aromatic mono-, bi-, and poly-cyclic rings, whether fused, bridged, or spiro. Non-limiting examples of monocyclic carbocycles include the cycloalkyls group such as cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl or aryl groups such as phenyl, and the like. Thus, "carbocycle," as used herein, encompasses but is not limited to "aryl", "phenyl" and "biphenyl."

"Carbocyclylene" refers to a carbocyclyl or carbocycle as defined above having two monovalent radical centers derived by the removal of two hydrogen atoms from the same or two different carbon atoms of a parent carbocyclyl. Typical carbocyclylene radicals include, but are not limited to, phenylene. Thus, "carbocyclylene," as used herein, encompasses but is not limited to "arylene."

"Carbocyclylalkyl" refers to an acyclic alkyl radical in which one of the hydrogen atoms bonded to a carbon atom, typically a terminal or sp3 carbon atom, is replaced with a carbocyclyl radical as defined above. Typical carbocyclylalkyl groups include, but are not limited to the arylalkyl groups such as benzyl, 2-phenylethan-1-yl, naphthylmethyl, 2-naphthylethan-1-yl, naphthobenzyl, 2-naphthophenylethan-1-yl or the cycloalkylalkyl groups such as cyclopropylmethyl, cyclobutylethyl, cyclohexylmethyl and the like. The arylalkyl group can comprise 6 to 20 carbon atoms, e.g., the alkyl moiety is 1 to 6 carbon atoms and the aryl moiety is 6 to 14 carbon atoms. The cycloalkylalkyl group can comprise 4 to 20 carbon atoms, e.g., the alkyl moiety is 1 to 6 carbon atoms and the cycloalkyl group is 3 to 14 carbon atoms.

"Arylheteroalkyl" refers to a heteroalkyl as defined herein, in which a hydrogen atom, which may be attached either to a carbon atom or a heteroatom, has been replaced with an aryl group as defined herein. The aryl groups may be bonded to a carbon atom of the heteroalkyl group, or to a heteroatom of the heteroalkyl group, provided that the resulting arylheteroalkyl group provides a chemically stable moiety. For example, an arylheteroalkyl group can have the general formulae -alkylene-O-aryl, -alkylene-O-alkylene-aryl, -alkylene-NH-aryl, -alkylene-NH-alkylene-aryl, -alkylene-S-aryl, -alkylene-S-alkylene-aryl, and the like. In addition, any of the alkylene moieties in the general formulae above can be further substituted with any of the substituents defined or exemplified herein.

"Heteroarylalkyl" refers to an alkyl group, as defined herein, in which a hydrogen atom has been replaced with a heteroaryl group as defined herein. Non-limiting examples of heteroaryl alkyl include-$CH_2$-pyridinyl, —$CH_2$-pyrrolyl, —$CH_2$-oxazolyl, —$CH_2$-indolyl, —$CH_2$-isoindolyl, —$CH_2$-purinyl, —$CH_2$-furanyl, —$CH_2$-thienyl, —$CH_2$-benzofuranyl, —$CH_2$-benzothiophenyl, —$CH_2$-carbazolyl, —$CH_2$-imidazolyl, —$CH_2$-thiazolyl, —$CH_2$-isoxazolyl, —$CH_2$-pyrazolyl, —$CH_2$-isothiazolyl, —$CH_2$-quinolyl, —$CH_2$-isoquinolyl, —$CH_2$-pyridazyl, —$CH_2$-pyrimidyl, —$CH_2$-pyrazyl, —$CH(CH_3)$-pyridinyl, —$CH(CH_3)$-pyrrolyl, —$CH(CH_3)$-oxazolyl, —$CH(CH_3)$-indolyl, —$CH(CH_3)$-isoindolyl, —$CH(CH_3)$-purinyl, —$CH(CH_3)$-furanyl, —$CH(CH_3)$-thienyl, —$CH(CH_3)$-benzofuranyl, —$CH(CH_3)$-benzothiophenyl, —$CH(CH_3)$-carbazolyl, —$CH(CH_3)$-imidazolyl, —$CH(CH_3)$-thiazolyl, —$CH(CH_3)$-isoxazolyl, —$CH(CH_3)$-pyrazolyl, —$CH(CH_3)$-isothiazolyl, —$CH(CH_3)$-quinolyl, —$CH(CH_3)$-isoquinolyl, —$CH(CH_3)$-pyridazyl, —$CH(CH_3)$-pyrimidyl, —$CH(CH_3)$-pyrazyl, and the like.

The term "optionally substituted" in reference to a particular moiety of the compound of the Formulae of the invention, for example an optionally substituted aryl group, refers to a moiety having 0, 1, or more substituents.

The term "prodrug" as used herein refers to any compound that when administered to a biological system generates the drug substance, i.e., active ingredient, as a result of spontaneous chemical reaction(s), enzyme catalyzed chemical reaction(s), photolysis, and/or metabolic chemical reaction(s). A prodrug is thus a covalently modified analog or latent form of a therapeutically active compound.

One skilled in the art will recognize that substituents and other moieties of the compounds of the present description should be selected in order to provide a compound which is sufficiently stable to provide a pharmaceutically useful compound which can be formulated into an acceptably stable pharmaceutical composition.

Some compounds of the present description and their pharmaceutically acceptable salts may exist as different polymorphs or pseudopolymorphs. As used herein, crystalline polymorphism means the ability of a crystalline compound to exist in different crystal structures. Polymorphism generally can occur as a response to changes in temperature, pressure, or both. Polymorphism can also result from variations in the crystallization process.

Polymorphs can be distinguished by various physical characteristics known in the art such as x-ray diffraction patterns, solubility, and melting point. The crystalline polymorphism may result from differences in crystal packing (packing polymorphism) or differences in packing between different conformers of the same molecule (conformational polymorphism). As used herein, crystalline pseudopolymorphism means the ability of a hydrate or solvate of a compound to exist in different crystal structures. The pseudopolymorphs of some of the compounds of the present description may exist due to differences in crystal packing (packing pseudopolymorphism) or due to differences in packing between different conformers of the same molecule (conformational pseudopolymorphism). It is understood that all polymorphs and pseudopolymorphs of the compounds described herein and their pharmaceutically acceptable salts are included within the scope of the present description.

The compounds of the present description and their pharmaceutically acceptable salts may exist as an amorphous solid. As used herein, an amorphous solid is a solid in which there is no long-range order of the positions of the atoms in the solid. This definition applies as well when the crystal size is two nanometers or less. Additives, including solvents, may be used to create amorphous forms the compounds of the present description.

Certain of the compounds described herein contain one or more chiral centers or may otherwise be capable of existing as multiple stereoisomers. The scope of the present description includes mixtures of stereoisomers as well as purified enantiomers or enantiomerically/diastereomerically enriched mixtures. Also included within the scope of the present description are the individual isomers of the compounds described herein, as well as any wholly or partially equilibrated mixtures thereof. The compounds of the present description and their pharmaceutically acceptable salts also includes the individual isomers of the compounds represented by the formulas above as mixtures with isomers thereof in which one or more chiral centers are inverted.

The compounds of the present description may exist in solvated, for example hydrated, as well as unsolvated forms. Typically, but not absolutely, the salts of the compounds of the present description are pharmaceutically acceptable salts. Salts encompassed within the term "pharmaceutically acceptable salts" refer to non-toxic salts of the compounds of the present description.

Examples of suitable pharmaceutically acceptable salts include inorganic acid addition salts such as chloride, bromide, sulfate, phosphate, and nitrate; organic acid addition salts such as acetate, galactarate, propionate, succinate, lactate, glycolate, malate, tartrate, citrate, maleate, fumarate, methanesulfonate, p-toluenesulfonate, and ascorbate; salts with acidic amino acid such as aspartate and glutamate; alkali metal salts such as sodium salt and potassium salt; alkaline earth metal salts such as magnesium salt and calcium salt; ammonium salt; organic basic salts such as trimethylamine salt, triethylamine salt, pyridine salt, picoline salt, dicyclohexylamine salt, and N,N'-dibenzylethylenediamine salt; and salts with basic amino acid such as lysine salt and arginine salt. The salts may be in some cases hydrates or ethanol solvates.

The definitions and substituents for various genus and subgenus of the present compounds are described and illustrated herein. It should be understood by one skilled in the art that any combination of the definitions and substituents described above should not result in an inoperable species or compound. "Inoperable species or compounds" means compound structures that violates relevant scientific principles (such as, for example, a carbon atom connecting to more than four covalent bonds) or compounds too unstable to permit isolation and formulation into pharmaceutically acceptable dosage forms.

Pharmaceutical Compositions

The compounds of the present description can be formulated with conventional carriers and excipients, which will be selected in accordance with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the *Handbook of Pharmaceutical Excipients* (1986), herein incorporated by reference in its entirety. Excipients include ascorbic acid and other antioxidants, chelating agents such as EDTA, carbohydrates such as dextrin, hydroxyalkylcellulose, hydroxyalkylmethylcellulose, stearic acid and the like. The pH of the formulations ranges from about 3 to about 11 but is ordinarily about 7 to 10.

While it is possible for the active ingredients to be administered alone it may be preferable to present them as pharmaceutical formulations. The formulations of the invention, both for veterinary and for human use, comprise at least one active ingredient, together with one or more acceptable carriers and optionally other therapeutic ingredients.

The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.), herein incorporated by reference in its entirety. Such methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent.

Molded tablets may be made by molding in a suitable machine a mixture of the powdered active ingredient moistened with an inert liquid diluent. The tablets may optionally be coated or scored and optionally are formulated so as to provide slow or controlled release of the active ingredient.

Pharmaceutical formulations according to the present description include one or more compounds together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation.

Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth herein, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned herein. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose, any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations for rectal administration may be presented as a suppository with a suitable base comprising for example cocoa butter or a salicylate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

The compounds of the present description can also be formulated to provide controlled release of the active ingredient to allow less frequent dosing or to improve the pharmacokinetic or toxicity profile of the active ingredient. Accordingly, there is also provided compositions comprising one or more compounds of the present description formulated for sustained or controlled release.

The effective dose of an active ingredient depends at least on the nature of the condition being treated, toxicity, whether the compound is being used prophylactically (lower doses) or against an active disease or condition, the method of delivery, and the pharmaceutical formulation, and will be determined by the clinician using conventional dose escalation studies. The effective dose can be expected to be from about 0.0001 to about 10 mg/kg body weight per day, typically from about 0.001 to about 1 mg/kg body weight per day, more typically from about 0.01 to about 1 mg/kg body weight per day, even more typically from about 0.05 to about 0.5 mg/kg body weight per day. For example, the daily candidate dose for an adult human of approximately 70 kg body weight will range from about 0.05 mg to about 100 mg, or between about 0.1 mg and about 25 mg, or between about 0.4 mg and about 4 mg, and may take the form of single or multiple doses.

SGK-1 and Associated Conditions

The present description relates to compounds or pharmaceutically acceptable salts thereof, for the treatment various conditions treatable by inhibiting SGK-1. For example, the condition can be Long QT syndrome (LQTS), such as genetic LQTS or acquired LQTS, or other cardiovascular diseases (e.g., dilated cardiomyopathy-genetic or acquired) that are treatable by inhibiting SGK-1. Without being bound by theory, it is believed that SGK-1 inhibition in vivo has a protective effect and can alleviate symptoms associated with LOTS; can reduce and alleviate symptoms associated with heart failure, arrhythmia, ischemic injury, ischemic infarction, cardiac fibrosis, vascular proliferation, restenosis, genetic or acquired dilated cardiomyopathy, hypertrophic cardiomyopathy, and stent failure.

Long QT syndrome (LQTS) can be genetic (e.g. caused by a mutation in the KCNQ1 gene, the KCNH2 gene, or the SCN5a gene). Alternatively, Long QT syndrome is not associated with a genetic mutation and is acquired as a result of exposure to an external stimulus. For instance, acquired Long QT syndrome can be a side effect of drugs such as erythromycin or haloperidol. Acquired Long QT syndrome is also associated with other heart conditions such as myocardial ischemia.

The present description also relates to compounds or pharmaceutically acceptable salts thereof, for the treatment of other conditions related to SGK-1 mediated mechanisms, such as prostate cancer, colorectal cancer, breast cancer (e.g., resistant breast cancer), Parkinson's disease and Lafora disease.

Serine/threonine-protein kinase (SGK-1) (also known as serum/glucocorticoid-regulated kinase 1) is a protein kinase that plays a role in a cell's response to stress. In vivo, SGK-1 activates certain potassium, sodium, and chloride channels. For instance, the protein is known to regulate the myo-inositol transporter during osmotic stress. The term "inhibitor of SGK-1", as used herein, refers to any compound that can block, arrest, interfere with, or reduce the biological activity of SGK-1.

In some embodiments, the compounds of the present description can be used for increasing fetal hemoglobin (HbF) in erythrocytes. In some embodiments, the compounds of the present description can be used for the treatment of a β-hemoglobinopathy. In some embodiments, the compounds of the present description can be used for the treatment of sickle cell disease.

In some embodiments, the compounds of the present description can be used for the treatment of prostate cancer. In other embodiments, the compounds of the present description can be used for the treatment of epilepsy.

Inhibitors of SGK-1

The compounds of the present description and their pharmaceutically acceptable salts thereof are pharmacologically active compounds that modulate protein kinase activity, specifically the activity of serum and glucocorticoid regulated kinase isoform 1 (SGK-1). The compounds of the present description or their pharmaceutically acceptable salts can be suitable for the treatment of conditions in which SGK-1 activity is inappropriate. Non-limiting examples of such conditions can include Long QT syndrome, heart failure, arrhythmia, ischemic injury, ischemic infarction, cardiac fibrosis, vascular proliferation, restenosis, dilated cardiomyopathy, stent failure, prostate cancer and epilepsy. Other non-limiting examples of such conditions include ß-hemoglobinopathies, such as sickle cell disease.

In one aspect, compounds of Formula I, or pharmaceutically acceptable salts thereof are provided.

Formula I

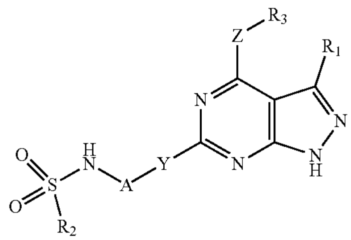

In some embodiments, Z is selected from the group consisting of a direct bond, —O—, —S—, —CH($R_9$)— and —N($R_{10}$)—, wherein Ry and $R_{10}$ are independently of one another selected from the group consisting of H and ($C_1$-$C_4$)-alkyl. In some embodiments, Z is selected from the group consisting of a direct bond, —O—, —S—, —$CH_2$— and —NH—. In some embodiments, Z is a direct bond. In some embodiments, Z is selected from the group consisting of —O— and —NH—.

In some embodiments, $R_3$ is selected from the group consisting of H, ($C_1$-$C_8$)-alkyl, $R_{30}$ and ($C_1$-$C_4$)-alkyl-$R_{30}$, wherein ($C_1$-$C_8$)-alkyl is unsubstituted or substituted by one or more identical or different substituents $R_{31}$. $R_{30}$ is a 3-membered to 12-membered, monocyclic or bicyclic, saturated, partially unsaturated or aromatic, cyclic group which comprises 0, 1, 2 or 3 identical or different ring heteroatoms selected from the group consisting of nitrogen, oxygen and sulfur, which is unsubstituted or substituted by one or more identical or different substituents $R_{32}$. $R_{31}$ is selected from the group consisting of halogen, —OH, —$CF_3$, —O—($C_1$-$C_4$)-alkyl, —N($R_{33}$)—$R_{34}$ and —CN. $R_{32}$ is selected from the group consisting of halogen, ($C_1$-$C_4$)-alkyl, ($C_3$-$C_7$)-cycloalkyl, —($C_1$-$C_4$)-alkyl-($C_3$-$C_7$)-cycloalkyl, —($C_1$-$C_4$)-alkyl-O—$R_{37}$, —($C_1$-$C_4$)-alkyl-N($R_{38}$)—$R_{39}$, —($C_1$-$C_4$)-alkyl-CN, —C(O)—($C_1$-$C_4$)-alkyl, —CN, —OH, =O, —O—($C_1$-$C_4$)-alkyl, —N($R_{40}$)—$R_{41}$, —C(O)—O—($C_1$-$C_4$)-alkyl and —C(O)—N($R_{42}$)—$R_{43}$.

In some embodiments, $R_{33}$ and $R_{34}$ are independently of one another selected from the group consisting of H, ($C_1$-

$C_4$)-alkyl and ($C_3$-$C_7$)-cycloalkyl, wherein ($C_1$-$C_4$)-alkyl and ($C_3$-$C_7$)-cycloalkyl are unsubstituted or substituted by one or more identical or different substituents $R_{50}$, wherein $R_{50}$ is selected from the group consisting of halogen, —OH, —O—($C_1$-$C_4$)-alkyl, —$CF_3$ and —CN. In some embodiments, $R_{37}$, $R_{38}$, $R_{39}$, $R_{40}$, $R_{41}$, $R_{42}$ and $R_{43}$ are independently of one another selected from the group consisting of H and ($C_1$-$C_4$)-alkyl.

In some embodiments, $R_3$ is selected from the group consisting of H, —$CH_2OH$, —$CH_3$,

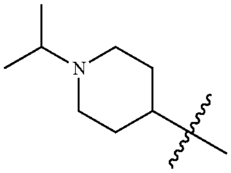,
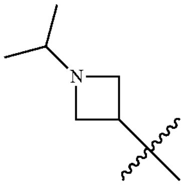,
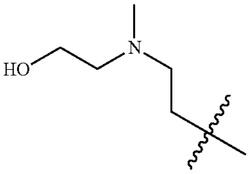,
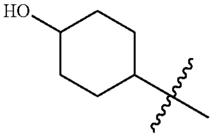,
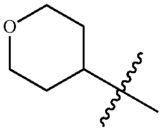,
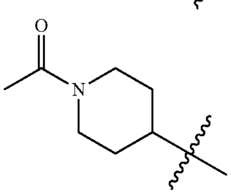,
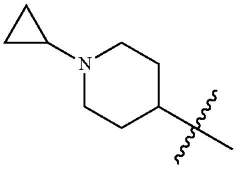,
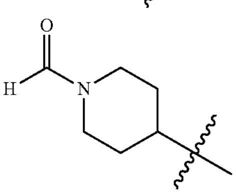,
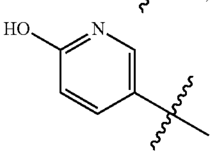,
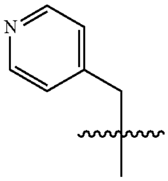,
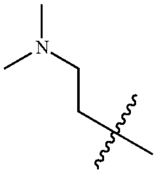,
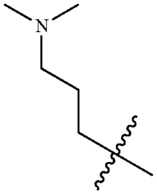,
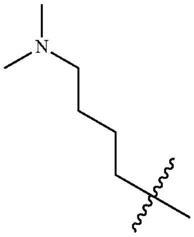
and
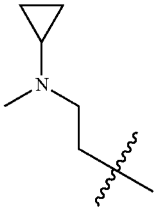.

In some embodiments, Z is a direct bond and $R_3$ is selected from the group consisting of H, —$CH_2OH$ and —$CH_3$. In other embodiments, Z is selected from the group consisting of —O— and —NH— and $R_3$ is selected from the group consisting of:

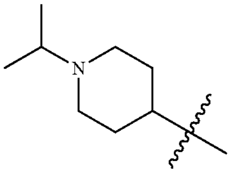,
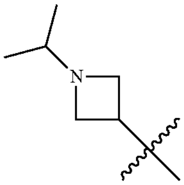,
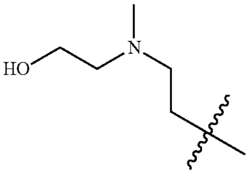,
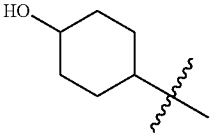,
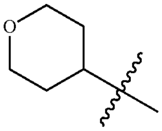,
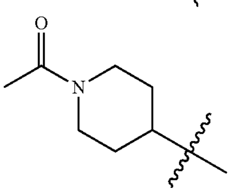,
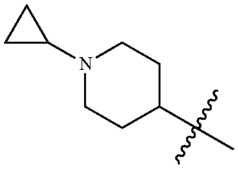,
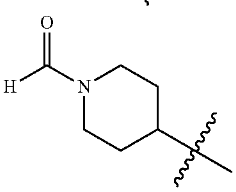,
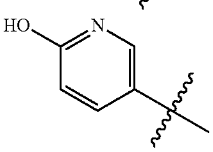,
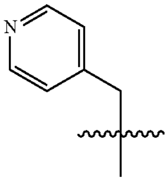,
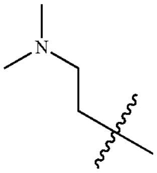,
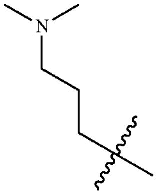,
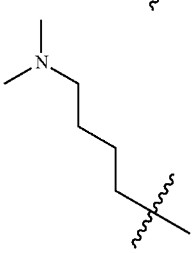
and
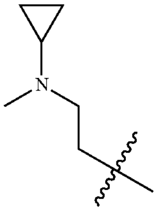.

In some embodiments, $R_1$ is selected from the group consisting of H, —N($R_{11}$)$R_{12}$, —N($R_{13}$)—C(O)—$R_{14}$, —$NR_{13}$—S(O)$_2$—$R_{15}$, —$NR_{13}$—C(O)—NH—$R_{16}$, —($C_1$-$C_4$)-alkyl, —($C_1$-$C_4$)-alkyl-$OR_{17}$ and —($C_1$-$C_4$)-alkyl-N($R_{18}$)$R_{19}$, wherein $R_{11}$, $R_{12}$, $R_{13}$, $R_{14}$, $R_{15}$, $R_{16}$, $R_{17}$, $R_{18}$ and $R_{19}$ are independently of one another selected from the group consisting of H and ($C_1$-$C_4$)-alkyl.

In some embodiments, $R_1$ is selected from the group consisting of —($C_1$-$C_4$)-alkyl, and —($C_1$-$C_4$)-alkyl-N($R_{18}$)

$R_{19}$. In some embodiments, $R_1$ is selected from the group consisting of —$CH_3$, —$CH_2N(CH_3)_2$ and —$CH_2$—$CH_2$—$N(CH_3)_2$.

In some embodiments, Y is selected from the group consisting of carbocyclylene and heterocyclylene, which is unsubstituted or substituted by one or more identical or different substituents $R_5$, wherein $R_5$ is selected from the group consisting of halogen, $(C_1-C_4)$-alkyl, —O—$(C_1-C_4)$-alkyl and —CN. In some embodiments, Y is selected from the group consisting of arylene and heteroarylene, which is unsubstituted or substituted by one or more identical or different substituents $R_5$.

In some embodiments, Y is selected from the group consisting of:

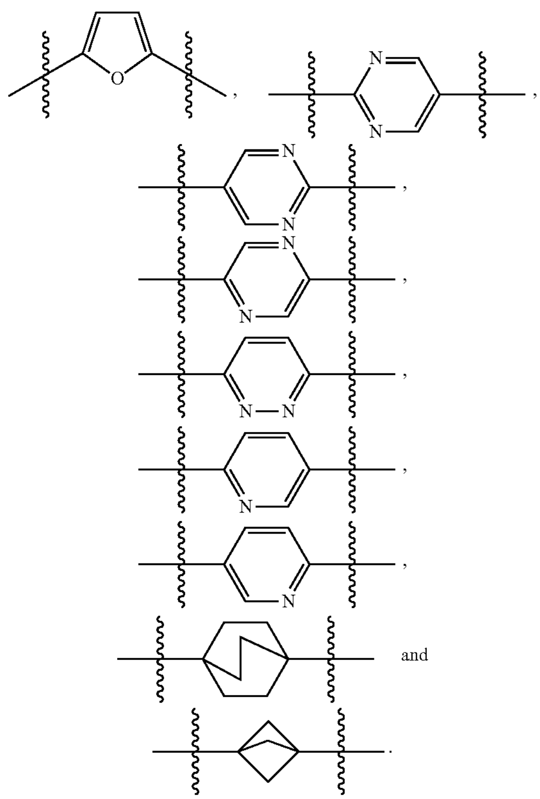

It is understood that when two symmetrical Y groups are listed, such as

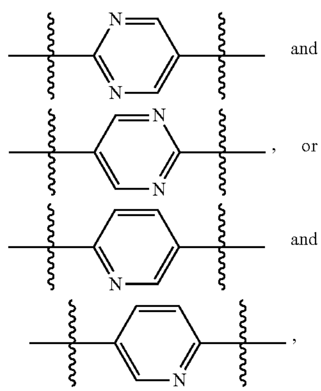

it is meant that both options:

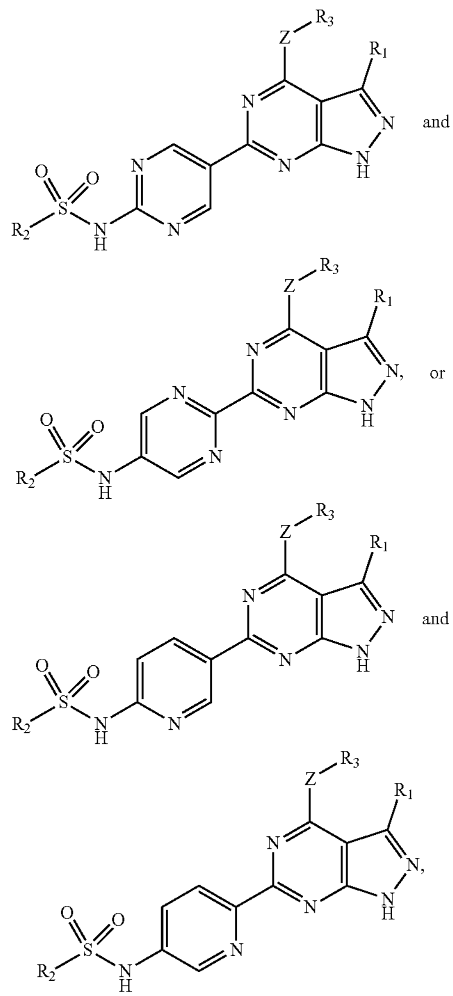

are included.

In some embodiments, A is selected from the group of a direct bond or —$CH_2$—. When A is a direct bond, —Y— is directly linked to the nitrogen of the sulfonamide group.

In some embodiments $R_2$ is selected from the group consisting of $(C_1-C_4)$-alkyl, $(C_3-C_7)$-cycloalkyl, $(C_2-C_4)$-alkenyl, $(C_2-C_4)$-alkynyl, phenyl and a 5-membered or 6-membered monocyclic, saturated, partially unsaturated or aromatic, heterocyclic group which comprises 1, 2 or 3 identical or different ring heteroatoms selected from the group consisting of nitrogen, oxygen and sulfur, and is bonded via a ring carbon atom or a ring nitrogen atom, wherein $R_2$ is unsubstituted or substituted by one or more identical or different substituents $R_{20}$, wherein $R_{20}$ is selected from the group consisting of halogen, —$CF_3$, $(C_1-C_4)$-alkyl, —$OR_{21}$, —$N(R_{22})R_{23}$, $(C_1-C_4)$-alkyl-$OR_{24}$, $(C_1-C_4)$-alkyl-$N(R_{25})R_{26}$ and —CN, and wherein $R_{21}$, $R_{22}$, $R_{23}$, $R_{24}$, $R_{25}$ and $R_{26}$ are independently of one another selected from the group consisting of H and $(C_1-C_4)$-alkyl.

In some embodiments, when Y is not 1,4-phenylene, or when Y is 1,4-phenylene and $R_1$ is —$(C_1-C_4)$-alkyl-$N(R_{18})R_{19}$: $R_2$ is selected from the group consisting of $(C_1-C_4)$-alkyl, $(C_3-C_7)$-cycloalkyl, $(C_2-C_4)$-alkenyl, $(C_2-C_4)$-alkynyl, phenyl and a 5-membered or 6-membered monocyclic, saturated, partially unsaturated or aromatic, heterocyclic group which comprises 1, 2 or 3 identical or different ring heteroatoms selected from the group consisting of nitrogen, oxygen and sulfur, and is bonded via a ring carbon atom or a ring nitrogen atom, wherein $R_2$ is unsubstituted or substituted by one or more identical or different substituents $R_{20}$, wherein $R_{20}$ is selected from the group consisting of halogen, —$CF_3$, $(C_1$-$C_4)$-alkyl, —$OR_{21}$, —$N(R_{22})R_{23}$, $(C_1$-$C_4)$-alkyl-$OR_{24}$, $(C_1$-$C_4)$-alkyl-$N(R_{25})R_{26}$ and —CN, and wherein $R_{21}$, $R_{22}$, $R_{23}$, $R_{24}$, $R_{25}$ and $R_{26}$ are independently of one another selected from the group consisting of H and $(C_1$-$C_4)$-alkyl.

In other embodiments, when Y is 1,4-phenylene and $R_1$ is H, —$N(R_{11})R_{12}$, —$N(R_{13})$—C(O)—$R_{14}$, —$NR_{13}$—S(O)$_2$—$R_{15}$, —$NR_{13}$—C(O)—NH—$R_{16}$, —$(C_1$-$C_4)$-alkyl or —$(C_1$-$C_4)$-alkyl-$OR_{17}$, $R_2$ is selected from the group consisting of $(C_1$-$C_4)$-alkyl, $(C_3$-$C_7)$-cycloalkyl, $(C_2$-$C_4)$-alkenyl, $(C_2$-$C_4)$-alkynyl and a 5-membered or 6-membered monocyclic, saturated or partially unsaturated, heterocyclic group which comprises 1, 2 or 3 identical or different ring heteroatoms selected from the group consisting of nitrogen, oxygen and sulfur, and is bonded via a ring carbon atom or a ring nitrogen atom, wherein $R_2$ is unsubstituted or substituted by one or more identical or different substituents $R_{20}$, wherein $R_{20}$ from is selected the group consisting of halogen, —$CF_3$, $(C_1$-$C_4)$-alkyl, —$OR_{21}$, —$N(R_{22})R_{23}$, $(C_1$-$C_4)$-alkyl-$OR_{24}$, $(C_1$-$C_4)$-alkyl-$N(R_{25})R_{26}$ and —CN, and wherein $R_{21}$, $R_{22}$, $R_{23}$, $R_{24}$, $R_{25}$ and $R_{26}$ are independently of one another selected from the group consisting of H and $(C_1$-$C_4)$-alkyl.

In some embodiments, $R_2$ is selected from the group consisting of:

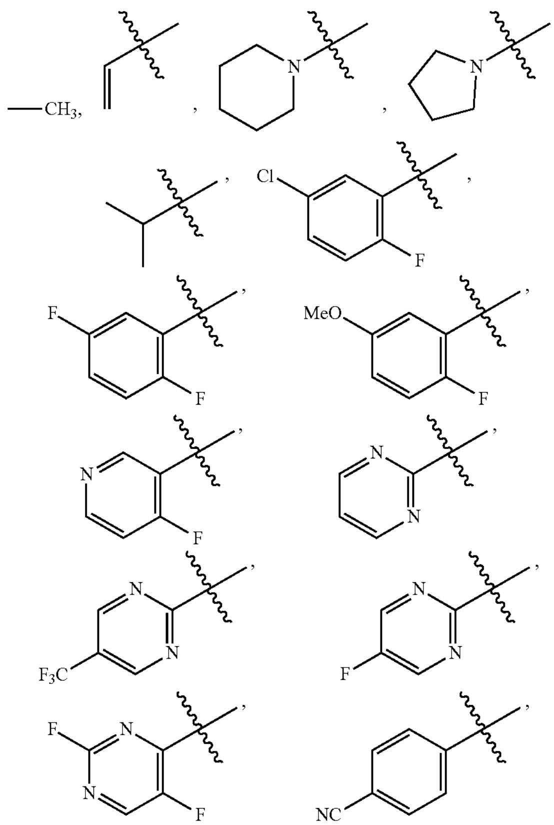

-continued

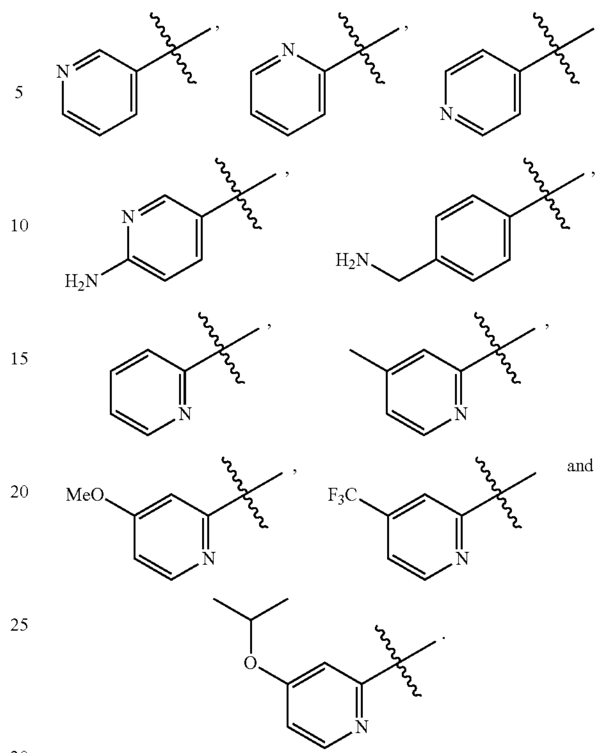

and

In some embodiments, Y is 1,4-phenylene and $R_2$ is selected from the group consisting of: —$CH_3$,

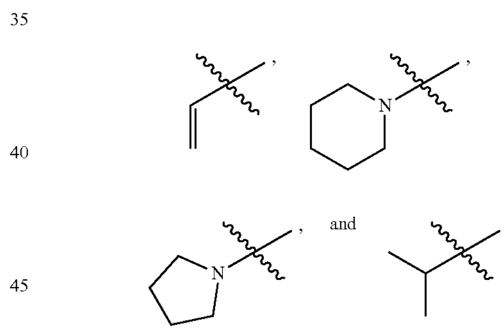

and

In some embodiments, the compound of Formula I is selected from the group consisting of:

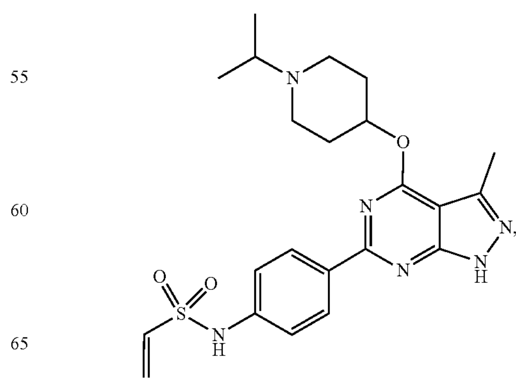

-continued
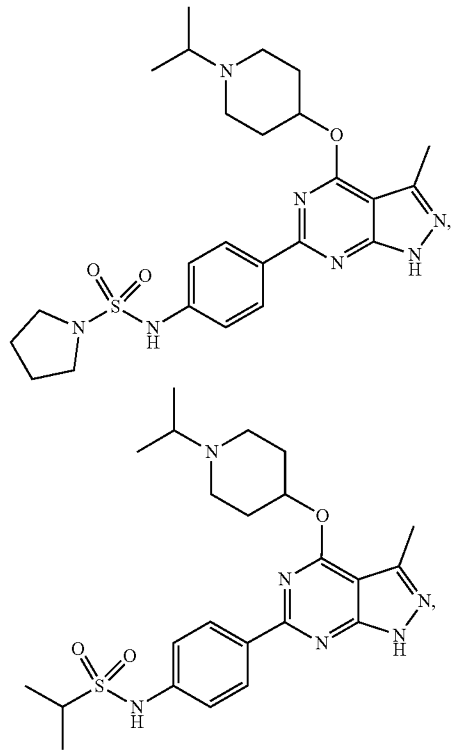
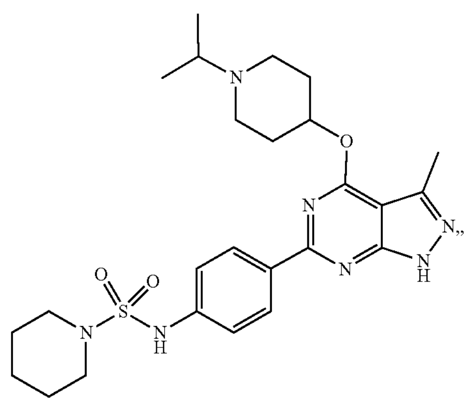
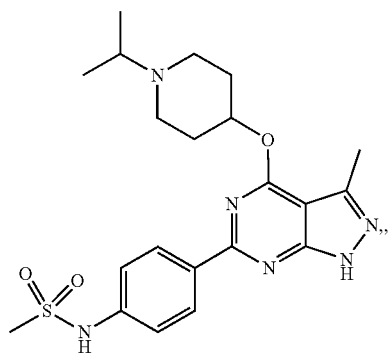
-continued
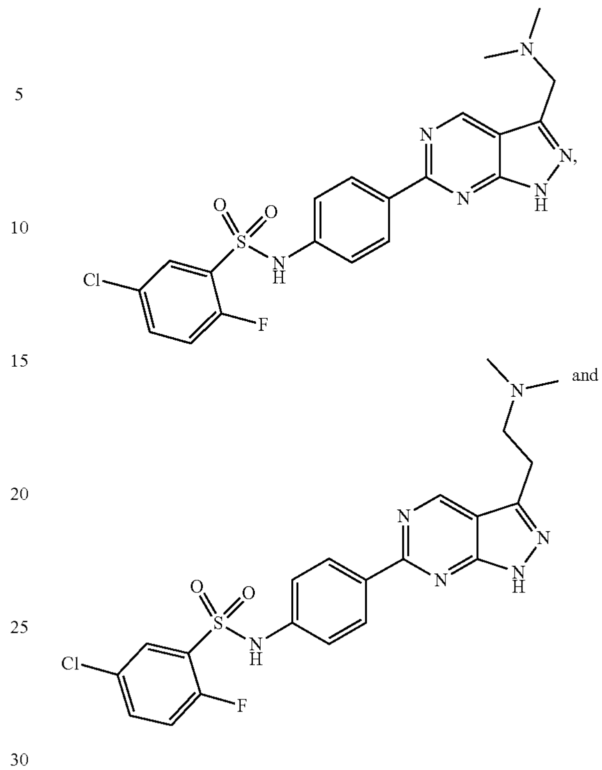
and
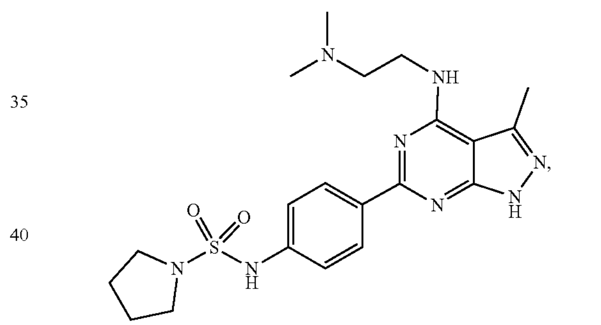
or a pharmaceutically acceptable salt thereof.
In some embodiments, the compound of Formula I is selected from the group consisting of:
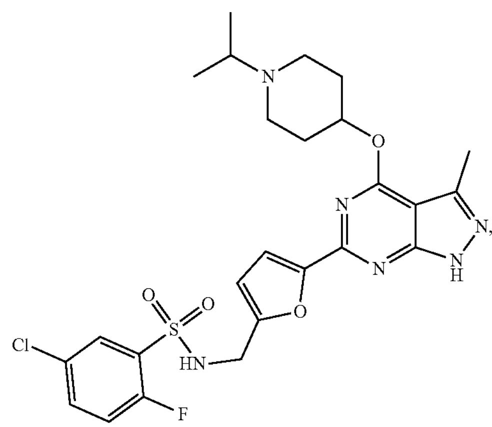

-continued
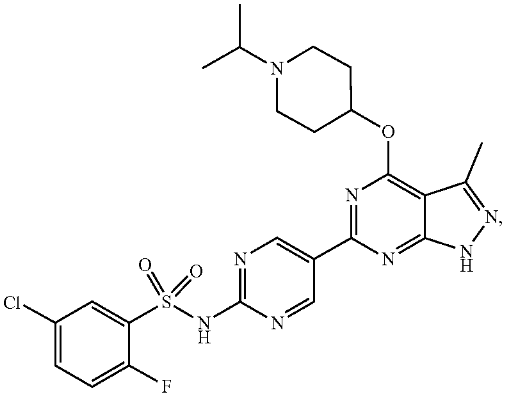
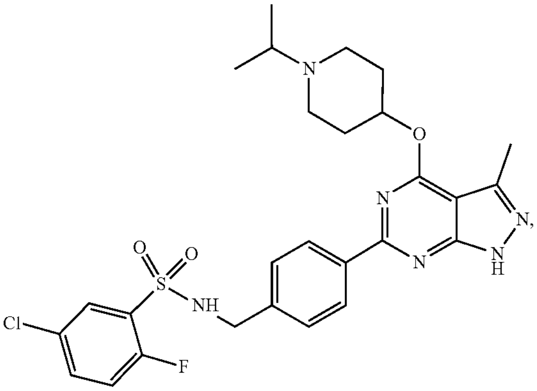
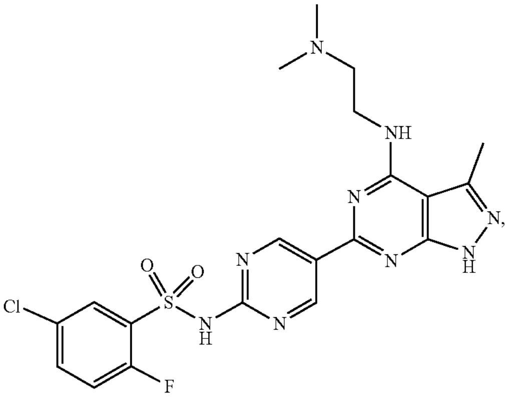
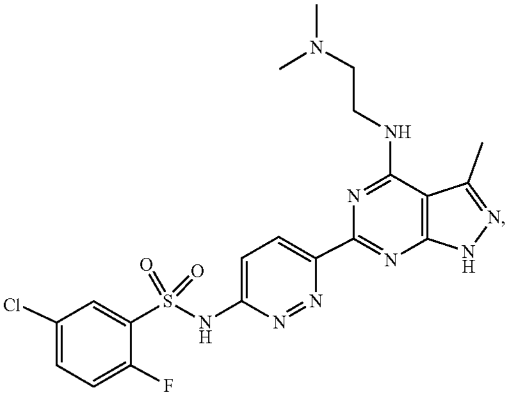
-continued
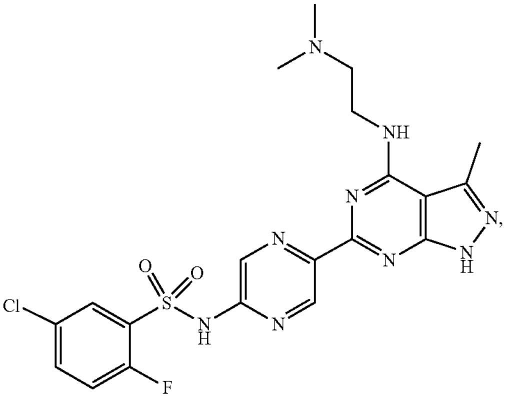
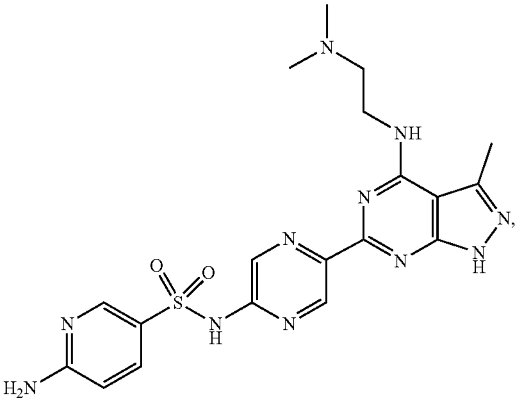
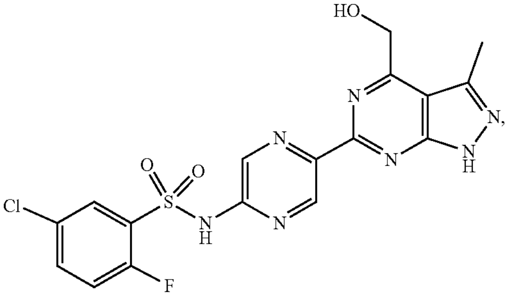
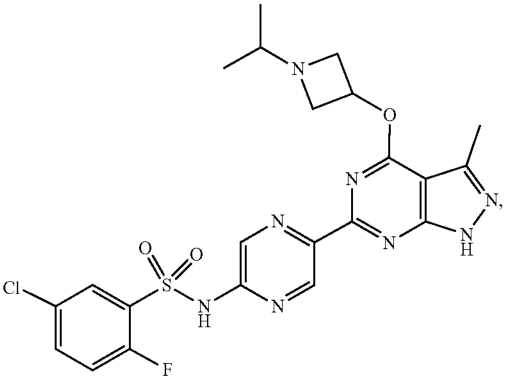

-continued

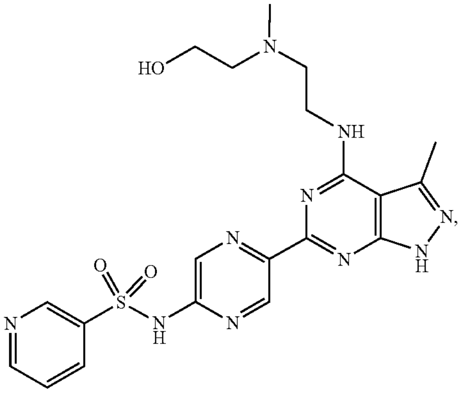

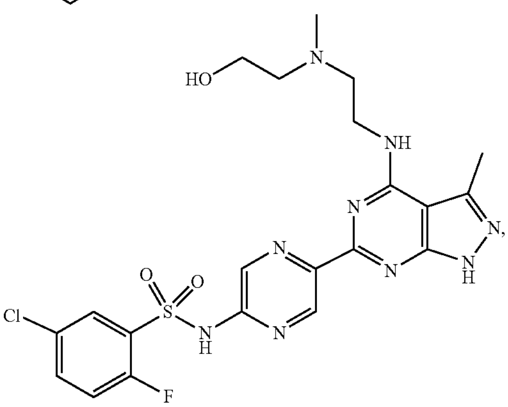

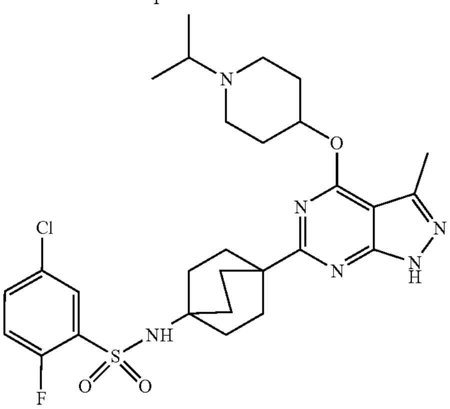

and

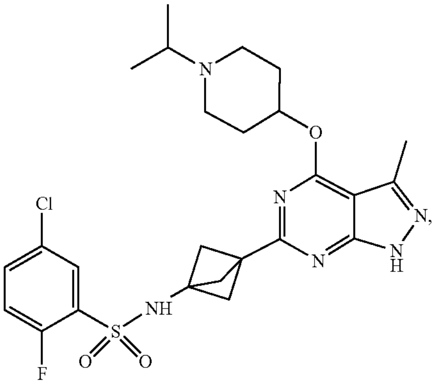

or a pharmaceutically acceptable salt thereof.

In another aspect, compounds of Formula II, or pharmaceutically acceptable salts thereof, are provided:

Formula II

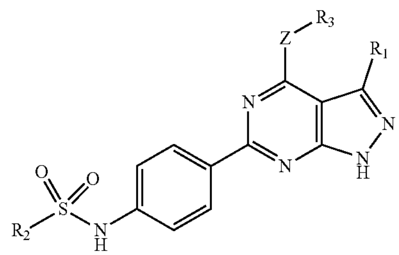

wherein:

Z is selected from the group consisting of O, $CH_2$, S and NH;

$R_1$ is selected from the group consisting of H, and —($C_1$-$C_4$)-alkyl;

$R_3$ is selected from the group consisting of —$(CH_2)_p$—$N(R_{33})\ R_{34}$;

p is 1, 2, 3 or 4;

$R_2$ is selected from the group consisting of a 5-membered or 6-membered monocyclic, aromatic or heteroaromatic group which comprises 1, 2 or 3 identical or different ring heteroatoms selected from the group consisting of nitrogen, oxygen and sulfur, wherein $R_2$ is unsubstituted or substituted by one or more identical or different substituents $R_{20}$;

$R_{20}$ is selected from the group consisting of halogen, —$CF_3$, ($C_1$-$C_4$)-alkyl, —$OR_{21}$, —$N(R_{22})R_{23}$, ($C_1$-$C_4$)-alkyl-$OR_{24}$, ($C_1$-$C_4$)-alkyl-$N(R_{25})R_{26}$ and —CN;

$R_{21}$, $R_{22}$, $R_{23}$, $R_{24}$, $R_{25}$ and $R_{26}$, are independently of one another selected from the group consisting of H and ($C_1$-$C_4$)-alkyl;

$R_{33}$ and $R_{34}$ are independently of one another selected from the group consisting of —CH═O, ($C_1$-$C_4$)-alkyl and ($C_3$-$C_7$)-cycloalkyl, wherein ($C_1$-$C_4$)-alkyl and ($C_3$-$C_7$)-cycloalkyl are each unsubstituted or substituted by one or more identical or different substituents $R_{50}$; and $R_{50}$ is selected from the group consisting of halogen, —OH, —O—($C_1$-$C_4$)-alkyl, $CF_3$, and —CN.

In some embodiments, Z is NH. In other embodiments, Z is O. In some embodiments, $R_1$ is methyl. In some embodiments, p is 2, 3 or 4.

In some embodiments, $R_2$ is selected from the group consisting of:

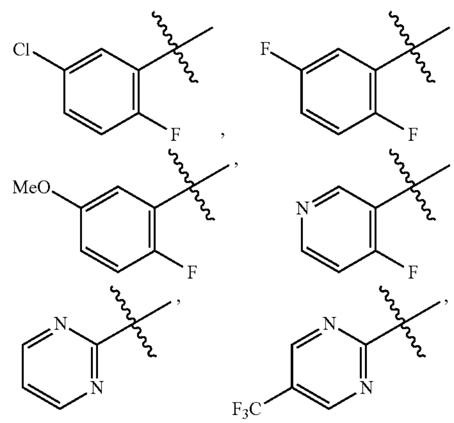

-continued
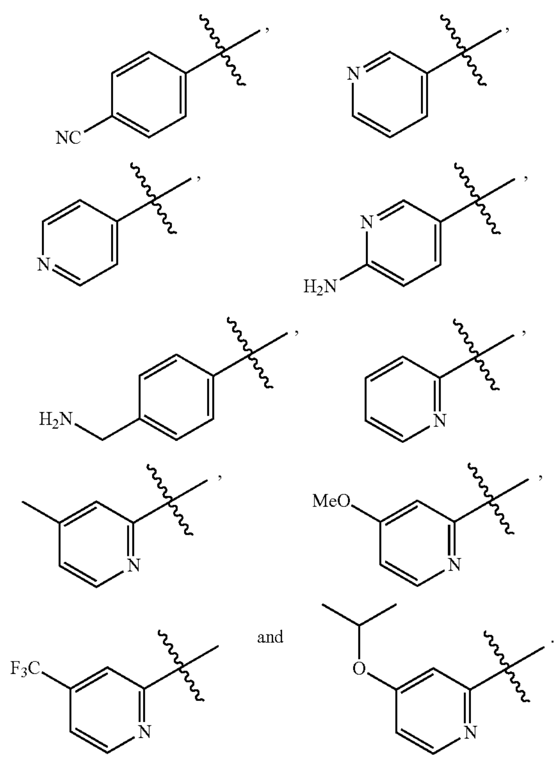
In some embodiments, $R_{33}$ is methyl. In some embodiments, $R_{34}$ is methyl.
In some embodiments, $R_3$ is selected from the group consisting of:
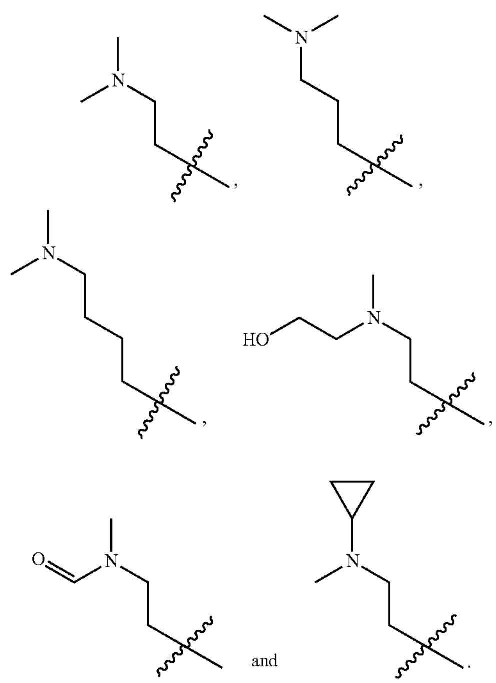
In some embodiments, the compound of Formula II is selected from the group consisting of:
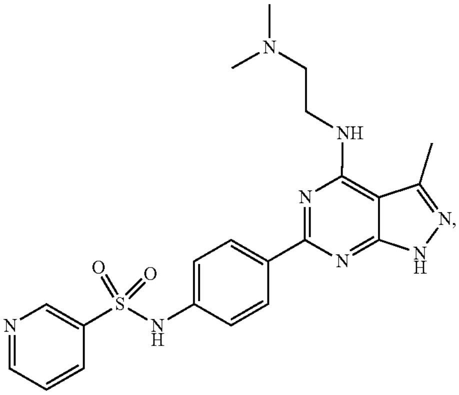
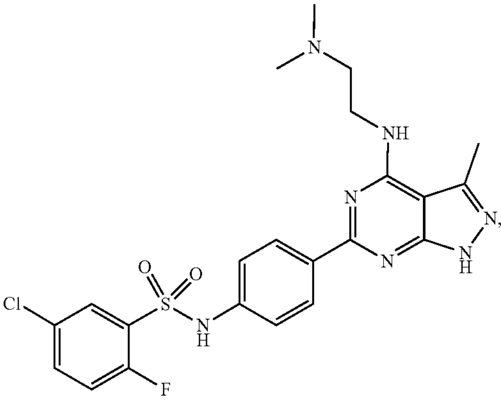
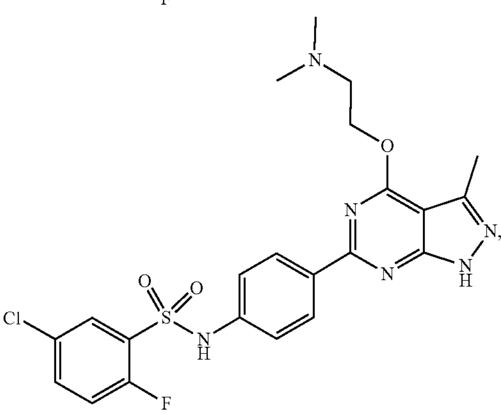
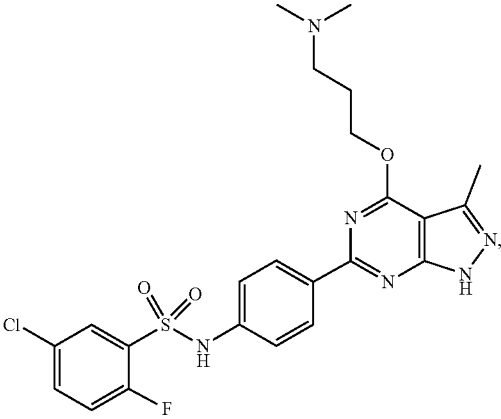

-continued
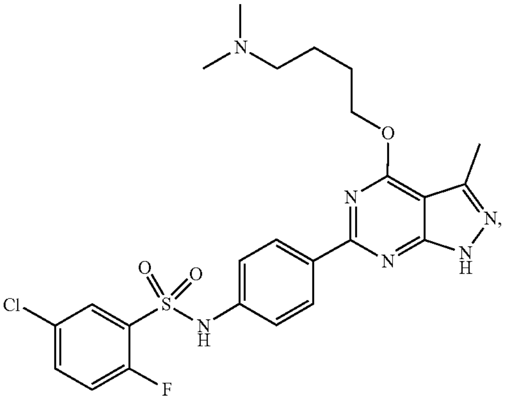
,
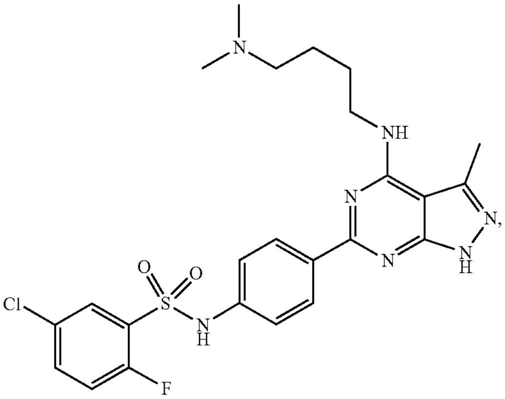
,
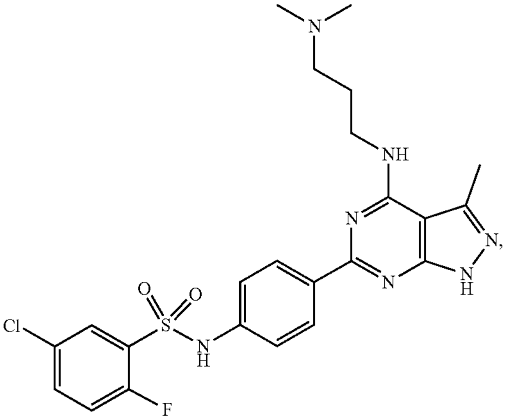
,
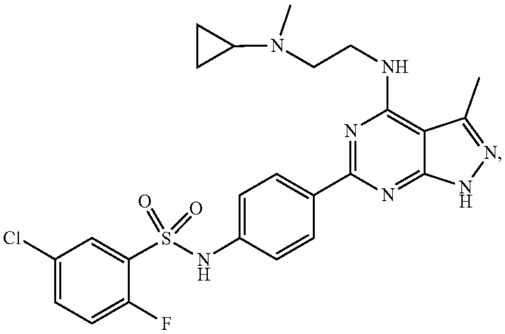
,
-continued
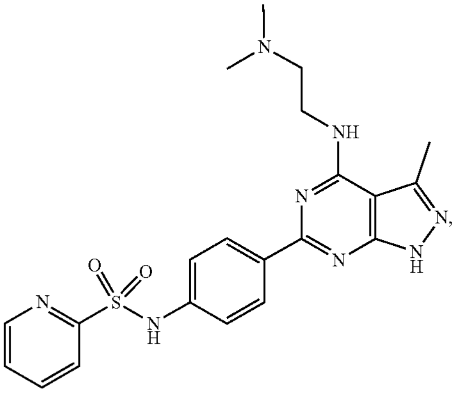
,
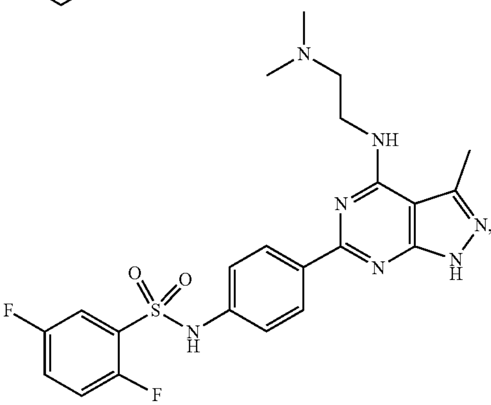
,
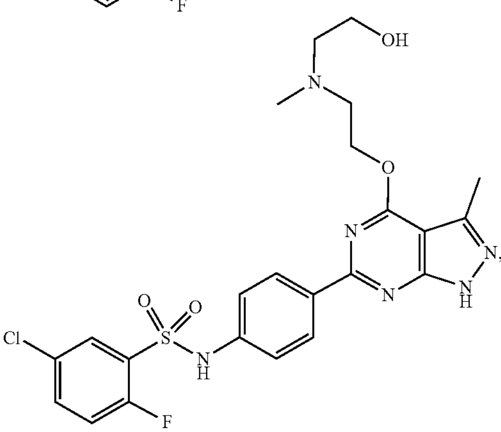
, and
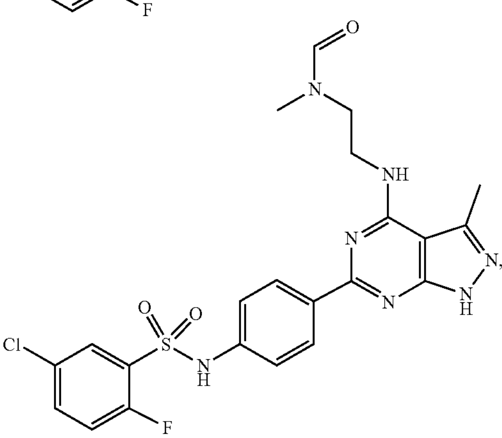
or a pharmaceutically acceptable salt thereof.
In yet another aspect, compounds of Formula II, or pharmaceutically acceptable salts thereof are provided:

Formula II

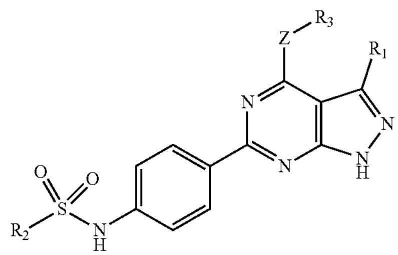

wherein:

Z is selected from the group consisting of a direct bond, O, S, $CH(R_9)$ and $N(R_{10})$;

$R_1$ is selected from the group consisting of H, $—N(R_{11})R_{12}$, $—N(R_{13})—C(O)—R_{14}$, $—NR_{13}—S(O)_2—R_{15}$, $—NR_{13}—C(O)—NH—R_{16}$, $—(C_1\text{-}C_4)$-alkyl, $—(C_1\text{-}C_4)$-alkyl-$OR_{17}$ and $—(C_1\text{-}C_4)$-alkyl-$N(R_{18})R_{19}$;

$R_3$ is selected from the group consisting of H, $(C_1\text{-}C_8)$-alkyl, $R_{30}$ and $(C_1\text{-}C_4)$-alkyl-$R_{30}$, wherein $(C_1\text{-}C_5)$-alkyl is unsubstituted or substituted by one or more identical or different substituents $R_{31}$;

$R_{30}$ is a 3-membered to 12-membered, monocyclic or bicyclic, saturated, partially unsaturated or aromatic, cyclic group which comprises 0, 1, 2 or 3 identical or different ring heteroatoms selected from the group consisting of nitrogen, oxygen and sulfur, which is unsubstituted or substituted by one or more identical or different substituents $R_{32}$ $R_{31}$ is selected from the group consisting of halogen, —OH, $—CF_3$, $—O—(C_1\text{-}C_4)$-alkyl, $—N(R_{33})—R_{34}$ and —CN;

$R_{32}$ is selected from the group consisting of halogen, $(C_1\text{-}C_4)$-alkyl, $(C_3\text{-}C_7)$-cycloalkyl, $—(C_1\text{-}C_4)$-alkyl-$(C_3\text{-}C_7)$-cycloalkyl, $—(C_1\text{-}C_4)$-alkyl-$O—R_{37}$, $—(C_1\text{-}C_4)$-alkyl-$N(R_{38})—R_{39}$, $—(C_1\text{-}C_4)$-alkyl-CN, $—C(O)—(C_1\text{-}C_4)$-alkyl, —CN, —OH, =O, $—O—(C_1\text{-}C_4)$-alkyl, $—N(R_{40})—R_{41}$, $—C(O)—O—(C_1\text{-}C_4)$-alkyl and $—C(O)—N(R_{42})—R_{43}$;

$R_2$ is a 6-membered monocyclic, heteroaromatic group which comprises 1 or 2 nitrogen atoms, wherein $R_2$ is unsubstituted or substituted by one or more identical or different substituents $R_{20}$;

$R_{20}$ is selected from the group consisting of halogen, $—CF_3$, $(C_1\text{-}C_4)$-alkyl, $—OR_{21}$, $—N(R_{22})R_{23}$, $(C_1\text{-}C_4)$-alkyl-$OR_{24}$, $(C_1\text{-}C_4)$-alkyl-$N(R_{25})R_{26}$ and —CN;

$R_9$, $R_{10}$, $R_{11}$, $R_{12}$, $R_{13}$, $R_{14}$, $R_{15}$, $R_{16}$, $R_{17}$, $R_{18}$, $R_{19}$, $R_{21}$, $R_{22}$, $R_{23}$, $R_{24}$, $R_{25}$, $R_{26}$, $R_{37}$, $R_{38}$, $R_{39}$, $R_{40}$, $R_{41}$, $R_{42}$ and $R_{43}$ are independently of one another selected from the group consisting of H and $(C_1\text{-}C_4)$-alkyl;

$R_{33}$ and $R_{34}$ are independently of one another selected from the group consisting of H, $(C_1\text{-}C_4)$-alkyl and $(C_3\text{-}C_7)$-cycloalkyl wherein $(C_1\text{-}C_4)$-alkyl and $(C_3\text{-}C_7)$-cycloalkyl are unsubstituted or substituted by one or more identical or different substituents $R_{50}$; and $R_{50}$ is selected from the group consisting of halogen, —OH, $—O—(C_1\text{-}C_4)$-alkyl, $—CF_3$ and —CN.

In some embodiments, $R_1$ is selected from the group consisting of $—(C_1\text{-}C_4)$-alkyl, and $—(C_1\text{-}C_4)$-alkyl-$N(R_{18})R_{19}$. For example, in some embodiments, $R_1$ is selected from the group consisting of $—CH_3$, $—CH_2N(CH_3)_2$ and $—CH_2—CH_2—N(CH_3)_2$.

In some embodiments, Z is selected from the group consisting of —O— and —NH—. In some embodiments, $R_3$ is selected from the of: group consisting

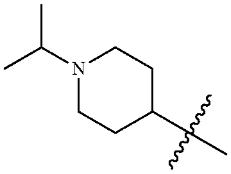,

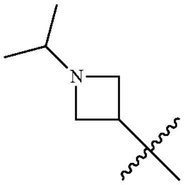,

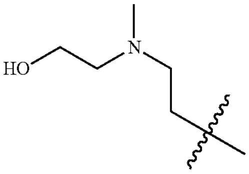,

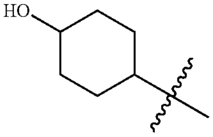,

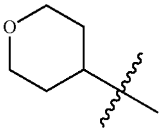,

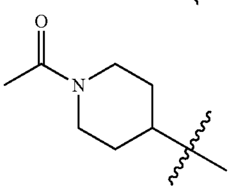,

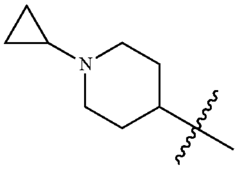,

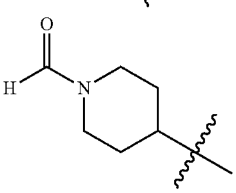,

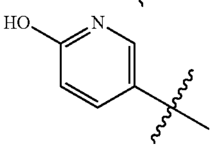,

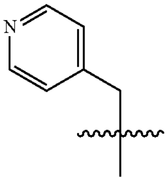,

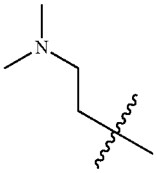,

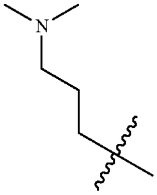,

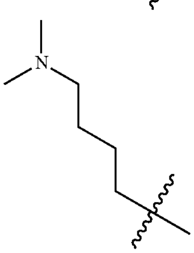

and

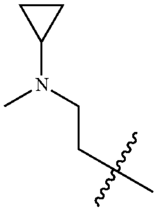.

In some embodiments, Z is a direct bond. In some embodiments, $R_3$ is selected from the group consisting of H, $—CH_2OH$ and $—CH_3$.

In some embodiments, $R_2$ is selected from the group consisting of:

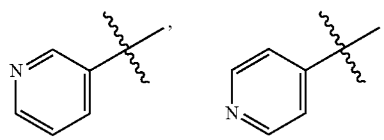

-continued
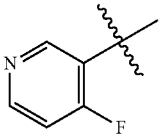 , 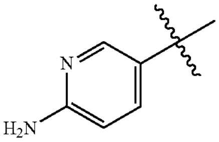 ,
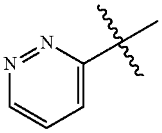 , 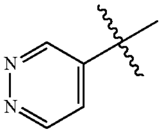 , 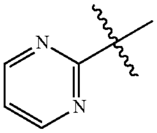 ,
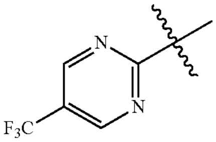 , 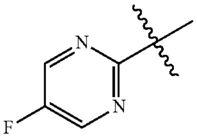 ,
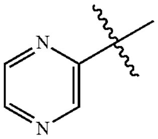 , 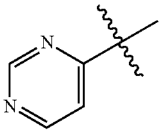 and
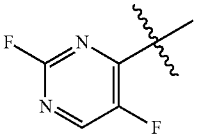 , 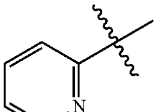 ,
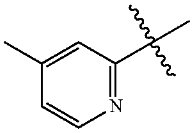 , 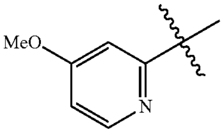 ,
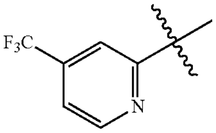 and 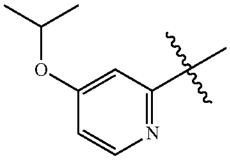 .
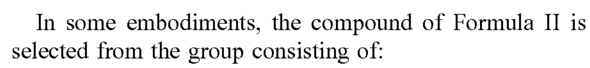
In some embodiments, the compound of Formula II is selected from the group consisting of:
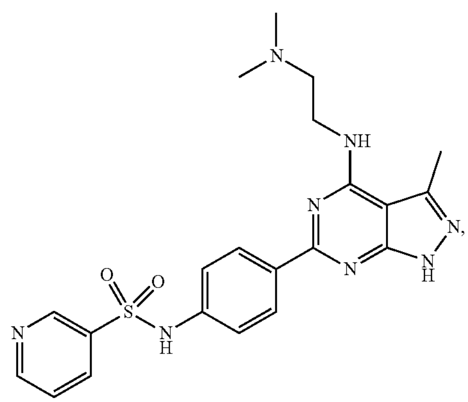
-continued
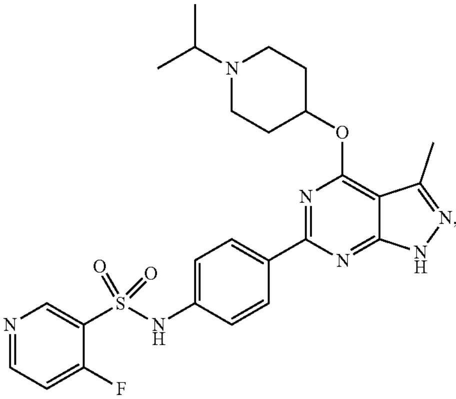
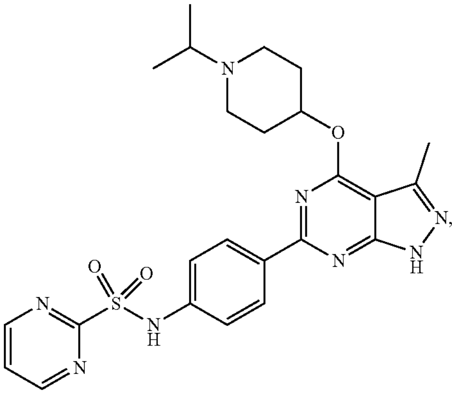
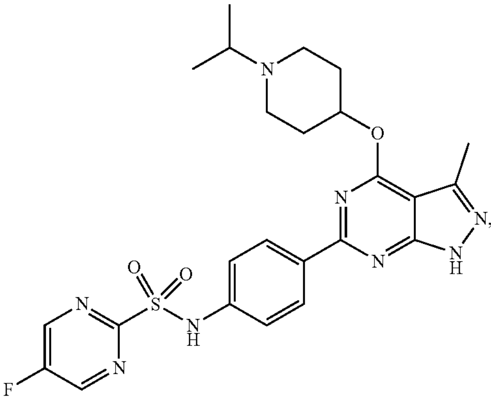
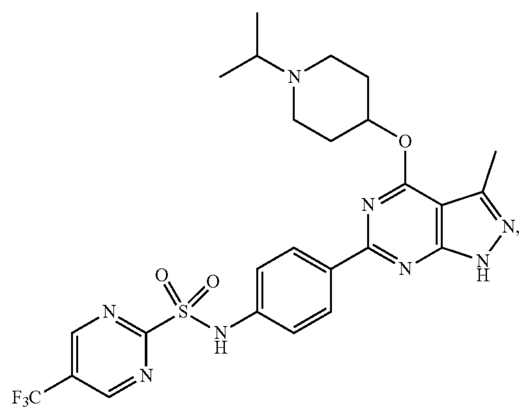

-continued

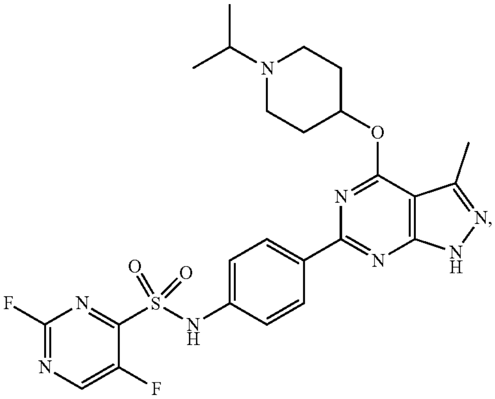

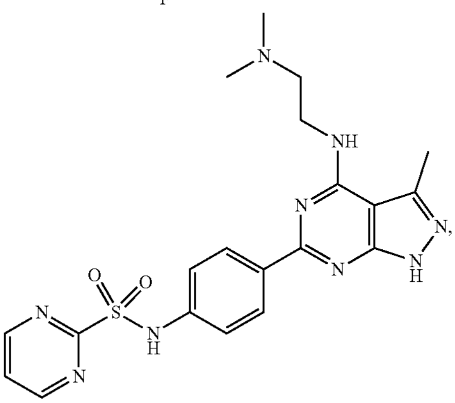

and

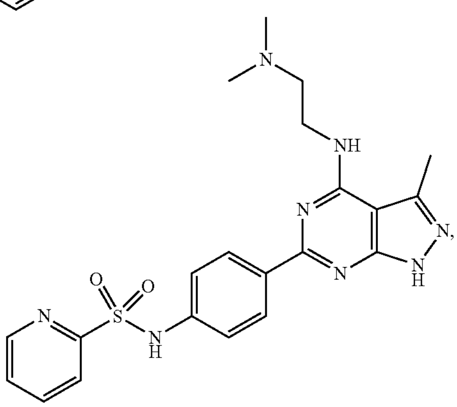

or a pharmaceutically acceptable salt thereof.

In yet another aspect, a compound of Formula III is provided:

Formula III

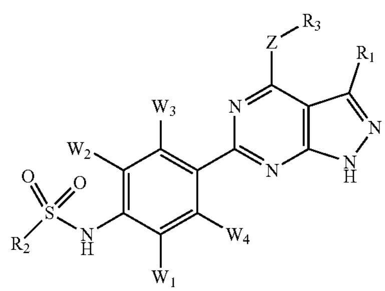

or a pharmaceutically acceptable salt thereof, wherein:

Z is selected from the group consisting of O, $CH_2$, S and NH;

$R_1$ is selected from the group consisting of H, and —($C_1$-$C_4$)-alkyl;

$R_3$ is selected from the group consisting of —$(CH_2)_p$—$N(R_{33})R_{34}$, wherein zero, one or two hydrogen atoms of the group —$(CH_2)_p$— are independently replaced with F;

p is 1, 2, 3 or 4;

$R_2$ is selected from the group consisting of a 5-membered or 6-membered monocyclic, aromatic or heteroaromatic group which comprises 1, 2 or 3 identical or different ring heteroatoms selected from the group consisting of nitrogen, oxygen and sulfur, wherein $R_2$ is unsubstituted or substituted by one or more identical or different substituents $R_{20}$;

$R_{20}$ is selected from the group consisting of halogen, —$CF_3$, ($C_1$-$C_4$)-alkyl, —$OR_{21}$, —$N(R_{22})R_{23}$, ($C_1$-$C_4$)-alkyl-$OR_{24}$, ($C_1$-$C_4$)-alkyl-$N(R_{25})R_{26}$ and —CN;

$R_{21}$, $R_{22}$, $R_{23}$, $R_{24}$, $R_{25}$ and $R_{26}$, are independently of one another selected from the group consisting of H and ($C_1$-$C_4$)-alkyl;

$R_{33}$ and $R_{34}$ are independently of one another selected from the group consisting of —CH═O, ($C_1$-$C_4$)-alkyl and ($C_3$-$C_7$)-cycloalkyl, wherein ($C_1$-$C_4$)-alkyl and ($C_3$-$C_7$)-cycloalkyl are each unsubstituted or substituted by one or more identical or different substituents $R_{50}$;

$R_{50}$ is selected from the group consisting of halogen, —$OR_{27}$, —O—($C_1$-$C_4$)-alkyl, $CF_3$, and —CN;

$R_{27}$ is selected from the group consisting of H, —C(═O)—($C_1$-$C_4$)-alkyl, a natural amino acid bound by the α-carboxyl group, or P(═O)$(OH)_2$; and $W_1$, $W_2$, $W_3$, $W_4$ are independently of one another selected from the group consisting of H, halogen, —$OR_{21}$, —$CF_3$, ($C_1$-$C_4$)-alkyl, and —CN.

In some embodiments, Z is NH. In other embodiments, Z is O. In some embodiments, $R_1$ is methyl. In some embodiments, p is 2, 3 or 4.

In some embodiments, $R_2$ is

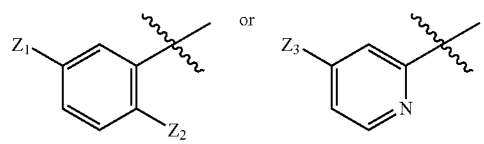

wherein $Z_1$ and $Z_2$ are independently from one another selected from the group consisting of Cl, F, —OMe and —CN, and $Z_3$ is selected from the group consisting of H, halogen, ($C_1$-$C_4$)alkyl, —OH, —O—($C_1$-$C_4$)alkyl, —$CF_3$ and —CN.

In some embodiments, $R_2$ is selected from the group consisting of:

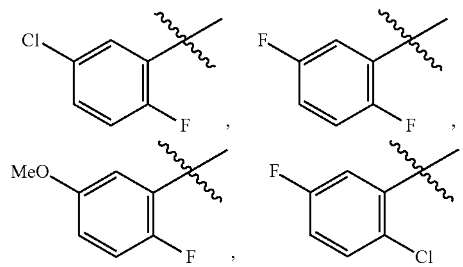

-continued

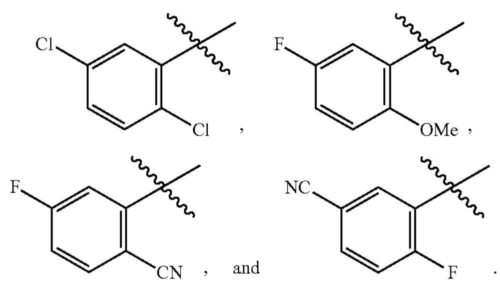

, , , and .

In some embodiments, $R_2$ is selected from the group consisting of:

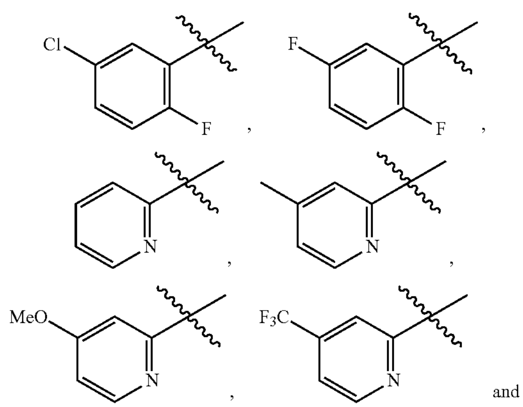

, , , , , and

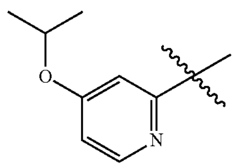

.

In some embodiments, $R_2$ is

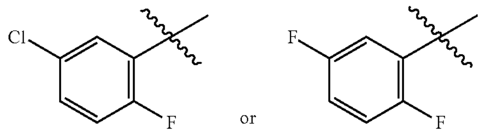

or .

In some embodiments, $R_2$ is

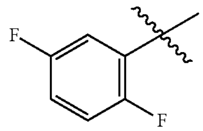

.

In some embodiments, $R_{33}$=methyl. In some embodiments, $R_{34}$=methyl.

In some embodiments, $R_3$ is selected from the group consisting of:

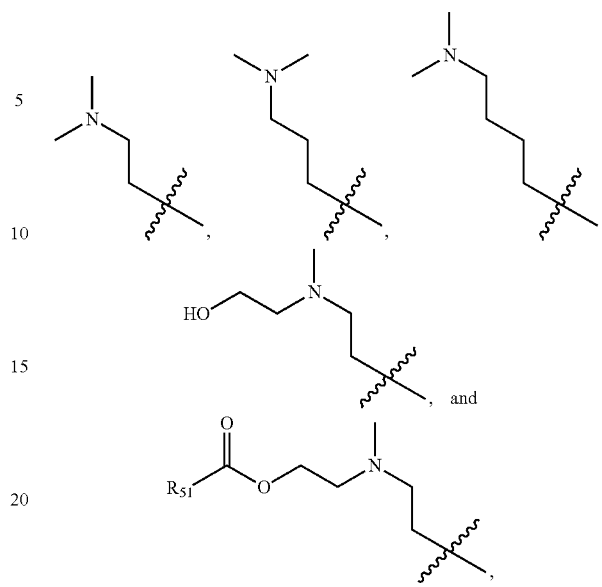

, , , , and , wherein $R_{51}$ is $(C_1-C_4)$-alkyl.

In some embodiments:

$W_1$, $W_2$, $W_3$ and $W_4$ are each H;

$W_1$ is F or Cl, $W_2$, $W_3$ and $W_4$ are each H; or $W_1$ and $W_2$ are each F, $W_3$ and $W_4$ are each H.

In some embodiments, $W_1$ is F or Cl, $W_2$ is H, $W_3$ is H and $W_4$ is H. In some embodiments, $W_1$ is F, $W_2$ is H, $W_3$ is H and $W_4$ is H. In some embodiments, $W_1$ is Cl, $W_2$ is H, $W_3$ is H and $W_4$ is H.

In yet another aspect, a compound of Formula III is provided:

Formula III

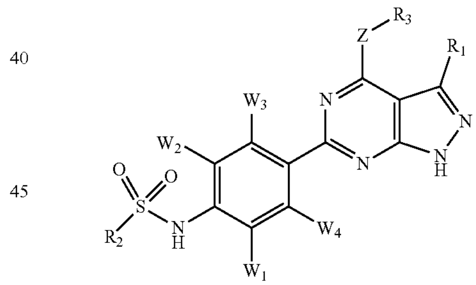

or a pharmaceutically acceptable salt thereof, wherein:

Z is selected from the group consisting of O and NH;

$R_1$ is selected from the group consisting of H and $(C_1-C_4)$-alkyl;

$R_3$ is selected from the group consisting of $-(CH_2)_p-N(R_{33})R_{34}$;

p is 2, 3 or 4;

$R_2$ is

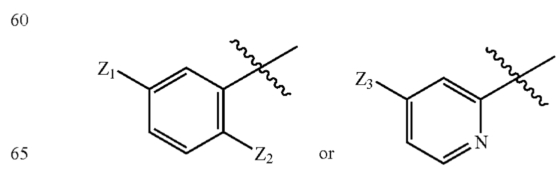

or ;

$Z_1$ and $Z_2$ are independently from one another selected from the group consisting of halogen, $(C_1\text{-}C_4)$alkyl, —OH, —O—$(C_1\text{-}C_4)$alkyl, —$CF_3$, and —CN;

$Z_3$ is selected from the group consisting of H, halogen, $(C_1\text{-}C_4)$alkyl, —OH, —O—$(C_1\text{-}C_4)$alkyl, —$CF_3$ and —CN;

$R_{33}$ and $R_{34}$ are independently of one another a $(C_1\text{-}C_4)$-alkyl;

$W_1$, $W_2$, $W_3$, $W_4$ are independently of one another selected from the group consisting of H, halogen, —$OR_{21}$, —$CF_3$, $(C_1\text{-}C_4)$-alkyl, and —CN; and $R_{21}$, is selected from the group consisting of H and $(C_1\text{-}C_4)$-alkyl.

In some embodiments, $R_1$ is methyl.

In some embodiments, $R_3$ is selected from the group consisting of:

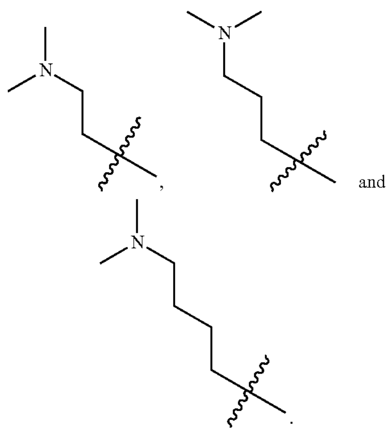

In some embodiments, $R_3$ is

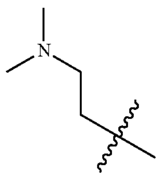

In some embodiments, $R_2$ is selected from the group consisting of:

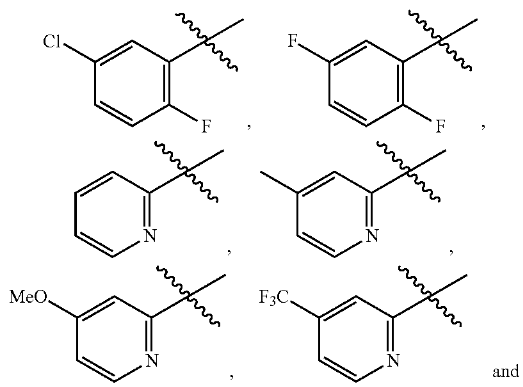

-continued

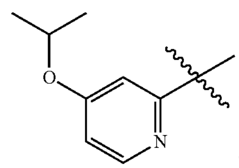

In some embodiments, $R_2$ is

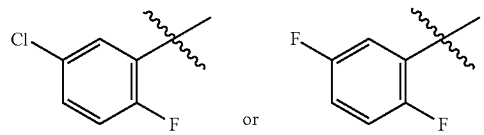

In some embodiments, $W_1$, $W_2$, $W_3$ and $W_4$ are each H;

$W_1$ is F, $W_2$, $W_3$ and $W_4$ are each H; or $W_1$ and $W_2$ are each F, $W_3$ and $W_4$ are each H.

In some embodiments, $W_1$ is F, $W_2$, $W_3$ and $W_4$ are each H.

In some embodiments, Z is NH.

In some embodiments, there is provided a compound selected from the group consisting of:

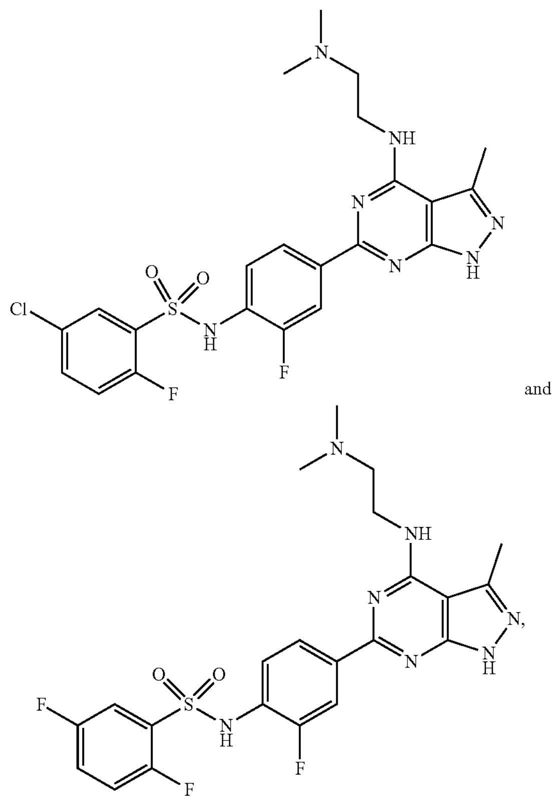

or a pharmaceutically acceptable sale thereof.

In yet another aspect, a compound of Formula III is provided:

Formula III

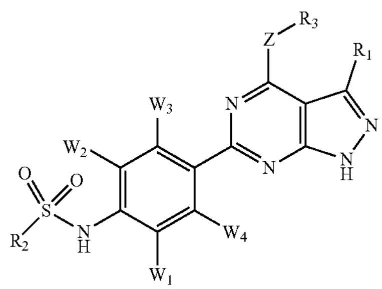

or a pharmaceutically acceptable salt thereof, wherein:

Z is selected from the group consisting of O, and NH;

$R_1$ is selected from the group consisting of H, and —($C_1$-$C_4$)-alkyl;

$R_3$ is a nitrogen-bearing heterocycle selected from the group consisting of

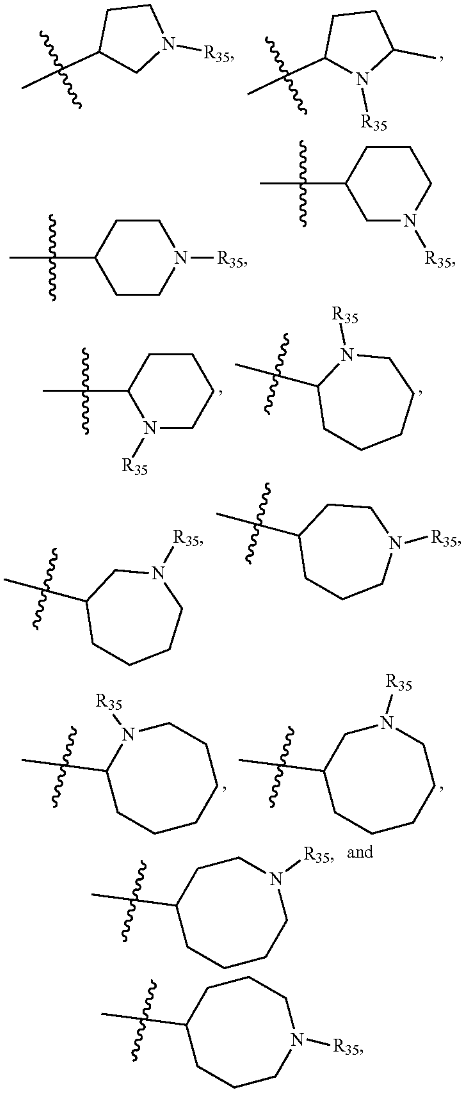

and wherein zero, one or two hydrogens on the —$CH_2$— groups of the nitrogen-bearing heterocycle is replaced with halogen, —OH, —CN, —$CF_3$ or ($C_1$-$C_4$)-alkyl;

$R_{35}$ is H or ($C_1$-$C_4$)-alkyl which is unsubstituted or substituted by one or more identical or different substituents $R_{50}$; and $R_{50}$ is selected from the group consisting of halogen, —OH, —O—($C_1$-$C_4$)-alkyl, $CF_3$, and —CN;

$R_2$ is

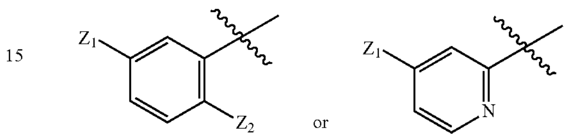

or ;

$Z_1$ and $Z_2$ are independently from one another selected from the group consisting of halogen, ($C_1$-$C_4$)alkyl, —OH, —O—($C_1$-$C_4$)alkyl, —$CF_3$, and —CN;

$Z_3$ is selected from the group consisting of H, halogen, ($C_1$-$C_4$)alkyl, —OH, —O—($C_1$-$C_4$)alkyl, —$CF_3$ and —CN;

$W_1$ is F;

$W_2$ is H or F;

$W_3$ is H; and $W_4$ is H.

In some embodiments, Z is O.

In some embodiments, $R_2$ is selected from the group consisting of

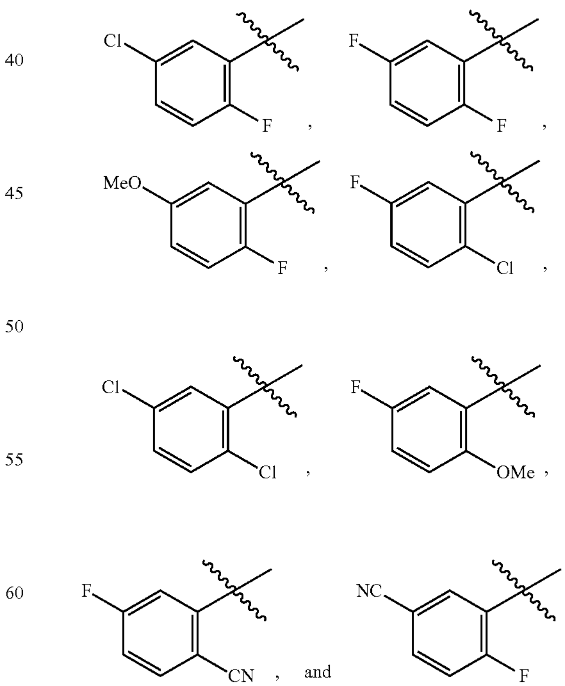

, , , , , , and .

In some embodiments, $R_2$ is selected from the group consisting of:

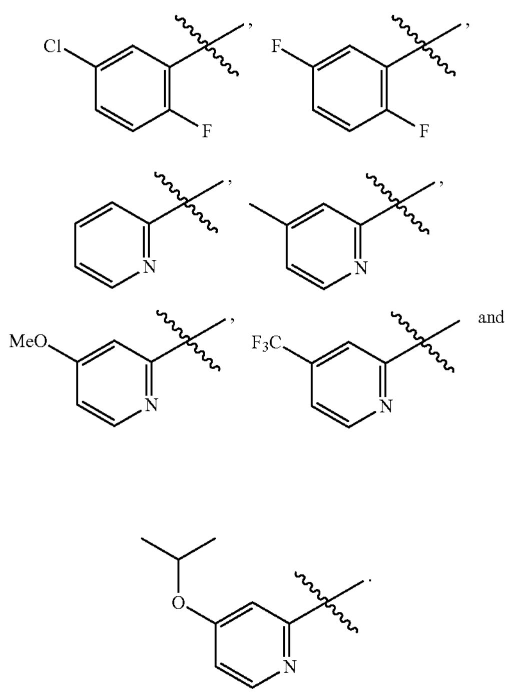

and

In some embodiments, $R_1$ is methyl.

In some embodiments, $R_3$ is

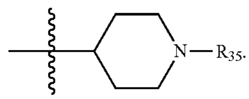

In some embodiments, $R_{35}$ is methyl or isopropyl.

In some embodiments, $W_2$ is H.

In yet another aspect, a compound of Formula III is provided:

Formula III

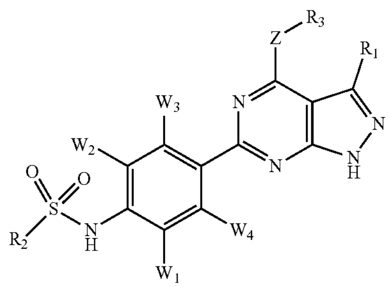

or a pharmaceutically acceptable salt thereof, wherein:

Z is selected from the group consisting of O, and NH;

$R_1$ is selected from the group consisting of H, and —($C_1$-$C_4$)-alkyl;

$R_3$ is a nitrogen-bearing heterocycle selected from the group consisting of

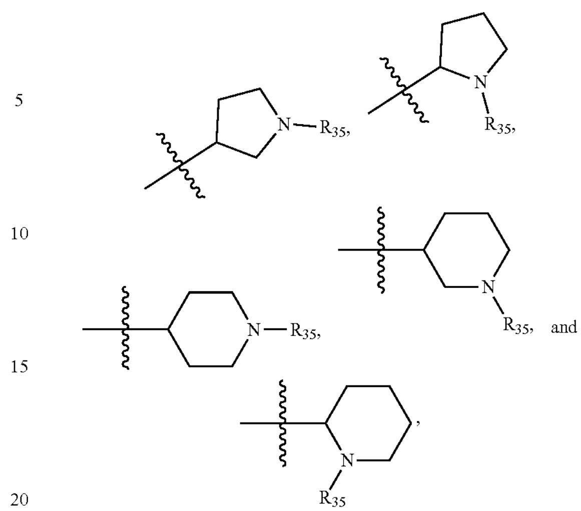

and wherein zero, one or two hydrogens on any of the —$CH_2$— groups of the nitrogen-bearing heterocycle is replaced with halogen, —OH, —CN, —$CF_3$ or ($C_1$-$C_4$)-alkyl;

$R_{35}$ is H or ($C_1$-$C_4$)-alkyl which is unsubstituted or substituted by one or more identical or different substituents $R_{50}$; and $R_{50}$ is selected from the group consisting of halogen, —OH, —O—($C_1$-$C_4$)-alkyl, $CF_3$, and —CN;

$R_2$ is

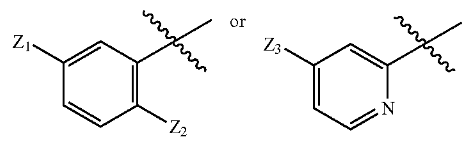

or $Z_1$ and $Z_2$ are independently from one another selected from the group consisting of halogen, ($C_1$-$C_4$)alkyl, —OH, —O—($C_1$-$C_4$)alkyl, —$CF_3$, and —CN;

$Z_3$ is selected from the group consisting of H, halogen, ($C_1$-$C_4$)alkyl, —OH, —O—($C_1$-$C_4$)alkyl, —$CF_3$ and —CN;

$W_1$ is F, Cl or OMe;

$W_2$ is H or F;

$W_3$ is H; and $W_4$ is H.

In some embodiments, Z is O.

In some embodiments, $R_1$ is methyl.

In some embodiments, $R_3$ is

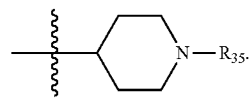

In some embodiments, $R_{35}$ is methyl or isopropyl.

In some embodiments, $W_2$ is H.

In some embodiments, $R_2$ is selected from the group consisting of:

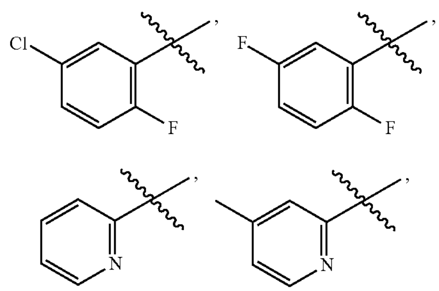

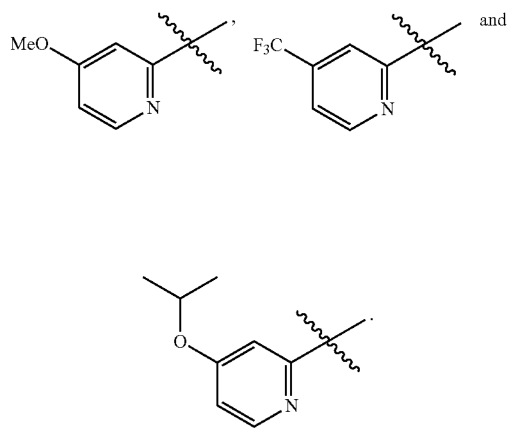

and

In some embodiments, $R_2$ is:

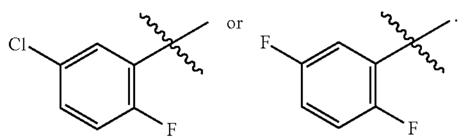 [SMILES: *c1cc(Cl)ccc1F ; *c1cc(F)ccc1F]

or

In some embodiments, there is provided a compound selected from the group consisting of:

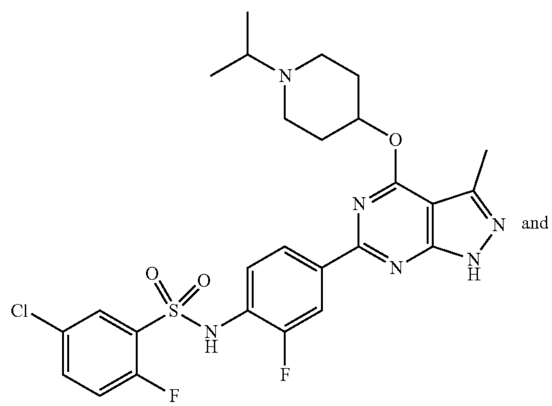

and

-continued

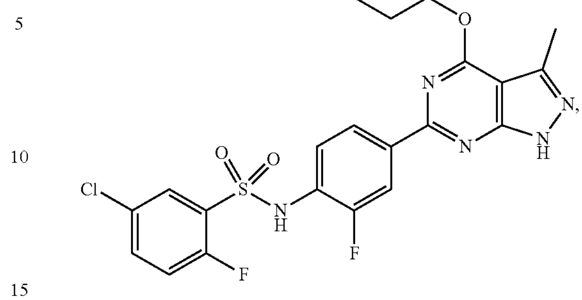

or a pharmaceutically acceptable sale thereof.

In yet another aspect, a compound of Formula III is provided:

Formula III

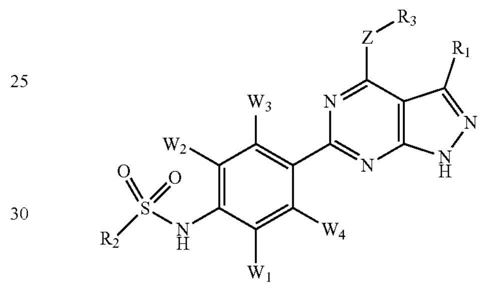

or a pharmaceutically acceptable salt thereof, wherein:

Z is selected from the group consisting of O, and NH;

$R_1$ is selected from the group consisting of H, and —($C_1$-$C_4$)-alkyl;

$R_3$ is a nitrogen-bearing heterocycle selected from the group consisting of

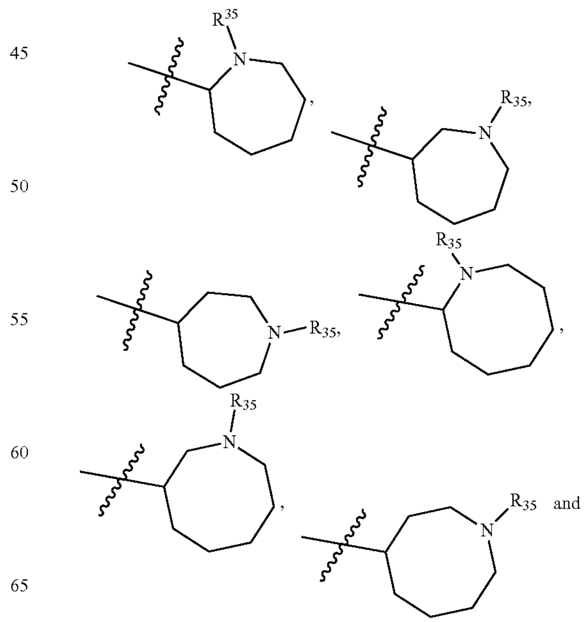

and

-continued

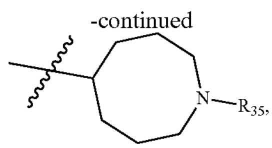

wherein zero, one or two hydrogens on any of the —$CH_2$— groups of the nitrogen-bearing heterocycle is replaced with halogen, —OH, —CN, —$CF_3$ or ($C_1$-$C_4$)-alkyl;

$R_{35}$ is H or ($C_1$-$C_4$)-alkyl which is unsubstituted or substituted by one or more identical or different substituents $R_{50}$; and $R_{50}$ is selected from the group consisting of halogen, —OH, —O—($C_1$-$C_4$)-alkyl, $CF_3$, and —CN;

$R_2$ is

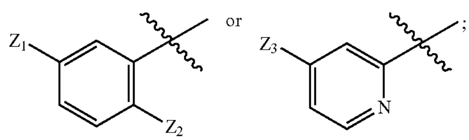

$Z_1$ and $Z_2$ are independently from one another selected from the group consisting of halogen, ($C_1$-$C_4$)alkyl, —OH, —O—($C_1$-$C_4$)alkyl, —$CF_3$, and —CN;

$Z_3$ is selected from the group consisting of H, halogen, ($C_1$-$C_4$)alkyl, —OH, —O—($C_1$-$C_4$)alkyl, —$CF_3$ and —CN;

$W_1$, $W_2$, $W_3$, $W_4$ are independently of one another selected from the group consisting of H, halogen, —$OR_{21}$, —$CF_3$, ($C_1$-$C_4$)-alkyl, and —CN, $R_{21}$ is selected from the group consisting of H and ($C_1$-$C_4$)-alkyl.

In some embodiments, Z is O.

In some embodiments, $R_1$ is methyl.

In some embodiments, $R_3$ is

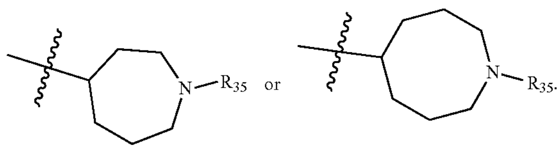

In some embodiments, $R_{35}$ is methyl or isopropyl.

In some embodiments, $W_1$ is H, F, Cl or OMe;

$W_2$ is H or F;

$W_3$ is H; and $W_4$ is H.

In some embodiments, $W_1$ is F, $W_2$ is H, $W_3$ is H and $W_4$ is H. In some embodiments, $W_1$ is Cl, $W_2$ is H, $W_3$ is H and $W_4$ is H.

In some embodiments, $R_2$ is selected from the group consisting of:

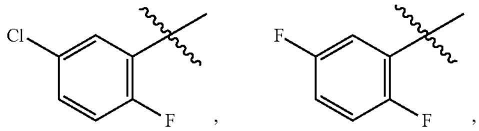

-continued

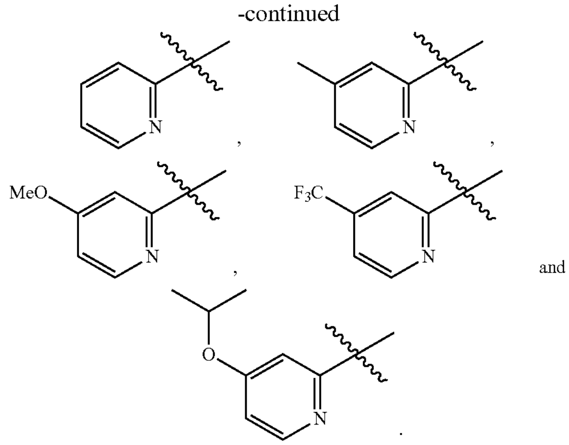

In some embodiments, $R_2$ is

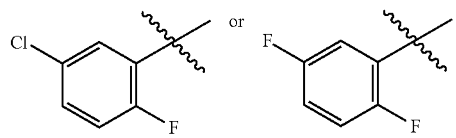

In some embodiments, there is provided a compound selected from the group consisting of:

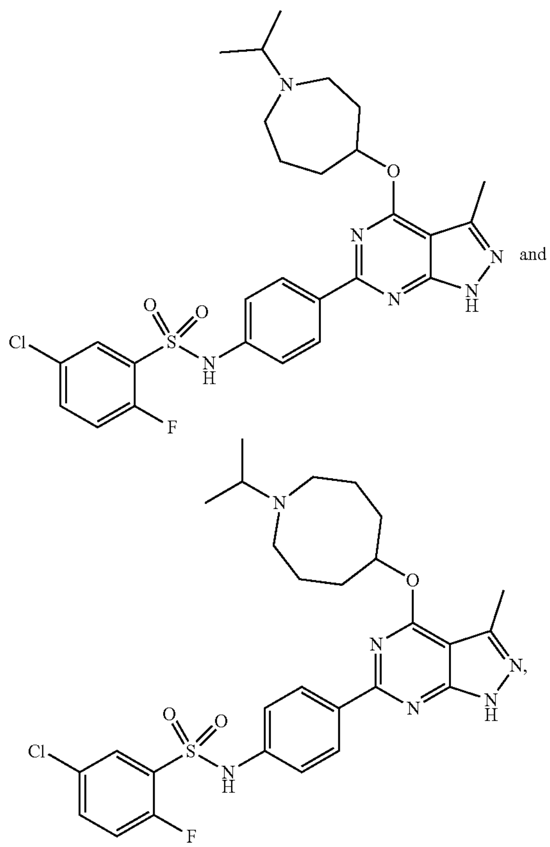

or a pharmaceutically acceptable sale thereof.

In yet another aspect, a compound of Formula IV is provided:

Formula IV

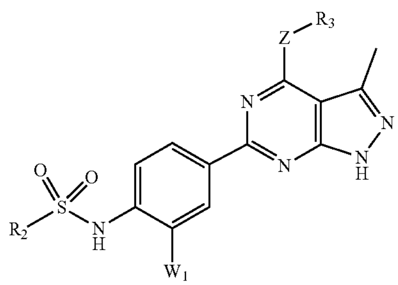

or a pharmaceutically acceptable salt thereof, wherein:

Z is selected from the group consisting of O and NH;

$R_3$ is selected from the group consisting of: —$(CH_2)_p$—$N(R_{33})R_{34}$,

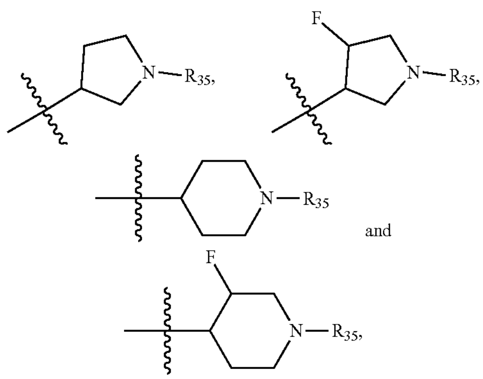

and p is 2, 3 or 4;

$R_{33}$ and $R_{34}$ are independently from one another a ($C_1$-$C_4$)-alkyl which is unsubstituted or substituted by one or more identical or different substituents $R_{50}$;

$R_{35}$ is H or a ($C_1$-$C_4$)-alkyl which is unsubstituted or substituted by one or more identical or different substituents $R_{50}$;

$R_{50}$ is selected from the group consisting of halogen, —$OR_{27}$, —O—($C_1$-$C_4$)-alkyl, —$CF_3$, and —CN;

$R_{27}$ is selected from the group consisting of H, —C(═O)—($C_1$-$C_4$)alkyl, a natural amino acid bound by the α-carboxyl group, and P(═O)$(OH)_2$;

$R_2$ is

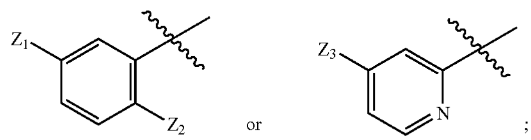

or ;

$Z_1$ and $Z_2$ are independently of one another selected from the group consisting of halogen, ($C_1$-$C_4$)alkyl, —OH, —O—($C_1$-$C_4$)alkyl, —$CF_3$, and —CN;

$Z_3$ is selected from the group consisting of H, halogen, ($C_1$-$C_4$)alkyl, —OH, —O—($C_1$-$C_4$)alkyl, —$CF_3$ and —CN; and $W_1$ is halogen.

In some embodiments, Z is O. In other embodiments, Z is NH.

In some embodiments, $R_{27}$ is selected from the group consisting of H or —C(═O)—($C_1$-$C_4$)alkyl.

In some embodiments, $R_3$ is —$(CH_2)_p$—$N(R_{33})R_{34}$. In some embodiments, p=2. In some embodiments, $R_{33}$ is methyl.

In some embodiments, $R_{34}$ is methyl. In other embodiments, $R_{34}$ is —$(CH_2)_2$—OH or —$(CH_2)_2$—O—C(═O)—($C_1$-$C_4$)alkyl.

In some embodiments, $R_3$ is

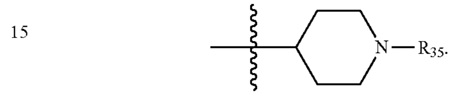

In some embodiments, $R_{35}$ is methyl or isopropyl.

In some embodiments, $R_3$ is

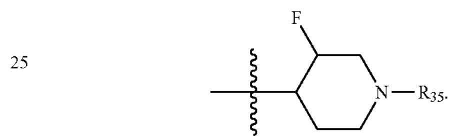

In some embodiments, $R_{35}$ is H.

In some embodiments, Z—$R_3$ is selected from the group consisting of

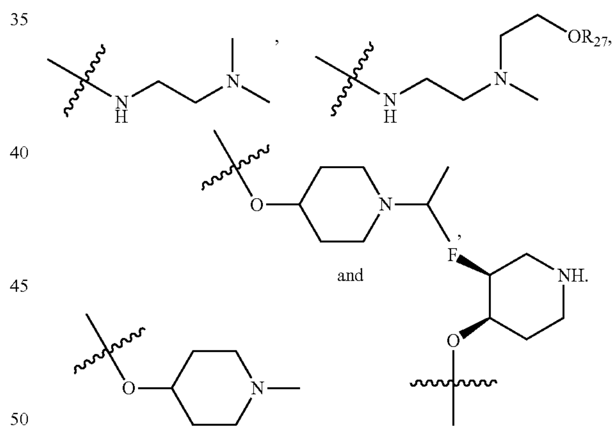

, , and

In some embodiments, Z—$R_3$ is selected from the group consisting of

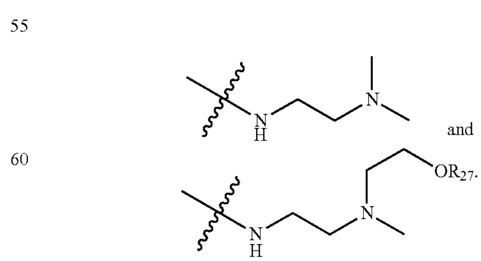

and

In some embodiments, Z—$R_3$ is selected from the group consisting of

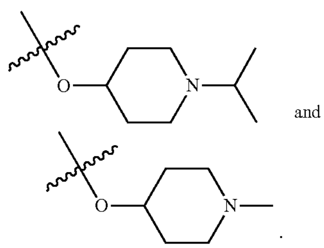

In some embodiments, $Z$—$R_3$ is

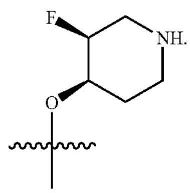

In some embodiments, $W_1$ is F. In other embodiments, $W_1$ is $C_1$.

In some embodiments, $R_2$ is

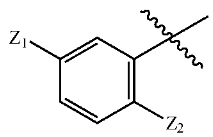

$Z_1$ and $Z_2$ can be independently from one another selected from the group consisting of Cl, F, —$CH_3$, —CN, —$OCH(CH_3)_2$ and —OMe.

In some embodiments, $R_2$ is

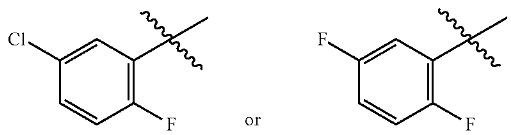

In some embodiments, $R_2$ is

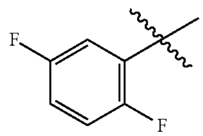

In some embodiments, $R_2$ is

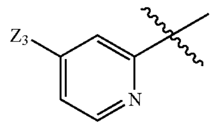

$Z_3$ can be selected from the group consisting of H, Cl, F, —$CH_3$, —CN, —$OCH(CH_3)_2$ and —OMe, or from the group consisting of H, —$CH_3$, —$CF_3$, —$OCH(CH_3)_2$ and —OMe, or from the group consisting of —$CH_3$, —$OCH(CH_3)_2$ and —OMe.

In some embodiments, the compound of Formula IV is a compound of Formula IVa:

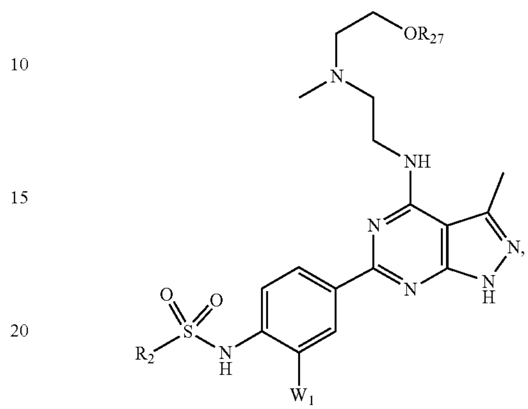

or a pharmaceutically acceptable salt thereof, wherein:

$R_2$ is selected from the group consisting of:

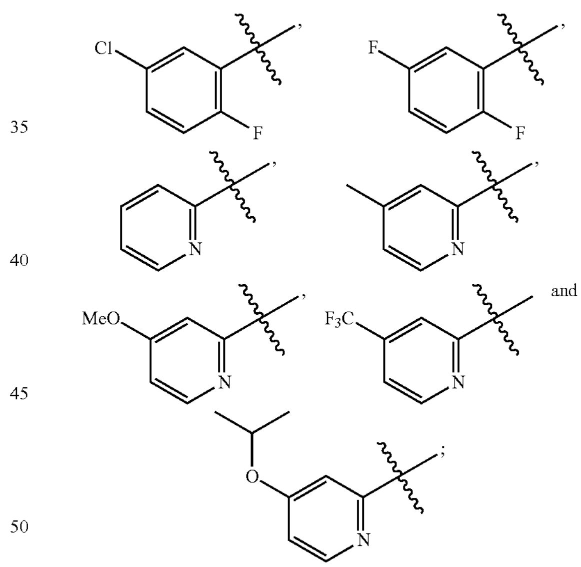

$W_1$ is selected from the group consisting of Cl and F; and $R_{27}$ is selected from the group consisting of: H,

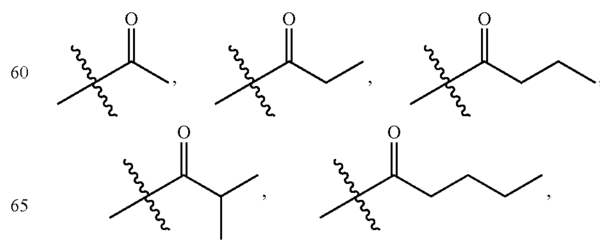

-continued

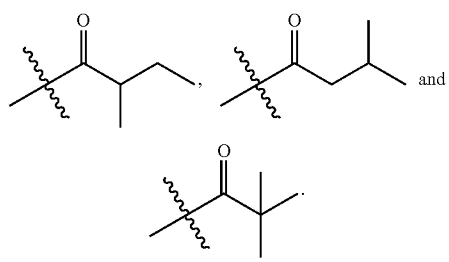

In some embodiments, the compound of Formula IV is a compound of Formula IVb:

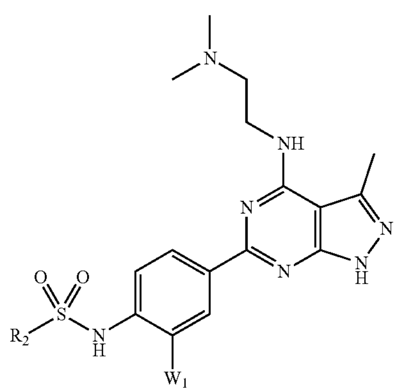

or a pharmaceutically acceptable salt thereof, wherein:

$R_2$ is selected from the group consisting of.

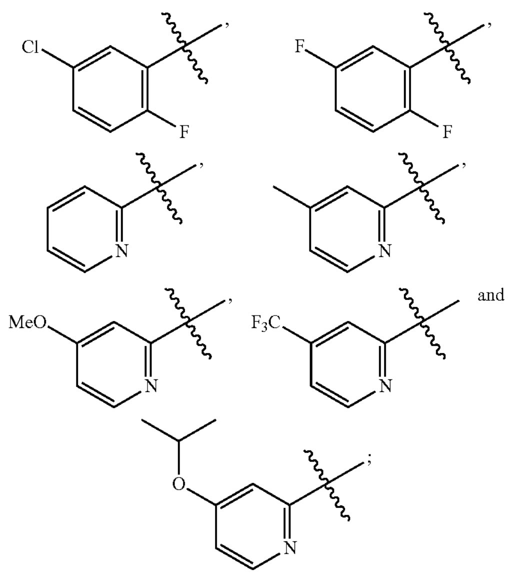

and $W_1$ is selected from the group consisting of Cl and F.

In some embodiments, the compound of Formula IV is a compound of Formula IVc:

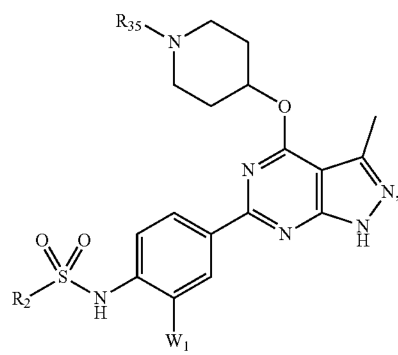

or a pharmaceutically acceptable salt thereof, wherein:

$R_2$ is selected from the group consisting of:

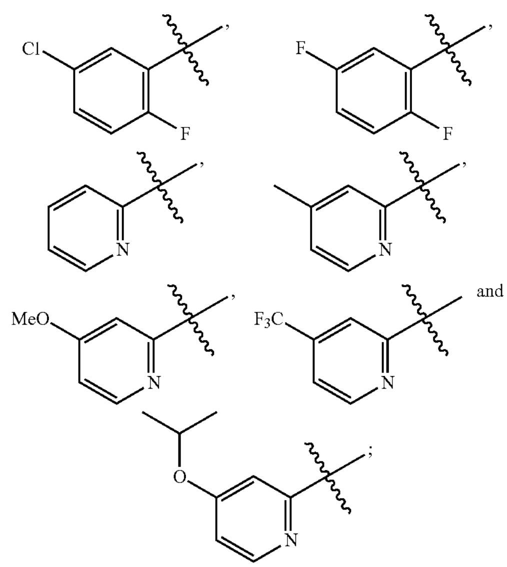

$W_1$ is selected from the group consisting of Cl and F; and $R_{35}$ is selected from the group consisting of methyl and isopropyl.

In some embodiments, the compound of Formula IV is a compound of Formula IVd:

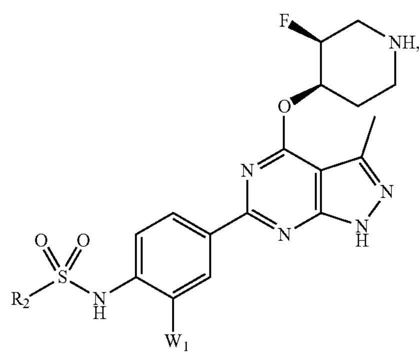

or a pharmaceutically acceptable salt thereof, wherein:

$R_2$ is selected from the group consisting of:

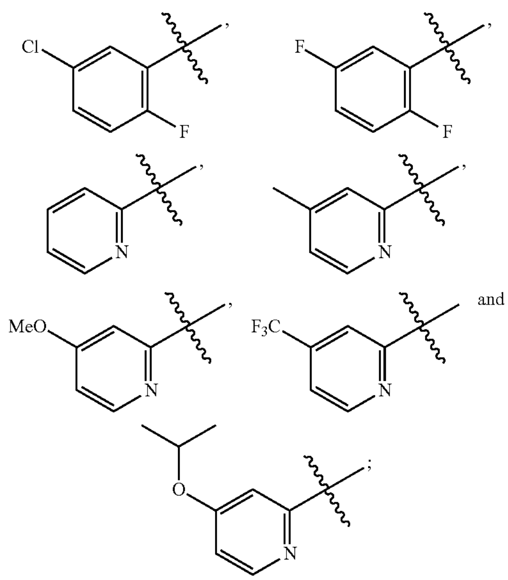

and $W_1$ is selected from the group consisting of Cl and F.

In some embodiments, the compound of Formula IV is selected from the group consisting of Compounds 28, 38, 78, 79, 84, 85, 99, 100, 101, 102, 103,104, 105, 107, 106, 108, 109, 110, 111, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 155, 156, 163, 164, 165, 166, 167, 168, 169, 170, 171, 172, 173 and 174, as numbered in Table A hereinbelow, or a pharmaceutically acceptable salt thereof.

In another aspect, a compound of Formula IV is provided:

Formula IV

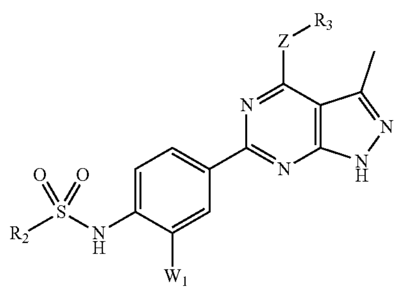

or a pharmaceutically acceptable salt thereof, wherein:

Z—$R_3$ is selected from the group consisting of:

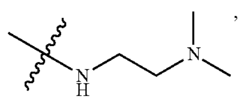

-continued

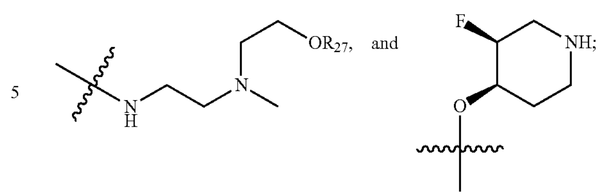

$R_{27}$ is selected from the group consisting of: H,

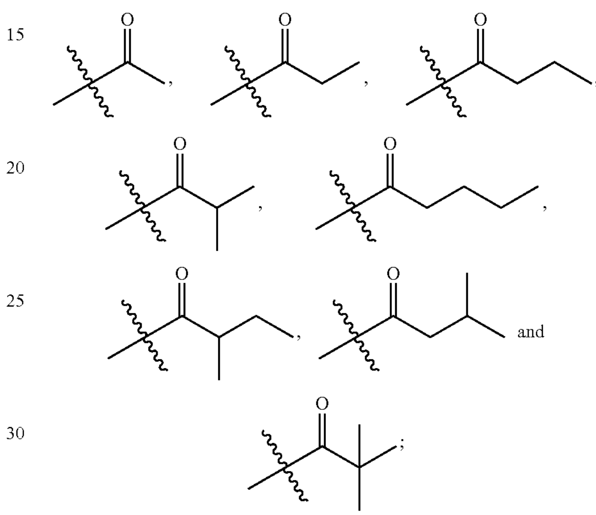

$R_2$ is selected from the group consisting of

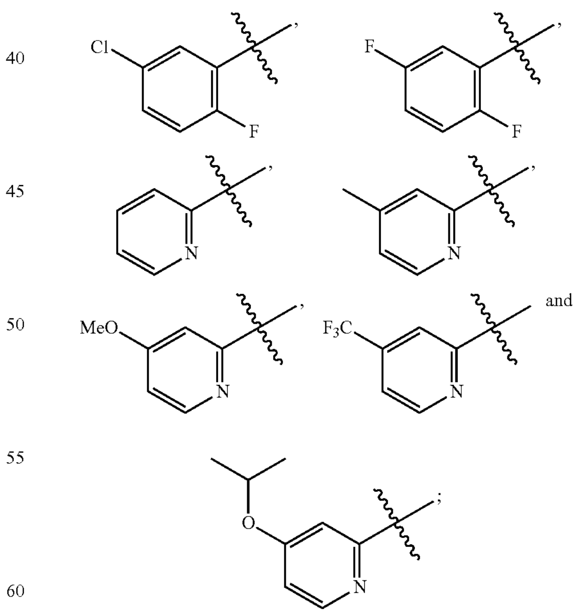

and $W_1$ is selected from the group consisting of Cl and F.

In some embodiments, $W_1$ is $C_1$. In other embodiments, $W_1$ is F. In some embodiments, $R_2$ is

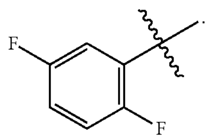 [SMILES: *c1cc(F)ccc1F]

In some embodiments, $R_{27}$ is H. In some embodiments, Z—$R_3$ is

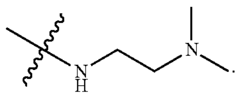 [SMILES: *NCCN(C)C]

In another aspect, a compound of Formula V is provided:

Formula V

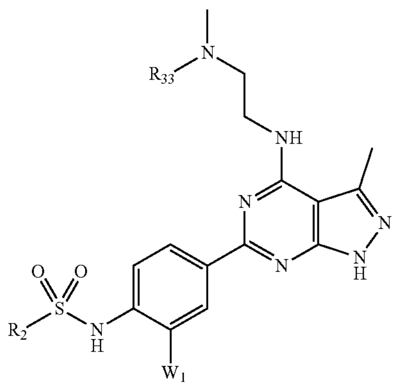

or a pharmaceutically acceptable salt thereof, wherein:

$R_2$ is

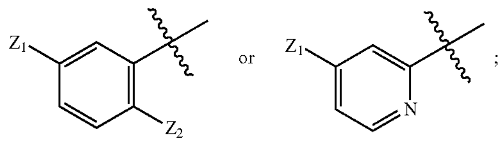

$Z_1$ and $Z_2$ are independently from one another selected from the group consisting of halogen, $(C_1$-$C_4)$alkyl, —OH, —O—$(C_1$-$C_4)$alkyl, —$CF_3$, and —CN;

$Z_3$ is selected from the group consisting of H, halogen, $(C_1$-$C_4)$alkyl, —OH, —O—$(C_1$-$C_4)$alkyl, —$CF_3$ and —CN;

$W_1$ is selected from the group consisting of H and halogen;

$R_{33}$ is —$CH_3$ or —$(CH_2)$—$(CH_2)$—$OR_{27}$; and $R_{27}$ is selected from the group consisting of H, —C(═O)—$(C_1$-$C_4)$alkyl, a natural amino acid bound by the α-carboxyl group, and —P(═O)$(OH)_2$.

In some embodiments, $W_1$ is F. In some embodiments, $W_1$ is Cl.

In some embodiments, $R_2$ is

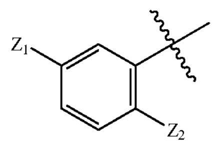

$Z_1$ and $Z_2$ can be independently from one another selected from the group consisting of Cl, F, —$CH_3$, —CN, —OCH$(CH_3)_2$ and —OMe.

In some embodiments, $R_2$ is

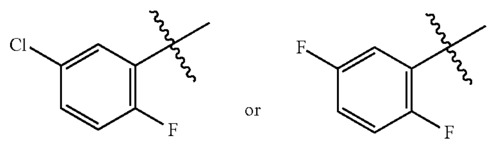

In some embodiments, $R_2$ is

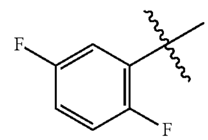

In some embodiments, $R_2$ is

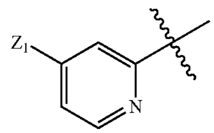

$Z_3$ can be selected from the group consisting of H, Cl, F, —$CH_3$, —CN, —OCH$(CH_3)_2$ and —OMe, or from the group consisting of H, —$CH_3$, —$CF_3$, —OCH$(CH_3)_2$ and —OMe, or from the group consisting of —$CH_3$, —OCH$(CH_3)_2$ and —OMe.

In some embodiments, $R_{33}$ is —$CH_3$. In other embodiments, $R_{33}$ is —$(CH_2)$—$(CH_2)$—$OR_{27}$. In some embodiments, $R_{27}$ is selected from the group consisting of H and —C(═O)—$(C_1$-$C_4)$alkyl.

In some embodiments, the compound of Formula V is a compound of Formula Va:

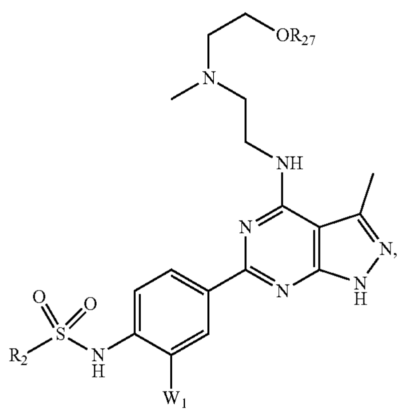

or a pharmaceutically acceptable salt thereof, wherein:

$R_2$ is selected from the group consisting of:

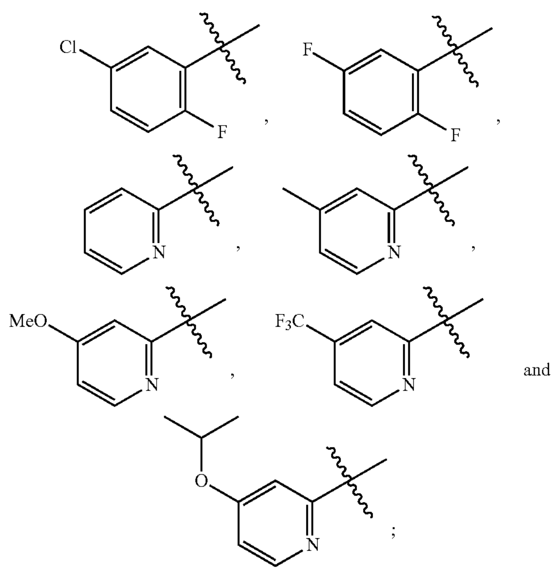

and $W_1$ is selected from the group consisting of H, Cl and F; and $R_{27}$ is selected from the group consisting of: H,

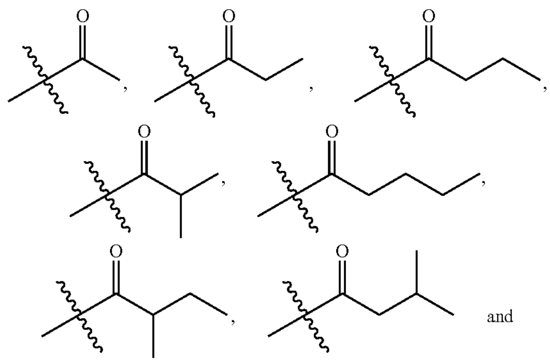

and

-continued

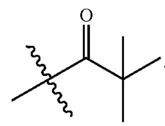

In some embodiments, the compound of Formula V is a compound of Formula Vb:

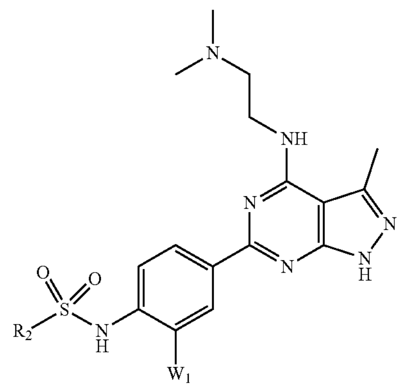

or a pharmaceutically acceptable salt thereof, wherein:

$R_2$ is selected from the group consisting of:

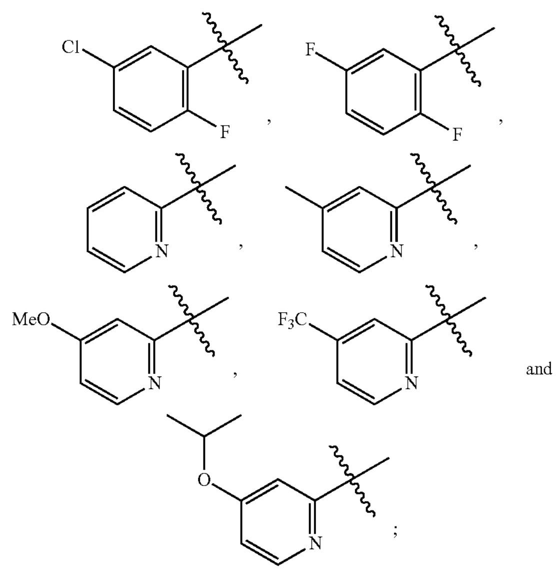

and and $W_1$ is selected from the group consisting of H, Cl and F.

In some embodiments, the compound of Formula V is selected from the group consisting of Compounds 9, 20, 22, 24, 27, 30, 38, 45, 72, 73, 78, 84, 85, 99, 100, 103, 104, 105, 106, 107, 108, 109, 110, 111, 112, 113, 114, 115, 116, 117, 118, 119, 120, 121, 122, 123, 124, 125, 150, 151, 152 and 153, as numbered in Table A hereinbelow, or a pharmaceutically acceptable salt thereof.

In one aspect, a compound of Formula Vb is provided:

Formula Vb

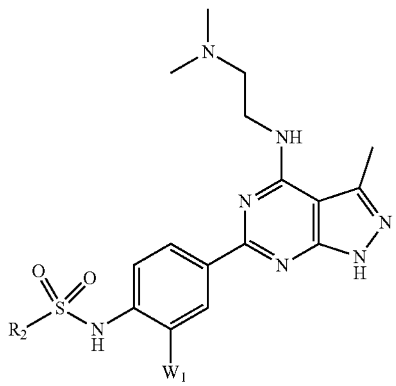

or a pharmaceutically acceptable salt thereof, wherein:

$R_2$ is

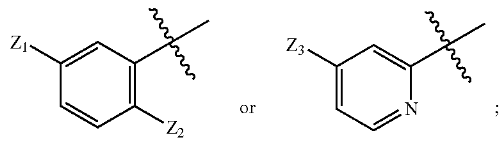

$Z_1$ and $Z_2$ are independently from one another selected from the group consisting of halogen, $(C_1-C_4)$alkyl, —OH, —O—$(C_1-C_4)$alkyl, —$CF_3$, and —CN;

$Z_3$ is selected from the group consisting of H, halogen, $(C_1-C_4)$alkyl, —OH, —O—$(C_1-C_4)$alkyl, —$CF_3$ and —CN; and $W_1$ is selected from the group consisting of H and halogen.

In some embodiments, $W_1$ is F. In other embodiments, $W_1$ is $C_1$.

In some embodiments, $R_2$ is

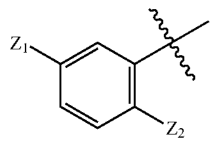

$Z_1$ and $Z_2$ can be independently from one another selected from the group consisting of Cl, F, —$CH_3$, —CN, —$OCH(CH_3)_2$ and —OMe.

In some embodiments, $R_2$ is

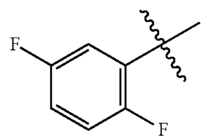

In some embodiments, $R_2$ is

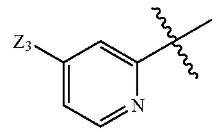

$Z_3$ can be selected from the group consisting of H, Cl, F, —$CH_3$, —CN, —$OCH(CH_3)_2$ and —OMe, or from the group consisting of H, —$CH_3$, —$CF_3$, —$OCH(CH_3)_2$ and —OMe, or from the group consisting of —$CH_3$, —$OCH(CH_3)_2$ and —OMe.

In some embodiments, the compound of Formula Vb is selected from the group consisting of Compounds 9, 38, 45, 84, 85 and 111, as numbered in Table A hereinbelow, or a pharmaceutically acceptable salt thereof.

In some embodiments, the compound of Formula Vb is selected from the group consisting of Compounds 24, 27, 30, 73, 100, 103, 104, 105, 106, 107, 108, 109, 110, 113 and 112, as numbered in Table A hereinbelow, or a pharmaceutically acceptable salt thereof.

In another aspect, there is provided a compound of Formula VI:

Formula VI

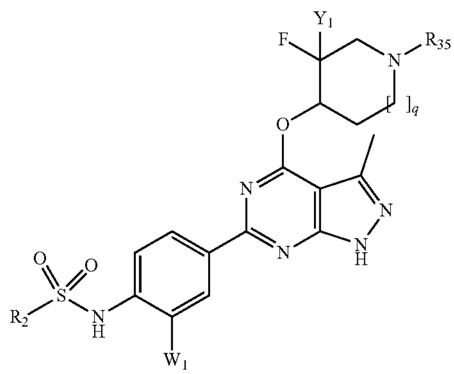

or a pharmaceutically acceptable salt thereof, wherein:

$Y_1$ is H or F;

q is 0 or 1;

$R_2$ is

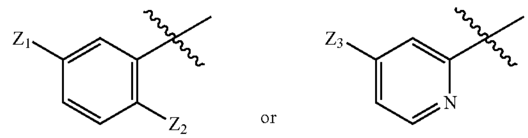

$Z_1$ and $Z_2$ are independently from one another selected from the group consisting of halogen, $(C_1-C_4)$alkyl, —OH, —O—$(C_1-C_4)$alkyl, —$CF_3$, and —CN;

$Z_3$ is selected from the group consisting of H, halogen, $(C_1-C_4)$alkyl, —OH, —O—$(C_1-C_4)$alkyl, —$CF_3$ and —CN;

$W_1$ is selected from the group consisting of H and halogen;

$R_{35}$ is H or a $(C_1-C_4)$-alkyl which is unsubstituted or substituted by one or more identical or different substituents $R_{50}$;

$R_{50}$ is selected from the group consisting of halogen, —$OR_{27}$, —O—($C_1$-$C_4$)-alkyl, —$CF_3$, and —CN;

$R_{27}$ is selected from the group consisting of H, —C(═O)—($C_1$-$C_4$)alkyl, a natural amino acid bound by the α-carboxyl group, and P(═O)$(OH)_2$.

In some embodiments, $Y_1$ is H.

In some embodiments, the compound of Formula VI is selected from the group consisting of:

Formula VIa

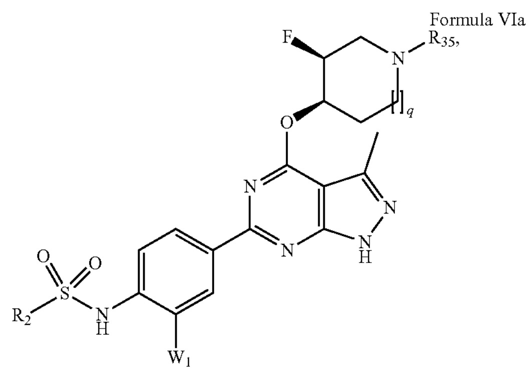

Formula VIb

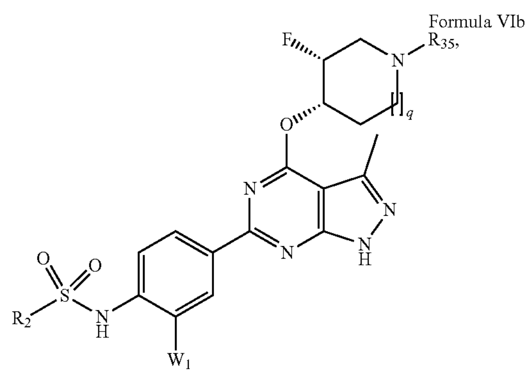

Formula VIc

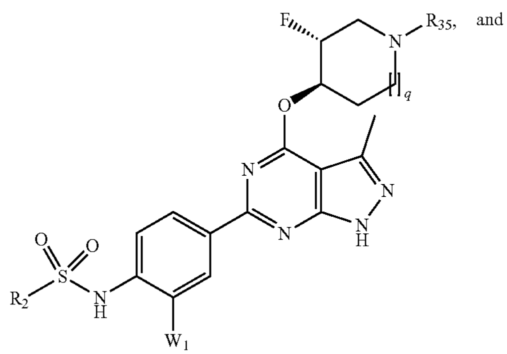

and

-continued

Formula VId

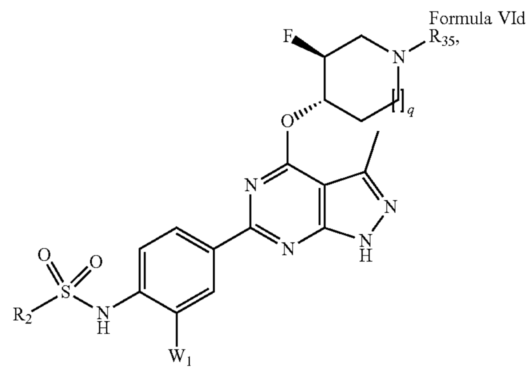

or a pharmaceutically acceptable salt thereof.

In some embodiments, the compound of Formula VI is a compound of Formula Via:

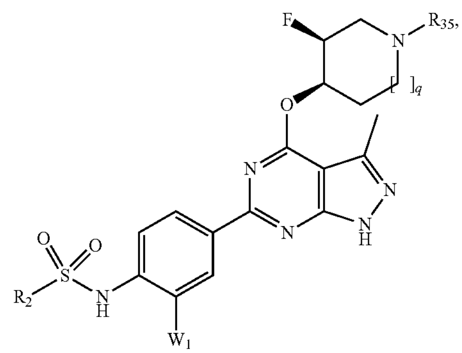

or a pharmaceutically acceptable salt thereof.

In some embodiments, q=1.

In some embodiments, $W_1$ is F. In other embodiments, $W_1$ is Cl.

In some embodiments, $R_2$ is

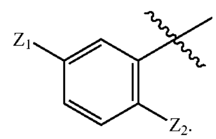

$Z_1$ and $Z_2$ can be independently from one another selected from the group consisting of Cl, F, —$CH_3$, —CN, —OCH$(CH_3)_2$ and —OMe.

In some embodiments, $R_2$ is

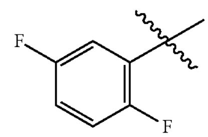

In some embodiments, $R_2$ is

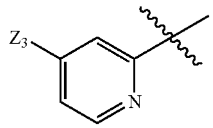

$Z_3$ can be selected from the group consisting of H, Cl, F, —$CH_3$, —CN, —$OCH(CH_3)_2$ and —OMe, or from the group consisting of H, —$CH_3$, —$CF_3$, —$OCH(CH_3)_2$ and —OMe, or from the group consisting of —$CH_3$, —OCH $(CH_3)_2$ and —OMe.

In some embodiments, $R_{27}$ is selected from the group consisting of H and —C(═O)—($C_1$-$C_4$)alkyl.

In some embodiments, $R_{35}$ is H or a ($C_1$-$C_4$)-alkyl a ($C_1$-$C_4$)-alkyl which is unsubstituted. In some embodiments, $R_{35}$ is H.

In some embodiments, the compound of Formula VI is a compound of Formula VIa:

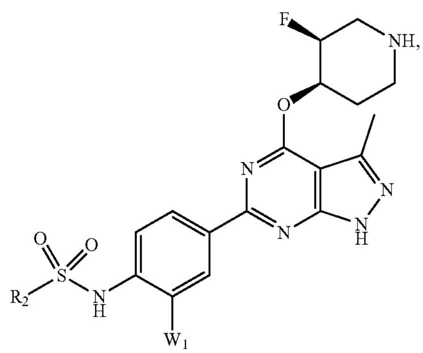

or a pharmaceutically acceptable salt thereof, wherein:

$R_2$ is selected from the group consisting of:

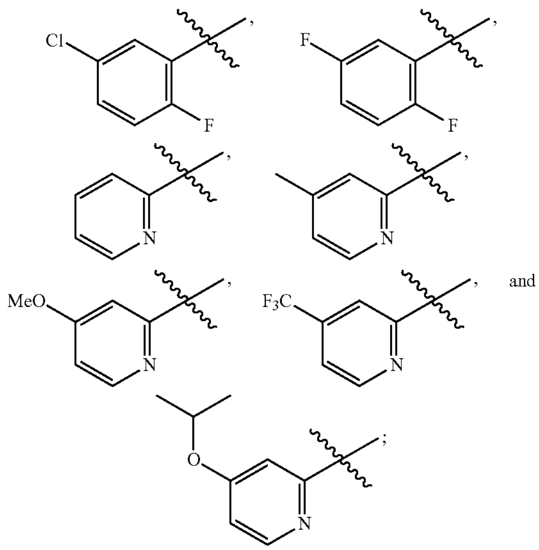

and $W_1$ is selected from the group consisting of H, Cl and F.

In some embodiments, the compound of Formula VI is selected from the group consisting of Compounds 29, 41, 42, 44, 46, 47, 49, 50, 53, 54, 56, 57, 58, 59, 60, 61, 62, 63, 64, 66, 67, 69, 70, 71, 92, 155 and 156, as numbered in Table A hereinbelow, or a pharmaceutically acceptable salt thereof.

For all the embodiments pertaining to Formula VI described herein, the compound of Formula VI is preferably not a compound of Formula VIa in racemic form:

Formula VIa

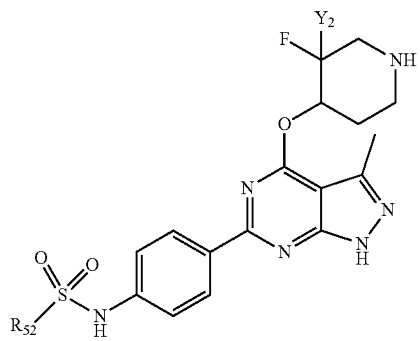

or a pharmaceutically acceptable salt thereof, wherein:

$Y_2$ is H or F; and $R_{52}$ is selected from the group consisting of:

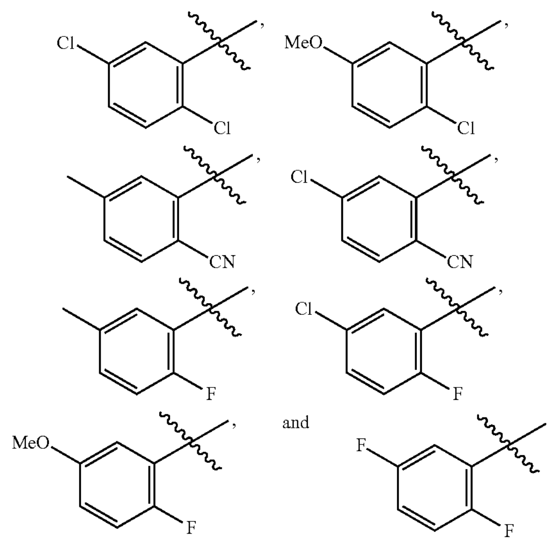

EXAMPLES

Some abbreviations and acronyms are used in the description of the experimental procedures and Examples below. Although most of these abbreviations and acronyms would be understood by a person skilled in the art.

Preparation of Compounds

ACS grade solvents and reagents were used without further purification.

The prepared compounds were in general characterized by spectroscopic data and chromatographic data, in particular mass spectra (MS) and/or nuclear magnetic resonance (NMR) spectra. $^1$H-NMR spectra were generally recorded at 600 MHz. In the NMR characterization, the chemical shift δ (in ppm), the number of hydrogen atoms (H), the coupling constant J (in Hz) and the multiplicity (s: singlet, d: doublet, dd: double doublet, t: triplet, dt: double triplet, m: multiplet; br: broad) of the peaks are given. In the MS characterization, the mass number (m/z) of the peak of the molecular ion (M) or of a related ion such as the ion [M+1], i.e. the protonated molecular ion [M+H)] or the ion [M−1], which was formed depending on the ionization method used, is given. Generally, the ionization method was electrospray ionization (ES+ or ES−).

Compound 1 N-(4-(4-((1-isopropylpiperidin-4-yl) oxy)-3-methyl-1H-pyrazolo[3,4-d]pyrimidin-6-yl) phenyl)ethenesulfonamide

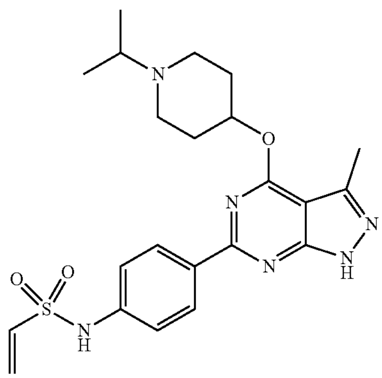 [SMILES: C=CS(=O)(=O)Nc1ccc(-c2nc(OC3CCN(C(C)C)CC3)c3c(C)n[nH]c3n2)cc1]

(i) 4,6-dichloro-3-methyl-1-(tetrahydro-2H-pyran-2-yl)-1H-pyrazolo[3,4-d]pyrimidine Commercially available 4,6-Dichloro-3-methyl-1H-pyrazolo[3,4-d]pyrimidine (1.00 g, 5.29 mmol, 1.00 equiv.) was dissolved in THF (13.3 ml, 0.4 M) in a reaction vessel containing a magnetic stirring bar, followed by addition of 3,4-dihydro-2H-pyran (2.42 ml, 26.5 mmol, 5.00 equiv.) and pyridinium 4-toluenesulfonate (66.3 mg, 0.264 mmol, 0.05 equiv.) at RT. The colorless reaction mixture was heated to 60° C. for 3 h (the solution became slightly yellow) and allowed to cool down before evaporation of the volatiles. The residue was dissolved in ethyl acetate (20 ml) and washed with a saturated aqueous sodium hydrogenocarbonate solution (3×20 ml), dried over sodium sulfate, filtered and evaporated to afford the desired product (1.28 g, 94% yield) as a slightly yellow solid.

(ii) 6-chloro-4-((1-isopropylpiperidin-4-yl)oxy)-3-methyl-1H-pyrazolo[3,4-d]pyrimidine 1-Isopropylpiperidin-4-ol (498 mg, 3.30 mmol, 4.74 equiv.) was dissolved in dry THF (5.00 ml) in a reaction vessel containing a magnetic stirring bar under an argon atmosphere, and the mixture cooled on an ice bath. Then sodium hydride (26.5 mg, 60% suspension in mineral oil) was added and the mixture stirred on an ice bath for approximately 30 min Addition of 4,6-dichloro-3-methyl-1-(tetrahydro-pyran-2-yl) 1H-pyrazolo3,4-dpyrimidine (200 mg, 0.70 mmol, 1.00 equiv.) dissolved in THF (2.00 ml). The ice bath was removed and the mixture stirred at RT until complete conversion of the starting material as monitored by TLC (AcOEt/hexanes). the reaction mixture was quenched with water (10 ml) and extracted with ethyl acetate (3×20 ml) and the combined organic phases dried over sodium sulfate, filtered and evaporated. The crude product was purified by flash chromatography on silica gel using a mixture of ethyl acetate and Hexanes as the eluent to afford the desired product after evaporation (241 mg, 88% yield) as a colorless oil. LCMS (ESI, m/z): 394.5 [M+H]+.

(iii) N-(4-(4,4,5,5-tetramethyl-1,3,2-dioxaborolan-2-yl)phenyl)ethenesulfonamide Ethenesulfonyl chloride (217 μL, 2.28 mmol, 1.00 equiv.) and 4-(4.4.5.5-tetramethyl-1,3,2-dioxaborolan-2-yl)phenylamine (500 mg, 2.28 mmol, 1.00 equiv.) were added to a reaction vessel containing a magnetic stirring bar, followed by 9.58 ml dry DCM and 196 μl pyridine. The reaction mixture was stirred at RT. After 20 h, the reaction mixture was cooled on an ice-bath and quenched with 1M aqueous Sodium hydroxide solution (formation of yellow solution). The organic phase was separated and the aqueous phase acidified with 2M aqueous hydrochloric acid (formation of a white precipitate) and extracted three times with ethyl acetate. The combined organic phases were washed with brine and dried over sodium sulfate and evaporated to afford the crude product. Purification by flash chromatography on silica gel using a mixture of ethyl acetate and hexanes as the eluent afforded the desired product as a white solid (234 mg, 33% yield). LCMS (ESI, m/z): 309.2 [M+H]+.

(iv) N-(4-(4-((1-isopropylpiperidin-4-yl)oxy)-3-methyl-1H-pyrazolo[3,4-d]pyrimidin-6-yl)phenyl) ethenesulfonamide N-(4-(4,4,5,5-Tetramethyl-1,3,2-dioxaborolan-2-yl)phenyl)ethanesulfonamide (60.0 mg, 1.00 equiv.) was added to a reaction vessel containing a magnetic stirring bar together with MK0016 (76.4 mg, 1.00 equiv.). BDFP (11.3 mg) and cesium carbonate (196 mg, 2.2 equiv.), followed by 1.94 mL Dioxane and 324 ul water, and the mixture heated to 100° C. under stirring. Reaction was monitored by LC-MS After 3 h the reaction mixture was cooled to RT and quenched with a saturated aqueous sodium hydrogencarbonate solution (10 ml) and extracted with ethyl acetate (3×10 ml). The combined aqueous phases were dried over sodium sulfate, filtered and evaporated to afford the crude product as a brown oil.

The crude product was dissolved in a mixture of 4M HCl in Diox (1 ml) and iPrOH (1 ml) and stirred for 2 h at RT before evaporation of the solvent. Reaction was monitored by LC-MS. The crude product was purified by C18 reversed phase column, elution with a water/MeCN gradient with 0.1% TFA. The fractions containing the product were lyophilized to yield pure desired product (18 mg, 20% yield) as an off-white TFA salt. LCMS (ESI, m/z): 457.7 [M+H]+. $^1$H NMR (600 MHZ, DMSO-$d_6$) δ 13.49 (brs, 1H), 10.40 (d, J=12.75 Hz, 1H), 9.41 (br s, 1H), 8.37 (dd, J=18.80, 8.99 Hz, 2H), 7.29 (dd, J=8.57, 4.81 Hz, 2H), 6.20 (dd, J=17.61, 5.14 Hz, 1H), 6.13-6.00 (m, 2H), 5.93-5.57 (m, 1H), 3.65-3.11 (m, 7H), 2.59 (s, 3H), 2.38-2.17 (m, 2H), 2.00 (t, J=13.57, 1H), 1.32 (d, J=6.88 Hz, 6H).

Compound 2 N-(4-(4-((1-isopropylpiperidin-4-yl)oxy)-3-methyl-1H-pyrazolo[3,4-d]pyrimidin-6-yl)phenyl)pyrrolidine-1-sulfonamide

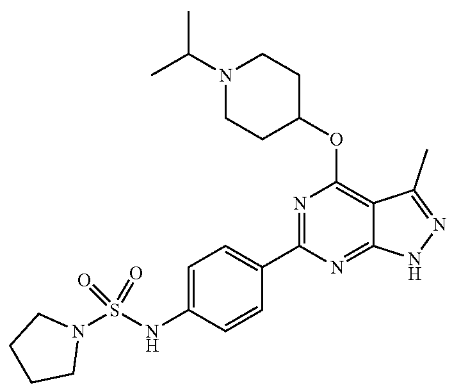 [SMILES: Cc1n[nH]c2nc(-c3ccc(NS(=O)(=O)N4CCCC4)cc3)nc(OC3CCN(C(C)C)CC3)c12]

This compound was prepared according to the procedure described in example 1. The desired product (5.6 mg, 8% yield) was obtained as an off-white TFA salt. LCMS (ESI, m/z): 500.7 [M+H]+. $^1$H NMR (600 MHZ, DMSO-$d_6$) δ 13.47 (brs, 1H), 10.21 (d, J=14.67 Hz, 1H), 9.39 (br s, 1H), 8.37 (dd, J=18.66, 9.03 Hz, 2H), 7.33 (br t, J=8.76 Hz, 2H), 5.87-5.66 (m, 1H), 3.58-3.36 (m, 10H), 2.59 (s, 3H), 2.40-2.16 (m, 2H), 2.11-1.93 (m, 1H), 1.76-1.69 (m, 4H), 1.46-1.41 (m, 1H), 1.32 (d, J=6.9 Hz, 6H).

Compound 3 4-cyano-N-(4-(4-((1-isopropylpiperidin-4-yl)oxy)-3-methyl-1H-pyrazolo[3,4-d]pyrimidin-6-yl)phenyl)benzenesulfonamide

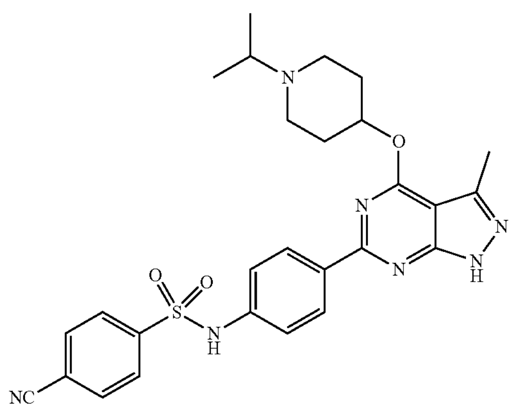 [SMILES: Cc1n[nH]c2nc(-c3ccc(NS(=O)(=O)c4ccc(C#N)cc4)cc3)nc(OC3CCN(C(C)C)CC3)c12]

This compound was prepared according to the procedure described in example 1. The desired product (103 mg, 75% yield) was obtained as an off-white TFA salt. LCMS (ESI, m/z): 532.4 [M+H]+. $^1$H NMR (600 MHZ, DMSO-$d_6$) δ 13.51 (br s, 1H), 10.95-10.93 (m, 1H), 9.43 (br d, 1H), 8.41-8.30 (m, 2H), 8.08-7.96 (m, 4H), 7.27-7.25 (m, 2H), 5.83-5.62 (m, 1H), 3.58-3.18 (m, 9H), 2.58-2.50 (m, 1H), 2.58 (s, 3H), 2.33-2.18 (m, 2H), 2.01-1.96 (m, 1H), 1.30 (d, J=6.6 Hz, 6H).

Compound 4 4-(aminomethyl)-N-(4-(4-((1-isopropylpiperidin-4-yl)oxy)-3-methyl-1H-pyrazolo[3,4-d]pyrimidin-6-yl)phenyl)benzenesulfonamide

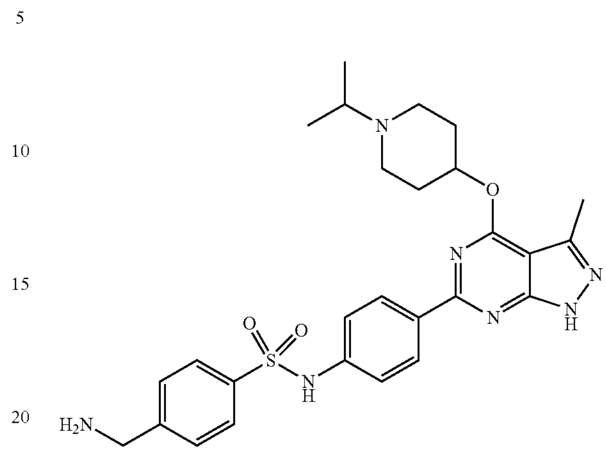

A solution of the compound 3 (33.5 mg. 0.07 mmol, 1.00 equiv.) in methanol (630 UL, 0.1M), at 0° C. was treated with cobalt (II) chloride (16.4 mg. 0.13 mmol, 2.00 equiv.) and the resulting mixture left to stir for 5 minutes prior to the addition of sodium borohydride (23.8 mg, 0.63 mmol, 10.0 equiv.). The resulting suspension was allowed to warm gradually to room temperature. After 16 hours 10 ml of 3N solution of hydrochloric acid was added and the mixture stirred for 10 minutes followed by of 1 ml of 880 Ammonia solution. The crude product was purified by C18 reversed phase column, elution with a water/MeCN gradient with 0.1% TFA. The fractions containing the product were lyophilized to yield pure desired product (15.7 mg, 47% yield) was obtained as an off-white TFA salt. LCMS (ESI, m/z): 536.7 [M+H]+. $^1$H NMR (400 MHZ, CDCl3): δ 13.45 (br s, 1H), 10.91-10.65 (m, 1H), 9.43-9.17 (br d 1H), 8.29 (d, J=8.6 Hz, 2H), 8.19 (br, s, 2H), 7.87 (dd, J=8.21, 3.91 Hz, 2H), 7.60 (d, J=8.60, 2H), 7.25 (dd, J=8.79, 4.10 Hz, 2H), 5.92-5.47 (m, 1H), 3.70-3.05 (m, 10H), 2.55 (s, 3H), 2.38-2.10 (m, 2H), 2.02-1.89 (m, 1H), 1.28 (d, J=6.6 Hz, 6H).

Compound 5 N-(4-(4-((1-isopropylpiperidin-4-yl)oxy)-3-methyl-1H-pyrazolo[3,4-d]pyrimidin-6-yl)phenyl)propane-2-sulfonamide

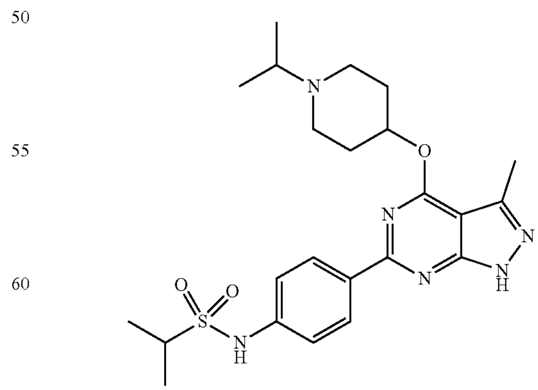

This compound was prepared according to the procedure described in example 1. The desired product (82.7 mg, 67% yield) was obtained as an off-white TFA salt. LCMS (ESI, m/z): 473.5 [M+H]+. $^1$H NMR (600 MHZ, DMSO-$d_6$) δ 13.45 (br s, 1H), 10.14-10.12 (m, 1H), 9.31 (br s, 1H), 8.41-8.36 (m, 2H), 7.39-7.36 (m, 1H), 5.86-5.55 (m, 1H), 3.57-3.18 (m, 5H), 2.58 (s, 3H), 2.30-2.21 (m, 2H), 1.99-1.97 (m, 1H), 1.47-1.41 (m, 2H), 1.30 (d, J=6.6 Hz, 6H).

Compound 6 N-(4-(4-((1-isopropylpiperidin-4-yl)oxy)-3-methyl-1H-pyrazolo[3,4-d]pyrimidin-6-yl)phenyl)piperidine-1-sulfonamide

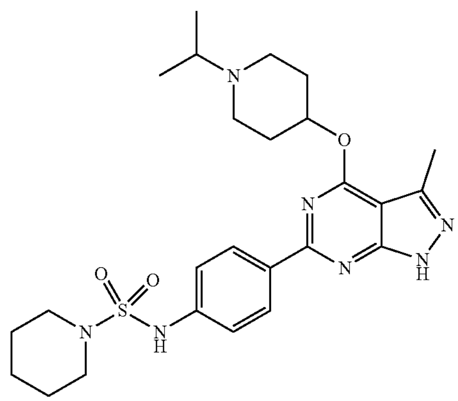 [SMILES: Cc1n[nH]c2nc(-c3ccc(NS(=O)(=O)N4CCCCC4)cc3)nc(OC3CCN(C(C)C)CC3)c12]

This compound was prepared according to the procedure described in example 1. The desired product (11.9 mg, 14% yield) was obtained as an off-white TFA salt. LCMS (ESI, m/z): 514.6 [M+H]+. $^1$H NMR (600 MHZ, CDCl3): δ 13.46 (br, s, 1H), 10.32-10.17 (m, 1H), 9.24 (br, d, 1H), 8.35 (dd, J=12.5, 8.99 Hz, 2H), 7.42-7.15 (m, 2H), 5.85 (m, 1H), 3.39-2.89 (m, 10H), 2.58 (s, 3H), 2.38-2.12 (m, 3H), 2.01-1.89 (m, 1H), 1.41-1.38 (m, 6H), 1.29 (d, J=6.64 Hz, 6H).

Compound 7 N-(4-(4-((1-isopropylpiperidin-4-yl)oxy)-3-methyl-1H-pyrazolo[3,4-d]pyrimidin-6-yl)phenyl)pyridine-2-sulfonamide

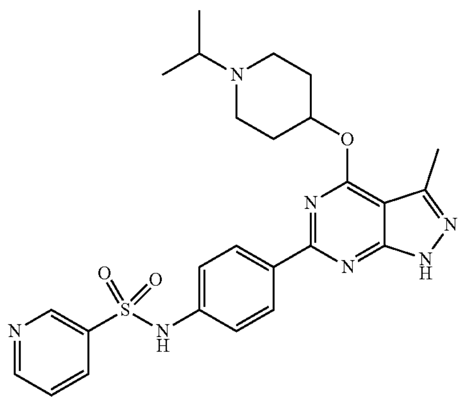 [SMILES: Cc1n[nH]c2nc(-c3ccc(NS(=O)(=O)c4cccnc4)cc3)nc(OC3CCN(C(C)C)CC3)c12]

This compound was prepared according to the procedure described in example 1. The desired product (113 mg, 79% yield) was obtained as an off-white TFA salt. LCMS (ESI, m/z): 508.6 [M+H]+. $^1$H NMR (600 MHZ, DMSO-$d_6$) δ 13.49 (br s, 1H), 10.91-10.89 (m, 1H), 9.41 (br s, 1H), 8.96-8.90 (m, 1H), 8.80-8.78 (m, 1H), 8.36-8.19 (m, 3H), 7.63-7.60 (m, 1H), 7.27-7.25 (m, 2H), 5.83-5.61 (m, 1H), 3.57-3.18 (m, 5H), 2.58 (s, 3H), 2.30-2.21 (m, 2H), 1.99-1.97 (m, 1H), 1.47-1.41 (m, 2H), 1.30 (d, J=6.6 Hz, 6H).

Compound 8 5-chloro-N-(4-(4-(2-(dimethylamino)ethoxy)-3-methyl-1H-pyrazolo[3,4-d]pyrimidin-6-yl)phenyl)-2-fluorobenzenesulfonamide

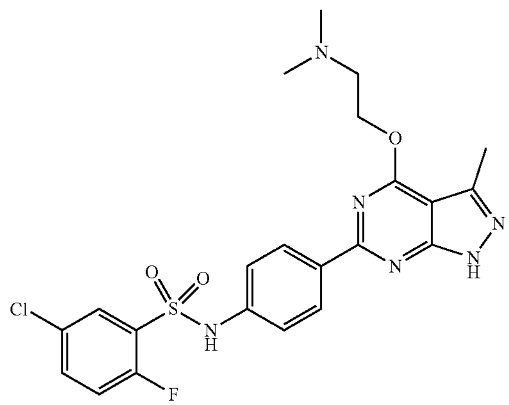 [SMILES: Cc1n[nH]c2nc(-c3ccc(NS(=O)(=O)c4cc(Cl)ccc4F)cc3)nc(OCCN(C)C)c12]

(i) 5-chloro-2-fluoro-N-[4-(4,4,5,5-tetramethyl-1,3,2-dioxaborolan-2-yl)phenyl]benzenesulfonamide A 50-mL 3-necked round-bottom flask was charged with 5-chloro-2-fluorobenzenesulfonyl chloride (1.00 g, 4.36 mmol, 1.00 equiv.), dichloromethane (10 mL), 4-(4,4,5,5-tetramethyl-1,3,2-dioxaborolan-2-yl)aniline (0.956 g, 4.36 mmol, 1.00 equiv.), pyridine (0.345 g, 4.36 mmol, 1.00 equiv.) under $N_2$. The reaction mixture was stirred overnight at room temperature and diluted with dichloromethane (50 mL). The resulting mixture was washed with water (3×20 mL), dried over anhydrous sodium sulfate, filtered and concentrated under reduced pressure. The residue was purified by silica gel column chromatography, eluted with ethyl acetate/hexane (1/3) to afford desired product 5-chloro-2-fluoro-N-[4-(4,4,5,5-tetramethyl-1,3,2-dioxaborolan-2-yl)phenyl]benzenesulfonamide (1.03 g, 57% yield) as a light yellow solid. LCMS (ESI, m/z): 412 [M+H]+.

(ii) 2-[[6-chloro-3-methyl-1-(oxan-2-yl)pyrazolo[3,4-d]pyrimidin-4-yl]oxy]ethyl)dimethylamine A 20-mL vial was charged with 4,6-dichloro-3-methyl-1-(oxan-2-yl)pyrazolo[3,4-d]pyrimidine (75.0 mg, 0.261 mmol, 1.00 equiv.), dimethylaminoethanol (23.8 mg, 0.261 mmol, 1.00 equiv.), potassium carbonate (72.2 mg, 0.522 mmol, 2.00 equiv.) and acetonitrile (3 mL). The resulting solution was stirred overnight at room temperature. The solids were filtered off and the filtrate was concentrated under reduce pressure. The residue was purified by silica gel column chromatography, eluted with dichloromethane/methanol (95/5) to afford desired product (65.0 mg, 73% yield) as an off-white solid. LCMS (ESI, m/z): 340 [M+H]+.

(iii) 5-chloro-N-(4-(4-(2-(dimethylamino)ethoxy)-3-methyl-1H-pyrazolo[3,4-d]pyrimidin-6-yl)phenyl)-2-fluorobenzenesulfonamide A 8 mL vial was charged with 5-chloro-2-fluoro-N-[4-(4,4,5,5-tetramethyl-1,3,2-dioxaborolan-2-yl)phenyl]benzenesulfonamide (87.3 mg, 0.212 mmol, 1.20 equiv.), (2-[[6-chloro-3-methyl-1-(oxan-2-yl)pyrazolo[3,4-d]pyrimidin-4-yl]oxy]ethyl)dimethylamine (60.0 mg, 0.177 mmol, 1.00 equiv.), 1,4-dioxane (2 mL), water (0.2 mL), cesium carbonate (115 mg, 0.353 mmol, 2.00 equiv.), [1,1'-bis(diphenylphosphino)ferrocene]dichloropalladium (14.4 mg, 0.0180 mmol, 0.10 equiv.) under $N_2$. The resulting solution was stirred overnight at 100° C. The solids were filtered off and the filtrate was concentrated under reduce pressure. The crude product was purified by reverse phase column chromatography with the following conditions: Column: Agela C18 Column, 120 g, Mobile Phase A: Water (0.05% TFA), Mobile Phase B: ACN; Flow rate: 40 mL/min; Gradient: 0% B to 45% B in 45 min; Detector: 220 nm to afford desired product 5-chloro-N-(4-[4-[2-(dimethylamino) ethoxy]-3-methyl-1-(oxan-2-yl)pyrazolo[3,4-d]pyrimidin-6-yl]phenyl)-2-fluorobenzenesulfonamide (50.0 mg, 40% yield) as a brown solid. LCMS (ESI, m/z): 589 [M+H]+.

A 25-mL 2-necked round-bottom flask was charged with 5-chloro-N-(4-[4-[2-(dimethylamino) ethoxy]-3-methyl-1-(oxan-2-yl)pyrazolo[3,4-d]pyrimidin-6-yl]phenyl)-2-fluorobenzenesulfonamide (54.0 mg, 0.092 mmol, 1.00 equiv.), isopropyl alcohol (2.6 mL), 2 M hydrochloric acid (gas) in 1,4-dioxane (1.5 mL). The resulting solution was stirred for 3 h at room temperature and concentrated under reduced pressure. The crude product was purified by Prep-HPLC with the following conditions: Column: Xselect CSH OBD Column 30×50 mm, 5 um, Mobile Phase A: Water (10 mmol/L NH4HCO3+0.1% NH3·H2O), Mobile Phase B: ACN; Flow rate: 60 mL/min; Gradient: 18% B to 38% B in 7 min; Detector: 220 nm to afford desired product 5-chloro-N-(4-(4-(2-(dimethylamino)ethoxy)-3-methyl-1H-pyrazolo[3,4-d]pyrimidin-6-yl)phenyl)-2-fluorobenzenesulfonamide (12.7 mg, 27% yield) as an off-white solid. LCMS (ESI, m/z): 505 [M+H]+. $^1$H NMR (400 MHZ, DMSO-$d_6$) δ 13.42 (s, 1H), 10.82 (s, 1H), 8.35-8.21 (m, 2H), 7.86-7.84 (m, 1H), 7.74-7.72 (m, 1H), 7.47 (t, J=8.0 Hz, 1H), 7.26-7.17 (m, 2H), 4.75 (t, J=4.0 Hz, 2H), 2.89 (t, J=6.0 Hz, 2H), 2.50 (s, 3H), 2.36 (s, 6H).

Compound 9 5-chloro-N-(4-(4-((2-(dimethylamino) ethyl)amino)-3-methyl-1H-pyrazolo[3,4-d]pyrimidin-6-yl)phenyl)-2-fluorobenzenesulfonamide

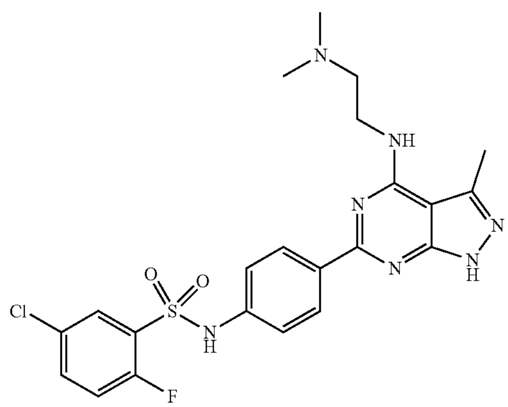 [SMILES: Cc1n[nH]c2nc(-c3ccc(NS(=O)(=O)c4cc(Cl)ccc4F)cc3)nc(NCCN(C)C)c12]

(i) 6-chloro-N-[2-(dimethylamino)ethyl]-3-methyl-1-(oxan-2-yl)pyrazolo[3,4-d]pyrimidin-4-amine A 8-mL vial was charged with 4,6-dichloro-3-methyl-1-(oxan-2-yl)-2H,3H-pyrazolo[3,4-d]pyrimidine (74.3 mg, 0.259 mmol, 1.00 equiv.), (2-aminoethyl)dimethylamine (22.8 mg, 0.259 mmol, 1.00 equiv.), dichloromethane (3.0 mL) and triethylamine (57.7 mg, 0.571 mmol, 2.20 equiv.). The resulting solution was stirred overnight at room temperature and concentrated under reduced pressure. The residue was purified by silica gel column chromatography, eluted with dichloromethane/methanol (95/5) to afford desired product 6-chloro-N-[2-(dimethylamino)ethyl]-3-methyl-1-(oxan-2-yl)pyrazolo[3,4-d]pyrimidin-4-amine (55.0 mg, 62% yield) as a colorless solid. LCMS (ESI, m/z): 339 [M+H]+.

(ii) 5-chloro-N-(4-(4-((2-(dimethylamino)ethyl) amino)-3-methyl-1H-pyrazolo[3,4-d]pyrimidin-6-yl) phenyl)-2-fluorobenzenesulfonamide A 8-mL vial was charged with 5-chloro-2-fluoro-N-[4-(4,4,5,5-tetramethyl-1,3,2-dioxaborolan-2-yl)phenyl]benzenesulfonamide (69.2 mg, 0.168 mmol, 1.00 equiv.), 6-chloro-N-[2-(dimethylamino)ethyl]-3-methyl-1-(oxan-2-yl) pyrazolo[3,4-d]pyrimidin-4-amine (prepared from 6-chloro-3-methyl-1H-pyrazolo 3,4-dipyrimidine analogously to the procedure described in example 8), (57.0 mg, 0.168 mmol, 1.00 equiv.), 1,4-dioxane (2.9 mL), water (0.3 mL), cesium carbonate (109 mg, 0.336 mmol, 2.00 equiv.), [1,1'-bis (diphenylphosphino)ferrocene]dichloropalladium (13.7 mg, 0.0170 mmol, 0.10 equiv.). The resulting solution was stirred overnight at 100° C. The solids were filtered off and the filtrate was concentrated under reduced pressure. The crude product was purified by reverse phase column chromatography with the following conditions: Column, Column: Agela C18 Column, 120 g, Mobile Phase A: Water (0.05% TFA), Mobile Phase B: ACN; Flow rate: 40 mL/min; Gradient: 0% B to 55% B in 45 min; Detector: 220 nm to afford desired product 5-chloro-N-[4-(4-[[2-(dimethylamino)ethyl]amino]-3-methyl-1-(oxan-2-yl)pyrazolo[3,4-d]pyrimidin-6-yl)phenyl]-2-fluorobenzenesulfonamide (50.0 mg, 51% yield) as a brown solid. LCMS (ESI, m/z): 588 [M+H]+.

A 25-mL 2-necked round-bottom flask was charged with 5-chloro-N-[4-(4-[[2-(dimethylamino)ethyl]amino]-3-methyl-1-(oxan-2-yl)pyrazolo[3,4-d]pyrimidin-6-yl)phenyl]-2-fluorobenzenesulfonamide (55.0 mg, 0.094 mmol, 1.00 equiv.), isopropanol (3 mL), 2M hydrochloric acid (gas) in 1,4-dioxane (1 mL). The resulting solution was stirred for 3 h at room temperature and concentrated under reduced pressure. The crude product was purified by Prep-HPLC with the following conditions: Column: Xselect CSH OBD Column 30×150 mm, 5 um. Mobile Phase A: Water (10 mmol/L NH4HCO3+0.1% NH3·H2O), Mobile Phase B: ACN; Flow rate: 60 mL/min; Gradient: 18% B to 38% B in 7 min; Detector: 220 nm to afford desired product 5-chloro-N-[4-(4-[[2-(dimethylamino)ethyl]amino]-3-methyl-1H-pyrazolo[3,4-d]pyrimidin-6-yl)phenyl]-2-fluorobenzenesulfonamide (13.6 mg, 29% yield) as an off-white solid. LCMS (ESI, m/z): 504 [M+H]+. $^1$H NMR (400 MHZ, DMSO-$d_6$): δ 12.95 (s, 1H), 10.69 (s, 1H), 8.27-8.20 (m, 2H), 7.83 (dd, J=6.0, 2.7 Hz, 1H), 7.73 (dt, J=8.6, 3.4 Hz, 1H), 7.46 (t, J=9.2 Hz, 1H), 7.16 (d, J=8.5 Hz, 2H), 7.02 (d, J=6.2 Hz, 1H), 3.79-3.71 (m, 2H), 2.74 (s, 2H), 2.51 (s, 3H), 2.38 (s, 6H).

Compound 10 5-chloro-N-(4-(4-(4-(dimethylamino)butoxy)-3-methyl-1H-pyrazolo[3,4-d]pyrimidin-6-yl)phenyl)-2-fluorobenzenesulfonamide

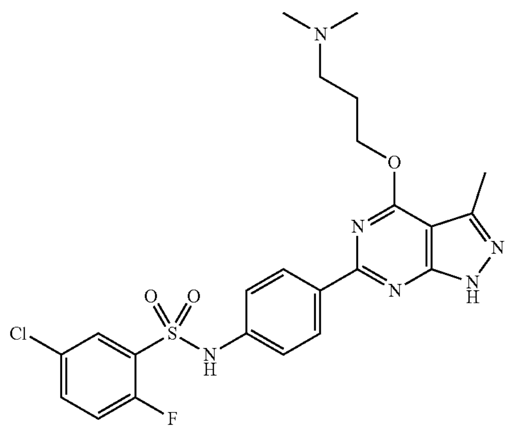 [SMILES: Cc1n[nH]c2nc(-c3ccc(NS(=O)(=O)c4cc(Cl)ccc4F)cc3)nc(OCCCN(C)C)c12]

This compound was prepared according to the procedure described in example 8. The desired product (18.4 mg, 39% yield) was obtained as an off-white solid. LCMS (ESI, m/z): 519 [M+H]+. $^1$H NMR (300 MHZ, DMSO-$d_6$) δ 13.39 (s, 1H), 8.33-8.17 (m, 2H), 7.84-7.81 (m, 1H), 7.71-7.69 (m, 1H), 7.43 (t, J=9.0 Hz, 1H), 7.31-7.10 (m, 2H), 4.65 (t, J=6.0 Hz, 2H), 2.67 (t, J=6.0 Hz, 2H), 2.50 (s, 3H), 2.36 (s, 6H), 2.08-1.99 (m, 2H).

Compound 11 5-chloro-N-(4-(4-((4-(dimethylamino)butyl)amino)-3-methyl-1H-pyrazolo[3,4-d]pyrimidin-6-yl)phenyl)-2-fluorobenzenesulfonamide

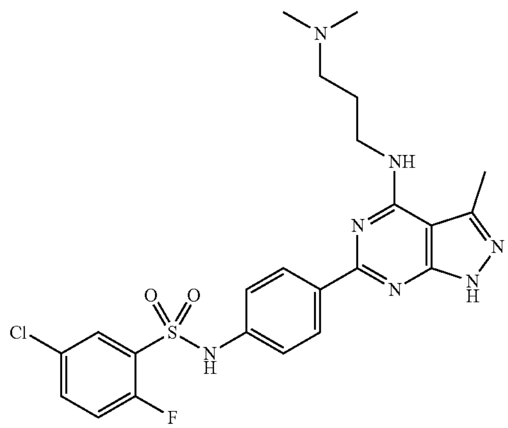 [SMILES: Cc1n[nH]c2nc(-c3ccc(NS(=O)(=O)c4cc(Cl)ccc4F)cc3)nc(NCCCN(C)C)c12]

This compound was prepared according to the procedure described in example 9. The desired product (17.3 mg, 40% yield) was obtained as an off-white solid. LCMS (ESI, m/z): 518 [M+H]+. 1H NMR (400 MHZ, DMSO-$d_6$): δ 12.90 (s, 1H), 8.21 (d, J=8.5 Hz, 2H), 7.82 (dd, J=6.0, 2.7 Hz, 1H), 7.69 (s, 1H), 7.44 (t, J=9.0 Hz, 2H), 7.13 (d, J=8.5 Hz, 2H), 3.69-3.62 (m, 2H), 2.57 (s, 2H), 2.51 (s, 3H), 2.32 (s, 6H), 1.90-1.82 (m, 2H).

Compound 12 5-chloro-2-fluoro-N-(5-(4-((1-isopropylpiperidin-4-yl)oxy)-3-methyl-1H-pyrazolo[3,4-d]pyrimidin-6-yl)pyrimidin-2-yl)benzenesulfonamide

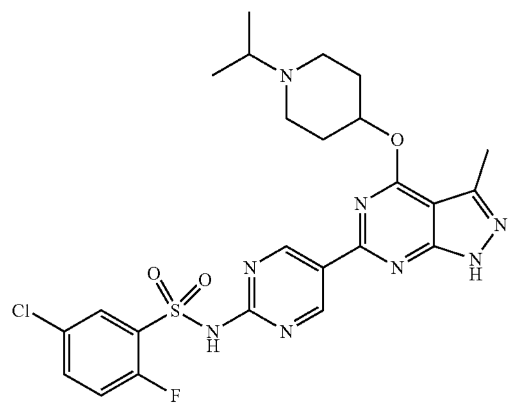 [SMILES: Cc1n[nH]c2nc(-c3cnc(NS(=O)(=O)c4cc(Cl)ccc4F)nc3)nc(OC3CCN(C(C)C)CC3)c12]

(i) N-(5-bromopyrimidin-2-yl)-5-chloro-2-fluorobenzenesulfonamide

To a solution of 5-bromopyrimidin-2-amine (1.50 g, 8.62 mmol, 1.00 equiv.) in tetrahydrofuran (60 mL) was added dropwise lithium hexamethyldisilazide (9.00 mL, 9.00 mmol, 1.05 equiv., 1M solution in THF) at −40° C. under $N_2$. The resulting mixture was stirred for 0.5 hour at −40° C. and more 1 hour at room temperature. Then a solution of 5-chloro-2-fluorobenzenesulfonyl chloride (2.40 g, 10.5 mmol, 1.20 equiv.) in tetrahydrofuran (5 mL) was added dropwise at −40° C. The resulting mixture was stirred at −40° C. for 1 hour and additional 16 hours at room temperature. The reaction mixture was quenched with saturated ammonium chloride solution (100 mL) at 0° C., extracted with ethyl acetate (3×100 mL). The organic layer was dried over anhydrous sodium sulfate and filtered. The filtrate was concentrated under reduced pressure. The residue was purified by silica gel column chromatography, eluting with 0-15% ethyl acetate in petroleum ether to afford the desired product (750 mg, 24% yield) as a yellow solid. LCMS (ESI, m/z): 366 [M+H]+.

(ii) 5-chloro-2-fluoro-N-[5-(4,4,5,5-tetramethyl-1,3,2-dioxaborolan-2-yl)pyrimidin-2-yl]benzenesulfonamide A mixture of N-(5-bromopyrimidin-2-yl)-5-chloro-2-fluorobenzenesulfonamide (700 mg, 1.53 mol, 1.00 equiv.), bis(pinacolato)diboron (900 mg, 3.54 mmol, 2.30 equiv.), potassium acetate (380 mg, 3.87 mmol, 2.50 equiv.) and [1,1'-bis(diphenylphosphino)ferrocene]dichloropalladium (112 mg, 0.150 mmol, 0.10 equiv.) in 1,4-dioxane (30 mL)

was stirred for 16 hours at 85° C. under $N_2$ and diluted with water (100 mL). The mixture was extracted with ethyl acetate (3×100 mL). The organic layer was dried over anhydrous sodium sulfate and filtered. The filtrate was concentrated under reduced pressure. The residue was purified by reverse phase column chromatography with the following condition: Column: Agela C18 Column, Mobile Phase A: Water, Mobile Phase B: ACN; Flow rate: 40 mL/min; Gradient: 0% B to 80% B in 7 min; Detector: 220 nm to afford desired product (140 mg, 18% yield) as a light yellow solid. LCMS (ESI, m/z): 332 [M+H−82]+

(iii) 5-chloro-2-fluoro-N-(5-(4-((1-isopropylpiperidin-4-yl)oxy)-3-methyl-1-(tetrahydro-2H-pyran-2-yl)-1H-pyrazolo[3,4-d]pyrimidin-6-yl)pyrimidin-2-yl)benzenesulfonamide A mixture of 5-chloro-2-fluoro-N-[5-(4,4,5,5-tetramethyl-1,3,2-dioxaborolan-2-yl)pyrimidin-2-yl]benzenesulfonamide (90.0 mg, 0.220 mmol, 1.20 equiv.), 4-[[6-chloro-3-methyl-1-(oxan-2-yl)pyrazolo[3,4-d]pyrimidin-4-yl]oxy]-1-isopropylpiperidine (prepared from 6-chloro-3-methyl-1H-pyrazolo 3,4-dipyrimidine analogously to the procedure described in example 1 (75.0 mg, 0.190 mmol, 1.00 equiv.), sodium bicarbonate (31 mg, 0.370 mmol, 2.00 equiv.) and [1,1'-bis(diphenylphosphino)ferrocene]dichloropalladium (16.00 mg, 0.022 mmol, 0.10 equiv.) in 1,4-dioxane (3.5 mL)/ethanol (1.5 mL)/water (2.0 mL) was stirred for 2 hours at 80° C. under $N_2$ and concentrated under reduced pressure. The residue was purified by reverse phase column chromatography with the following condition: Column: Agela C18 Column, 120 g, Mobile Phase A: Water (0.05% TFA), Mobile Phase B: ACN; Flow rate: 40 mL/min; Gradient: 30% B to 80% B in 7 min; Detector: 220 nm to afford desired product (30.0 mg, 25% yield) as a light yellow solid. LCMS (ESI, m/z): 645 [M+H]+.

(iv) 5-chloro-2-fluoro-N-(5-(4-((1-isopropylpiperidin-4-yl)oxy)-3-methyl-1H-pyrazolo[3,4-d]pyrimidin-6-yl)pyrimidin-2-yl)benzenesulfonamide To a solution of 5-chloro-2-fluoro-N-(5-[4-[(1-isopropylpiperidin-4-yl)methyl]-3-methyl-1-(oxan-2-yl)-2H,3H-pyrazolo[3,4-d]pyrimidin-6-yl]pyrimidin-2-yl)benzenesulfonamide (30.0 mg, 0.046 mmol, 1.00 equiv.) in methanol (2 mL) was added 4M HCl (gas) in 1,4-dioxane (0.2 mL) at 0° C. The resulting mixture was stirred for 3 hours at room temperature and concentrated under reduced pressure. The residue was purified by Prep-HPLC with the following conditions: Column: XSelect CSH Prep C18 OBD Column, 19×250 mm, 5 um; Mobile Phase A: Water (10 mmol/L $NH_4HCO_3$), Mobile Phase B: ACN; Flow rate: 25 mL/min; Gradient: 54% B to 74% B in 8 min; Detector: 254 nm to afford desired product (8.4 mg, 32% yield) as a white solid.

LCMS (ESI, m/z): 561 [M+H]+. $^1H$ NMR (300 MHZ, DMSO-$d_6$) δ 13.62 (brs, 1H), 9.36-9.10 (m, 2H), 7.99-7.82 (m, 1H), 7.82-7.79 (m, 1H), 7.50 (t, J=8.7 Hz, 1H), 5.91-5.71 (m, 1H), 3.57-3.06 (m, 9H), 2.58-2.50 (m, 1H), 2.31-1.82 (m, 3H), 1.30 (d, J=6.6 Hz, 6H).

Compound 13 5-chloro-2-fluoro-N-(4-(3-methyl-4-((pyridin-4-ylmethyl)amino)-1H-pyrazolo[3,4-d]pyrimidin-6-yl)phenyl)benzenesulfonamide

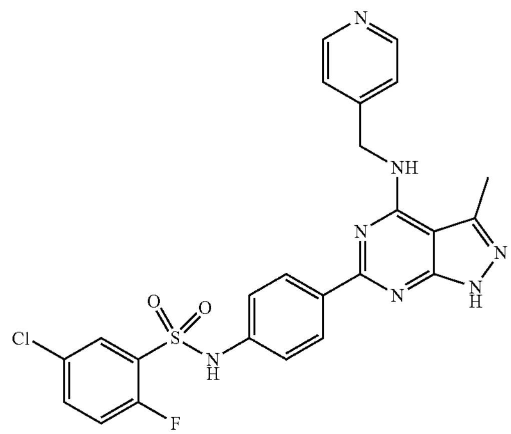 [SMILES: Cc1n[nH]c2nc(-c3ccc(NS(=O)(=O)c4cc(Cl)ccc4F)cc3)nc(NCc3ccncc3)c12]

(i) 6-chloro-3-methyl-1-(oxan-2-yl)-N-(pyridin-4-ylmethyl)pyrazolo[3,4-d]pyrimidin-4-amine A 20-mL vial was charged with 4,6-dichloro-3-methyl-1-(oxan-2-yl)pyrazolo[3,4-d]pyrimidine (150 mg, 0.522 mmol, 1.00 equiv.), dichloromethane (3 mL), 4-pyridinemethaneamine (62.1 mg, 0.575 mmol, 1.10 equiv.), trimethylamine (58.2 mg, 0.575 mmol, 1.10 equiv.). The resulting solution was stirred overnight at room temperature and quenched with water (10 mL). The mixture was extracted with dichloromethane (3×10 mL) and the organic layers were combined, washed with water (3×10 mL), dried over anhydrous sodium sulfate, filtered and concentrated under reduced pressure. The crude product was purified by reverse phase column chromatography with the following conditions: Column: Agela C18 Column, 120 g, Mobile Phase A: Water, Mobile Phase B: ACN; Flow rate: 40 mL/min; Gradient: 5% B to 95% B in 35 min; Detector: 220 nm to afford desired product (120 mg, 64% yield)) as an off-white solid. LCMS (ESI, m/z): 359 [M+H]+.

(ii) 5-chloro-2-fluoro-N-(4-(3-methyl-4-((pyridin-4-ylmethyl)amino)-1H-pyrazolo[3,4-d]pyrimidin-6-yl)phenyl)benzenesulfonamide The desired product (20.0 mg, 51% yield) was obtained as a beige solid following the general procedure described in example 1. LCMS (ESI, m/z): 524 [M+H]+. $^1H$ NMR (300 MHz, DMSO-$d_6$): δ 13.03 (s, 1H), 11.00 (s, 1H), 8.52-8.44 (m, 2H), 8.17-8.08 (m, 2H), 7.84 (dd, J=6.0, 2.7 Hz, 2H), 7.76 (ddd, J=8.8, 4.1, 2.7 Hz, 1H), 7.54-7.42 (m, 1H), 7.46-7.38 (m, 2H), 7.21-7.10 (m, 2H), 4.83 (d, J=5.7 Hz, 2H), 2.61 (s, 3H).

Compound 14 5-chloro-2-fluoro-N-((5-(4-((1-isopropylpiperidin-4-yl)oxy)-3-methyl-1H-pyrazolo[3,4-d]pyrimidin-6-yl)furan-2-yl)methyl)benzenesulfonamide-2,2,2-trifluoroacetaldehyde

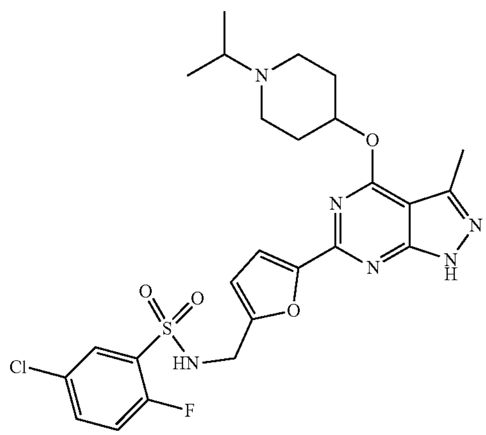 [SMILES: Cc1n[nH]c2nc(-c3ccc(CNS(=O)(=O)c4cc(Cl)ccc4F)o3)nc(OC3CCN(C(C)C)CC3)c12]

(i) 5-(4-((1-isopropylpiperidin-4-yl)oxy)-3-methyl-1-(tetrahydro-2H-pyran-2-yl)-1H-pyrazolo[3,4-d]pyrimidin-6-yl) furan-2-carbaldehyde A mixture of 4-[[6-chloro-3-methyl-1-(oxan-2-yl)pyrazolo[3,4-d]pyrimidin-4-yl]oxy]-1-isopropylpiperidine, (prepared from 6-chloro-3-methyl-1H-pyrazolo 3,4-dipyrimidine analogously to the procedure described in example 1) (500 mg, 1.27 mmol, 1.00 equiv.) and 5-formylfuran-2-ylboronic acid (300 mg, 2.14 mmol, 1.69 equiv.), [1,1'-bis(diphenylphosphino)ferrocene]dichloropalladium (103 mg, 0.140 mmol, 0.11 equiv.) and cesium carbonate (799 mg, 2.45 mmol, 1.93 equiv.) in 1,4-dioxane (12 mL) and water (2 mL) was stirred at 100° C. for 4 hours under $N_2$ and quenched with water (50 mL). The mixture was extracted with ethyl acetate (3×100 mL). The organic layer was dried over anhydrous sodium sulfate and filtered. The filtrate was concentrated under reduced pressure. The residue was purified by silica gel column chromatography, eluting with 0-100% ethyl acetate in petroleum ether to afford 5-(4-((1-isopropylpiperidin-4-yl)oxy)-3-methyl-1-(tetrahydro-2H-pyran-2-yl)-1H-pyrazolo[3,4-d]pyrimidin-6-yl)furan-2-carbaldehyde (450 mg, 78% yield) as a light brown solid. LCMS (ESI, m/z): 454[M+H]+.

(ii) (E)-5-(4-((1-isopropylpiperidin-4-yl)oxy)-3-methyl-1-(tetrahydro-2H-pyran-2-yl)-1H-pyrazolo[3,4-d]pyrimidin-6-yl)furan-2-carbaldehyde oxime A mixture of 5-[4-[(1-isopropylpiperidin-4-yl)oxy]-3-methyl-1-(oxan-2-yl)pyrazolo[3,4-d]pyrimidin-6-yl]furan-2-carbaldehyde (430 mg, 0.95 mmol, 1.00 equiv.), sodium acetate (172 mg, 2.10 mmol, 2.20 equiv.) and hydroxylamine hydrochloride (86.0 mg, 1.24 mmol, 1.30 equiv.) in ethanol (20 mL) was stirred for 1 h at 50° C. and concentrated under reduced pressure. The residue was diluted with water (50 mL). The mixture was extracted with ethyl acetate (3×100 mL). The organic layer was dried over anhydrous sodium sulfate and filtered. The filtrate was concentrated under reduced pressure to afford (E)-5-(4-((1-isopropylpiperidin-4-yl)oxy)-3-methyl-1-(tetrahydro-2H-pyran-2-yl)-1H-pyrazolo[3,4-d]pyrimidin-6-yl)furan-2-carbaldehyde oxime (350 mg, crude) as brown oil, which was used in the next step without any further purification. LCMS (ESI, m/z): 469 [M+H]+.

(iii) (5-(4-((1-isopropylpiperidin-4-yl)oxy)-3-methyl-1-(tetrahydro-2H-pyran-2-yl)-1H-pyrazolo[3,4-d]pyrimidin-6-yl)furan-2-yl)methanamine To a solution of (E)-N-[(5-[4-[(1-isopropylpiperidin-4-yl)oxy]-3-methyl-1-(oxan-2-yl)pyrazolo[3,4-d]pyrimidin-6-yl]furan-2-yl)methylidene]hydroxylamine (300 mg, 0.64 mmol, 1.00 equiv.) in acetic acid (10 mL) was added zinc powder (419 mg, 6.39 mmol, 10.0 equiv.). The resulting mixture was stirred for 2 h at 50° C. The solids were filtered off and the filter cake was washed with acetic acid (2×10 mL). The combined filtrate was concentrated under reduced pressure. The residue was purified by reverse phase column chromatography with the following condition: Column: Agela C18 Column, 120 g, Mobile Phase A: Water (0.05% TFA), Mobile Phase B: ACN; Flow rate: 40 mL/min; Gradient: 50% B to 80% B in 10 min; Detector: 254 nm to afford (5-(4-((1-isopropylpiperidin-4-yl)oxy)-3-methyl-1-(tetrahydro-2H-pyran-2-yl)-1H-pyrazolo[3,4-d]pyrimidin-6-yl)furan-2-yl)methanamine (50.0 mg, 17% yield) as a light brown solid. LCMS (ESI, m/z): 455 [M+H]+.

5-chloro-2-fluoro-N-((5-(4-((1-isopropylpiperidin-4-yl)oxy)-3-methyl-1-(tetrahydro-2H-pyran-2-yl)-1H-pyrazolo[3,4-d]pyrimidin-6-yl)furan-2-yl)methyl) benzenesulfonamide To a solution of 1-(5-[4-[(1-isopropylpiperidin-4-yl)oxy]-3-methyl-1-(oxan-2-yl)pyrazolo[3,4-d]pyrimidin-6-yl]furan-2-yl)methanamine (50.0 mg, 0.110 mmol, 1.00 equiv.) and trimethylamine (17.0 mg, 0.160 mmol, 1.50 equiv.) in dichloromethane (3 mL) was added 5-chloro-2-fluorobenzenesulfonyl chloride (27.0 mg, 0.110 mmol, 1.00 equiv.) at 0° C. under $N_2$. The resulting mixture was stirred for 3 hours at room temperature and quenched with water (20 mL). The mixture was extracted with dichloromethane (3×50 mL). The organic layer was dried over anhydrous sodium sulfate and filtered. The filtrate was concentrated under reduced pressure to afford 5-chloro-2-fluoro-N-((5-(4-((1-isopropylpiperidin-4-yl)oxy)-3-methyl-1-(tetrahydro-2H-pyran-2-yl)-1H-pyrazolo[3,4-d]pyrimidin-6-yl)furan-2-yl)methyl) benzenesulfonamide (15.0 mg, crude) as brown oil which was used in the next step without any further purification. LCMS (ESI, m/z): 647 [M+H]+.

(iv) 5-chloro-2-fluoro-N-((5-(4-((1-isopropylpiperidin-4-yl)oxy)-3-methyl-1H-pyrazolo[3,4-d]pyrimidin-6-yl)furan-2-yl)methyl)benzenesulfonamide-2,2,2-trifluoroacetaldehyde A mixture of 5-chloro-2-fluoro-N-((5-(4-((1-isopropylpiperidin-4-yl)oxy)-3-methyl-1-(tetrahydro-2H-pyran-2-yl)-1H-pyrazolo[3,4-d]pyrimidin-6-yl)furan-2-yl)methyl)benzenesulfonamide (15.0 mg, 0.023 mmol, 1.00 equiv.) in methanol (2 mL) was added 4M HCl (gas) in 1,4-dioxane (0.2 mL) at 0° C. The resulting mixture was stirred at room temperature for 3 hours and concentrated under reduced pressure. The residue was purified by Prep-HPLC with the following conditions: Column: XBridge Prep OBD C18 Column, 19×250 mm, 5 um; Mobile Phase A: Water (0.05% TFA), Mobile Phase B: ACN; Flow rate: 25 mL/min; Gradient: 23% B to 42% B in 7 min; Detector: 254 nm to afford 5-chloro-2-fluoro-N-((5-(4-((1-isopropylpiperidin-4-yl)oxy)-3-methyl-1H-pyrazolo[3,4-d]pyrimidin-6-yl)furan-2-yl)methyl)benzenesulfonamide-2,2,2-trifluoroacetaldehyde (6.5 mg, 42% yield) as a white solid. LCMS (ESI, m/z): 563 [M+H—CF3COOH]+. $^1$H NMR (400 MHz, DMSO-$d_6$) δ13.48 (brs, 1H), 8.86-8.83 (m, 1H), 7.60-7.53 (m, 2H), 7.33-6.99 (m, 3H), 6.41 (d, J=3.9 Hz, 1H), 5.74-5.51 (m, 1H), 4.30 (d, J=5.2 Hz, 2H), 3.58-3.20 (m, 7H), 2.70-2.58 (m, 2H), 2.31-1.96 (m, 3H), 1.40-1.20 (m, 6H).

Compound 15 N-[4-(4-[[2-(dimethylamino)ethyl]amino]-3-methyl-1H-pyrazolo[3,4-d]pyrimidin-6-yl)phenyl]-3-fluoropyridine-4-sulfonamide

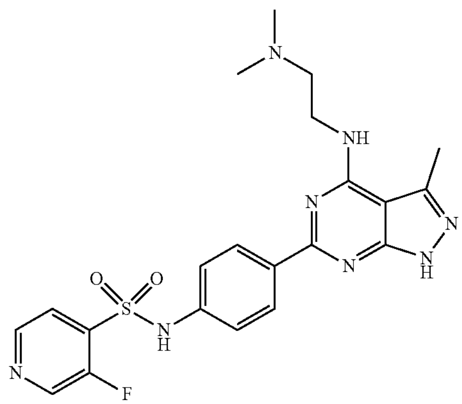 [SMILES: Cc1n[nH]c2nc(-c3ccc(NS(=O)(=O)c4ccncc4F)cc3)nc(NCCN(C)C)c12]

(i) 4-(benzylsulfanyl)-3-fluoropyridine

Into a 4-chloro-3-fluoropyridine (2.00 g, 15.2 mmol, 1.00 equiv.) solution of acetonitrile (7.5 mL) were added potassium carbonate (4.20 g, 30.4 mmol, 2.00 equiv.), then, added benzyl mercaptan (1.89 g, 0.0150 mmol, 1.00 equiv.) solution of acetonitrile (15 mL) at 0° C. Then finally the mixture was stirred at room temperature, concentrated under reduced pressure. The reaction was quenched with water at room temperature. The resulting mixture was extracted with dichloromethane (2×50 mL). The combined organic layers were washed with brine (3×50 mL), dried over anhydrous sodium sulfate. After filtration, the filtrate was concentrated under reduced pressure. T The residue was purified by silica gel column chromatography, eluted with ethyl acetate/hexane (1/3) to afford desired product 4-(benzylsulfanyl)-3-fluoropyridine (2.5 g, 72% yield) as a Brown yellow oil. LCMS (ESI, m/z): 220 [M+H]+.

(ii) 3-fluoropyridine-4-sulfonyl chloride

To a stirred solution of hydrochloric acid (12 mL) in dichloromethane (8 mL) was added NaClO (10 mL), 4-(benzylsulfanyl)-3-fluoropyridine (800 mg, 3.65 mmol, 1.00 equiv.) at −5° C. under air atmosphere. The resulting mixture was stirred for 1 h at −5° C. under air atmosphere. The reaction was added with dichloromethane at room temperature. The combined organic layers were washed with brine (3×30 mL), dried over anhydrous sodium sulfate. After filtration, the filtrate was concentrated under reduced pressure. The crude product 3-fluoropyridine-4-sulfonyl chloride was used in the next step directly without further purification. LCMS (ESI, m/z): 196 $[M+H]^+$.

(iii) 4,6-dichloro-3-methyl-1-(oxan-2-yl)pyrazolo[3,4-d]pyrimidine

A 50-mL 3-necked round-bottom flask was charged with 4,6-dichloro-3-methyl-1H-pyrazolo[3,4-d]pyrimidine (750 mg, 3.69 mmol, 1.00 equiv.), tetrahydrofuran (20 mL), dihydropyran (2.25 mL, 26.7 mmol, 7.10 equiv.), pyridinium p-toluenesulfonate (50.0 mg, 0.199 mmol, 0.05 equiv.) under $N_2$. The resulting solution was stirred for 3 h at 60° C. and concentrated under reduced pressure. The mixture was diluted with dichloromethane (30 mL), washed with saturated sodium bicarbonate (3×20 mL) dried over anhydrous sodium sulfate, filtered and concentrated under reduced pressure. The residue was purified by silica gel column chromatography, eluted with ethyl acetate/hexane (3/7) to afford desired product 4,6-dichloro-3-methyl-1-(oxan-2-yl)pyrazolo[3,4-d]pyrimidine (750 mg, 71% yield) as an off-white solid. LCMS (ESI, m/z): 287 [M+H]+.

(iv) 6-chloro-N-[2-(dimethylamino)ethyl]-3-methyl-1-(oxan-2-yl)pyrazolo[3,4-d]pyrimidin-4-amine A 8-mL vial was charged with 4,6-dichloro-3-methyl-1-(oxan-2-yl)-2H,3H-pyrazolo[3,4-d]pyrimidine (74.3 mg, 0.259 mmol, 1.00 equiv.), (2-aminoethyl)dimethylamine (22.8 mg, 0.259 mmol, 1.00 equiv.), dichloromethane (3.0 mL) and triethylamine (57.7 mg, 0.571 mmol, 2.20 equiv.). The resulting solution was stirred overnight at room temperature and concentrated under reduced pressure. The residue was purified by silica gel column chromatography, eluted with dichloromethane/methanol (95/5) to afford desired product 6-chloro-N-[2-(dimethylamino)ethyl]-3-methyl-1-(oxan-2-yl)pyrazolo[3,4-d]pyrimidin-4-amine (55.0 mg, 62% yield) as a colorless solid. LCMS (ESI, m/z): 339 [M+H]+.

(v) 6-(4-aminophenyl)-N-[2-(dimethylamino)ethyl]-3-methyl-1-(oxan-2-yl)pyrazolo[3,4-d]pyrimidin-4-amine To a stirred solution of 6-chloro-N-[2-(dimethylamino)ethyl]-3-methyl-1-(oxan-2-yl)pyrazolo[3,4-d]pyrimidin-4-amine (100 mg, 0.295 mmol, 1.00 equiv.) and 4-(4,4,5,5-tetramethyl-1,3,2-dioxaborolan-2-yl)aniline (77.6 mg, 0.354 mmol, 1.20 equiv.) in dioxane (2 mL) was added [1,1'-bis(diphenylphosphino)ferrocene]dichloropalladium (32.4 mg, 0.0440 mmol, 0.150 equiv.), cesium carbonate (192 mg, 0.590 mmol, 2.00 equiv.), water (0.3 mL) portions at room temperature under $N_2$ atmosphere. The resulting mixture was stirred for 3 h at 100° C. under $N_2$ atmosphere. The resulting mixture was concentrated under reduced pressure. The residue was purified by reverse flash chromatography with the following conditions: Column, Column: Agela C18 Column, 120 g, Mobile Phase A: Water (0.05% trifluoro acetic acid), Mobile Phase B: acetonitrile; Flow rate: 40 mL/min; Gradient: 0% B to 55% B in 45 min; Detector: 220 nm to afford 6-(4-aminophenyl)-N-[2-(dimethylamino) ethyl]-3-methyl-1-(oxan-2-yl)pyrazolo[3,4-d]pyrimidin-4-amine (89 mg, 76% yield) as a Brown yellow solid. LCMS (ESI, m/z): 396 [M+H]+.

(vi) N-[4-(4-[[2-(dimethylamino)ethyl]amino]-3-methyl-1-(oxan-2-yl)pyrazolo[3,4-d]pyrimidin-6-yl) phenyl]-3-fluoropyridine-4-sulfonamide To a stirred solution of 6-(4-aminophenyl)-N-[2-(dimethylamino)ethyl]-3-methyl-1-(oxan-2-yl) pyrazolo[3,4-d]pyrimidin-4-amine (50.0 mg, 0.126 mmol, 1.00 equiv.) and 3-fluoropyridine-4-sulfonyl chloride (123 mg, 0.632 mmol, 5.00 equiv.) in dichloromethane (8 mL) was added pyridine (50.0 mg, 0.632 mmol, 5.00 equiv.) at room temperature under air atmosphere. The resulting mixture was stirred for overnight at room temperature under air atmosphere. The reaction was quenched with Water (30 mL) at room temperature. The resulting mixture was extracted with dichloromethane (3×20 mL). The combined organic layers were washed with brine (3×30 mL), dried over anhydrous sodium sulfate. After filtration, the filtrate was concentrated under reduced pressure. The residue was purified by reverse flash chromatography with the following conditions: Column, Column: Agela C18 Column, 120 g, Mobile Phase A: Water (0.05% trifluoroacetic acid), Mobile Phase B: acetonitrile; Flow rate: 40 mL/min; Gradient: 0% B to 55% B in 45 min; Detector: 220 nm to afford N-[4-(4-[[2-(dimethylamino) ethyl]amino]-3-methyl-1-(oxan-2-yl) pyrazolo[3,4-d]pyrimidin-6-yl)phenyl]-3-fluoropyridine-4-sulfonamide (60.0 mg, 42% yield) as a brown yellow solid. LCMS (ESI, m/z): 555 [M+H]+.

(vii) N-[4-(4-[[2-(dimethylamino)ethyl]amino]-3-methyl-1H-pyrazolo[3,4-d]pyrimidin-6-yl)phenyl]-3-fluoropyridine-4-sulfonamide To a stirred solution of N-[4-(4-[[2-(dimethylamino) ethyl]amino]-3-methyl-1-(oxan-2-yl) pyrazolo[3,4-d]pyrimidin-6-yl)phenyl]-3-fluoropyridine-4-sulfonamide (35.0 mg, 0.0630 mmol, 1.00 equiv.) in isopropanol (1 mL) was added trifluoroacetic acid (1 mL) at room temperature under air atmosphere. The resulting mixture was stirred for 3 h at room temperature under air atmosphere. The resulting mixture was concentrated under reduced pressure. The residue was purified by reverse flash chromatography with the following conditions: Column: YMC-Actus Triart C18 30*250.5 um; Mobile Phase A: Water (10 mmol/L $NH_4HCO_3$+0.1% $NH_3 \cdot H_2O$), Mobile Phase B: ACN; Flow rate: 60 mL/min; Gradient: 7% B to 32% B in 7 min; 254 nm; Rt: 6.47 min; detector, UV 254 nm. This resulted in N-[4-(4-[[2-(dimethylamino)ethyl]amino]-3-methyl-1H-pyrazolo[3,4-d]pyrimidin-6-yl)phenyl]-3-fluoropyridine-4-sulfonamide (5.9 mg, 19% yield) as an off-white solid. LCMS (ESI, m/z): 471 [M+H]+. $^1$H NMR (400 MHZ, DMSO-$d_6$): δ 12.90 (s, 1H), 10.51 (s, 1H), 8.69 (s, 1H), 8.54 (d, J=8.0 Hz, 1H), 8.16-8.14 (m, 2H), 7.75 (t, J=8.0 Hz, 1H), 7.06-6.98 (m, 3H), 3.80-3.75 (m, 2H), 2.89-2.83 (m, 2H), 2.52 (s, 3H), 2.44 (s, 6H).

Compound 16 6-amino-N-[4-(4-[[2-(dimethylamino)ethyl]amino]-3-methyl-1H-pyrazolo[3,4-d]pyrimidin-6-yl)phenyl]pyridine-3-sulfonamide

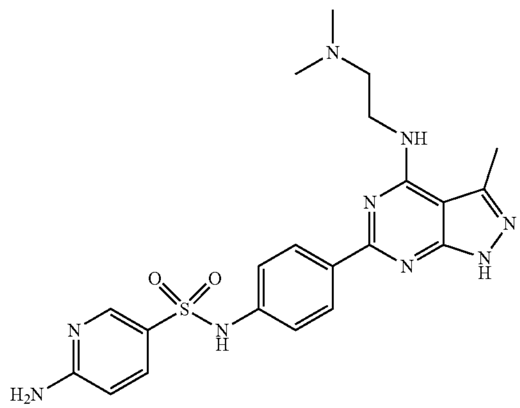 [SMILES: Cc1n[nH]c2nc(-c3ccc(NS(=O)(=O)c4ccc(N)nc4)cc3)nc(NCCN(C)C)c12]

(i) 6-chloro-N-[4-(4,4,5,5-tetramethyl-1,3,2-dioxaborolan-2-yl)phenyl]pyridine-3-sulfonamide To a stirred solution of 6-chloropyridine-3-sulfonyl chloride (200 mg, 0.943 mmol, 1.00 equiv.) and 4-(4,4,5,5-tetramethyl-1,3,2-dioxaborolan-2-yl)aniline (206 mg, 0.943 mmol, 1.00 equiv.) in dichloromethane (10 mL) was added Pyridine (85.8 mg, 1.085 mmol, 1.15 equiv.) dropwise at 0° C. under air atmosphere. The resulting mixture was stirred for overnight at room temperature under air atmosphere. The reaction was quenched with Water at room temperature. The resulting mixture was extracted with dichloromethane (3×20 mL). The combined organic layers were washed with brine (3×30 mL), dried over anhydrous sodium sulfate. After filtration, the filtrate was concentrated under reduced pressure. The residue was purified by silica gel column chromatography, eluted with ethyl acetate/hexane (1/1) to afford desired product 6-chloro-N-[4-(4,4,5,5-tetramethyl-1,3,2-dioxaborolan-2-yl)phenyl]pyridine-3-sulfonamide (270 mg, 72% yield) as a yellow solid. LCMS (ESI, m/z): 361 $[M+H]^+$.

(ii) 6-[[(4-methoxyphenyl)methyl]amino]-N-[4-(4,4,5,5-tetramethyl-1,3,2-dioxaborolan-2-yl)phenyl] pyridine-3-sulfonamide To a stirred solution of 6-chloro-N-[4-(4,4,5,5-tetramethyl-1,3,2-dioxaborolan-2-ylphenyl]pyridine-3-sulfonamide (100 mg, 0.253 mmol, 1.00 equiv.) in 1-methyl-2-pyrrolidinone (7.5 mL) was added benzenemethanamine, 4-methoxy-(52.1 mg, 0.380 mmol, 1.50 equiv.) dropwise at room temperature under air atmosphere. The resulting mixture was stirred for overnight at 60° C. under air atmosphere. The reaction was quenched with Water at room temperature. The resulting mixture was extracted with ethyl acetate (3×20 mL). The combined organic layers were washed with brine (3×20 mL), dried over anhydrous sodium sulfate. After filtration, the filtrate was concentrated under reduced pressure. The residue was purified by silica gel column chromatography, eluted with ethyl acetate/hexane (1/1) to afford desired product This resulted in 6-[[(4-methoxyphenyl) methyl]amino]-N-[4-(4,4,5,5-tetramethyl-1,3,2-dioxaborolan-2-yl)phenyl]pyridine-3-sulfonamide (90.0 mg, 71% yield) as a Brown yellow solid. LCMS (ESI, m/z): 496 $[M+H]^+$.

(iii) 4,6-dichloro-3-methyl-1-(oxan-2-yl)pyrazolo[3,4-d]pyrimidine

A 50-mL 3-necked round-bottom flask was charged with 4,6-dichloro-3-methyl-1H-pyrazolo[3,4-d]pyrimidine (750 mg, 3.69 mmol, 1.00 equiv.), tetrahydrofuran (20 mL), dihydropyran (2.25 mL, 26.7 mmol, 7.10 equiv.), pyridinium p-toluenesulfonate (50.0 mg, 0.199 mmol, 0.05 equiv.) under $N_2$. The resulting solution was stirred for 3 h at 60° C. and concentrated under reduced pressure. The mixture was diluted with dichloromethane (30 mL), washed with saturated sodium bicarbonate (3×20 mL) dried over anhydrous sodium sulfate, filtered and concentrated under reduced pressure. The residue was purified by silica gel column chromatography, eluted with ethyl acetate/hexane (3/7) to afford desired product 4,6-dichloro-3-methyl-1-(oxan-2-yl)pyrazolo[3,4-d]pyrimidine (750 mg, 71% yield) as an off-white solid. LCMS (ESI, m/z): 287 $[M+H]^+$.

(iv) 6-chloro-N-[2-(dimethylamino)ethyl]-3-methyl-1-(oxan-2-yl)pyrazolo[3,4-d]pyrimidin-4-amine A 8-mL vial was charged with 4,6-dichloro-3-methyl-1-(oxan-2-yl)-2H,3H-pyrazolo[3,4-d]pyrimidine (74.3 mg, 0.259 mmol, 1.00 equiv.), (2-aminoethyl)dimethylamine (22.8 mg, 0.259 mmol, 1.00 equiv.), dichloromethane (3.0 mL) and triethylamine (57.7 mg, 0.571 mmol, 2.20 equiv.). The resulting solution was stirred overnight at room temperature and concentrated under reduced pressure. The residue was purified by silica gel column chromatography, eluted with dichloromethane/methanol (95/5) to afford desired product 6-chloro-N-[2-(dimethylamino)ethyl]-3-methyl-1-(oxan-2-yl)pyrazolo[3,4-d]pyrimidin-4-amine (55.0 mg, 62% yield) as a colorless solid. LCMS (ESI, m/z): 339 $[M+H]^+$.

(v) N-[4-(4-[[2-(dimethylamino)ethyl]amino]-3-methyl-1-(oxan-2-yl)pyrazolo[3,4-d]pyrimidin-6-yl)phenyl]-6-[[(4-methoxyphenyl)methyl]amino]pyridine-3-sulfonamide To a stirred solution of 6-[[(4-methoxyphenyl)methyl]amino]-N-[4-(4,4,5,5-tetramethyl-1,3,2-dioxaborolan-2-yl)phenyl]pyridine-3-sulfonamide (90.0 mg, 0.182 mmol, 1.00 equiv.) and 6-chloro-N-[2-(dimethylamino)ethyl]-3-methyl-1-(oxan-2-yl)pyrazolo[3,4-d]pyrimidin-4-amine (61.5 mg, 0.182 mmol, 1.00 equiv.) in dioxane (2 mL) was added [1,1'-bis(diphenylphosphino)ferrocene] dichloropalladium (19.9 mg, 0.0270 mmol, 0.150 equiv.), cesium carbonate (118 mg, 0.363 mmol, 2.00 equiv.), water (0.3 mL) at room temperature under $N_2$ atmosphere. The resulting mixture was stirred for 3 h at 100° C. under $N_2$ atmosphere. The crude product was purified by reverse phase column chromatography with the following conditions: Column, Column: Agela C18 Column, 120 g, Mobile Phase A: Water (0.05% trifluoroacetic acid), Mobile Phase B: acetonitrile; Flow rate: 40 mL/min; Gradient: 0% B to 55% B in 45 min; Detector: 220 nm to afford N-[4-(4-[[2-(dimethylamino)ethyl]amino]-3-methyl-1-(oxan-2-yl)pyrazolo[3,4-d]pyrimidin-6-yl)phenyl]-6-[[(4-methoxyphenyl)methyl]amino]pyridine-3-sulfonamide (62.0 mg, 50% yield) as a Brown yellow solid. LCMS (ESI, m/z): 672 $[M+H]^+$.

(vi) 6-amino-N-[4-(4-[[2-(dimethylamino)ethyl]amino]-3-methyl-1H-pyrazolo[3,4-d]pyrimidin-6-yl)phenyl]pyridine-3-sulfonamide To a stirred solution of N-[4-(4-[[2-(dimethylamino)ethyl]amino]-3-methyl-1-(oxan-2-yl)pyrazolo[3,4-d]pyrimidin-6-yl)phenyl]-6-[[(4-methoxyphenyl)methyl]amino]pyridine-3-sulfonamide (30.0 mg, 0.0450 mmol, 1.00 equiv.) was added trifluoroacetic acid (2 mL) at 0° C. under air atmosphere. The resulting mixture was stirred for overnight at 25° C. under air atmosphere. The resulting mixture was concentrated under reduced pressure. The residue was purified by reverse flash chromatography with the following conditions: Column: XSelect CSH Prep C18 OBD Column, 5 um, 19*150 mm; Mobile Phase A: Water (10 mmol/L $NH_4HCO3$+0.1% $NH_3 \cdot H_2O$), Mobile Phase B: ACN; Flow rate: 25 mL/min; Gradient: 10 B to 30 B in 7 min; 220 nm; RT1:5.93; RT2; Injection Volum: ml; Number Of Runs; detector, UV 254 nm to afford 6-amino-N-[4-(4-[[2-(dimethylamino)ethyl]amino]-3-methyl-1H-pyrazolo[3,4-d]pyrimidin-6-yl)phenyl]pyridine-3-sulfonamide (1.9 mg, 9% yield) as an off-white solid. LCMS (ESI, m/z): 468 $[M+H]^+$. $^1H$ NMR (400 MHZ, DMSO-$d_6$): δ 12.93 (s, 1H), 11.03 (s, 1H), 8.26-8.22 (m, 2H), 7.63-7.60 (m, 1H), 7.18-7.15 (m, 2H), 7.01-6.98 (m, 1H), 6.87 (s, 3H), 6.43-6.40 (m, 1H), 3.70-3.68 (m, 2H), 2.50-2.48 (m, 2H), 2.47 (s, 3H), 2.25 (s, 6H).

Compound 17 5-chloro-2-fluoro-N-(4-[4-[(1-isopropylazetidin-3-yl)oxy]-3-methyl-1H-pyrazolo[3,4-d]pyrimidin-6-yl]phenyl)benzenesulfonamide

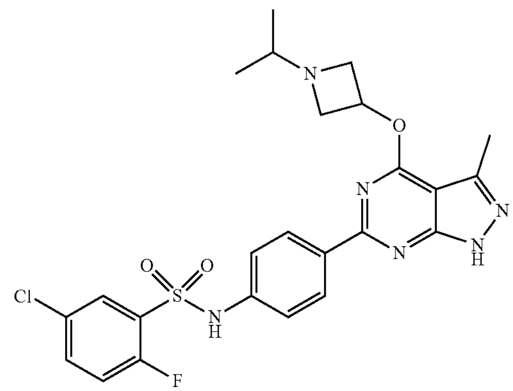 [SMILES: Cc1n[nH]c2nc(-c3ccc(NS(=O)(=O)c4cc(Cl)ccc4F)cc3)nc(OC3CN(C(C)C)C3)c12]

This compound was prepared according to the procedure described in example 1. The desired product as an off-white solid (35.0 mg, 50%). LCMS (ESI, m/z): 531 $[M+H]^+$. $^1H$ NMR (300 MHZ, DMSO-$d_6$) δ 13.45 (s, 1H), 8.24-8.21 (d, J=9.0 Hz 2H), 7.84-7.81 (m, 1H), 7.74-7.69 (m, 1H), 7.48-7.42 (t, J=9.0 Hz, 1H), 5.46-5.38 (m, 1H), 3.96-3.91 (t, J=9.0 Hz, 1H), 3.37-3.32 (m, 3H), 2.49 (s, 3H), 0.99-0.97 (d, J=6.0 Hz 6H).

Compound 18 N-[2-([6-[4-(5-chloro-2-fluorobenzenesulfonamide)phenyl]-3-methyl-1H-pyrazolo[3,4-d]pyrimidin-4-yl]amino)ethyl]-N-methylformamide

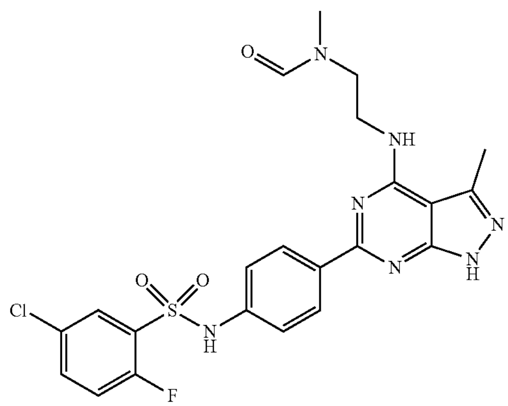 [SMILES: Cc1n[nH]c2nc(-c3ccc(NS(=O)(=O)c4cc(Cl)ccc4F)cc3)nc(NCCN(C)C=O)c12]

(i) tert-butyl N-(2-[[6-chloro-3-methyl-1-(oxan-2-yl)pyrazolo[3,4-d]pyrimidin-4-yl]amino]ethyl)-N-methylcarbamate To a stirred solution of 4,6-dichloro-3-methyl-1-(oxan-2-yl)pyrazolo[3,4-d]pyrimidine (100 mg, 0.348 mmol, 1.00 equiv.) and tert-butyl N-(2-aminoethyl)-N-methylcarbamate (91.0 mg, 0.522 mmol, 1.50 equiv.) in dichloromethane (4 mL), trimethylamine (70.9 mg, 0.697 mmol, 2.00 equiv.) was added dropwise at room temperature under $N_2$ atmosphere. The resulting mixture was stirred for overnight at room temperature under air atmosphere. The resulting solution was diluted with 20 mL of dichloromethane. The resulting mixture was washed with 2×10 ml of water. The resulting mixture was concentrated under vacuum. This resulted in 130 mg (83%) of tert-butyl N-(2-[[6-chloro-3-methyl-1-(oxan-2-yl)pyrazolo[3,4-d]pyrimidin-4-yl]amino]ethyl)-N-methylcarbamate as a light yellow solid. LCMS29 (ESI, m/z): 425 [M+H]+.

(ii) tert-butyl N-[2-([6-[4-(5-chloro-2-fluorobenzenesulfonamido)phenyl]-3-methyl-1-(oxan-2-yl)pyrazolo[3,4-d]pyrimidin-4-yl]amino)ethyl]-N-methylcarbamate To a stirred solution of 5-chloro-2-fluoro-N-[4-(4,4,5,5-tetramethyl-1,3,2-dioxaborolan-2-yl)phenyl]benzenesulfonamide (151 mg, 0.367 mmol, 1.20 equiv.) and tert-butyl N-(2-[[6-chloro-3-methyl-1-(oxan-2-yl)pyrazolo[3,4-d]pyrimidin-4-yl]amino]ethyl)-N-methylcarbamate (130 mg, 0.306 mmol, 1.00 equiv.) in dioxane (2 mL) was added cesium carbonate (199 mg, 0.612 mmol, 2.00 equiv.), and water (0.30 mL) then added [1,1'-bis(diphenylphosphino)ferrocene]dichloropalladium(II) (38.5 mg, 0.0470 mmol, 0.180 equiv.) at room temperature under $N_2$ atmosphere. The resulting mixture was stirred for 3 h at 100° C. under $N_2$ atmosphere. The reaction mixture was cooled. The solids were filtered out. The crude product was purified by Flash-Prep-HPLC with the following conditions (IntelFlash-1): Column, C18 silica gel; mobile phase, ACN/water=5/95 increasing to ACN/water=56/44 within 30; Detector, 220 nm. This resulted in 140 mg (64%) of tert-butyl N-[2-([6-[4-(5-chloro-2-fluorobenzenesulfonamido)phenyl]-3-methyl-1-(oxan-2-yl)pyrazolo[3,4-d]pyrimidin-4-yl]amino)ethyl]-N-methylcarbamate as a light brown solid. LCMS (ESI, m/z): 674 $[M+H]^+$.

(iii) 5-chloro-2-fluoro-N-(4-(3-methyl-4-((2-(methylamino)ethyl)amino)-1H-pyrazolo[3,4-d]pyrimidin-6-yl)phenyl)benzenesulfonamide To a stirred solution of tert-butyl N-[2-([6-[4-(5-chloro-2-fluorobenzenesulfonamido)phenyl]-3-methyl-1-(oxan-2-yl)pyrazolo[3,4-d]pyrimidin-4-yl]amino)ethyl]-N-methylcarbamate (140 mg) in dichloromethane (2 mL) was added trifluoroacetic acid (1 mL) at room temperature under $N_2$ atmosphere. The resulting mixture was stirred for 3 h at room temperature under air atmosphere. The resulting mixture was concentrated under reduced pressure. The residue 70.0 mg 5-chloro-2-fluoro-N-(4-(3-methyl-4-((2-(methylamino)ethyl)amino)-1H-pyrazolo[3,4-d]pyrimidin-6-yl)phenyl)benzenesulfonamide was used directly. LCMS (ESI, m/z): 490 $[M+H]^+$.

(iv) N-[2-([6-[4-(5-chloro-2-fluorobenzenesulfonamido)phenyl]-3-methyl-1H-pyrazolo[3,4-d]pyrimidin-4-yl]amino)ethyl]-N-methylformamide To a stirred solution of 5-chloro-2-fluoro-N-[4-(3-methyl-4-[[2-(methylamino)ethyl]amino]-1H-pyrazolo[3,4-d]pyrimidin-6-yl)phenyl]benzene sulfonamide (70.00 mg, 0.163 mmol, 1.00 equiv.) in NMP (2 mL) was added 1,1,3-trioxo-1lambda6,2-benzothiazole-2-carbaldehyde (34.5 mg, 0.163 mmol, 1.00 equiv.) at room temperature under air atmosphere. The resulting mixture was stirred for 1 h at room temperature under $N_2$ atmosphere. The resulting mixture was concentrated under reduced pressure. The crude product was purified by Prep-HPLC with the following conditions: Column: XBridge Prep C18 OBD Column, 19*150 mm 5 um; Mobile Phase A: Water (10 MMOL/L $NH_4HCO3$+0.1% $NH_3 \cdot H_2O$), Mobile Phase B: ACN; Flow rate: 25 mL/min; Gradient: 18 B to 38 B in 7 min; Director: 220 nm. This resulted in 23.2 mg (29%) of N-[2-([6-[4-(5-chloro-2-fluorobenzenesulfonamido)phenyl]-3-methyl-1H-pyrazolo[3,4-d]pyrimidin-4-yl]amino)ethyl]-N-methylformamide as a solid. LCMS (ESI, m/z): 518 $[M+H]^+$. $^1$H NMR (400 MHz, DMSO-$d_6$) δ 12.99 (s, 1H), 11.02 (s, 1H), 11.13 (s, 1H), 8.32-8.25 (m, 2H), 8.01-7.84 (m, 3H), 7.77-7.76 (m, 1H), 7.52-7.48 (m, 2H), 7.32-7.20 (s, 1H), 3.79-3.73 (m, 2H), 3.57-3.53 (m, 2H), 2.98-2.80 (m, 3H), 2.67 (s, 3H).

Compound 19 N-(4-(4-(2-(dimethylamino)ethylamino)-3-methyl-1H-pyrazolo[3,4-d]pyrimidin-6-yl)phenyl)-4-methoxypyridine-3-sulfonamide

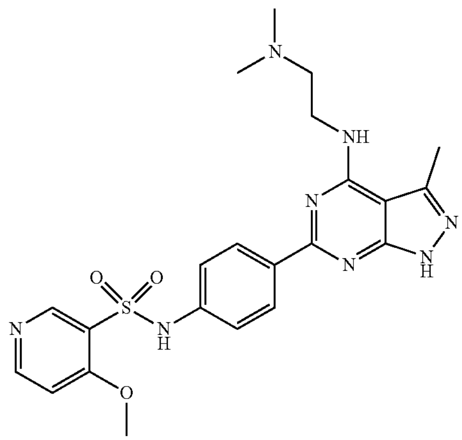 [SMILES: COc1ccncc1S(=O)(=O)Nc1ccc(-c2nc(NCCN(C)C)c3c(C)n[nH]c3n2)cc1]

(i) 4-chloro-N-(4-(4,4,5,5-tetramethyl-1,3,2-dioxaborolan-2-yl)phenyl)pyridine-3-sulfonamide Into a 50-mL round-bottom flask, was placed 4-chloropyridine-3-sulfonyl chloride (900.00 mg, 4.244 mmol, 1.00 equiv.), 4-(4,4,5,5-tetramethyl-1,3,2-dioxaborolan-2-yl)aniline (929.92 mg, 4.244 mmol, 1.00 equiv.), DCM (15.00 mL), pyridine (671.48 mg, 8.488 mmol, 2.00 equiv.). The resulting solution was stirred for overnight at room temperature. The resulting solution was diluted with 50 mL of DCM. The resulting mixture was washed with 2×30 ml of brine and 1×30 ml of water. The mixture was dried over anhydrous sodium sulfate and concentrated. The residue was applied onto a silica gel column with ethyl acetate/petroleum ether (0:100 to 20:80). The collected fractions were combined and concentrated. This resulted in 700 mg (37.61%) of 4-chloro-N-[4-(4,4,5,5-tetramethyl-1,3,2-dioxaborolan-2-yl)phenyl]pyridine-3-sulfonamide as a off-white solid. LCMS (ESI, m/z): 395 $[M+H]^+$.

(ii) 4-(4-methoxypyridine-3-sulfonamido)phenylboronic acid

Into a 25-mL round-bottom flask, was placed 4-chloro-N-[4-(4,4,5,5-tetramethyl-1,3,2-dioxaborolan-2-yl)phenyl]pyridine-3-sulfonamide (650.00 mg, 1.647 mmol, 1.00 equiv.), MeOH (3.00 mL, 0.094 mmol, 0.06 equiv.), CH3ONa (1.00 mL). The resulting solution was stirred for overnight at 70° C. in an oil bath. The resulting mixture was concentrated. The resulting solution was diluted with 10 mL of $H_2O$. The resulting mixture was washed with 2×10 ml of DCM. The pH value of the solution was adjusted to 2-3 with HCl (2 mol/L). The resulting mixture was washed with 2×10 mL of EA. The water layer was concentrated. This resulted in 350 mg (crude) of 4-(4-methoxypyridine-3-sulfonamido)phenylboronic acid as light yellow oil. LCMS (ESI, m/z): 309 [M+H]+.

(iii) N-(4-(4-(2-(dimethylamino)ethylamino)-3-methyl-1-(tetrahydro-2H-pyran-2-yl)-1H-pyrazolo[3,4-d]pyrimidin-6-yl)phenyl)-4-methoxypyridine-3-sulfonamide Into a 50-mL 3-necked round-bottom flask purged and maintained with an inert atmosphere of $N_2$, was placed 4-(4-methoxypyridine-3-sulfonamido)phenylboronic acid (NaN mg, 0.649 mmol, 2.75 equiv., 60%), 6-chloro-N-[2-(dimethylamino)ethyl]-3-methyl-1-(oxan-2-yl)pyrazolo[3,4-d]pyrimidin-4-amine (80.00 mg, 0.236 mmol, 1.00 equiv.), dioxane (4.00 mL), $Cs_2CO_3$ (230.78 mg, 0.708 mmol, 3.00 equiv.), water (1.00 mL), $Pd(dppf)Cl_2$ (17.28 mg, 0.024 mmol, 0.10 equiv.). The resulting solution was stirred for 40 hours at 100° C. in an oil bath. The reaction mixture was cooled with a water bath. The resulting solution and E08786-007 were diluted with 20 ml of water. The resulting mixture was washed with 2×20 ml of DCM. The resulting mixture was concentrated. The residue was applied onto a C18 gel with $H_2O$ (0.5% NH4HCO3)/ACN (90:10 to 10:90) in 45 minutes. The collected fractions were combined and concentrated. This resulted in 50 mg (33.63%) of N-[4-(4-[[2-(dimethylamino)ethyl]amino]-3-methyl-1-(oxan-2-yl)pyrazolo[3,4-d]pyrimidin-6-yl)phenyl]-4-methoxypyridine-3-sulfonamide as light yellow oil. LCMS (ESI, m/z): 567 $[M+H]^+$ (iv) N-(4-(4-(2-(dimethylamino)ethylamino)-3-methyl-1H-pyrazolo[3,4-d]pyrimidin-6-yl)phenyl)-4-methoxypyridine-3-sulfonamide Into a 50-mL round-bottom flask, was placed N-[4-(4-[[2-(dimethylamino)ethyl]amino]-3-methyl-1-(oxan-2-yl)pyrazolo[3,4-d]pyrimidin-6-yl)phenyl]-4-methoxypyridine-3-sulfonamide (50.00 mg, 0.088 mmol, 1.00 equiv.), IPA (5.00 mL), HCl (gas) in 1,4-dioxane (5.00 mL, 0.073 mmol, 0.83 equiv.). The resulting solution was stirred for 3 hours at room temperature. The resulting mixture was concentrated. The crude product was purified by prep HPLC. Column: Xselect CSH OBD Column 30*150 mm*5 um, Mobile Phase A: Water (10 MMOL/L $NH_4HCO_3$+0.1% $NH_3 \cdot H_2O$), Mobile Phase B: ACN; flow rate: 60 ml/min; Gradient: 13% B to 38% B in 7 min; 254/220 nm; Rt: 5.13 min (detected by lcms and collected). The combined fractions were lyophilized to afford the desired product 14.1 mg as a white solid. LCMS (ESI, m/z): 483 $[M+H]^+$. $^1$H NMR (400 MHZ, DMSO-$d_6$) δ 8.81 (s, 1H), 8.55 (d, J=6.0 Hz, 1H), 8.27-8.30 (m, 2H), 7.21-7.24 (m, 3H), 4.63 (s, 1H), 4.06 (s, 3H), 3.88 (t, J=6.7 Hz, 2H), 2.75 (t, J=6.7 Hz, 2H), 2.62 (s, 3H), 2.40 (s, 7H).

Compound 20 N-[4-[4-([2-[(2-hydroxyethyl)(methyl)amino]ethyl]amino)-5-methyl-7-(oxan-2-yl)pyrrolo[2,3-d]pyrimidin-2-yl]phenyl]pyridine-2-sulfonamide

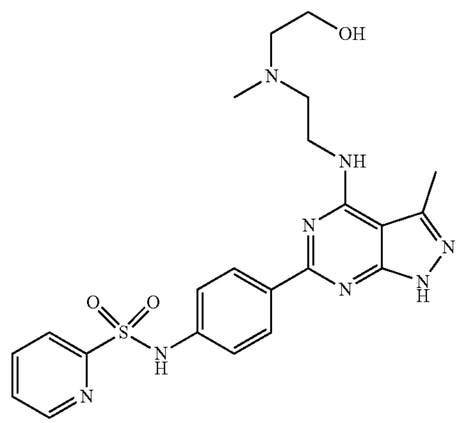 [SMILES: Cc1n[nH]c2nc(-c3ccc(NS(=O)(=O)c4ccccn4)cc3)nc(NCCN(C)CCO)c12]

This compound was prepared according to the procedure described in example 9. The desired product as an off-white solid (13.9 mg). LCMS (ESI, m/z): 482 $[M+H]^+$. $^1$H NMR (300 MHz, CD3OD) δ 8.66-8.64 (m, 1H), 8.27-8.22 (m, 2H), 8.01-7.96 (m, 2H), 7.57-7.52 (m, 1H), 7.25-7.21 (m, 2H), 3.85-3.81 (t, J=6.6 Hz 2H), 3.69-3.65 (t, J=6.0 Hz 2H), 2.83-2.78 (t, J=6.0 Hz 2H), 2.68-2.64 (t, J=6.0 Hz 2H), 2.58 (s, 3H), 2.43 (s, 3H).

Compound 21 N-[4-[4-([2-[(2-hydroxyethyl)(methyl)amino]ethyl]amino)-3-methyl-1H-pyrazolo[3,4-d]pyrimidin-6-yl]phenyl]pyridine-3-sulfonamide

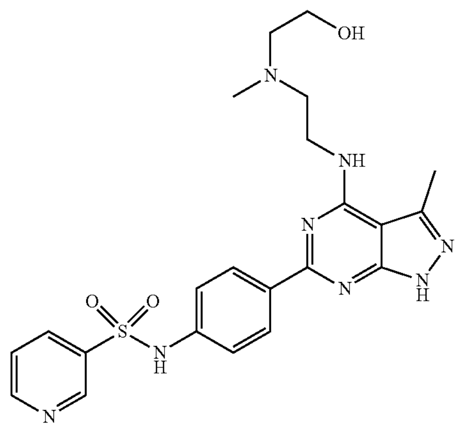 [SMILES: Cc1n[nH]c2nc(-c3ccc(NS(=O)(=O)c4cccnc4)cc3)nc(NCCN(C)CCO)c12]

This compound was prepared according to the procedure described in example 9. The desired product as an off-white solid (41.2 mg, 60% yield). LCMS (ESI, m/z): 483 $[M+H]^+$. $^1$H NMR (400 MHZ, DMSO-$d_6$): δ 12.95 (s, 1H), 10.64 (s, 1H), 8.93 (s, 1H), 8.77-8.75 (m, 1H), 8.25-8.23 (m, 2H), 8.17-8.14 (m, 1H), 7.61-7.58 (m, 1H), 7.19-7.17 (m, 2H), 7.00-6.97 (m, 1H), 4.45 (s, 1H), 3.72-3.67 (m, 2H), 3.50 (t, J=8.0 Hz, 2H), 2.71-2.69 (m, 2H), 2.55-2.52 (m, 2H), 2.50 (s, 3H), 2.33 (s, 3H).

Compound 22 5-chloro-2-fluoro-N-[4-[4-([2-[(2-hydroxyethyl)(methyl)amino]ethyl]amino)-3-methyl-1H-pyrazolo[3,4-d]pyrimidin-6-yl]phenyl]benzenesulfonamide

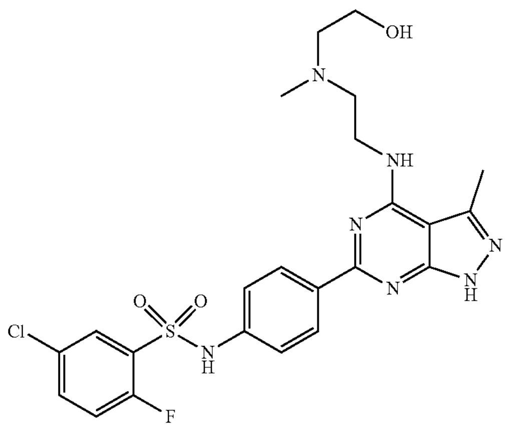 [SMILES: Cc1n[nH]c2nc(-c3ccc(NS(=O)(=O)c4cc(Cl)ccc4F)cc3)nc(NCCN(C)CCO)c12]

This compound was prepared according to the procedure described in example 9. The desired product as an off-white solid (28.8 mg, 29%). LCMS (ESI, m/z): 534 $[M+H]^+$. $^1$H NMR (400 MHZ, DMSO-$d_6$) δ 12.94 (s, 1H), 13.00 (s, 1H), 10.82 (s, 1H), 8.24-8.22 (d, J=8.0 Hz, 2H), 7.84-7.82 (m, 1H), 7.75-7.72 (m, 1H), 7.48-7.44 (t, J=8.0 Hz, 1H), 7.17-7.15 (d, J=8.0 Hz, 2H), 7.01-6.98 (d, J=8.0 Hz, 1H), 4.50 (s, 1H), 3.74-3.71 (t, J=4.0 Hz, 2H), 3.53-3.50 (t, J=4.0 Hz, 2H), 2.77-2.74 (t, J=6.0 Hz, 2H), 2.67 (s, 3H), 2.33 (s, 3H).

Compound 23 N-[4-(4-[[2-(dimethylamino)ethyl]amino]-3-methyl-1H-pyrazolo[3,4-d]pyrimidin-6-yl)phenyl]pyridine-3-sulfonamide

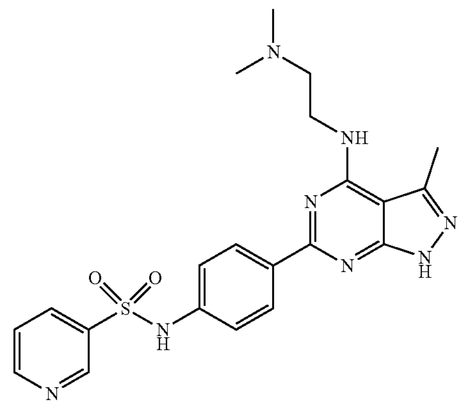 [SMILES: Cc1n[nH]c2nc(-c3ccc(NS(=O)(=O)c4cccnc4)cc3)nc(NCCN(C)C)c12]

This compound was prepared according to the procedure described in example 9. The desired product as an off-white solid (26.9 mg, 31% yield). LCMS (ESI, m/z): 453 $[M+H]^+$. $^1$H NMR (400 MHZ, DMSO-$d_6$): δ 12.95 (s, 1H), 11.15 (s, 1H), 8.93 (s, 1H), 8.77-8.75 (m, 1H), 8.25-8.23 (d, J=8.0 Hz, 2H), 8.17-8.14 (m, 1H), 7.61-7.58 (m, 1H), 7.19-7.17 (m, 2H), 7.01 (t, J=4.0 Hz, 1H), 3.74-3.69 (m, 2H), 2.62 (t, J=8.0 Hz, 2H), 2.52 (s, 3H), 2.29 (s, 6H).

Compound 24 N-[4-(4-[[2-(dimethylamino)ethyl]amino]-3-methyl-1H-pyrazolo[3,4-d]pyrimidin-6-yl)phenyl]pyridine-2-sulfonamide

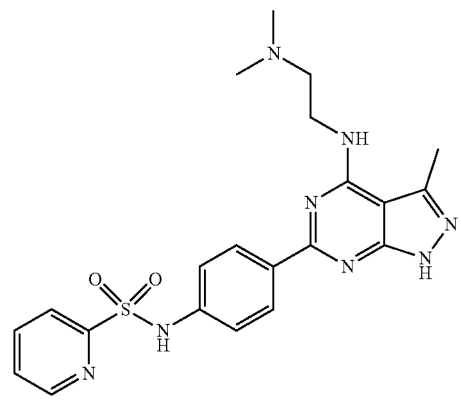 [SMILES: Cc1n[nH]c2nc(-c3ccc(NS(=O)(=O)c4ccccn4)cc3)nc(NCCN(C)C)c12]

This compound was prepared according to the procedure described in example 9. The desired product as an off-white solid (14.9 mg, 17.67%). LCMS29 (ESI, m/z): 453 $[M+H]^+$.

$^1$H NMR (400 MHZ, DMSO-$d_6$) δ 12.93 (s, 1H), 10.77 (s, 1H), 8.72-8.70 (m, 1H), 8.22-8.01 (m, 2H), 8.07-8.01 (m, 3H), 7.65-7.62 (m, 1H), 7.23-7.21 (d, J=8.0 Hz, 2H), 7.00-6.98 (t, J=4.0 Hz, 1H), 3.72-3.67 (m, 2H), 2.58-2.55 (t, J=8.0 Hz, 3H), 2.52 (s, 2H), 2.25 (s, 6H).

Compound 25 5-chloro-2-fluoro-N-(4-(4-((1-isopropylazetidin-3-yl)amino)-3-methyl-1H-pyrazolo[3,4-d]pyrimidin-6-yl)phenyl)benzenesulfonamide

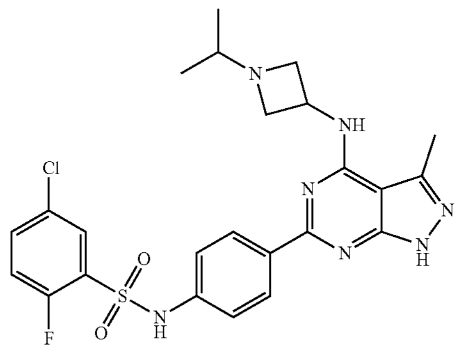 [SMILES: Cc1n[nH]c2nc(-c3ccc(NS(=O)(=O)c4cc(Cl)ccc4F)cc3)nc(NC3CN(C(C)C)C3)c12]

(i) 3-methyl-6-(4-nitrophenyl)-1,3a,7,7a-tetrahydro-4H-pyrazolo[3,4-d]pyrimidin-4-one To a stirred mixture of 3-amino-5-methyl-2H-pyrazole-4-carboxamide (1 g, 7.143 mmol, 1.0 equiv.) in ACN (20 mL) was added 4-nitrobenzaldehyde (2.15 g, 14.29 mmol, 2.0 equiv.) and 12 (3.63 g, 14.290 mmol, 2.0 equiv.) at room temperature. The resulting mixture was stirred for 4 hours at 90° C. The resulting mixture was cooled at room temperature and filtered, the filter cake was washed with ACN (2×100 mL) and dried under IR lamp to afford 3-methyl-6-(4-nitrophenyl)-1H-pyrazolo[3,4-d]pyrimidin-4-ol (900 mg, crude) as a pink solid. LCMS (ESI, m/z): 272 $[M+H]^+$ (ii) 4-chloro-3-methyl-6-(4-nitrophenyl)-3a,4,7,7a-tetrahydro-1H-pyrazolo[3,4-d]pyrimidine To a stirred mixture of 3-methyl-6-(4-nitrophenyl)-1H-pyrazolo[3,4-d]pyrimidin-4-ol (2 g, 7.35 mmol, 1.0 equiv.) in $SOCl_2$ (17.50 g, 147 mmol, 20.0 equiv.) was DMF (0.536 g, 7.35 mmol, 1.0 equiv.) at room temperature. The resulting mixture was stirred for 4 hours at 80° C. The resulting mixture was cooled and quenched with water (100 mL) at room temperature, and filtered, the filter cake was washed with $Et_2O$ (2×100 mL) and dried under IR lamp to afford 4-chloro-3-methyl-6-(4-nitrophenyl)-1H-pyrazolo[3,4-d]pyrimidine (1.6 g, 88% purity, 75.05% yield) as a yellow solid. LCMS (ESI, m/z): 290 $[M+H]^+$.

(iii) N-(1-isopropylazetidin-3-yl)-3-methyl-6-(4-nitrophenyl)-1H-pyrazolo[3,4-d]pyrimidin-4-amine To a stirred mixture of 4-chloro-3-methyl-6-(4-nitrophenyl)-1H-pyrazolo[3,4-d]pyrimidine (300 mg, 1.034 mmol, 1.0 equiv.) in DMF (5 mL) was DIEA (668.5 mg, 5.172 mmol, 5.0 equiv.) and 1-isopropylazetidin-3-amine (235 mg, 2.068 mmol, 2.0 equiv.) at room temperature. The resulting mixture was stirred for 2 hours at 50° C. The mixture was then diluted with water and extracted with EtOAc. The organic layer was dried over $Na_2SO_4$, concentrated, and purified by column chromatography to give the compound of 1-isopropyl-N-[3-methyl-6-(4-nitrophenyl)-1H-pyrazolo[3,4-d]pyrimidin-4-yl]azetidin-3-amine 160 mg (93% purity, white solid) in 46% yield. LCMS (ESI, m/z): 368 $[M+H]^+$.

(iv) 6-(4-aminophenyl)-N-(1-isopropylazetidin-3-yl)-3-methyl-1H-pyrazolo[3,4-d]pyrimidin-4-amine 1-isopropyl-N-[3-methyl-6-(4-nitrophenyl)-1H-pyrazolo[3,4-d]pyrimidin-4-yl]azetidin-3-amine (160 mg, 0.435 mmol, 1.0 equiv.) and 20% Pd/C (230 mg, 0.217 mmol, 0.5 equiv.) were dissolved under $H_2$ (5 bar) atmosphere in DMF (5 mL). The mixture was stirred for 18 hours at 25° C. The resulting mixture was filtered, the filtrate was removed under reduced pressure to afford the white solid crude of N-[6-(4-aminophenyl)-3-methyl-1H-pyrazolo[3,4-d]pyrimidin-4-yl]-1-isopropylazetidin-3-amine (130 mg, 86.4% purity, 88.4% yield, white solid). LCMS (ESI, m/z): 338 $[M+H]^+$ (v) 5-chloro-2-fluoro-N-(4-(4-((1-isopropylazetidin-3-yl)amino)-3-methyl-1H-pyrazolo[3,4-d]pyrimidin-6-yl)phenyl)benzenesulfonamide A solution of N-[6-(4-aminophenyl)-3-methyl-1H-pyrazolo[3,4-d]pyrimidin-4-yl]-1-isopropylazetidin-3-amine (130 mg, 0.385 mmol, 1.0 equiv.) and Pyridine (30.8 mg, 0.385 mmol, 1.0 equiv.) in anhydrous DMF (1 mL) was stirred with chloro(5-chloro-2-fluorophenyl)methylidene-lambda6-sulfanone (87.3 mg, 0.385 mmol, 1.0 equiv.) for 24 hours at room temperature. The organic layer was worked up with aqueous HCl (5%, 10 mL) and DCM (10 mL), dried over anhydrous $Na_2SO_4$, evaporated in vacuo and purified by HPLC(Column: XBridge Shield RP18 OBD Column, 19*250 mm, 10 um; Mobile Phase A: Water (10 MMOL/L $NH_4HCO_3$+0.1% $NH_3 \cdot H_2O$), Mobile Phase B: ACN; Flow rate: 25 mL/min; Gradient: 18 B to 48 B in 10 min, 220 nm; RT1:9.60) provide the 5-chloro-2-fluoro-N-(4-[4-[(1-isopropylazetidin-3-yl)amino]-3-methyl-1H-pyrazolo[3,4-d]pyrimidin-6-yl]phenyl)benzenesulfonamide (17.8 mg, 95.7% purity, 8.73% yield, yellow solid). LCMS (ESI, m/z): 530.2 $[M+H]^+$. $^1$H NMR (300 MHZ, DMSO-$d_6$) δ 12.99 (s, 1H), 8.20 (d, J=8.5 Hz, 2H), 7.82 (dd, J=6.0, 2.7 Hz, 1H), 7.70 (dt, J=8.8, 3.4 Hz, 1H), 7.44 (dd, J=10.9, 7.5 Hz, 1H), 7.17 (dd, J=15.9, 6.9 Hz, 3H), 4.77 (q, J=6.8 Hz, 1H), 3.86 (s, 2H), 2.98 (s, 2H), 2.58 (s, 3H), 1.18 (d, J=6.8 Hz, 1H), 0.96 (d, J=6.2 Hz, 6H).

Compound 26 5-chloro-2-fluoro-N-(4-(3-methyl-4-((2-morpholinoethyl)amino)-1H-pyrazolo[3,4-d]pyrimidin-6-yl)phenyl)benzenesulfonamide

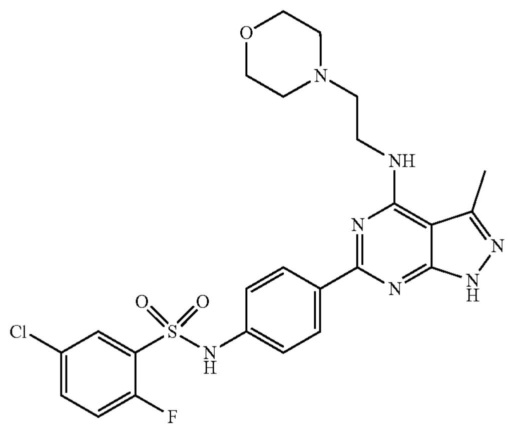 [SMILES: Cc1n[nH]c2nc(-c3ccc(NS(=O)(=O)c4cc(Cl)ccc4F)cc3)nc(NCCN3CCOCC3)c12]

(i) 6-chloro-3-methyl-N-(2-morpholinoethyl)-1H-pyrazolo[3,4-d]pyrimidin-4-amine

Into a 50-mL round-bottom flask, was placed 4,6-dichloro-3-methyl-1H-pyrazolo[3,4-d]pyrimidine (150.00 mg, 0.739 mmol, 1.00 equiv.), DCM (15.00 mL), DIEA (286.46 mg, 2.216 mmol, 3 equiv.), N-aminoethylmorpholine (115.42 mg, 0.887 mmol, 1.20 equiv.). The resulting solution was stirred for 16 hr at room temperature. The resulting solution was extracted with 2×30 mL of ethyl acetate dried over anhydrous sodium sulfate and concentrated. This resulted in 200 mg (82.10%) of 6-chloro-3-methyl-N-[2-(morpholin-4-yl)ethyl]-1H-pyrazolo[3,4-d]pyrimidin-4-amine as a yellow solid. LCMS (ES. m/z): 297 $[M+H]^+$.

(ii) 5-chloro-2-fluoro-N-(4-(3-methyl-4-((2-morpholinoethyl)amino)-1H-pyrazolo[3,4-d]pyrimidin-6-yl)phenyl)benzenesulfonamide Into a 50-mL round-bottom flask, was placed 6-chloro-3-methyl-N-[2-(morpholin-4-yl)ethyl]-1H-pyrazolo[3,4-d]pyrimidin-4-amine (200.00 mg, 0.674 mmol, 1.00 equiv.), dioxane (16.00 mL), $H_2O$ (4.00 mL), 5-chloro-2-fluoro-N-[4-(4,4,5,5-tetramethyl-1,3,2-dioxaborolan-2-yl)phenyl]benzenesulfonamide (305.19 mg, 0.741 mmol, 1.10 equiv.), $CS_2CO_3$ (658.75 mg, 2.022 mmol, 3 equiv.), $Pd(dppf)Cl_2$ (49.31 mg, 0.067 mmol, 0.1 equiv.). The resulting solution was stirred for 3 hr at 100° C. The resulting solution was extracted with 3×50 mL of ethyl acetate dried in an oven under reduced pressure and concentrated. The crude product was purified by Flash-Prep-HPLC with the following conditions: Column, silica gel C18 (210 g); mobile phase A: Water-10 mM $NH_4HCO_3$, mobile phase B: Acetonitrile; Flow rate: 50 mL/min; Gradient: 55 B to 60 B; 254 nm. The solution was concentrated. The solid was washed with $CH_3CN$ (3 mL×2). The solid was collected by filtration. This resulted in 65.3 mg (17.05%) of 5-chloro-2-fluoro-N-[4-(3-methyl-4-[[2-(morpholin-4-yl)ethyl]amino]-1H-pyrazolo[3,4-d]pyrimidin-6-yl)phenyl]benzenesulfonamide as a light brown solid. $^1$H-NMR ($CD_3OD$, 300 MHZ) δ (ppm): 8.29 (d, J=9.0 Hz, 2H), 7.86-7.89 (m, 1H), 7.60-7.64 (m, 1H), 7.21-7.32 (m, 3H), 3.85-3.91 (m, 2H), 3.70-3.73 (m, 4H), 2.71-2.80 (m, 2H), 2.67 (s, 7H). LCMS (ES. m/z): 546 $[M+H]^+$.

Compound 27 N-(4-(4-((2-(dimethylamino)ethyl)amino)-3-methyl-1H-pyrazolo[3,4-d]pyrimidin-6-yl)phenyl)-4-methoxypyridine-2-sulfonamide

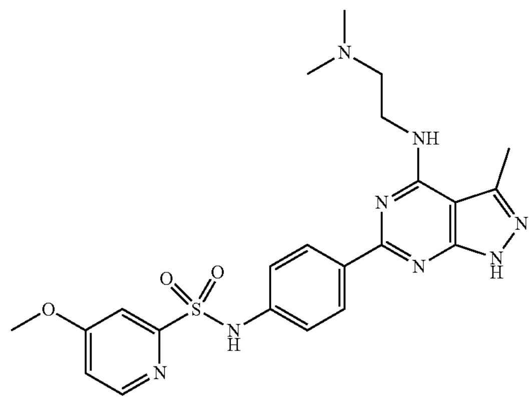 [SMILES: COc1ccnc(S(=O)(=O)Nc2ccc(-c3nc(NCCN(C)C)c4c(C)n[nH]c4n3)cc2)c1]

This compound was prepared according to the procedure described in example 9. The desired product as an off-white solid (21.9 mg, 11.6% yield). LCMS (ESI, m/z): 483.3 $[M+H]^+$. $^1$H NMR (300 MHZ, DMSO-$d_6$) δ 12.95 (s, 1H), 8.52 (d, J=5.6 Hz, 1H), 8.27-8.18 (m, 2H), 7.51 (d, J=2.5 Hz, 1H), 7.29-7.17 (m, 3H), 7.02 (t, J=5.7 Hz, 1H), 3.90 (s, 3H), 3.72 (q, J=6.5 Hz, 2H), 2.62 (t, J=6.8 Hz, 2H), 2.52 (s, 3H). 2.29 (s, 6H).

Compound 28 5-chloro-2-fluoro-N-(4-(4-((1-isopropylpiperidin-4-yl)oxy)-3-methyl-1H-pyrazolo[3,4-d]pyrimidin-6-yl)phenyl)benzenesulfonamide

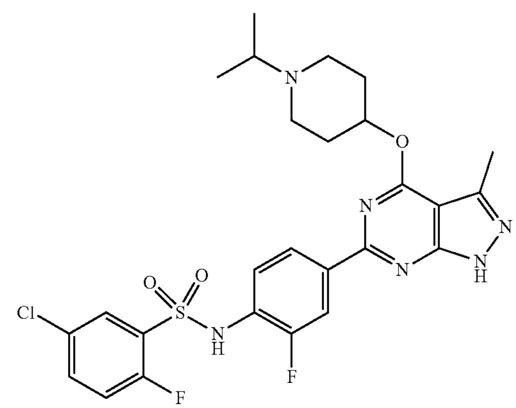 [SMILES: Cc1n[nH]c2nc(-c3ccc(NS(=O)(=O)c4cc(Cl)ccc4F)c(F)c3)nc(OC3CCN(C(C)C)CC3)c12]

This compound was prepared according to the procedure described in example 9. The desired product as a white solid (37.6 mg, 32.16%). $^1$H-NMR (DMSO-$d_6$, 300 MHZ) δ(ppm): 13.6 (s, 1H), 7.89-7.96 (m, 2H), 7.69-7.23 (m, 1H), 7.53-7.57 (m, 1H), 7.25-7.34 (m, 2H), 5.70 (s, 1H), 3.61 (s, 1H), 3.22 (s, 4H), 2.48 (s, 3H), 1.97-2.27 (m, 4H), 1.25 (d, J=6.6 Hz, 6H). LCMS (ES. m/z): 577 $[M+H]^+$.

Compound 29 5-chloro-2-fluoro-N-(4-(4-(((3S,4R)-3-fluoropiperidin-4-yl)oxy)-3-methyl-1H-pyrazolo[3,4-d]pyrimidin-6-yl)phenyl)benzenesulfonamide

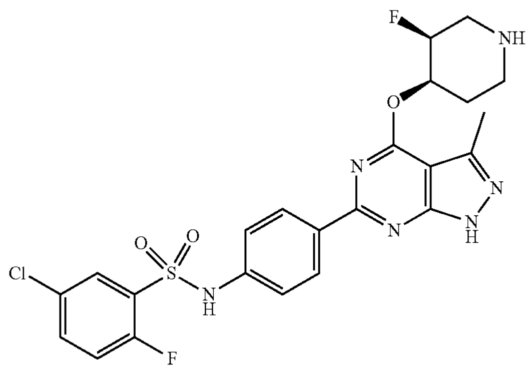 [SMILES: Cc1n[nH]c2nc(-c3ccc(NS(=O)(=O)c4cc(Cl)ccc4F)cc3)nc(O[C@@H]3CCNC[C@@H]3F)c12]

(i) tert-butyl-(3S,4R)-4-((6-chloro-3-methyl-1H-pyrazolo[3,4-d]pyrimidin-4-yl)oxy)-3-fluoropiperidine-1-carboxylate Into a 50-mL round-bottom flask, was placed 4,6-dichloro-3-methyl-1H-pyrazolo[3,4-d]pyrimidine (100.00 mg, 0.493 mmol, 1.00 equiv.), tert-butyl (3S,4R)-3-fluoro-4-hydroxypiperidine-1-carboxylate (118.79 mg, 0.542 mmol, 1.10 equiv.), THF (10.00 mL). The resulting solution was stirred for 20 min at room temperature. Then added NaH (59.10 mg, 2.463 mmol, 5 equiv.) at 0° C. The resulting solution was stirred for 2 hr at room temperature. The reaction was then quenched by the addition of water. The resulting solution was extracted with 2×50 mL of ethyl acetate dried over anhydrous sodium sulfate and concentrated. The resulting mixture was washed with EtOAc. The solids were collected by filtration. This resulted in 110 mg (52.10%) of tert-butyl (3S,4R)-4-([6-chloro-3-methyl-1H-pyrazolo[3,4-d]pyrimidin-4-yl]oxy)-3-fluoropiperidine-1-carboxylate as a light yellow solid. LCMS (ES. m/z): 386 $[M+H]^+$.

(ii) tert-butyl (3S,4R)-4-((6-(4-((5-chloro-2-fluorophenyl)sulfonamido)phenyl)-3-methyl-1H-pyrazolo[3,4-d]pyrimidin-4-yl)oxy)-3-fluoropiperidine-1-carboxylate Into a 40-mL sealed tube purged and maintained with an inert atmosphere of $N_2$, was placed tert-butyl (3S,4R)-4-([6-chloro-3-methyl-1H-pyrazolo[3,4-d]pyrimidin-4-yl]oxy)-3-fluoropiperidine-1-carboxylate (100.00 mg, 0.259 mmol, 1.00 equiv.), dioxane (8.00 mL), $H_2O$ (2.00 mL), 5-chloro-2-fluoro-N-[4-(4,4,5,5-tetramethyl-1,3,2-dioxaborolan-2-yl)phenyl]benzenesulfonamide (106.70 mg, 0.259 mmol, 1.00 equiv.), Cs2CO3 (126.67 mg, 0.389 mmol, 1.5 equiv.), $Pd(dppf)Cl_2$ (37.93 mg, 0.052 mmol, 0.2 equiv.). The resulting solution was stirred for 16 hr at 100° C. The resulting mixture was concentrated. The residue was purified by preparative TLC (DCM:MeOH=20:1). This resulted in 150 mg (72.90%) of tert-butyl (3S,4R)-4-([6-[4-(5-chloro-2-fluorobenzenesulfonamido)phenyl]-3-methyl-1H-pyrazolo[3,4-d]pyrimidin-4-yl]oxy)-3-fluoropiperidine-1-carboxylate as a yellow solid. LCMS (ES. m/z): 635 $[M+H]^+$.

(iii) 5-chloro-2-fluoro-N-(4-(4-(((3S,4R)-3-fluoropiperidin-4-yl)oxy)-3-methyl-1H-pyrazolo[3,4-d]pyrimidin-6-yl)phenyl)benzenesulfonamide Into a 50-mL round-bottom flask, was placed tert-butyl (3S,4R)-4-([6-[4-(5-chloro-2-fluorobenzenesulfonamido) phenyl]-3-methyl-1H-pyrazolo[3,4-d]pyrimidin-4-yl]oxy)-3-fluoropiperidine-1-carboxylate (130.00 mg, 0.205 mmol, 1.00 equiv.), DCM (5.00 mL), HCl (4M in 1,4-dioxane) (5.00 mL, 87.587 mmol, 427.88 equiv.). The resulting solution was stirred for 2 hr at room temperature. The resulting mixture was concentrated. The solid by Prep-HPLC (Column: YMC-Actus Triart C18, 30 mm×150 mm, 5 um; Mobile Phase A: Water (10 MMOL/L $NH_4HCO_3$+ 0.1% $NH_3 \cdot H_2O$), Mobile Phase B: ACN; Flow rate: 60 mL/min; Gradient: 25 B to 45 B in 7 min, 254 nm; RT1:6.73; RT2; Injection Volumn: ml; Number Of Runs). This resulted in 20.7 mg (18.18%) of 5-chloro-2-fluoro-N-[4-(4-[[(3S,4R)-3-fluoropiperidin-4-yl]oxy]-3-methyl-1H-pyrazolo[3,4-d]pyrimidin-6-yl)phenyl]benzenesulfonamide as a white solid. $^1$H-NMR (CD3OD, 300 MHZ) δ (ppm): 8.32 (d, J=9 Hz, 2H), 7.86-7.89 (m, 1H), 7.57-7.62 (m, 1H), 7.22-7.30 (m, 3H), 5.68-5.89 (m, 1H), 5.08 (s, 1H), 3.06-3.21 (m, 2H), 2.79-3.02 (m, 2H), 2.59 (s, 3H), 2.04-3.01 (m, 2H). LCMS (ES. m/z): 535 $[M+H]^+$.

Compound 30 N-(4-(4-((2-(dimethylamino)ethyl)amino)-3-methyl-1H-pyrazolo[3,4-d]pyrimidin-6-yl)phenyl)-4-(trifluoromethyl)pyridine-2-sulfonamide

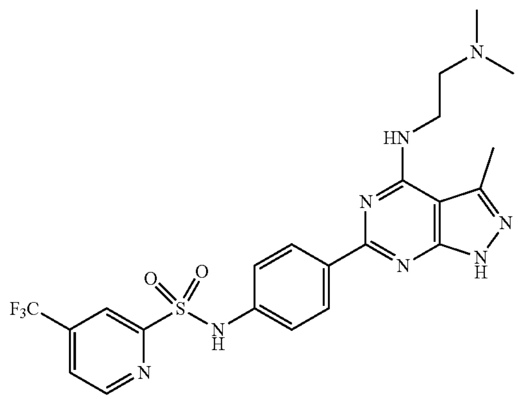 [SMILES: Cc1n[nH]c2nc(-c3ccc(NS(=O)(=O)c4cc(C(F)(F)F)ccn4)cc3)nc(NCCN(C)C)c12]

This compound was prepared according to the procedure described in example 9. The desired product as a white solid (41.6 mg). $^1$H NMR (300 MHZ, DMSO-$d_6$) δ 12.91 (s, 1H), 8.98 (d, J=5.0 Hz, 1H), 8.24-8.15 (m, 3H), 8.10-7.99 (m, 1H), 7.19 (d, J=8.7 Hz, 2H), 6.99 (t, J=5.6 Hz, 1H), 3.72 (d, J=6.3 Hz, 2H), 2.66 (t, J=6.7 Hz, 2H), 2.50 (s, 3H), 2.31 (s, 6H). LCMS (ES, m/z): 521 $[M+H]^+$.

Compound 31 N-(4-(4-((2-(dimethylamino)ethyl)amino)-3-methyl-1H-pyrazolo[3,4-d]pyrimidin-6-yl)phenyl)-5-(trifluoromethyl)pyridine-2-sulfonamide

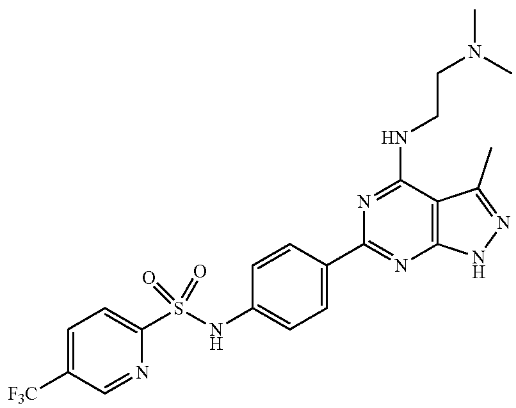 [SMILES: Cc1n[nH]c2nc(-c3ccc(NS(=O)(=O)c4ccc(C(F)(F)F)cn4)cc3)nc(NCCN(C)C)c12]

This compound was prepared according to the procedure described in example 9. The desired product as a white solid (17.8 mg). $^1$H NMR (300 MHZ, DMSO-$d_6$) δ 12.94 (s, 1H), 9.14 (s, 1H), 8.48 (dd, J=8.3, 2.3 Hz, 1H), 8.20 (dd, J=8.3, 5.1 Hz, 3H), 7.20 (d, J=8.5 Hz, 2H), 7.02 (s, 1H), 3.72 (d, J=6.2 Hz, 2H), 2.70 (s, 2H), 2.50 (s, 3H), 2.34 (s, 6H). LCMS (ES, m/z): 521 $[M+H]^+$.

Compound 32 N-(4-(4-((2-(diethylamino)ethyl)amino)-3-methyl-1H-pyrazolo[3,4-d]pyrimidin-6-yl)phenyl)-2,5-difluorobenzenesulfonamide

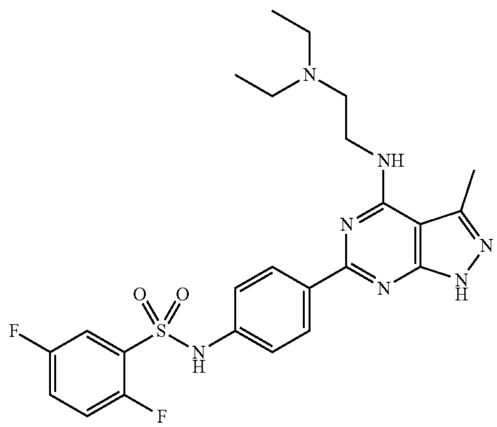 [SMILES: CCN(CC)CCNc1nc(-c2ccc(NS(=O)(=O)c3cc(F)ccc3F)cc2)nc2[nH]nc(C)c12]

This compound was prepared according to the procedure described in example 28. The desired product as an off-white solid (39.1 mg, 16.4%). $^1$H-NMR (DMSO-$d_6$, 300 MHZ) δ (ppm): 12.95 (s, 1H), 10.63 (s, 1H), 8.22 (d, J=8.7 Hz, 2H), 7.69-7.63 (m, 1H), 7.57 (d, J=3.6 Hz, 2H), 7.15 (d, J=8.7 Hz, 2H), 7.03-6.99 (m, 1H), 3.71 (d, J=5.7 Hz, 2H), 2.82-2.78 (m, 2H), 2.72-2.61 (m, 4H), 2.53 (s, 3H), 1.08 (s, 6H). LCMS (ES. m/z): 516 $[M+H]^+$.

Compound 33 2,5-difluoro-N-(4-(3-methyl-4-((2-(pyrrolidin-1-yl)ethyl)amino)-1H-pyrazolo[3,4-d]pyrimidin-6-yl)phenyl)benzenesulfonamide

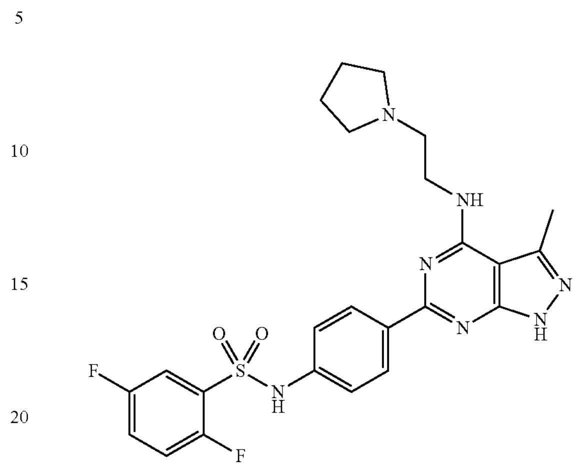

This compound was prepared according to the procedure described in example 28. The desired product as a white solid to provide (60.0 mg, 99.4% purity). LCMS (ESI, m/z): 514.4 $[M+H]^+$. $^1$H NMR (300 MHZ, DMSO-$d_6$) δ 12.94 (s, 1H), 8.29-8.13 (m, 2H), 7.65 (ddd, J=8.0, 5.4, 3.1 Hz, 1H), 7.56-7.38 (m, 2H), 7.21-7.00 (m, 3H), 3.77 (q, J=6.4 Hz, 2H), 2.89 (t, J=6.7 Hz, 2H), 2.75 (d, J=6.3 Hz, 4H), 2.53 (s, 3H), 1.74 (h, J=3.0 Hz, 4H).

Compound 34 2,5-difluoro-N-(4-(3-methyl-4-((1-methylazetidin-3-yl)oxy)-1H-pyrazolo[3,4-d]pyrimidin-6-yl)phenyl)benzenesulfonamide

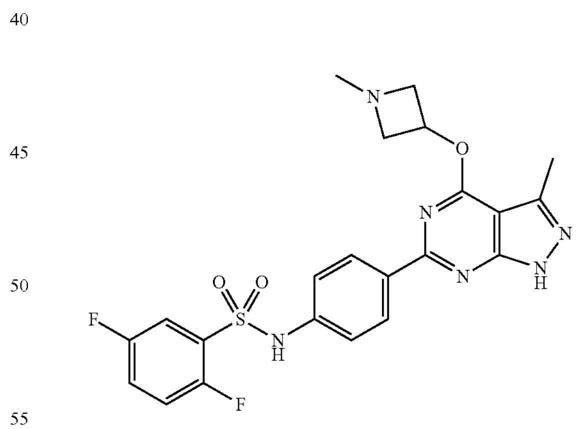

This compound was prepared according to the procedure described in example 8. The desired product as a white solid to provide the desired product as a TFA salt (9.1 mg, 99.1% purity). $^1$H NMR (300 MHZ, DMSO-$d_6$) δ 13.62 (s, 1H), 11.18 (s, 1H), 8.28 (d, J=8.5 Hz, 2H), 7.79-7.69 (m, 1H), 7.56 (dtd, J=18.3, 9.0, 8.6, 4.2 Hz, 2H), 7.32-7.23 (m, 2H), 5.71 (s, 1H), 4.71 (s, 2H), 4.41 (s, 2H), 2.97 (s, 3H), 2.58 (s, 3H), 1.24 (s, 1H)). LCMS (ESI, m/z): 487.1 $[M+H]^+$.

Compound 35 5-chloro-2-fluoro-N-(4-(4-((2-((2-hydroxyethyl)(methyl)amino)ethyl)(methyl)amino)-3-methyl-1H-pyrazolo[3,4-d]pyrimidin-6-yl)phenyl) benzene sulfonamide

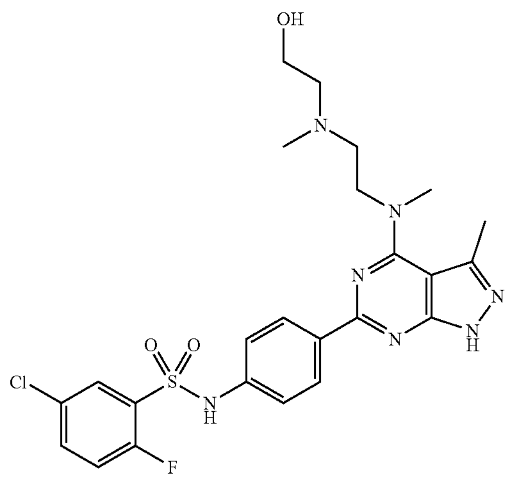 [SMILES: Cc1n[nH]c2nc(-c3ccc(NS(=O)(=O)c4cc(Cl)ccc4F)cc3)nc(N(C)CCN(C)CCO)c12]

(i) tert-butyl (2-((2-hydroxyethyl)(methyl)amino) ethyl)(methyl)carbamate

A mixture of 2-(methylamino)ethan-1-ol (1.10 g, 14.67 mmol), tert-butyl (2-(methylamino)ethyl)carbamate (2.54 g, 14.67 mmol), Sodium triacetoxyborohydride (6.22 g, 29.34 mmol) and AcOH (0.1 mL) in $CHCl_3$ (40 mL) was stirred for 16 hours at room temperature. The reaction mixture was washed with saturated aqueous $NaHCO_3$ (20 mL) then brine (20 mL). The organic layer was dried anhydrous $Na_2SO_4$ and filtered The filtrate was concentrated in vacuo. This resulted in tert-butyl (2-((2-hydroxyethyl)(methyl)amino) ethyl)(methyl)carbamate (720 mg, Y=23%) as light yellow oil, which was used in the next step directly without any further purification. LCMS (ES, m/z): 233 $[M+H]^+$.

(ii) 2-(methyl(2-(methylamino)ethyl)amino)ethan-1-ol

To a solution of tert-butyl (2-((2-hydroxyethyl)(methyl) amino)ethyl)(methyl) carbamate (720 mg, 3.09 mmol) in DCM (12 mL) was added TFA (4 mL). The resulting mixture was stirred for 16 hours at room temperature. The reaction mixture was concentrated in vacuo. This resulted in 2-(methyl(2-(methylamino)ethyl)amino)ethan-1-ol (530 mg crude, TFA salt form) as light brown oil, which was used in the next step directly without any further purification. LCMS (ES, m/z): 133 $[M+H]^+$.

(iii) 2-((2-((6-chloro-3-methyl-1H-pyrazolo[3,4-d] pyrimidin-4-yl)(methyl)amino)ethyl)(methyl)amino) ethan-1-ol A mixture of 4,6-dichloro-3-methyl-1H-pyrazolo[3,4-d] pyrimidine (200 mg, 0.99 mmol), 2-(methyl(2-(methylamino)ethyl)amino)ethan-1-ol (530 mg crude, TFA salt form) and DIPEA (1.67 mL, 9.99 mmol) in DCM (10 mL) was stirred for 16 hours at room temperature. The reaction mixture was concentrated in vacuo. The residue was purified by reverse phase chromatography with the following condition: (Column: Agela C18 Column, 120 g; Mobile Phase A: Water (10 mmol/L $NH_4HCO_3$), Mobile Phase B: ACN; Flow rate: 40 mL/min; Gradient: 0 B to 100% B in 20 min; 254 nm. This resulted in 2-((2-((6-chloro-3-methyl-1H-pyrazolo[3,4-d]pyrimidin-4-yl)(methyl)amino)ethyl) (methyl)amino)ethan-1-ol (280 mg, Y=95%) as a light yellow solid. LCMS (ES, m/z): 299 $[M+H]^+$.

(iv) 5-chloro-2-fluoro-N-(4-(4-((2-((2-hydroxyethyl) (methyl)amino)ethyl)(methyl)amino)-3-methyl-1H-pyrazolo[3,4-d]pyrimidin-6-yl)phenyl)benzenesulfonamide trifluoroacetate A mixture of 2-((2-((6-chloro-3-methyl-1H-pyrazolo[3,4-d]pyrimidin-4-yl)(methyl)amino)ethyl)(methyl)amino) ethan-1-ol (100 mg, 0.33 mmol), 5-chloro-2-fluoro-N-(4-(4,4,5,5-tetramethyl-1,3,2-dioxaborolan-2-yl)phenyl) benzenesulfonamide (204 mg, 0.50 mmol), cesium carbonate (196 mg, 0.60 mmol) and Pd(dppf)$Cl_2$ (22 mg, 0.03 mmol) in 1,4-dioxane (4 mL) and water (1 mL) was degassed and refilled with $N_2$ for three times, then stirred at 100° C. for 3 hours under $N_2$. The reaction mixture was cooled to ambient temperature and filtered. The filtrate was purified by prep-HPLC with the following condition: Column: YMC-Actus Triart C18, 30 mm×150 mm, 5 um; Mobile Phase A: Water (0.05% TFA), Mobile Phase B: ACN; Flow rate: 60 mL/min; Gradient: 20% B to 50% B in 7 min; 254 nm; RT: 5.12. This resulted in 5-chloro-2-fluoro-N-(4-(4-((2-((2-hydroxyethyl)(methyl)amino)ethyl) (methyl)amino)-3-methyl-1H-pyrazolo[3,4-d]pyrimidin-6-yl)phenyl)benzenesulfonamide trifluoroacetate (11.9 mg) as a white solid. $^1$H NMR (400 MHz, DMSO-$d_6$) δ 13.27 (brs, 1H), 11.08 (s, 1H), 9.36 (s, 1H), 8.32-8.24 (m, 2H), 7.86 (dd, J=6.1, 2.7 Hz, 1H), 7.80 (ddd, J=8.8, 4.2, 2.7 Hz, 1H), 7.52 (t, J=9.3 Hz, 1H), 7.29-7.20 (m, 2H), 4.27-4.16 (m, 2H), 3.80-3.50 (m, 4H), 3.50-3.30 (m, 4H), 3.20 (dd, J=13.1, 5.7 Hz, 1H), 2.89 (d, J=4.3 Hz, 3H), 2.61 (s, 3H). LCMS (ES, m/z): 548 $[M+H]^+$-114.

Compound 36 2,5-difluoro-N-(3-methyl-4-(3-methyl-4-((2-(pyrrolidin-1-yl)ethyl)amino)-1H-pyrazolo[3,4-d]pyrimidin-6-yl)phenyl)benzenesulfonamide

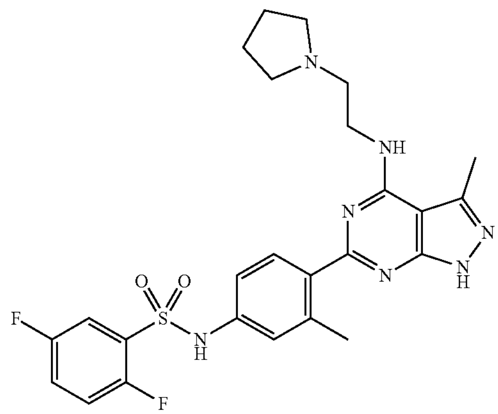 [SMILES: Cc1cc(NS(=O)(=O)c2cc(F)ccc2F)ccc1-c1nc(NCCN2CCCC2)c2c(C)n[nH]c2n1]

This compound was prepared according to the procedure described in example 9. The desired product was obtained as a white a TFA salt (40.6 mg, 99.6% purity). $^1$H NMR (300 MHz, DMSO-$d_6$) δ10.96 (s, 1H), 9.56 (s, 1H), 7.77-7.67 (m, 2H), 7.58 (dtt, J=18.3, 9.1, 4.8 Hz, 2H), 7.41 (s, 1H), 7.11-7.00 (m, 2H), 3.84 (d, J=5.8 Hz, 2H), 3.61 (s, 2H), 3.41 (t, J=5.7 Hz, 2H), 3.01 (s, 2H), 2.59 (s, 3H), 2.44 (s, 3H), 1.90 (s, 2H), 1.66 (s, 2H). LCMS (ESI, m/z): 528 $[M+H]^+$.

Compound 37 5-chloro-2-fluoro-N-(4-(3-methyl-4-((2-(pyrrolidin-1-yl)ethyl)amino)-1H-pyrazolo[3,4-d]pyrimidin-6-yl)phenyl)benzenesulfonamide

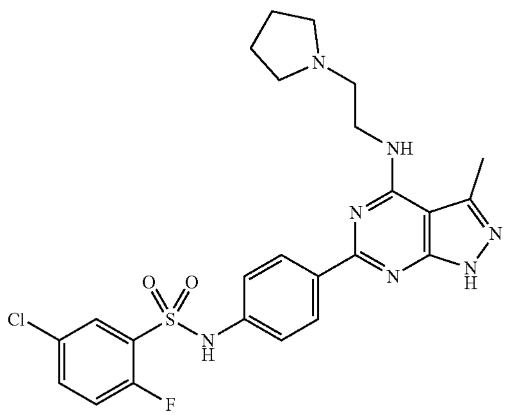 [SMILES: Cc1n[nH]c2nc(-c3ccc(NS(=O)(=O)c4cc(Cl)ccc4F)cc3)nc(NCCN3CCCC3)c12]

This compound was prepared according to the procedure described in example 9. The desired product was obtained as a white TFA salt solid (14.3 mg, 99.6% purity). $^1$H NMR (300 MHZ, DMSO-$d_6$) δ 11.09 (s, 1H), 9.58 (s, 1H), 8.34-8.24 (m, 2H), 7.90-7.75 (m, 2H), 7.53 (t, J=9.3 Hz, 1H), 7.39-7.19 (m, 3H), 3.95 (d, J=6.0 Hz, 2H), 3.73-3.59 (m, 2H), 3.54-3.40 (m, 2H), 3.11 (d, J=9.6 Hz, 2H), 2.57 (s, 3H), 2.00 (s, 2H), 1.90-1.73 (m, 2H). LCMS (ESI, m/z): 530 $[M+H]^+$.

Compound 38 5-chloro-N-(4-(4-((2-(dimethylamino)ethyl)amino)-3-methyl-1H-pyrazolo[3,4-d]pyrimidin-6-yl)-2-fluorophenyl)-2-fluorobenzenesulfonamide

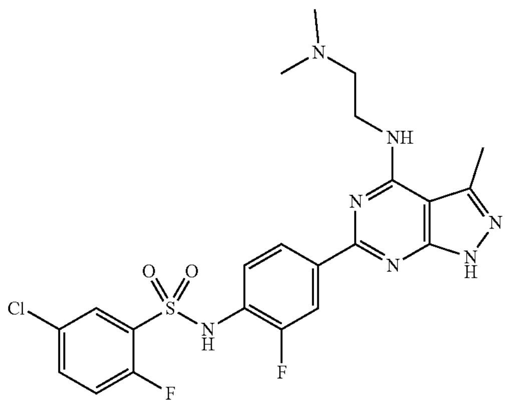 [SMILES: Cc1n[nH]c2nc(-c3ccc(NS(=O)(=O)c4cc(Cl)ccc4F)c(F)c3)nc(NCCN(C)C)c12]

This compound was prepared according to the procedure described in example 9. The desired product was obtained as a white TFA salt solid (28.6 mg, 19%). LCMS (ES. m/z): 522 $[M+H]^+$. $^1$H-NMR (CD3OD, 300 MHZ) δ (ppm): 8.19-8.10 (m, 1H), 8.09-8.06 (m, 1H), 7.81-7.78 (m, 1H), 7.68-7.53 (m, 2H), 7.35-7.29 (m, 1H), 4.16-4.12 (m, 2H), 3.57-3.53 (m, 2H), 2.98 (s, 6H), 2.65 (s, 3H).

Compound 39 N-(4-(4-((2-(dimethylamino)ethyl)amino)-3-ethyl-1H-pyrazolo[3,4-d]pyrimidin-6-yl)phenyl)-2,5-difluorobenzenesulfonamide

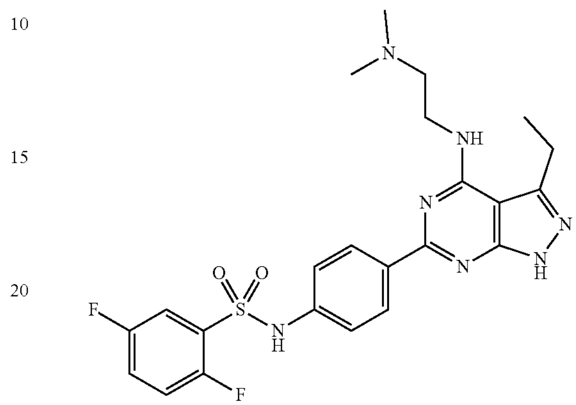

(i) 6-chloro-N-[2-(dimethylamino)ethyl]-1H-pyrazolo[3,4-d]pyrimidin-4-amine

A solution of 4,6-dichloro-1H-pyrazolo[3,4-d]pyrimidine (2.0 g, 10.5 mmol, 1.0 equiv.) and (2-aminoethyl)dimethylamine (2.72 g, 21.1 mmol, 1.0 equiv.) in anhydrous THF (20 mL) was added DIEA (1.12 g, 10.5 mmol, 1.0 equiv.) in 0° C., and stirred for 4 h at room temperature. The organic layer was worked up with $H_2O$ (20 mL), extracted with DCM (30 mL), dried over anhydrous $Na_2SO_4$, and evaporated in vacuo to provide the crude of the desired product (1.3 g, 93% purity, light yellow solid).

(ii) N-[4-(4-[[2-(dimethylamino)ethyl]amino]-1H-pyrazolo[3,4-d]pyrimidin-6-yl)phenyl]-2,5-difluorobenzenesulfonamide To the solution of 6-chloro-N-[2-(dimethylamino)ethyl]-1H-pyrazolo[3,4-d]pyrimidin-4-amine (1.3 g, 5.39 mmol, 1.0 equiv.), Pd(dppf)$Cl_2$ (788.6 mg, 1.08 mmol, 0.2 equiv.), and $Cs_2CO_3$ (2.64 mg, 8.09 mmol, 1.5 equiv.) in 1.4-dioxane (24 mL) and $H_2O$ (6 ml) was added 2,5-difluoro-N-[4-(4,4,5,5-tetramethyl-1,3,2-dioxaborolan-2-yl)phenyl]benzenesulfonamide (2.34 g, 5.93 mmol, 1.1 equiv.) under an atmosphere of nitrogen at room temperature. The reaction mixture was purged with nitrogen 3 times and stirred at 100° C. for 12 hours under nitrogen. The reaction was cooled to the room temperature and neutralized with saturated aqueous 1 N HCl to pH 7~8 and washed by DCM (3*100 mL). The combined organic phase was dried over $Na_2SO_4$ and concentrated under reduced pressure to provide the crude. Then the crude purified by HPLC chromatography to provide the desired product (350.0 mg, 90% purity, off-white solid).

(iii) N-[4-(4-[[2-(dimethylamino)ethyl]amino]-3-iodo-1H-pyrazolo[3,4-d]pyrimidin-6-yl)phenyl]-2,5-difluorobenzenesulfonamide To a stirred solution of the N-[4-(4-[[2-(dimethylamino)ethyl]amino]-1H-pyrazolo[3,4-d]pyrimidin-6-yl)phenyl]-2, 5-difluorobenzenesulfonamide (300.0 mg, 0.634 mmol, 1.0 equiv.) in HOAc (10 mL) was added NIS (143 mg, 0.634 mol, 1.0 eq), The resulting mixture was stirred for overnight at rt. The resulting mixture was concentrated under reduced pressure and diluted with water (100 mL). The residue was acidified to pH=7 with NaOH aq. (1 M). The mixture was extracted with DCM. The organic layer was dried over $Na_2SO_4$, concentrated and purified by column chromatography to give the desired product (Peak A: 90 mg, 70% purity, off-white solid; Peak B: 120 mg, 55% purity, off-white solid).

(iv) N-[4-(4-[[2-(dimethylamino)ethyl]amino]-5-ethenyl-7H-pyrrolo[2,3-d]pyrimidin-2-yl)phenyl]-2,5-difluorobenzenesulfonamide To the solution of N-[4-(4-[[2-(dimethylamino)ethyl]amino]-5-iodo-7H-pyrrolo[2,3-d]pyrimidin-2-yl)phenyl]-2,5-difluorobenzenesulfonamide (120 mg, 0.2 mmol, 1.0 equiv.), $Pd(dppf)Cl_2$ (43.9 mg, 0.06 mmol, 0.3 equiv.), and $K_2CO_3$ (55.2 mg, 0.4 mmol, 2 eq) in dioxane (4 mL) and $H_2O$ (1 ml) was added 2-ethenyl-4,4,5,5-tetramethyl-1,3,2-dioxaborolane (93 mg, 0.6 mmol, 3 equiv.) under an atmosphere of nitrogen at room temperature. The reaction mixture was purged with nitrogen 3 times and stirred at 100° C. for 18 h under nitrogen. The reaction was cooled to the room temperature and neutralized with saturated aqueous 1 N HCl to pH 7~8 and washed by DCM (3*5 mL). The combined organic phase was dried over $Na_2SO_4$ and concentrated under reduced pressure to provide the crude. Then the crude purified by reversed-phase chromatography (10 mmol/L $NH_4HCO_3$/ACN) to provide the desired product (75 mg, 50% purity, off-white solid).

(v) N-[4-(4-[[2-(dimethylamino)ethyl]amino]-5-ethyl-7H-pyrrolo[2,3-d]pyrimidin-2-yl)phenyl]-2,5-difluorobenzenesulfonamide To the solution of N-[4-(4-[[2-(dimethylamino)ethyl]amino]-5-ethenyl-7H-pyrrolo[2,3-d]pyrimidin-2-yl)phenyl]-2,5-difluorobenzenesulfonamide (75 mg, 0.15 mmol, 1.0 equiv.) in $CH_3OH$ (5 mL) and DMF (5 mL) was add Pd/C (32 mg, 0.03 mmol, 0.2 equiv.) under an atmosphere of $H_2$ at room temperature. The reaction mixture was purged with nitrogen 3 times and stirred at 25° C. for 20 h. The combined organic phase was filtrated and concentrated under reduced pressure to provide the crude. Then the crude purified by reversed-phase chromatography (Column: Xselect CSH OBD Column 30*150 mm 5 um, n; Mobile Phase A: Water (0.05% TFA), Mobile Phase B: ACN; Flow rate: 60 mL/min; Gradient: 9% B to 39% B in 9 min, 39% B; Wave Length: 254 nm; RT1 (min): 7.58; Number Of Runs: 0) to provide the desired product as a TFA salt (24 mg, 96.5% purity, white solid). LCMS (ESI, m/z): 502 $[M-2TFA+H]^+$. $^1H$ NMR (300 MHZ, DMSO-$d_6$) δ 11.10 (s, 1H), 9.49 (s, 1H), 8.33-8.24 (m, 2H), 7.76-7.49 (m, 3H), 7.29-7.18 (m, 3H), 3.97 (d, J=5.7 Hz, 2H), 3.41 (d, J=5.7 Hz, 2H), 2.98 (q, J=7.5 Hz, 2H), 2.88 (d, J=4.7 Hz, 6H), 1.28 (t, J=7.5 Hz, 3H).

Compound 40 N-(2-((6-(4-((5-chloro-2-fluorophenyl)sulfonamido)-2-methylphenyl)-3-methyl-1H-pyrazolo[3,4-d]pyrimidin-4-yl)amino)ethyl)-N-methylformamide

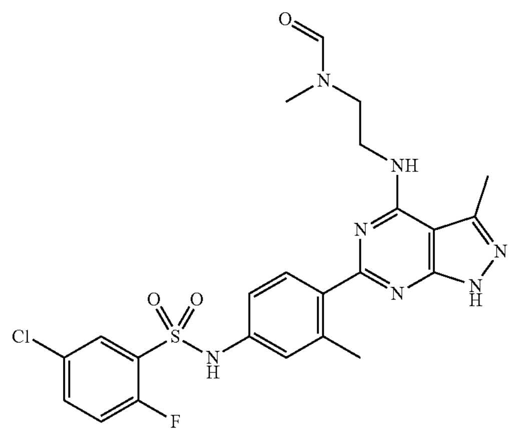 [SMILES: Cc1cc(NS(=O)(=O)c2cc(Cl)ccc2F)ccc1-c1nc(NCCN(C)C=O)c2c(C)n[nH]c2n1]

(i) tert-butyl (2-(N-methylformamido)ethyl)carbamate

A suspension of tert-butyl N-[2-(methylamino)ethyl]carbamate (2.00 g, 11.478 mmol) in ethyl formate (6 mL, 72.87 mmol) was stirred for 3 hours at 60° C. The resulting mixture was cooled, concentrated in vacuo. The residue was applied onto a silica gel column with 0-3% MeOH in DCM. This resulted in tert-butyl N-[2-(N-methylformamido)ethyl]carbamate (2.12 g, Y=82%) as yellow oil. LCMS (ESI, m/z): 203 $[M+H]^+$.

(ii) N-(2-aminoethyl)-N-methylformamide

To a solution of tert-butyl (2-(N-methylformamido)ethyl)carbamate (2.12 g, 10.50 mmol) in DCM (30 mL) was added TFA (10 mL). The resulting mixture was stirred for 16 hours at room temperature. The reaction mixture was concentrated in vacuo. This resulted in N-(2-aminoethyl)-N-methylformamide (2.00 g crude, TFA salt form) as light brown oil, which was used in the next step directly without any further purification. LCMS (ES, m/z): 103 [M+H]+

(iii) N-(2-((6-chloro-3-methyl-1H-pyrazolo[3,4-d]pyrimidin-4-yl)amino)ethyl)-N-methylformamide A mixture of 4,6-dichloro-3-methyl-1H-pyrazolo[3,4-d]pyrimidine (1.97 g, 9.54 mmol), N-(2-aminoethyl)-N-methylformamide (2.00 mg crude, TFA salt form) and DIPEA (15.7 mL, 95.4 mmol) in DCM (30 mL) was stirred for 16 hours at room temperature. The reaction mixture was concentrated in vacuo. The residue was purified by reverse phase chromatography with the following condition: (Column: Agela C18 Column, 330 g; Mobile Phase A: Water (10 mmol/L $NH_4HCO_3$), Mobile Phase B: ACN; Flow rate: 40 mL/min; Gradient: 0% B to 100% B in 20 min; 254 nm. This resulted in N-(2-((6-chloro-3-methyl-1H-pyrazolo[3,4-d]pyrimidin-4-yl)amino)ethyl)-N-methylformamide (2.05 g, Y=73%) as a light yellow solid. LCMS (ES, m/z): 269 $[M+H]^+$.

(iv) 5-chloro-2-fluoro-N-(3-methyl-4-(4,4,5,5-tetramethyl-1,3,2-dioxaborolan-2-yl)phenyl)benzenesulfonamide A mixture of 5-chloro-2-fluorobenzenesulfonyl chloride (97 mg, 0.429 mmol), pyridine (101 mg, 1.28 mmol) and 3-methyl-4-(4,4,5,5-tetramethyl-1,3,2-dioxaborolan-2-yl) aniline (100 mg, 0.429 mmol) in DCM (5 mL) was stirred for 16 hours at room temperature. The resulting mixture was concentrated in vacuo. The residue was applied onto a silica gel column with ethyl acetate/petroleum ether (1/3). This resulted in 5-chloro-2-fluoro-N-(3-methyl-4-(4,4,5,5-tetramethyl-1,3,2-dioxaborolan-2-yl)phenyl)benzenesulfonamide (148 mg, Y=81%) as a white solid. LCMS (ESI, m/z): 424 [M−1].

(v) N-(2-((6-(4-((5-chloro-2-fluorophenyl)sulfonamido)-2-methylphenyl)-3-methyl-1H-pyrazolo[3,4-d]pyrimidin-4-yl)amino)ethyl)-N-methylformamide A mixture of 5-chloro-2-fluoro-N-[3-methyl-4-(4,4,5,5-tetramethyl-1,3,2-dioxaborolan-2-yl)phenyl]benzenesulfonamide (80 mg, 0.194 mmol) N-[2-([6-chloro-3-methyl-1H-pyrazolo[3,4-d]pyrimidin-4-yl]amino)ethyl]-N-methylformamide (50 mg, 0.194 mmol), Pd(dppf) $Cl_2 \cdot CH_2Cl_2$ (15.83 mg, 0.019 mmol), and $Cs_2CO_3$ (126.63 mg, 0.389 mmol) in dioxane (2 mL) and water (0.5 mL) was stirred for 3 hours at 100° C. under nitrogen. The reaction mixture was cooled, concentrated in vacuo. The residue was purified by reverse flash chromatography with the following conditions: Column: Xselect CSH OBD Column 30*150 mm 5 um, n; Mobile Phase A: Water (0.05% TFA), Mobile Phase B: ACN; Flow rate: 60 mL/min; Gradient: 5% B to 50% B in 13 min; 254 nm; RT: 7.55. This resulted in N-[2-([6-[4-(5-chloro-2-fluorobenzenesulfonamido)-2-methylphenyl]-3-methyl-1H-pyrazolo[3,4-d]pyrimidin-4-yl]amino)ethyl]-N-methylformamide as a TFA salt (14.9 mg) as a white solid. $^1H$ NMR (400 MHZ, DMSO-$d_6$) δ 11.04 (brs, 1H), 7.92-7.80 (m, 3H), 7.75-7.73 (m, 1H), 7.55-7.49 (m, 1H), 7.11-7.04 (m, 2H), 3.76-3.65 (m, 3H), 3.64-3.59 (m, 2H), 2.94-2.71 (m, 3H), 2.67-2.58 (m, 2H), 2.51-2.42 (m, 3H). LCMS (ES, m/z): 532 $[M+H]^+$-114.

Compound 41 5-chloro-2-fluoro-N-(4-(4-(((3S,4R)-3-fluoro-1-isopropylpiperidin-4-yl)oxy)-3-methyl-1H-pyrazolo[3,4-d]pyrimidin-6-yl)phenyl)benzenesulfonamide

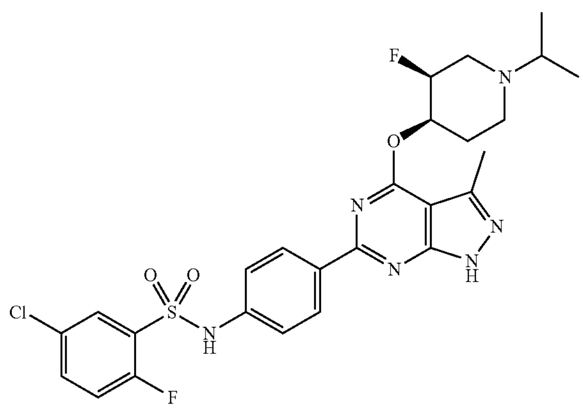 [SMILES: Cc1n[nH]c2nc(-c3ccc(NS(=O)(=O)c4cc(Cl)ccc4F)cc3)nc(O[C@@H]3CCN(C(C)C)C[C@@H]3F)c12]

(i) 5-chloro-2-fluoro-N-[4-(4-[[(3S,4R)-3-fluoro-1-isopropylpiperidin-4-yl]oxy]-3-methyl-1H-pyrazolo[3,4-d]pyrimidin-6-yl)phenyl]benzenesulfonamide To a stirred mixture of (3S,4R)-4-([6-chloro-3-methyl-1H-pyrazolo[3,4-d]pyrimidin-4-yl]oxy)-3-fluoro-1-isopropylpiperidine (50 mg, 0.153 mmol, prepared following the procedure in example 29) and (3S,4R)-4-([6-chloro-3-methyl-1H-pyrazolo[3,4-d]pyrimidin-4-yl]oxy)-3-fluoro-1-isopropylpiperidine (50 mg, 0.153 mmol) in 1,4-dioxane (3.0 mL) and $H_2O$ (1.0 mL) were added Pd(dppf) $Cl_2 \cdot CH_2Cl_2$ (13 mg, 0.015 mmol) and $Cs_2CO_3$ (100 mg, 0.306 mmol). The flask was evacuated and flushed with nitrogen for three times. The resulting mixture stirred at 100° C. for 3 hours under nitrogen. The reaction mixture was cooled to ambient temperature and filtered. The filtrate was purified by prep-HPLC with the following condition: Column: YMC-Actus Triart C18, 30 mm×150 mm, 5 um; Mobile Phase A: Water (0.05% TFA), Mobile Phase B: ACN; Flow rate: 60 mL/min; Gradient: 20% B to 50% B in 7 min; 254 nm; RT: 5.12. This resulted in afford 5-chloro-2-fluoro-N-[4-(4-[[(3S,4R)-3-fluoro-1-isopropylpiperidin-4-yl]oxy]-3-methyl-1H-pyrazolo[3,4-d]pyrimidin-6-yl)phenyl]benzenesulfonamide trifluoroacetic acid (11.3 mg, Y=11%, mixture of two enantiomers) as a white solid. $^1H$ NMR (400 MHZ, DMSO-$d_6$) δ 13.57 (s, 1H), 11.18 (s, 1H), 9.50-9.30 (m, 1H), 8.40-8.35 (m, 2H), 7.88-7.86 (m, 2H), 7.55-7.51 (m, 1H), 7.29-7.27 (m, 2H), 5.85-5.45 (m, 2H), 3.82-3.47 (m, 4H), 2.68-2.66 (m, 2H), 2.52-2.50 (m, 3H), 2.33-2.32 (m, 1H), 1.32 (d, J=6.24 Hz, 6H). LCMS (ES, m/z): 577 $[M+H]^+$-114.

Compound 42 5-chloro-2-fluoro-N-(4-(4-(((3R,4S)-4-fluoropyrrolidin-3-yl)oxy)-3-methyl-1H-pyrazolo[3,4-d]pyrimidin-6-yl)phenyl)benzenesulfonamide

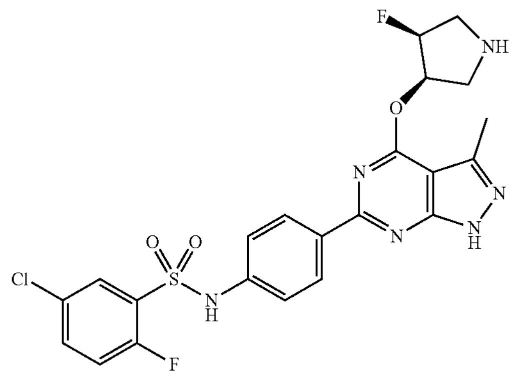 [SMILES: Cc1n[nH]c2nc(-c3ccc(NS(=O)(=O)c4cc(Cl)ccc4F)cc3)nc(O[C@@H]3CNC[C@@H]3F)c12]

This compound was prepared according to the procedure described in example 29. The desired product was obtained as a white TFA salt (40.2 mg, 99.5% purity). LCMS (ESI, m/z): 521 $[M-TFA+H]^+$. $^1H$ NMR (300 MHZ, DMSO-$d_6$) δ 13.63 (s, 1H), 11.21 (s, 1H), 9.57 (d, J=112.0 Hz, 2H), 8.41-8.32 (m, 2H), 7.92-7.77 (m, 2H), 7.53 (t, J=9.3 Hz, 1H), 7.33-7.24 (m, 2H), 5.97 (dtd, J=20.4, 7.9, 3.7 Hz, 1H), 5.82-5.56 (m, 1H), 3.98 (s, 2H), 3.76 (s, 2H), 3.68 (s, 1H), 3.43 (t, J=10.1 Hz, 1H), 2.53 (s, 3H).

Compound 43 5-chloro-2-fluoro-N-(4-(4-(((3S,4R)-3-fluoropiperidin-4-yl)oxy)-3-methyl-1H-pyrazolo[3,4-d]pyrimidin-6-yl)-3-methylphenyl)benzenesulfonamide

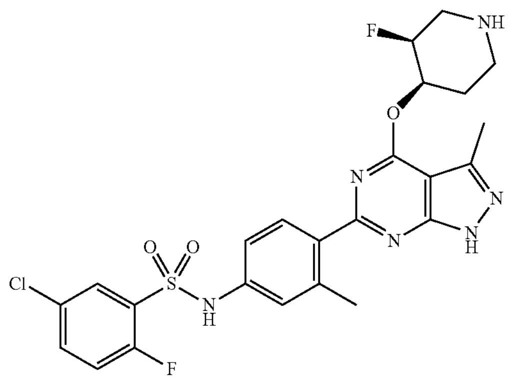 [SMILES: Cc1cc(NS(=O)(=O)c2cc(Cl)ccc2F)ccc1-c1nc(O[C@@H]2CCNC[C@@H]2F)c2c(C)n[nH]c2n1]

This compound was prepared according to the procedure described in example 29. The desired product was obtained as a white TFA salt (30.8 mg, 23%). $^1$H-NMR (CD3OD, 300 MHz) δ (ppm): 7.87-7.81 (m, 2H), 7.65-7.60 (m, 1H), 7.33-7.27 (m, 1H), 7.14-7.07 (m, 2H), 5.84-5.71 (m, 1H), 5.43-5.27 (m, 1H), 3.81-3.73 (m, 1H), 3.62-3.46 (m, 2H), 3.31-3.39 (m, 1H), 2.59 (s, 6H), 2.39 (m, 2H). LCMS (ES. m/z): 549 $[M+H]^+$.

Compound 44 (R)-5-chloro-N-(4-(4-((3,3-difluoropiperidin-4-yl)oxy)-3-methyl-1H-pyrazolo[3,4-d]pyrimidin-6-yl)phenyl)-2-fluorobenzenesulfonamide

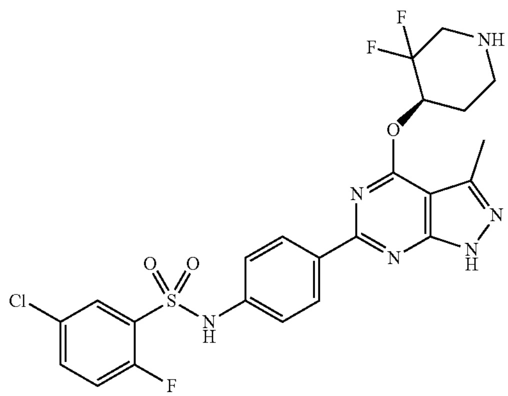 [SMILES: Cc1n[nH]c2nc(-c3ccc(NS(=O)(=O)c4cc(Cl)ccc4F)cc3)nc(O[C@@H]3CCNCC3(F)F)c12]

This compound was prepared according to the procedure described in example 29. The desired product was obtained as a white TFA salt (4.8 mg, 5%). $^1$H-NMR (CD3OD, 400 MHz) δ (ppm): 8.33 (d, J=8.7 Hz, 2H), 7.89-7.87 (m, 1H), 7.61-7.57 (m, 1H), 7.29-7.22 (m, 3H), 5.99-5.96 (m, 1H), 3.28-2.85 (m, 4H), 2.59 (s, 3H), 2.39-2.01 (m, 2H). LCMS (ES. m/z): 553 $[M+H]^+$.

Compound 45 N-(4-(4-((2-(dimethylamino)ethyl)amino)-3-methyl-1H-pyrazolo[3,4-d]pyrimidin-6-yl)phenyl)-2,5-difluorobenzenesulfonamide

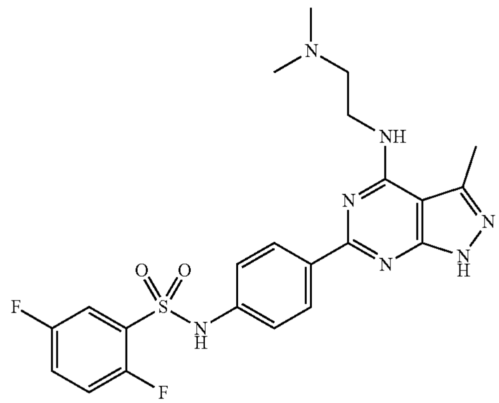 [SMILES: Cc1n[nH]c2nc(-c3ccc(NS(=O)(=O)c4cc(F)ccc4F)cc3)nc(NCCN(C)C)c12]

This compound was prepared according to the procedure described in example 9. The desired product was obtained as a white TFA salt (21.5 mg, 22%). $^1$H NMR (400 MHZ, DMSO-$d_6$): δ 13.15 (s, 1H), 11.1 (s, 1H), 9.41-9.25 (m, 1H), 8.26 (d, J=8.60 Hz, 2H), 7.66-7.72 (m, 1H), 7.62-7.55 (m, 1H), 7.54-7.47 (m, 1H), 7.22 (d, J=8.60 Hz, 2H), 3.42-3.32 (m, 2H), 3.42-3.32 (m, 2H), 2.54 (s, 3H), 1.10 (s, 6H). LCMS (ES. m/z): 488.5 $[M+H]^+$.

Compound 46 5-chloro-2-fluoro-N-(4-(4-(((3R,4S)-3-fluoropiperidin-4-yl)oxy)-3-methyl-1H-pyrazolo[3,4-d]pyrimidin-6-yl)phenyl)benzenesulfonamide

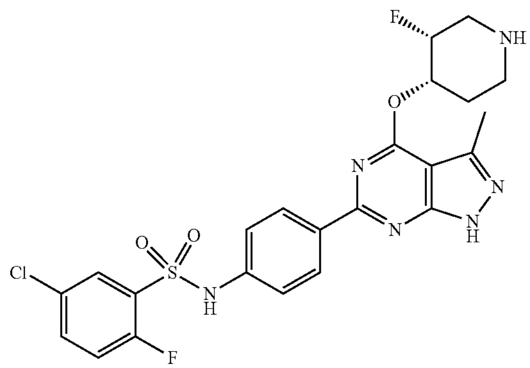 [SMILES: Cc1n[nH]c2nc(-c3ccc(NS(=O)(=O)c4cc(Cl)ccc4F)cc3)nc(O[C@H]3CCNC[C@H]3F)c12]

A solution of 4,6-dichloro-3-methyl-1H-pyrazolo[3,4-d]pyrimidine (200 mg, 0.984 mmol) and tert-butyl (3R,4S)-3-fluoro-4-hydroxypiperidine-1-carboxylate (218 mg, 0.984 mmol) in anhydrous DMF (2 mL) was added NaH (60 mg, 1.476 mmol) in 0° C., and stirred for 2 hours at room temperature. The organic layer was worked up with $H_2O$ (10 mL), extracted with DCM (15 mL), dried over anhydrous $Na_2SO_4$, and evaporated in vacuo to provide the crude of tert-butyl (3R,4S)-4-((6-chloro-3-methyl-1H-pyrazolo[3,4-d]pyrimidin-4-yl)oxy)-3-fluoropiperidine-1-carboxylate (160 mg, 85% purity, white solid). LCMS (ESI, m/z): 386 [M+H]+.

(i) tert-butyl (3R,4S)-4-((6-(4-((5-chloro-2-fluorophenyl)sulfonamido)phenyl)-3-methyl-1H-pyrazolo[3,4-d]pyrimidin-4-yl)oxy)-3-fluoropiperidine-1-carboxylate To the solution of tert-butyl (3R,4S)-4-((6-chloro-3-methyl-1H-pyrazolo[3,4-d]pyrimidin-4-yl)oxy)-3-fluoropiperidine-1-carboxylate (160 mg, 0.43 mmol, 1.0 equiv.), Pd(dppf)$Cl_2$ (63.4 mg, 0.09 mmol, 0.2 equiv.), and $Cs_2CO_3$ (212 mg, 0.65 mmol, 1.5 equiv.) in 1.4-dioxane (12 mL) and $H_2O$ (3 mL) was added 5-chloro-2-fluoro-N-(4-(4,4,5,5-tetramethyl-1,3,2-dioxaborolan-2-yl)phenyl)benzenesulfonamide (196 mg, 0.48 mmol, 1.1 equiv.) under an atmosphere of nitrogen at room temperature. The reaction mixture was purged with nitrogen 3 times and stirred at 100° C. for 16 hours under nitrogen. The reaction was cooled to the room temperature and neutralized with aqueous 1 N HCl to pH 7~8 and washed by DCM (3*20 mL). The combined organic phase was dried over $Na_2SO_4$ and concentrated under reduced pressure to provide the crude. Then the crude purified by reversed-phase chromatography (C18 column; mobile phase, MeCN in water, 10% to 36% gradient in 18 min; detector, UV 254 nm) to provide the desired product (130 mg, 48% purity, light brown solid). LCMS (ESI, m/z): 635 [M+H]+

(ii) 5-chloro-2-fluoro-N-(4-(4-(((3R,4S)-3-fluoropiperidin-4-yl)oxy)-3-methyl-1H-pyrazolo[3,4-d]pyrimidin-6-yl)phenyl)benzenesulfonamide trifluoroacetic acid A solution of tert-butyl (3R,4S)-4-((6-(4-((5-chloro-2-fluorophenyl)sulfonamido)phenyl)-3-methyl-1H-pyrazolo[3,4-d]pyrimidin-4-yl)oxy)-3-fluoropiperidine-1-carboxylate (130 mg, 0.204 mmol) in ACN (2 mL) was added $CF_3COOH$ (2 mL) in 25° C., and stirred for 10 hours at room temperature. The mixture was concentrated under reduced pressure to provide the crude. Then the crude purified by reversed-phase chromatography (Column: XBridge Shield RP18 OBD Column, 19*150 mm, 5 um; Mobile Phase A: Water (0.05% TFA), Mobile Phase B: ACN; Flow rate: 25 mL/min; Gradient: 20% B to 50% B in 9 min, 50% B; Wave Length: 254 nm; RT1 (min): 7.38; Number Of Runs: 0) to provide 5-chloro-2-fluoro-N-(4-(4-(((3R,4S)-3-fluoropiperidin-4-yl)oxy)-3-methyl-1H-pyrazolo[3,4-d]pyrimidin-6-yl)phenyl)benzenesulfonamide trifluoroacetic acid (55.8 mg, 99.5% purity, white solid). LCMS (ESI, m/z): 535 [M-TFA+H]+. $^1$H NMR (300 MHZ, DMSO-$d_6$) δ 13.56 (s, 1H), 9.11 (s, 1H), 8.44-8.31 (m, 2H), 7.93-7.72 (m, 2H), 7.53 (t, J=9.3 Hz, 1H), 7.32-7.23 (m, 2H), 6.07-5.71 (m, 1H), 5.38 (d, J=48.2 Hz, 1H), 3.71-3.47 (m, 2H), 3.35-3.23 (m, 4H), 2.58 (s, 3H), 2.26 (td, J=15.9, 15.0, 4.8 Hz, 2H).

Compound 47 5-chloro-2-fluoro-N-(4-(4-(((3S,4S)-3-fluoropiperidin-4-yl)oxy)-3-methyl-1H-pyrazolo[3,4-d]pyrimidin-6-yl)phenyl)benzenesulfonamide

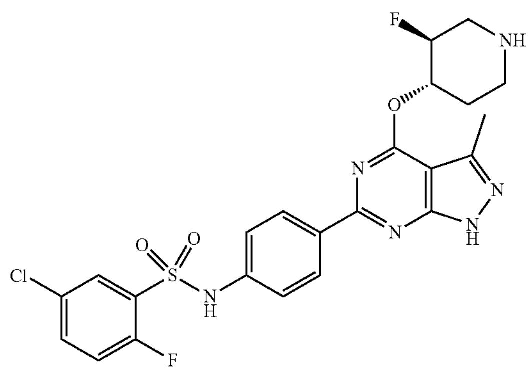 [SMILES: Cc1n[nH]c2nc(-c3ccc(NS(=O)(=O)c4cc(Cl)ccc4F)cc3)nc(O[C@H]3CCNC[C@@H]3F)c12]

This compound was prepared according to the procedure described in example 46. The desired product was obtained as a light pink TFA salt (66.5 mg, 95.8% purity). LCMS (ESI, m/z): 535 [M-TFA+H]+. $^1$H NMR (300 MHZ, DMSO-$d_6$) δ 13.56 (s, 1H), 8.39-8.28 (m, 2H), 7.89 (dd, J=6.0, 2.7 Hz, 1H), 7.80 (ddd, J=8.8, 4.2, 2.7 Hz, 1H), 7.53 (t, J=9.3 Hz, 1H), 7.35-7.23 (m, 2H), 5.95-5.82 (m, 1H), 5.30-5.02 (m, 1H), 3.69-3.49 (m, 2H), 3.27 (d, J=11.7 Hz, 4H), 2.55 (s, 3H), 2.39 (s, 1H), 2.17-2.06 (m, 1H).

Compound 48 5-chloro-2-fluoro-N-(4-{3-methyl-4-[(3S)-pyrrolidin-3-yloxy]-1H-pyrazolo[3,4-d]pyrimidin-6-yl}phenyl)benzenesulfonamide

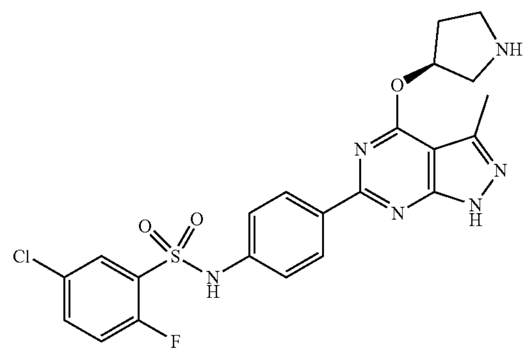 [SMILES: Cc1n[nH]c2nc(-c3ccc(NS(=O)(=O)c4cc(Cl)ccc4F)cc3)nc(O[C@H]3CCNC3)c12]

This compound was prepared according to the procedure described in example 47. The desired product was obtained as a white TFA salt (19.5 mg, Y=21%). LCMS (ES. m/z): 503 [M+H]+. $^1$H-NMR ($CD_3OD$, 300 MHZ) δ (ppm): 8.37 (d, J=8.7 Hz, 2H), 7.88-7.86 (m, 1H), 7.64-7.59 (m, 1H), 7.32-7.25 (m, 3H), 6.11 (d, J=3.0 Hz, 1H), 3.83-3.71 (m, 2H), 3.59-3.55 (m, 2H), 2.59-2.49 (m, 5H).

Compound 49 5-chloro-N-(4-{4-[(4,4-difluoropyrrolidin-3-yl)oxy]-3-methyl-1H-pyrazolo[3,4-d]pyrimidin-6-yl}phenyl)-2-fluorobenzenesulfonamide

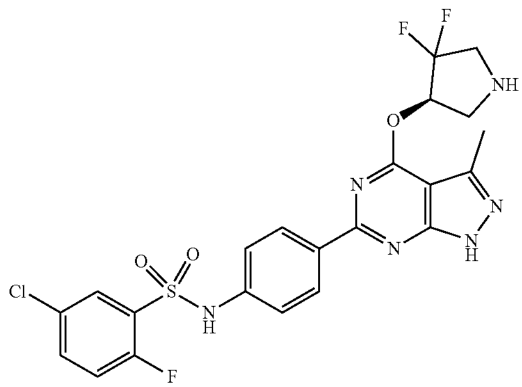 [SMILES: Cc1n[nH]c2nc(-c3ccc(NS(=O)(=O)c4cc(Cl)ccc4F)cc3)nc(O[C@@H]3CNCC3(F)F)c12]

This compound was prepared according to the procedure described in example 47. The desired product was obtained as an off-white TFA salt (12.2 mg, 98.4% purity). LCMS (ESI, m/z): 539 [M-TFA+H]+. $^1$H NMR (300 MHZ, DMSO-$d_6$) δ 13.67 (s, 1H), 11.17 (s, 1H), 10.08 (s, 1H), 8.47-8.31 (m, 2H), 7.98-7.73 (m, 2H), 7.53 (t, J=9.3 Hz, 1H), 7.29 (dd, J=9.8, 3.0 Hz, 2H), 6.34-6.07 (m, 1H), 4.15-3.87 (m, 3H), 3.78 (dt, J=13.5, 2.8 Hz, 1H), 2.56 (s, 3H).

Compound 50 5-chloro-2-fluoro-N-[4-(4-{[(3S,4R)-3-fluoro-1-(2-hydroxyethyl)piperidin-4-yl]oxy}-3-methyl-1H-pyrazolo[3,4-d]pyrimidin-6-yl)phenyl]benzenesulfonamide

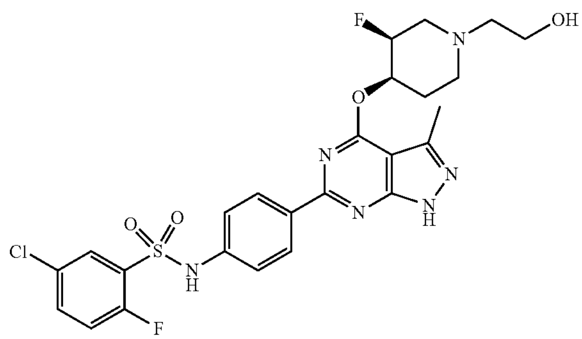 [SMILES: Cc1n[nH]c2nc(-c3ccc(NS(=O)(=O)c4cc(Cl)ccc4F)cc3)nc(O[C@@H]3CCN(CCO)C[C@@H]3F)c12]

(i) 2-[(3S,4R)-4-({6-chloro-3-methyl-1H-pyrazolo[3,4-d]pyrimidin-4-yl}oxy)-3-fluoropiperidin-1-yl]ethanol A solution of (3S,4R)-4-({6-chloro-3-methyl-1H-pyrazolo[3,4-d]pyrimidin-4-yl}oxy)-3-fluoropiperidine (150 mg, 0.499 mmol, 1.0 equiv.) and 2-bromoethanol (311 mg, 2.495 mmol, 5.0 equiv.) in anhydrous DMF (2 mL) was added DIEA (257 mg, 1.996 mmol, 4.0 equiv.), and stirred for 2 hours at room temperature. The organic layer was worked up with $H_2O$ (20 mL), extracted with DCM (20 mL), dried over anhydrous $Na_2SO_4$, and evaporated in vacuo to provide the crude. The residue was purified by reverse flash chromatography with the following conditions: column, silica gel; mobile phase, MeCN in water, 10% to 35% gradient in 18 min; detector, UV 254 nm and the purified product (120 mg, 93% purity, white solid) was obtained. LCMS (ESI, m/z): 330 [M+H]+.

(ii) 5-chloro-2-fluoro-N-[4-(4-{[(3S,4R)-3-fluoro-1-(2-hydroxyethyl)piperidin-4-yl]oxy}-3-methyl-1H-pyrazolo[3,4-d]pyrimidin-6-yl)phenyl]benzenesulfonamide To the solution of 2-[(3S,4R)-4-({6-chloro-3-methyl-1H-pyrazolo[3,4-d]pyrimidin-4-yl}oxy)-3-fluoropiperidin-1-yl]ethanol (120 mg, 0.338 mmol, 1.0 equiv.), Pd(dppf)$Cl_2$ (49.5 mg, 0.068 mmol, 0.2 eq), and $Cs_2CO_3$ (165 mg, 0.51 mmol, 1.5 eq) in 1.4-dioxane (8 mL) and $H_2O$ (2 mL) was added 5-chloro-2-fluoro-N-(4-(4,4,5,5-tetramethyl-1,3,2-dioxaborolan-2-yl)phenyl)benzenesulfonamide (170 mg, 0.37 mmol, 1.1 eq) under an atmosphere of nitrogen at room temperature. The reaction mixture was purged with nitrogen 3 times and stirred at 100° C. for 16 hours under nitrogen. The reaction was cooled to the room temperature and neutralized with saturated aqueous 1 N HCl to pH 7~8 and washed by DCM (3*20 mL). The combined organic phase was dried over $Na_2SO_4$ and concentrated under reduced pressure to provide the crude. Then the crude purified by reversed-phase chromatography (Column: Xselect CSH OBD Column 30*150 mm 5 um, n; Mobile Phase A: Water (0.05% TFA), Mobile Phase B: ACN; Flow rate: 60 mL/min; Gradient: 18% B to 28% B in 13 min, 28% B; Wave Length: 254 nm; RT1 (min): 11.52; Number Of Runs: 0) to provide 5-chloro-2-fluoro-N-[4-(4-{[(3S,4R)-3-fluoro-1-(2-hydroxyethyl)piperidin-4-yl]oxy}-3-methyl-1H-pyrazolo[3,4-d]pyrimidin-6-yl)phenyl]benzenesulfonamide; trifluoroacetic acid (34.6 mg, 99.5% purity, yellow solid). LCMS (ESI, m/z): 579 [M-TFA+H]+. $^1$H NMR (300 MHZ, Methanol-d4) δ 8.46-8.34 (m, 2H), 7.91 (dd, J=6.1, 2.7 Hz, 1H), 7.65 (ddd, J=8.9, 4.2, 2.7 Hz, 1H), 7.41-7.26 (m, 3H), 5.97 (dt, J=27.9, 7.9 Hz, 1H), 5.50 (d, J=48.0 Hz, 1H), 4.22-3.40 (m, 8H), 2.65 (s, 3H), 2.54 (d, J=7.7 Hz, 2H).

Compound 51 5-chloro-2-fluoro-N-[4-(4-{[1-(2-hydroxyethyl)piperidin-4-yl]oxy}-3-methyl-1H-pyrazolo[3,4-d]pyrimidin-6-yl)phenyl]benzenesulfonamide

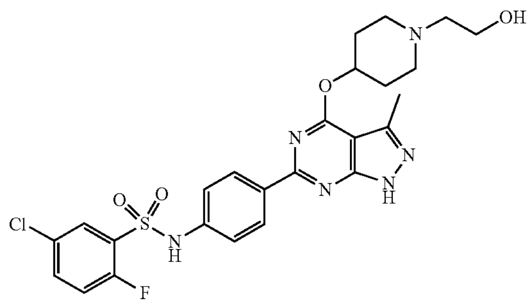 [SMILES: Cc1n[nH]c2nc(-c3ccc(NS(=O)(=O)c4cc(Cl)ccc4F)cc3)nc(OC3CCN(CCO)CC3)c12]

(i) tert-butoxy[4-({6-chloro-3-methyl-1H-pyrazolo[3,4-d]pyrimidin-4-yl}oxy)piperidin-1-yl]methanol A solution of 4,6-dichloro-3-methyl-1H-pyrazolo[3,4-d]pyrimidine (300 mg, 1.404 mmol, 1.0 eq) and tert-butyl 4-hydroxypiperidine-1-carboxylate (339 mg, 1.685 mmol, 1.2 equiv.) in anhydrous DMF (2 mL) was added NaH (84.22 mg, 2.106 mmol, 3.0 equiv.) in 0° C., and stirred for 2 hours at room temperature. The organic layer was worked up with $H_2O$ (10 mL), extracted with DCM (15 mL), dried over anhydrous $Na_2SO_4$, and evaporated in vacuo to provide the crude of tert-butoxy[4-({6-chloro-3-methyl-1H-pyrazolo[3,4-d]pyrimidin-4-yl}oxy)piperidin-1-yl]methanol (230 mg, 75% purity, orange oil). LCMS (ESI, m/z): 368 [M+H]+.

(ii) 4-({6-chloro-3-methyl-1H-pyrazolo[3,4-d]pyrimidin-4-yl}oxy)piperidine

A solution of tert-butyl 4-({6-chloro-3-methyl-1H-pyrazolo[3,4-d]pyrimidin-4-yl}oxy)piperidine-1-carboxylate (230 mg, 0.470 mmol, 1.0 eq) in ACN (3 mL) was added $CF_3COOH$ (3 mL), and stirred for 16 hours at room temperature. The mixture was concentrated under reduced pressure to provide the crude. Then the crude purified by reversed-phase chromatography with the following conditions: C18 column; mobile phase, MeCN in water, 10% to 35% gradient in 15 min; detector, UV 254 nm to provide the desired product (150 mg, 90% purity, white solid). LCMS (ESI, m/z): 268 [M+H]+.

(iii) 2-[4-({6-chloro-3-methyl-1H-pyrazolo[3,4-d]pyrimidin-4-yl}oxy)piperidin-1-yl]ethanol A solution of 4-({6-chloro-3-methyl-1H-pyrazolo[3,4-d]pyrimidin-4-yl}oxy)piperidine (150 mg, 0.504 mmol, 1.0 equiv.) and 2-bromoethanol (315 mg, 2.520 mmol, 5.0 equiv.) in anhydrous DMF (2 mL) was added DIEA (260 mg, 2.016 mmol, 4.0 equiv.), and stirred for 16 hours at room temperature. The organic layer was worked up with $H_2O$ (20 mL), extracted with DCM (20 mL), dried over anhydrous $Na_2SO_4$, and evaporated in vacuo to provide the crude. The residue was purified by reverse flash chromatography with the following conditions: column, silica gel; mobile phase, MeCN in water, 10% to 37% gradient in 15 min; detector, UV 254 nm and the purified product (130 mg, 94% purity, white solid) was obtained. LCMS (ESI, m/z): 312 [M+H]+.

(iv) 5-chloro-2-fluoro-N-[4-(4-{[1-(2-hydroxyethyl)piperidin-4-yl]oxy}-3-methyl-1H-pyrazolo[3,4-d]pyrimidin-6-yl)phenyl]benzenesulfonamide To the solution of 2-[4-({6-chloro-3-methyl-1H-pyrazolo[3,4-d]pyrimidin-4-yl}oxy)piperidin-1-yl]ethanol (130 mg, 0.392 mmol), Pd(dppf)Cl2 (57.3 mg, 0.078 mmol), and Cs2CO3 (127.7 mg, 0.392 mmol) in 1.4-dioxane (8 mL) and $H_2O$ (2 mL) was added the boronic acid (233 mg, 0.51 mmol, 1.3 eq) under an atmosphere of nitrogen at room temperature. The reaction mixture was purged with nitrogen 3 times and stirred at 100° C. for 16 hours under nitrogen. The reaction was cooled to the room temperature and neutralized with aqueous 1 N HCl to pH 7~8 and washed by DCM (3*20 mL). The combined organic phase was dried over $Na_2SO_4$ and concentrated under reduced pressure to provide the crude. Then the crude purified by reversed-phase chromatography (Column: YMC-Actus Triart C18 ExRS, 30*150 mm, 5 um; Mobile Phase A: Water (0.05% TFA), Mobile Phase B: ACN; Flow rate: 60 mL/min; Gradient: 20% B to 25% B in 16 min, 25% B; Wave Length: 254 nm; RT1 (min): 12.55) to provide the desired product (39.9 mg, 99.9% purity, white solid). LCMS (ESI, m/z): 561 [M+H]+. 1H NMR (300 MHZ, Methanol-d4) δ 8.43-8.32 (m, 2H), 7.89 (dd, J=6.1, 2.6 Hz, 1H), 7.68-7.58 (m, 1H), 7.30 (dd, J=14.3, 8.8 Hz, 3H), 5.98-5.57 (m, 1H), 3.95 (dd, J=6.3, 4.0 Hz, 2H), 3.74 (dd, J=43.1, 12.8 Hz, 2H), 3.38 (t, J=5.3 Hz, 4H), 2.70-2.12 (m, 7H).

Compound 52 5-chloro-2-fluoro-N-[4-(4-{[1-(2-hydroxyethyl)pyrrolidin-3-yl]oxy}-3-methyl-1H-pyrazolo[3,4-d]pyrimidin-6-yl)phenyl]benzenesulfonamide

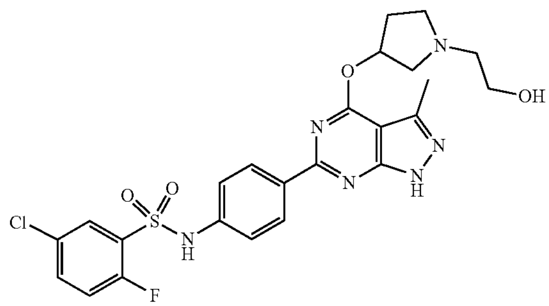 [SMILES: Cc1n[nH]c2nc(-c3ccc(NS(=O)(=O)c4cc(Cl)ccc4F)cc3)nc(OC3CCN(CCO)C3)c12]

This compound was prepared according to the procedure described in example 51. The desired product was obtained as a white free base (9.1 mg, 99.3% purity, white solid). LCMS (ESI, m/z): 547 [M+H]+. $^1$H NMR (300 MHZ, DMSO-$d_6$) δ 13.42 (s, 1H), 8.34-8.21 (m, 2H), 7.85 (dd, J=6.0, 2.7 Hz, 1H), 7.77-7.68 (m, 1H), 7.46 (t, J=9.3 Hz, 1H), 7.25-7.15 (m, 2H), 5.73 (td, J=6.8, 3.3 Hz, 1H), 4.58 (s, 1H), 3.52 (d, J=7.0 Hz, 2H), 3.16 (dd, J=11.3, 6.3 Hz, 1H), 2.98-2.85 (m, 2H), 2.64 (t, J=6.1 Hz, 3H), 2.47-2.35 (m, 4H), 2.09-1.92 (m, 1H).

Compound 53 5-chloro-2-fluoro-N-[4-(4-{[(3R,4R)-3-fluoropiperidin-4-yl]oxy}-3-methyl-1H-pyrazolo[3,4-d]pyrimidin-6-yl)phenyl]benzenesulfonamide

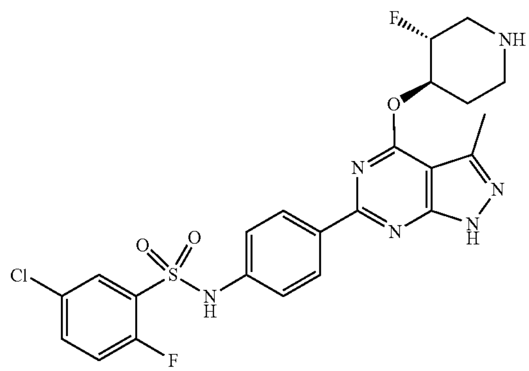 [SMILES: Cc1n[nH]c2nc(-c3ccc(NS(=O)(=O)c4cc(Cl)ccc4F)cc3)nc(O[C@@H]3CCNC[C@H]3F)c12]

This compound was prepared according to the procedure described in example 47. The desired product was obtained as a white TFA Salt (16.8 mg, 54%). LCMS (ES. m/z): 535 [M+H]+. $^1$H-NMR (DMSO-$d_6$, 300 MHZ) δ (ppm): 13.55 (s, 1H), 9.28 (s, 1H), 8.33 (d, J=8.7 Hz, 2H), 7.89-7.78 (m, 2H), 7.55-7.49 (m, 1H), 7.28 (d, J=8.7 Hz, 2H), 5.87 (s, 1H), 5.26-5.09 (m, 1H), 3.70-3.27 (m, 4H), 3.62 (s, 3H), 2.27 (s, 2H), 2.14-2.08 (m, 1H).

Compound 54 5-chloro-N-[4-(4-{[(3S,4R)-1-ethyl-3-fluoropiperidin-4-yl]oxy}-3-methyl-1H-pyrazolo[3,4-d]pyrimidin-6-yl)phenyl]-2-fluorobenzenesulfonamide

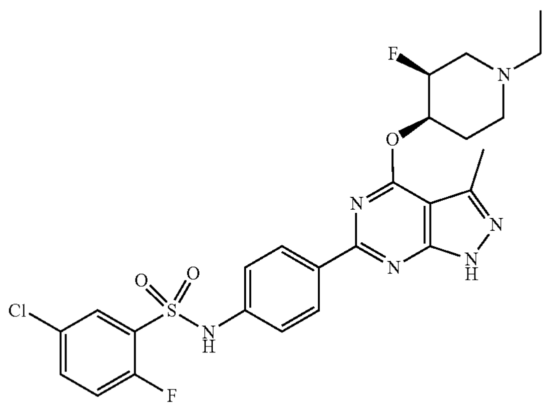 [SMILES: CCN1CC[C@@H](Oc2nc(-c3ccc(NS(=O)(=O)c4cc(Cl)ccc4F)cc3)nc3[nH]nc(C)c23)[C@@H](F)C1]

(i) tert-butyl (3S,4R)-4-([6-chloro-3-methyl-1H-pyrazolo[3,4-d]pyrimidin-4-yl]oxy)-3-fluoropiperidine-1-carboxylate Into a 50-mL round-bottom flask, was placed 4,6-dichloro-3-methyl-1H-pyrazolo[3,4-d]pyrimidine (300.00 mg, 1.478 mmol, 1.00 equiv.), THF (15.00 mL), tert-butyl (3S,4R)-3-fluoro-4-hydroxypiperidine-1-carboxylate (323.98 mg, 1.478 mmol, 1.00 equiv.). The resulting solution was stirred for 30 min at room temperature. Then added NaH (177.30 mg, 4.433 mmol, 3 equiv., 60%) at 0° C. The resulting solution was stirred for 2 hr at room temperature. The resulting mixture was concentrated. The solid was washed with ethylether. The solids were collected by filtration. This resulted in 280 mg (44.20%) of tert-butyl (3S,4R)-4-([6-chloro-3-methyl-1H-pyrazolo[3,4-d]pyrimidin-4-yl]oxy)-3-fluoropiperidine-1-carboxylate as a yellow solid. LCMS (ES. m/z): 386 [M+H]+.

(ii) (3S,4R)-4-([6-chloro-3-methyl-1H-pyrazolo[3,4-d]pyrimidin-4-yl]oxy)-3-fluoropiperidine hydrochloride Into a 50-mL round-bottom flask, was placed tert-butyl (3S,4R)-4-([6-chloro-3-methyl-1H-pyrazolo[3,4-d]pyrimidin-4-yl]oxy)-3-fluoropiperidine-1-carboxylate (280.00 mg, 0.726 mmol, 1.00 equiv.), DCM (6.00 mL), HCl (4M in 1,4-dioxane) (6.00 mL, 105.105 mmol, 115.86 equiv.). The resulting solution was stirred for 2 hr at room temperature. The resulting mixture was concentrated. This resulted in 200 mg (76.99%) of the desired compound as a white solid. LCMS (ES. m/z): 286 [M+H]+.

(iii) (3S,4R)-4-({6-chloro-3-methyl-1H-pyrazolo[3,4-d]pyrimidin-4-yl}oxy)-1-ethyl-3-fluoropiperidine A solution of (3S,4R)-4-({6-chloro-3-methyl-1H-pyrazolo[3,4-d]pyrimidin-4-yl}oxy)-3-fluoropiperidine hydrochloride (180 mg, 0.559 mmol, 1.00 equiv.), MeOH (6 mL, 148.193 mmol, 265.24 equiv.), Acetaldehyde (49.23 mg, 1.118 mmol, 2 equiv.), AcOH (33.55 mg, 0.559 mmol, 1.00 equiv.), $H_2O$ (0.5 mL, 27.754 mmol, 49.68 equiv.) was stirred for 30 min at room temperature. $NaBH_3CN$ (70.22 mg, 1.118 mmol, 2 equiv.) was added and the mixture was stirred for 3 h at 60° C. Then added $NaBH_3CN$ (70.22 mg, 1.118 mmol, 2 equiv.) was stirred for 16 h at 60° C. The mixture was allowed to cool down to room temperature. The reaction was quenched with Water. The resulting mixture was extracted with EtOAc (3×30 mL), dried over anhydrous $Na_2SO_4$. After filtration, the filtrate was concentrated under reduced pressure. The residue was purified by Prep-TLC (CH2Cl2/MeOH 15:1) to afford the desired product (100 mg, 51.34%) as a yellow oil. LCMS (ES. m/z): 314 [M+H]+.

(iv) 5-chloro-N-[4-(4-{[(3S,4R)-1-ethyl-3-fluoropiperidin-4-yl]oxy}-3-methyl-1H-pyrazolo[3,4-d]pyrimidin-6-yl)phenyl]-2-fluorobenzenesulfonamide A solution of (3S,4R)-4-({6-chloro-3-methyl-1H-pyrazolo[3,4-d]pyrimidin-4-yl}oxy)-1-ethyl-3-fluoropiperidine (100 mg, 0.319 mmol, 1.00 equiv.), 5-chloro-2-fluoro-N-[4-(4,4,5,5-tetramethyl-1,3,2-dioxaborolan-2-yl)phenyl]benzenesulfonamide (144.33 mg, 0.351 mmol, 1.1 equiv.), Pd(dppf)Cl2 (46.64 mg, 0.064 mmol, 0.2 equiv.), $Cs_2CO_3$ (155.77 mg, 0.479 mmol, 1.5 equiv.) and $Cs_2CO_3$ (155.77 mg, 0.479 mmol, 1.5 equiv.) in dioxane (4 mL, 47.216 mmol, 148.15 equiv.), $H_2O$ (1 mL, 55.508 mmol, 174.16 equiv.) was stirred for 16 h at 100° C. under nitrogen atmosphere. The mixture was allowed to cool down to room temperature. The resulting mixture was concentrated under vacuum. The sloid was purified by flash with the following conditions (Column, C18 (40 g); mobile phase A: Water-10 mM NH4HCO3, mobile phase B: Acetonitrile; Flow rate: 40 mL/min; Gradient 60 B to 65 B; 254 nm). Then The crude product was purified by Prep-HPLC with the following conditions (Column: Xselect CSH OBD Column 30×150 mm 5 um, n; Mobile Phase A: Water (0.05% TFA), Mobile Phase B: ACN; Flow rate: 60 mL/min; Gradient: 20% B to 35% B in 9 min, 35% B; Wave Length: 254 nm; RT1 (min): 7.48) to afford the desired product (19.3 mg, 8.91%) as a white solid. LCMS (ES. m/z): 563 [M+H]+. $^1$H-NMR ($CD_3OD$, 300 MHz) δ (ppm): 7.58 (d, J=8.7 Hz, 2H), 7.09-7.06 (m, 1H), 6.85-6.82 (m, 1H), 6.23-6.46 (m, 3H), 4.92-5.13 (m, 1H), 4.76-4.60 (m, 1H), 3.21 (d, J=9.3 Hz, 1H), 2.26-3.02 (m, 5H), 1.79-1.64 (m, 5H), 0.66-0.61 (m, 3H).

Compound 55 5-chloro-2-fluoro-N-{4-[3-methyl-4-(piperidin-4-yloxy)-1H-pyrazolo[3,4-d]pyrimidin-6-yl]phenyl}benzenesulfonamide

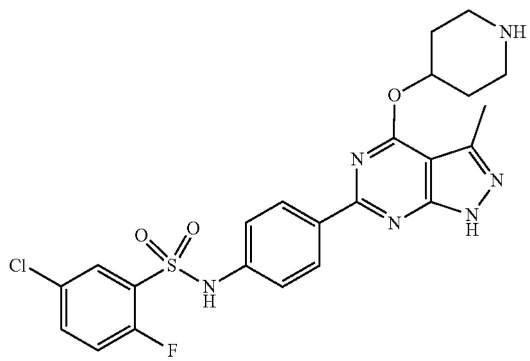 [SMILES: Cc1n[nH]c2nc(-c3ccc(NS(=O)(=O)c4cc(Cl)ccc4F)cc3)nc(OC3CCNCC3)c12]

This compound was prepared according to the procedure described in example 47. The desired product was obtained as a white TFA Salt (3.4 mg, 8.29%). LCMS (ES. m/z): 517 [M+H]+. $^1$H-NMR (300 MHZ, DMSO-$d_6$) δ (ppm): 13.49 (s, 1H), 11.16 (s, 1H), 8.67-8.41 (m, 2H), 8.33 (d, J=9.0 Hz, 2H), 7.82-7.78 (m, 2H), 7.56-7.49 (m, 1H), 7.27 (d, J=8.7 Hz, 2H), 5.74-5.71 (m, 1H), 3.58-3.48 (m, 4H), 2.59 (s, 3H), 2.13-2.25 (m, 2H), 1.96-2.05 (m, 2H).

Compound 56 5-chloro-N-[4-(4-{[(3R,4S)-1-ethyl-4-fluoropyrrolidin-3-yl]oxy}-3-methyl-1H-pyrazolo[3,4-d]pyrimidin-6-yl)phenyl]-2-fluorobenzenesulfonamide

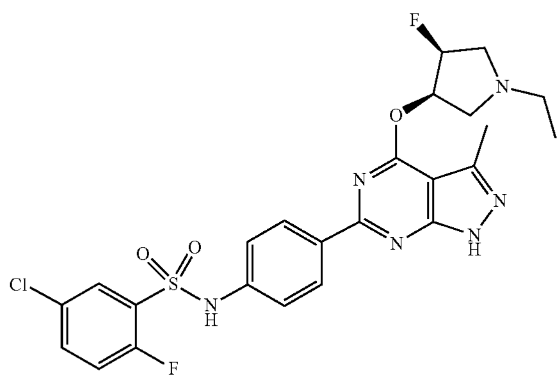 [SMILES: CCN1C[C@H](F)[C@H](Oc2nc(-c3ccc(NS(=O)(=O)c4cc(Cl)ccc4F)cc3)nc3[nH]nc(C)c23)C1]

This compound was prepared according to the procedure described in example 47. The desired product was obtained as an off white TFA Salt (20.9 mg, 9.41%). LCMS (ES. m/z): 549 [M+H]+. $^1$H-NMR ($CD_3OD$, 300 MHZ) δ (ppm): 8.40-8.37 (m, 2H), 7.88-7.85 (m, 1H), 7.64-7.59 (m, 1H), 7.32-7.26 (m, 3H), 6.16-6.10 (m, 1H), 5.85-5.68 (m, 1H), 3.65-4.23 (m, 4H), 3.48-3.41 (m, 2H), 2.61 (s, 3H), 1.44-1.39 (m, 3H).

Compound 57 5-chloro-2-fluoro-N-[4-(4-{[(3R,4S)-4-fluoro-1-isopropylpyrrolidin-3-yl]oxy}-3-methyl-1H-pyrazolo[3,4-d]pyrimidin-6-yl)phenyl]benzenesulfonamide

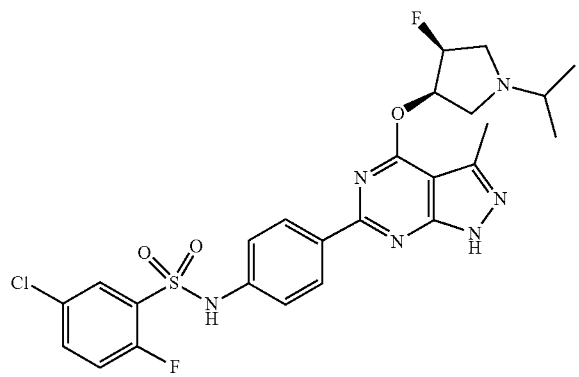 [SMILES: Cc1n[nH]c2nc(-c3ccc(NS(=O)(=O)c4cc(Cl)ccc4F)cc3)nc(O[C@@H]3CN(C(C)C)C[C@@H]3F)c12]

(i) (3R,4S)-3-({6-chloro-3-methyl-1H-pyrazolo[3,4-d]pyrimidin-4-yl}oxy)-4-fluoro-1-isopropylpyrrolidine To a solution of (3R,4S)-3-({6-chloro-3-methyl-1H-pyrazolo[3,4-d]pyrimidin-4-yl}oxy)-4-fluoropyrrolidin hydrochloride (200 mg, 0.649 mmol, 1.00 equiv.) in MeOH (10.00 mL, 246.97 mmol, 380.54 equiv.) was added acetone (376.97 mg, 6.490 mmol, 10 equiv.) The mixture was stirred for 30 min. $NaBH_3CN$ (81.58 mg, 1.298 mmol, 2 equiv.) was added and the mixture was stirred for 16 h at rt. The resulting mixture was concentrated under reduced pressure. The crude product was purified by flash with the following conditions (Column, C18 (80 g); mobile phase A: Water-10 mM $NH_4HCO_3$, mobile phase B: Acetonitrile; Flow rate: 50 mL/min; Gradient 48 B to 60 B; 254 nm) to afford the desired product (120 mg, 53.03%) as a yellow oil. LCMS (ES. m/z): 314 [M+H]+.

(ii) 5-chloro-2-fluoro-N-[4-(4-{[(3R,4S)-4-fluoro-1-isopropylpyrrolidin-3-yl]oxy}-3-methyl-1H-pyrazolo[3,4-d]pyrimidin-6-yl)phenyl]benzenesulfonamide A solution of (3R,4S)-3-({6-chloro-3-methyl-1H-pyrazolo[3,4-d]pyrimidin-4-yl}oxy)-4-fluoro-1-isopropylpyrrolidine (120 mg, 0.382 mmol, 1.00 equiv.), 5-chloro-2-fluoro-N-[4-(4,4,5,5-tetramethyl-1,3,2-dioxaborolan-2-yl)phenyl]benzenesulfonamide (173.20 mg, 0.420 mmol, 1.1 equiv.), $Pd(dppf)Cl_2$ (55.97 mg, 0.076 mmol, 0.2 equiv.) and $Cs_2CO_3$ (186.92 mg, 0.573 mmol, 1.5 equiv.) in dioxane (2.40 mL, 28.295 mmol, 74.07 equiv.), $H_2O$ (0.60 mL, 33.265 mmol, 87.08 equiv.) was stirred for 16 h at 100° C. under nitrogen atmosphere. The resulting mixture was concentrated under reduced pressure. The solid was purified by flash with the following conditions (Column, C18 (80 g); mobile phase A: Water-10 mM NH4HCO3, mobile phase B: Acetonitrile; Flow rate: 50 mL/min; Gradient 65 B to 72 B; 254 nm). The crude product was purified by Prep-HPLC with the following conditions (Column: Kinetex EVO C18 Column, 30×150, 5 um; Mobile Phase A: Water (0.05% TFA), Mobile Phase B: ACN; Flow rate: 60 mL/min; Gradient: 20% B to 40% B in 9 min, 40% B; Wave Length: 254 nm; RT1 (min): 6.78; Number Of Runs: 0) to afford (26.1 mg, 10.00%) as an off-white solid. LCMS (ES. m/z): 563 [M+H]+. $^1$H-NMR ($CD_3OD$, 300 MHZ) δ (ppm): 8.37 (d, J=8.7 Hz, 2H), 7.88-7.85 (m, 1H), 7.64-7.58 (m, 1H), 7.31-7.25 (m, 3H), 6.13-6.08 (m, 1H), 5.84-5.66 (m, 1H), 4.07-3.59 (m, 5H), 2.59 (s, 3H), 1.47-1.44 (m, 6H).

Compound 58 5-chloro-2-fluoro-N-[4-(4-{[(3R,4S)-4-fluoro-1-methylpyrrolidin-3-yl]oxy}-3-methyl-1H-pyrazolo[3,4-d]pyrimidin-6-yl)phenyl]benzenesulfonamide

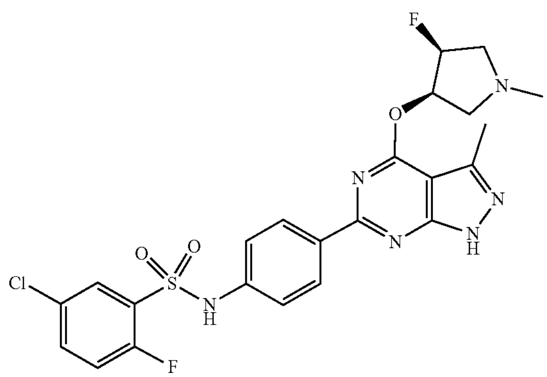 [SMILES: Cc1n[nH]c2nc(-c3ccc(NS(=O)(=O)c4cc(Cl)ccc4F)cc3)nc(O[C@@H]3CN(C)C[C@@H]3F)c12]

This compound was prepared according to the procedure described in example 57. The desired product was obtained as an off white TFA Salt (14.3 mg, Y=6.95%). LCMS (ES. m/z): 535 [M+H]+. $^1$H-NMR ($CD_3OD$, 300 MHZ) δ (ppm): 8.38 (d, J=8.7 Hz, 2H), 7.88-7.85 (m, 1H), 7.65-7.59 (m, 1H), 7.32-7.26 (m, 3H), 6.18-6.08 (m, 1H), 5.86-5.68 (m, 1H), 4.13-3.52 (m, 4H), 3.07 (s, 3H), 2.61 (s, 3H).

Compound 59 5-chloro-N-[4-(4-{[(4R)-1-ethyl-3,3-difluoropiperidin-4-yl]oxy}-3-methyl-1H-pyrazolo[3,4-d]pyrimidin-6-yl)phenyl]-2-fluorobenzenesulfonamide

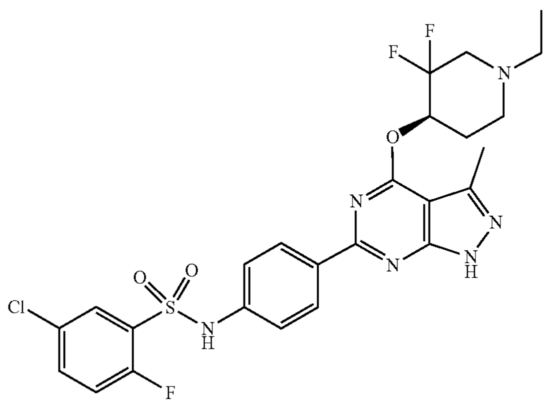 [SMILES: CCN1CC[C@@H](Oc2nc(-c3ccc(NS(=O)(=O)c4cc(Cl)ccc4F)cc3)nc3[nH]nc(C)c23)C(F)(F)C1]

This compound was prepared according to the procedure described in example 57. The desired product was obtained as a white TFA Salt (29.9 mg, Y=10.92%) LCMS (ES. m/z): 581 [M+H]+. $^1$H-NMR ($CD_3OD$, 300 MHZ) δ (ppm): 8.38 (d, J=8.7 Hz, 2H), 7.89-7.86 (m, 1H), 7.64-7.59 (m, 1H), 7.31-7.25 (m, 3H), 6.22-6.15 (m, 1H), 3.94 (s, 2H), 3.54-3.36 (m, 4H), 2.62-2.51 (m, 5H), 1.46-1.41 (m, 3H).

Compound 60 5-chloro-N-[4-(4-{[(4R)-3,3-difluoro-1-methylpiperidin-4-yl]oxy}-3-methyl-1H-pyrazolo[3,4-d]pyrimidin-6-yl)phenyl]-2-fluorobenzenesulfonamide

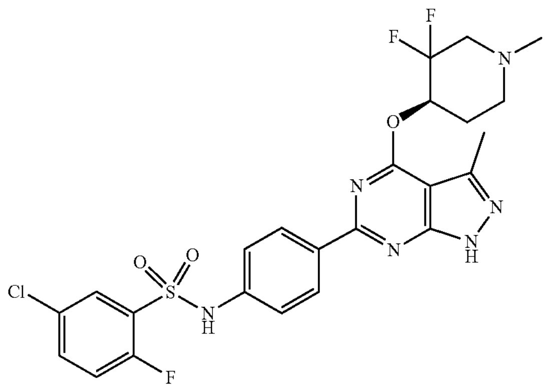 [SMILES: Cc1n[nH]c2nc(-c3ccc(NS(=O)(=O)c4cc(Cl)ccc4F)cc3)nc(O[C@@H]3CCN(C)CC3(F)F)c12]

This compound was prepared according to the procedure described in example 57. The desired product was obtained as a white TFA Salt (16.3 mg, 12.55%). LCMS (ES. m/z): 567 [M+H]+. $^1$H-NMR ($CD_3OD$, 300 MHZ) δ (ppm): 8.39-8.36 (m, 2H), 7.89-7.86 (m, 1H), 7.64-7.60 (m, 1H), 7.31-7.25 (m, 3H), 6.19-6.12 (m, 1H), 3.97-3.89 (m, 2H), 3.53 (s, 2H), 3.06 (s, 3H), 2.62-2.52 (m, 5H).

Compound 61 5-chloro-2-fluoro-N-[4-(4-{[(3R,4S)-4-fluoro-1-(2-hydroxyethyl)pyrrolidin-3-yl]oxy}-3-methyl-1H-pyrazolo[3,4-d]pyrimidin-6-yl)phenyl]benzenesulfonamide

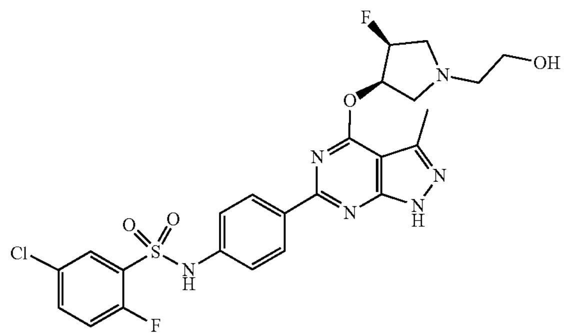 [SMILES: Cc1n[nH]c2nc(-c3ccc(NS(=O)(=O)c4cc(Cl)ccc4F)cc3)nc(O[C@@H]3CN(CCO)C[C@@H]3F)c12]

This compound was prepared according to the procedure described in example 50. The desired product was obtained as a white TFA Salt (12.7 mg, 7.22%). LCMS (ES. m/z): 565 [M+H]+. $^1$H-NMR ($CD_3OD$, 400 MHZ) δ (ppm): 8.38 (d, J=8.8 Hz, 2H), 7.88-7.86 (m, 1H), 7.64-7.60 (m, 1H), 7.31-7.26 (m, 3H), 6.13-6.08 (m, 1H), 5.82-5.69 (m, 1H), 4.15-4.07 (m, 2H), 3.93-3.78 (m, 4H), 3.55-3.50 (m, 2H), 2.61 (s, 3H).

Compound 62 N-[4-(4-{[(3S,4R)-3-fluoro-1-methylpiperidin-4-yl]oxy}-3-methyl-1H-pyrazolo[3,4-d]pyrimidin-6-yl)phenyl]-4-methoxypyridine-2-sulfonamide

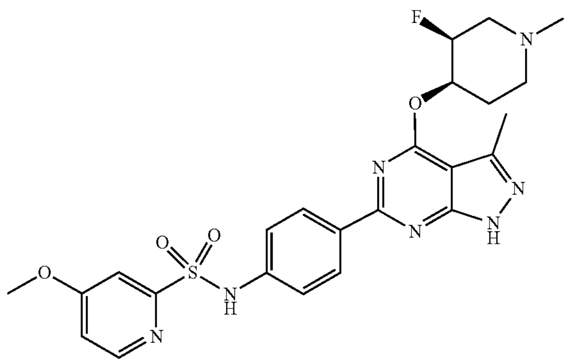

This compound was prepared according to the procedure described in example 57. The desired product was obtained as a white solid and a TFA salt (52.2 mg, 26.58%). 1H-NMR (DMSO-$d_6$, 300 MHZ) δ (ppm): 10.92 (s, 1H), 9.94 (s, 1H), 8.52 (d, J=5.7 Hz, 1H), 8.30 (d, J=9.0 Hz, 2H), 7.53 (d, J=2.4 Hz, 1H), 7.32-7.21 (m, 3H), 5.67-5.94 (m, 1H), 5.53-5.37 (m, 1H), 3.91 (s, 3H), 3.76-3.42 (m, 4H), 2.87 (s, 3H), 2.58 (s, 3H), 2.48-2.19 (m, 2H). LCMS (ES. m/z): 528 [M+H]+.

Compound 63 N-[4-(4-{[(3S,4R)-3-fluoro-1-methylpiperidin-4-yl]oxy}-3-methyl-1H-pyrazolo[3,4-d]pyrimidin-6-yl)phenyl]-4-(trifluoromethyl)pyridine-2-sulfonamide

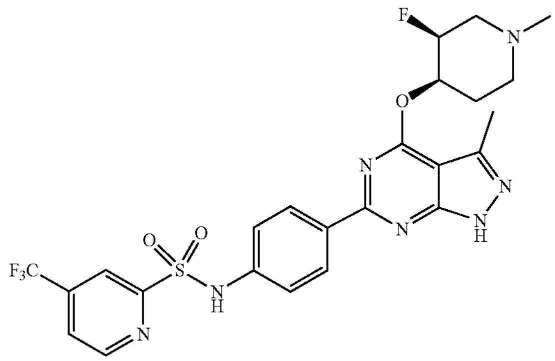 [SMILES: Cc1n[nH]c2nc(-c3ccc(NS(=O)(=O)c4cc(C(F)(F)F)ccn4)cc3)nc(O[C@@H]3CCN(C)C[C@@H]3F)c12]

This compound was prepared according to the procedure described in example 57. The desired product was obtained as a white solid and a TFA salt (34.1 mg, 16.5%). 1H-NMR ($DMSO-d_6$, 300 MHZ) δ (ppm): 13.56 (s, 1H), 11.15 (s, 1H), 9.95 (s, 1H), 9.03 (d, J=4.8 Hz, 2H), 8.34-8.12 (m, 4H), 7.33 (d, J=8.7 Hz, 1H), 5.62-5.97 (m, 1H), 5.53-5.29 (m, 1H), 3.92-3.43 (m, 4H), 2.95 (s, 3H), 2.59 (s, 3H), 2.47-2.23 (m, 2H). LCMS (ES. m/z): 566 [M+H]+.

Compound 64 5-chloro-N-[4-(4-{[(3S,4R)-1-(2,2-difluoroethyl)-3-fluoropiperidin-4-yl]oxy}-3-methyl-1H-pyrazolo[3,4-d]pyrimidin-6-yl)phenyl]-2-fluorobenzenesulfonamide

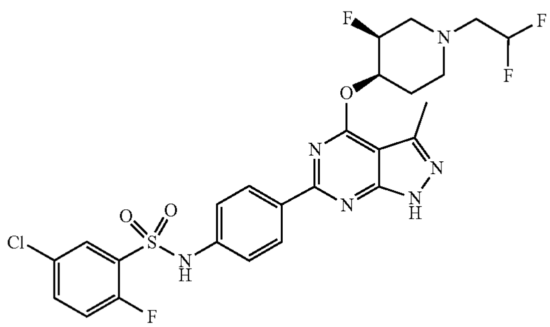 [SMILES: Cc1n[nH]c2nc(-c3ccc(NS(=O)(=O)c4cc(Cl)ccc4F)cc3)nc(O[C@@H]3CCN(CC(F)F)C[C@@H]3F)c12]

(i) (3S,4R)-3-fluoropiperidin-4-ol hydrochloride

To a solution of tert-butyl (3S,4R)-3-fluoro-4-hydroxypiperidine-1-carboxylate (1.00 g, 4.561 mmol, 1.00 equiv.) in DCM (15 mL, 235.951 mmol, 51.73 equiv.). HCl (4M in 1,4-dioxane) (15 mL, 416.667 mmol, 91.36 equiv.) was added and stirred for 2 h at rt. The resulting mixture was concentrated under reduced pressure. This resulted in (3S,4R)-3-fluoropiperidin-4-ol hydrochloride (700 mg, 88.77%) as a yellow solid. LCMS (ES. m/z): 120 [M+H—HCl]+.

(ii) (3S,4R)-1-(2,2-difluoroethyl)-3-fluoropiperidin-4-ol

A solution of (3S,4R)-3-fluoropiperidin-4-ol hydrochloride (680.94 mg, 4.376 mmol, 1.4 equiv.), 1,1-difluoro-2-iodoethane (600 mg, 3.126 mmol, 1.00 equiv.) and $NaHCO_3$ (787.8 mg, 9.378 mmol, 3.00 equiv.) in EtOH (20 mL, 344.271 mmol, 110.1 equiv.) was stirred for 36 h at 80° C. The solution was collected by filtration. The resulting mixture was concentrated under reduced pressure. The crude product was re-crystallized from DCM/MeOH (98%/2%) to afford (3S,4R)-1-(2,2-difluoroethyl)-3-fluoropiperidin-4-ol (30 mg, 4.72%) as a yellow oil. LCMS (ES. m/z): 184 [M+H]+.

(iii) (3S,4R)-4-({6-chloro-3-methyl-1H-pyrazolo[3,4-d]pyrimidin-4-yl}oxy)-1-(2,2-difluoroethyl)-3-fluoropiperidine To a solution of (3S,4R)-1-(2,2-difluoroethyl)-3-fluoropiperidin-4-ol (30.0 mg, 0.164 mmol, 1.00 equiv.) in THF (4.00 mL, 51.7 mmol, 315.6 equiv.) was added NaH (26.20 mg, 0.66 mmol, 4.00 equiv.) at 0° C. The mixture was stirred for 30 min. 4,6-dichloro-3-methyl-1H-pyrazolo[3,4-d]pyrimidine (36.58 mg, 0.180 mmol, 1.10 equiv.) was added and the mixture was allowed to warm to RT and stirred for 16 h at rt. The reaction was quenched with Water. The resulting mixture was extracted with EtOAc (3×30 mL), dried over anhydrous $Na_2SO_4$. After filtration, the filtrate was concentrated under reduced pressure. The solid was purified by flash Prep-HPLC with the following conditions (Column, C18 spherical 20-35 um 100 A (40 g); mobile phase A: Water-10 mM $NH_4HCO_3$, mobile phase B: Acetonitrile; Flow rate: 35 mL/min; Gradient: 56 B to 67 B; 254 nm) to afford (3S,4R)-4-({6-chloro-3-methyl-1H-pyrazolo[3,4-d]pyrimidin-4-yl}oxy)-1-(2,2-difluoroethyl)-3-fluoropiperidine (20 mg, 31.42%) as a white solid. LCMS (ES. m/z): 350 [M+H]+.

(iv) 5-chloro-N-[4-(4-{[(3S,4R)-1-(2,2-difluoroethyl)-3-fluoropiperidin-4-yl]oxy}-3-methyl-1H-pyrazolo[3,4-d]pyrimidin-6-yl)phenyl]-2-fluorobenzenesulfonamide A mixture of (3S,4R)-4-({6-chloro-3-methyl-1H-pyrazolo[3,4-d]pyrimidin-4-yl}oxy)-1-(2,2-difluoroethyl)-3-fluoropiperidine (30 mg, 0.086 mmol, 1.00 equiv.), 5-chloro-2-fluoro-N-[4-(4,4,5,5-tetramethyl-1,3,2-dioxaborolan-2-yl)phenyl]benzenesulfonamide (38.84 mg, 0.095 mmol, 1.10 equiv.), $Pd(dppf)Cl_2$ (12.55 mg, 0.017 mmol, 0.2 equiv.) and $Cs_2CO_3$ (41.92 mg, 0.129 mmol, 1.5 equiv.) in 1,4-dioxane (3.00 mL, 34.05 mmol, 397.0 equiv.), $H_2O$ (0.75 mL, 41.63 mmol, 485.34 equiv.) was stirred for 16 h at 100° C. under nitrogen atmosphere. The resulting mixture was concentrated under reduced pressure. The solid was purified by flash Prep-HPLC with the following conditions (Column, C18 spherical 20-35 um 100 A (40 g); mobile phase A: Water-10 mM $NH_4HCO_3$, mobile phase B: Acetonitrile; Flow rate: 35 mL/min; Gradient: 60 B to 68 B; 254 nm). The resulting mixture was concentrated under reduced pressure. The crude product was purified by Prep-HPLC with the following conditions (Column: XBridge Shield RP18 OBD Column, 30×150 mm, 5 um; Mobile Phase A: Water (0.05% TFA), Mobile Phase B: ACN; Flow rate: 60 mL/min; Gradient: 34% B to 55% B in 7 min, 55% B; Wave Length: 254 nm; RT1 (min): 6.58) to afford 5-chloro-N-[4-(4-{[(3S,4R)-1-(2,2-difluoroethyl)-3-fluoropiperidin-4-yl]oxy}-3-methyl-1H-pyrazolo[3,4-d]pyrimidin-6-yl)phenyl]-2-fluorobenzenesulfonamide; trifluoroacetic acid (8.6 mg, 13.71%) as an off-white solid. $^1H$-NMR ($DMSO-d_6$, 300 MHZ) δ (ppm): 11.14 (s, 1H), 8.31 (d, J=8.4 Hz, 2H), 7.89-7.77 (m, 2H), 7.46-7.58 (m, 1H), 7.27 (d, J=8.7 Hz, 2H), 6.03-6.49 (m, 1H), 5.83-5.75 (m, 1H), 5.14-4.92 (m, 1H), 3.25-2.73 (m, 6H), 2.59 (s, 3H), 2.12-2.05 (m, 2H). LCMS (ES. m/z): 599 [M+H]+.

Compound 65 5-chloro-2-fluoro-N-(4-(4-(((3S,4R)-3-fluoro-1-(methyl-d3)piperidin-4-yl)oxy)-3-methyl-1H-pyrazolo[3,4-d]pyrimidin-6-yl)phenyl)benzenesulfonamide

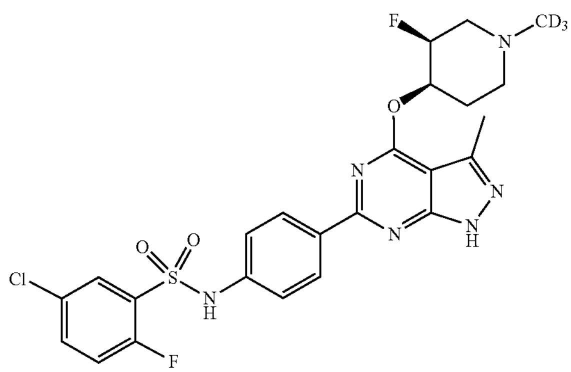 [SMILES: [2H]C([2H])([2H])N1CC[C@@H](Oc2nc(-c3ccc(NS(=O)(=O)c4cc(Cl)ccc4F)cc3)nc3[nH]nc(C)c23)[C@@H](F)C1]

(i) 6-chloro-4-(((3S,4R)-3-fluoro-1-(methyl-$d_3$)piperidin-4-yl)oxy)-3-methyl-1H-pyrazolo[3,4-d]pyrimidine A solution of and (3S,4R)-4-({6-chloro-3-methyl-1H-pyrazolo[3,4-d]pyrimidin-4-yl}oxy)-3-fluoropiperidine hydrochloride (300 mg, 0.931 mmol, 1.00 equiv.), CD3l (134.98 mg, 0.931 mmol, 1 equiv.), DIEA (361 mg, 2.79 mmol, 3.00 equiv.) in DMF (8.00 mL, 103.4 mmol, 111.0 equiv.) was stirred for 16 h at room temperature. The resulting mixture was extracted with EtOAc (3×40 mL), dried over anhydrous $Na_2SO_4$. After filtration, the filtrate was concentrated under reduced pressure. The solid was purified by flash Prep-HPLC with the following conditions (Column, C18 spherical 20-35 um 100 A (120 g); mobile phase A: Water-10 mM $NH_4HCO_3$, mobile phase B: Acetonitrile; Flow rate: 50 mL/min; Gradient: 49 B to 68 B; 254 nm) to afford 6-chloro-4-(((3S,4R)-3-fluoro-1-(methyl-d3)piperidin-4-yl)oxy)-3-methyl-1H-pyrazolo[3,4-d]pyrimidine (120 mg, 38.31%) as a yellow solid. LCMS (ES. m/z): 303 [M+H]+.

(ii) 5-chloro-2-fluoro-N-(4-(4-(((3S,4R)-3-fluoro-1-(methyl-d3)piperidin-4-yl)oxy)-3-methyl-1H-pyrazolo[3,4-d]pyrimidin-6-yl)phenyl)benzenesulfonamide A mixture of (3S,4R)-4-({6-chloro-3-methyl-1H-pyrazolo[3,4-d]pyrimidin-4-yl}oxy)-3-fluoro-1-($2H_3$)methylpiperidine (120 mg, 0.396 mmol, 1.00 equiv.), 5-chloro-2-fluoro-N-[4-(4,4,5,5-tetramethyl-1,3,2-dioxaborolan-2-yl)phenyl]benzenesulfonamide (179.5 mg, 0.436 mmol, 1.10 equiv.), Pd(dppf)$Cl_2$ (58.00 mg, 0.079 mmol, 0.2 equiv.) and $Cs_2CO_3$ (193.7 mg, 0.59 mmol, 1.50 equiv.) in 1,4-dioxane (4 mL) and water (1 ml) was stirred for 16 h at 100° C. under nitrogen atmosphere. The resulting mixture was concentrated under reduced pressure. The solid was purified by flash Prep-HPLC with the following conditions (Column, C18 spherical 20-35 um 100 A (80 g); mobile phase A: Water-10 mM $NH_4HCO_3$, mobile phase B: Acetonitrile; Flow rate: 40 mL/min; Gradient: 40 B to 51 B; 254 nm). The resulting mixture was concentrated under reduced pressure. The crude product was purified by Prep-HPLC with the following conditions (Column: XBridge Shield RP18 OBD Column, 30×150 mm, 5 um; Mobile Phase A: Water (0.05% TFA), Mobile Phase B: ACN; Flow rate: 60 mL/min; Gradient: 23% B to 43% B in 7 min, 43% B; Wave Length: 254 nm; RT1 (min): 4.93) to afford 5-chloro-2-fluoro-N-[4-(4-{[(3S,4R)-3-fluoro-1-($2H_3$)methylpiperidin-4-yl]oxy}-3-methyl-1H-pyrazolo[3,4-d]pyrimidin-6-yl)phenyl]benzenesulfonamide; trifluoroacetic acid (21.4 mg, 7.79%) as an off-white solid. $^1$H-NMR (DMSO-$d_6$, 300 MHZ) δ (ppm): 11.18 (s, 1H), 10.02 (s, 1H), 8.35 (d, J=8.7 Hz, 2H), 7.95-7.78 (m, 2H), 7.56-7.50 (m, 1H), 7.28 (d, J=8.7 Hz, 2H), 5.82-5.70 (m, 1H), 5.53-5.28 (m, 1H), 3.92-3.43 (m, 4H), 2.59 (s, 3H), 2.45-2.19 (m, 2H). LCMS (ES. m/z): 552 [M+H]+.

Compound 66 N-[4-(4-{[(3S,4R)-3-fluoro-1-methylpiperidin-4-yl]oxy}-3-methyl-1H-pyrazolo[3,4-d]pyrimidin-6-yl)phenyl]pyridine-2-sulfonamide

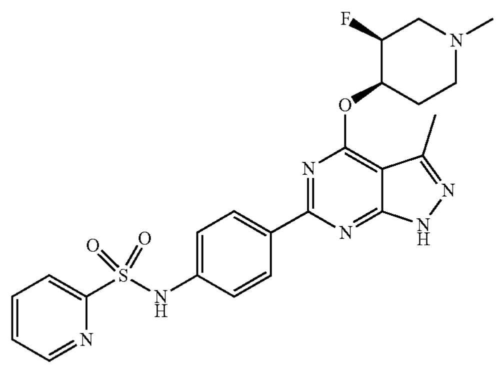 [SMILES: Cc1n[nH]c2nc(-c3ccc(NS(=O)(=O)c4ccccn4)cc3)nc(O[C@@H]3CCN(C)C[C@@H]3F)c12]

This compound was prepared according to the procedure described in example 57. The desired product was obtained as a white solid and a free base (4.6 mg, 9.10%). 1H NMR (300 MHz, DMSO-$d_6$) δ 13.54 (s, 1H), 10.95 (s, 1H), 9.96 (s, 1H), 8.72 (dt, J=4.7, 1.4 Hz, 1H), 8.33-8.22 (m, 2H), 8.20-7.96 (m, 2H), 7.67 (ddd, J=7.2, 4.7, 1.6 Hz, 1H), 7.46-7.28 (m, 3H), 7.04 (d, J=51.1 Hz, 1H), 5.81 (s, 1H), 5.40 (d, J=48.0 Hz, 1H), 3.51 (s, 3H), 2.84 (s, 3H), 2.52 (s, 3H), 2.36-2.15 (m, 2H). LCMS (ESI, m/z): 498[M+H]+.

Compound 67 N-[4-(4-{[(3S,4R)-3-fluoro-1-methylpiperidin-4-yl]oxy}-3-methyl-1H-pyrazolo[3,4-d]pyrimidin-6-yl)phenyl]pyridine-2-sulfonamide

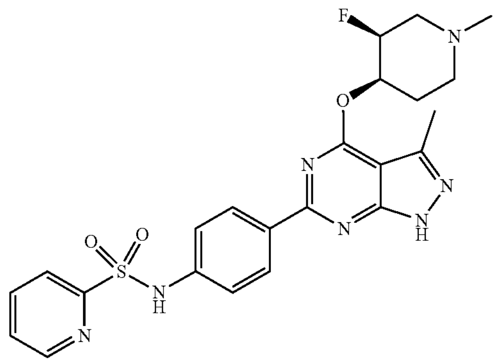 [SMILES: Cc1n[nH]c2nc(-c3ccc(NS(=O)(=O)c4ccccn4)cc3)nc(O[C@@H]3CCN(C)C[C@@H]3F)c12]

This compound was prepared according to the procedure described in example 57. The desired product was obtained as a white solid and a TFA salt (4.6 mg, 9.10%). 1H NMR (300 MHZ, DMSO-$d_6$) δ 13.54 (s, 1H), 10.95 (s, 1H), 9.96 (s, 1H), 8.72 (dt, J=4.7, 1.4 Hz, 1H), 8.33-8.22 (m, 2H), 8.20-7.96 (m, 2H), 7.67 (ddd, J=7.2, 4.7, 1.6 Hz, 1H), 7.46-7.28 (m, 3H), 7.04 (d, J=51.1 Hz, 1H), 5.81 (s, 1H), 5.40 (d, J=48.0 Hz, 1H), 3.51 (s, 3H), 2.84 (s, 3H), 2.52 (s, 3H), 2.36-2.15 (m, 2H). LCMS (ESI, m/z): 498[M+H]+.

Compound 67 N-[4-(4-{[(3R,4S)-4-fluoro-1-methylpyrrolidin-3-yl]oxy}-3-methyl-1H-pyrazolo[3,4-d]pyrimidin-6-yl)phenyl]-4-(trifluoromethyl)pyridine-2-sulfonamide

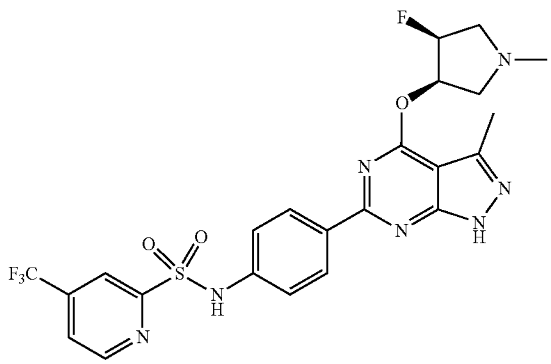 [SMILES: Cc1n[nH]c2nc(-c3ccc(NS(=O)(=O)c4cc(C(F)(F)F)ccn4)cc3)nc(O[C@@H]3CN(C)C[C@@H]3F)c12]

This compound was prepared according to the procedure described in example 57. The desired product was obtained as a white solid and a TFA salt (47.7 mg, 20.44%). $^1$H-NMR ($CD_3OD$, 300 MHZ) δ (ppm): 8.92 (d, J=4.8 Hz, 1H), 8.37 (d, J=8.7 Hz, 2H), 8.23 (s, 1H), 7.90 (d, J=4.8 Hz, 1H), 7.34 (d, J=8.7 Hz, 2H), 6.17-6.09 (m, 1H), 5.85-5.68 (m, 1H), 4.11-3.97 (m, 4H), 3.07 (s, 3H), 2.60 (s, 3H). LCMS (ES. m/z): 552 [M+H]+.

Compound 5-chloro-2-fluoro-N-[4-(4-{[(3S,4R)-3-fluoro-1-methylpiperidin-4-yl]oxy}-3-methyl-1H-pyrazolo[3,4-d]pyrimidin-6-yl)-3-methylphenyl]benzenesulfonamide

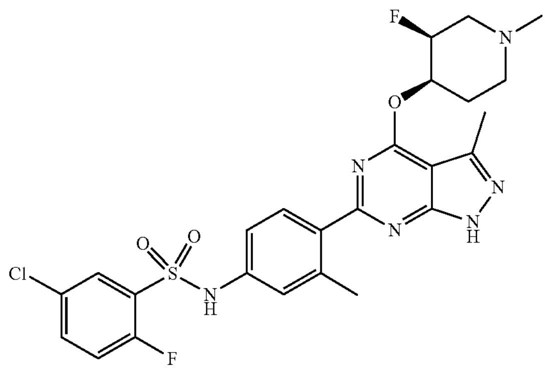 [SMILES: Cc1cc(NS(=O)(=O)c2cc(Cl)ccc2F)ccc1-c1nc(O[C@@H]2CCN(C)C[C@@H]2F)c2c(C)n[nH]c2n1]

This compound was prepared according to the procedure described in example 57. The desired product was obtained as a white solid and a TFA salt (24.4 mg, 10.78%). 1H-NMR ($CD_3OD$, 300 MHZ) δ (ppm): 7.87-7.81 (m, 2H), 7.66-7.61 (m, 1H), 7.33-7.27 (m, 1H), 7.13-7.07 (m, 2H), 5.85-5.64 (m, 1H), 5.48-5.22 (m, 1H), 3.67 (s, 1H), 3.69-3.48 (m, 2H), 3.42-3.35 (m, 1H), 2.96 (s, 3H), 2.60 (s, 6H), 2.53-2.38 (m, 2H). LCMS (ES. m/z): 563 [M+H]+.

Compound 69 5-chloro-2-fluoro-N-[2-fluoro-4-(4-{[(3S,4R)-3-fluoro-1-methylpiperidin-4-yl]oxy}-3-methyl-1H-pyrazolo[3,4-d]pyrimidin-6-yl)phenyl]benzenesulfonamide

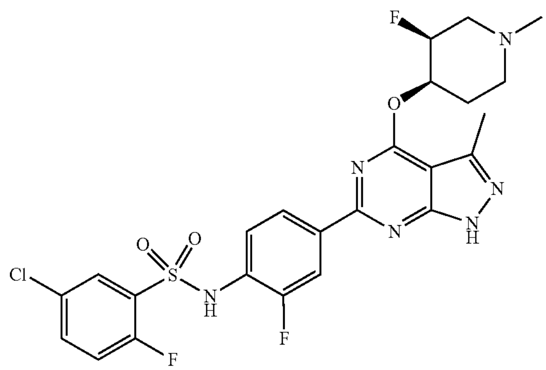 [SMILES: Cc1n[nH]c2nc(-c3ccc(NS(=O)(=O)c4cc(Cl)ccc4F)c(F)c3)nc(O[C@@H]3CCN(C)C[C@@H]3F)c12]

This compound was prepared according to the procedure described in example 57. The desired product was obtained as an off-white solid and a TFA salt (23.5 mg, 17.17%). $^1$H-NMR ($CD_3OD$, 300 MHZ) δ (ppm): 8.26 (d, J=8.4 Hz, 1 h), 8.16-8.12 (dd, J=1.8&11.7 Hz, 1H), 7.81-7.78 (dd, J=2.7&6 Hz, 1H), 7.67-7.62 (m, 1H), 7.59-7.54 (t, J=8.1 Hz, 1H), 7.35-7.29 (t, J=9.3 Hz, 1H), 5.95-5.78 (m, 1H), 5.43 (d, J=47.7 Hz, 1H), 3.77 (s, 1H), 3.79-3.59 (m, 2H), 3.49-3.46 (m, 1H), 3.00 (s, 3H), 2.65 (s, 3H), 2.53-2.42 (m, 2H). LCMS (ES. m/z): 567 [M+H]+.

Compound 70 N-[4-(4-{[(3R)-4,4-difluoro-1-methylpyrrolidin-3-yl]oxy}-3-methyl-1H-pyrazolo[3,4-d]pyrimidin-6-yl)phenyl]-4-(trifluoromethyl)pyridine-2-sulfonamide

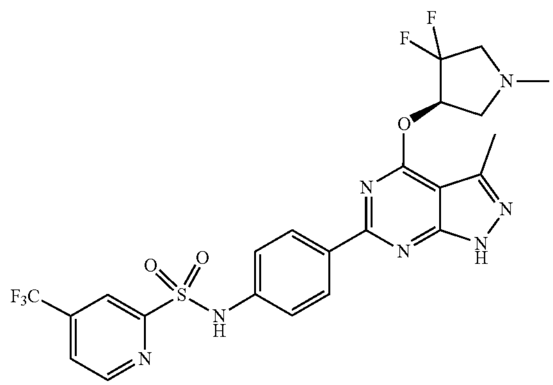 [SMILES: Cc1n[nH]c2nc(-c3ccc(NS(=O)(=O)c4cc(C(F)(F)F)ccn4)cc3)nc(O[C@@H]3CN(C)CC3(F)F)c12]

This compound was prepared according to the procedure described in example 57. The desired product was obtained as a white solid and a TFA salt (6.3 mg, 5.49%). 1H NMR ($CD_3OD$, 400 MHZ) δ 8.91 (d, J=4.8 Hz, 1H), 8.37 (d, J=8.4 Hz, 2H), 8.23 (s, 1H), 7.90-7.89 (m, 1H), 7.33-7.31 (m, 2H), 6.19 (d, J=10.4 Hz, 1H), 4.12 (m, 1H), 3.87-3.84 (m, 3H), 2.94 (s, 3H), 2.63 (s, 3H). LCMS (ESI, m/z): 570[M+H]+.

Compound 71 5-chloro-N-[4-(4-{[(4R)-3,3-difluoro-1-(2-hydroxyethyl)piperidin-4-yl]oxy}-3-methyl-1H-pyrazolo[3,4-d]pyrimidin-6-yl)phenyl]-2-fluorobenzenesulfonamide

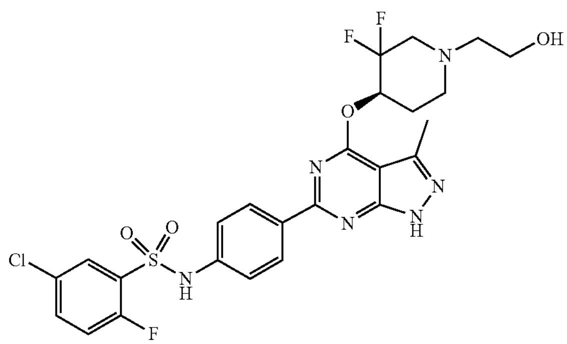 [SMILES: Cc1n[nH]c2nc(-c3ccc(NS(=O)(=O)c4cc(Cl)ccc4F)cc3)nc(O[C@@H]3CCN(CCO)CC3(F)F)c12]

This compound was prepared according to the procedure described in example 51. The desired product was obtained as a white solid and a TFA salt (18.7 mg, 21.5%) as a white solid. $^1$H-NMR (DMSO-$d_6$, 300 MHZ) δ (ppm): 8.34 (d, J=8.4 Hz, 2H), 7.92-7.74 (m, 2H), 7.51-7.40 (m, 1H), 7.23 (d, J=8.7 Hz, 2H), 5.98-5.95 (m, 1H), 4.85-4.81 (m, 1H), 4.40-4.27 (m, 2H), 3.84-3.71 (m, 2H), 3.24-2.77 (m, 4H), 2.68 (s, 3H), 2.23-2.19 (m, 1H), 1.95-1.79 (m, 1H). LCMS (ES. m/z): 597 [M+H]+.

Compound 72 N-{4-[4-({2-[(2-hydroxyethyl)(methyl)amino]ethyl}amino)-3-methyl-1H-pyrazolo[3,4-d]pyrimidin-6-yl]phenyl}-4-(trifluoromethyl)pyridine-2-sulfonamide

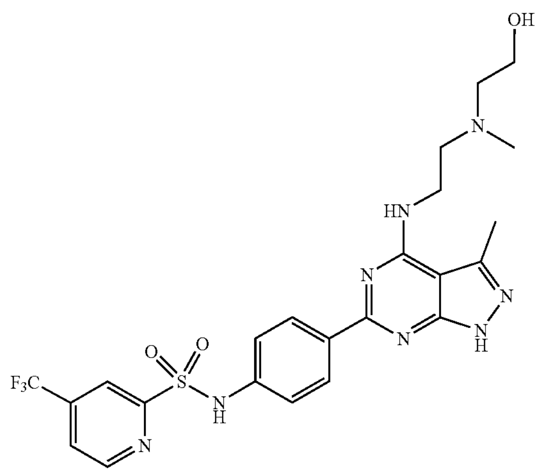 [SMILES: Cc1n[nH]c2nc(-c3ccc(NS(=O)(=O)c4cc(C(F)(F)F)ccn4)cc3)nc(NCCN(C)CCO)c12]

This compound was prepared according to the procedure described in example 51. The desired product was obtained as an off-white solid and a TFA salt (34.5 mg, 17.58%). $^1$H-NMR (DMSO-$d_6$, 300 MHZ) δ (ppm): 12.95 (s, 1H), 9.01 (d, J=4.8 Hz, 1H), 8.23 (d, J=8.7 Hz, 3H), 8.07 (d, J=4.8 Hz, 1H), 7.23 (d, J=8.7 Hz, 2H), 7.03-6.99 (m, 1H), 4.50 (s, 1H), 3.74-3.71 (m, 2H), 3.57-3.49 (m, 2H), 2.76-2.72 (m, 2H), 2.68-2.59 (m, 2H), 2.48 (s, 3H), 2.39 (s, 3H). LCMS (ES. m/z): 551 [M+H]+.

Compound 73 N-[4-(4-{[2-(dimethylamino)ethyl]amino}-3-methyl-1H-pyrazolo[3,4-d]pyrimidin-6-yl)phenyl]-4-isopropoxypyridine-2-sulfonamide

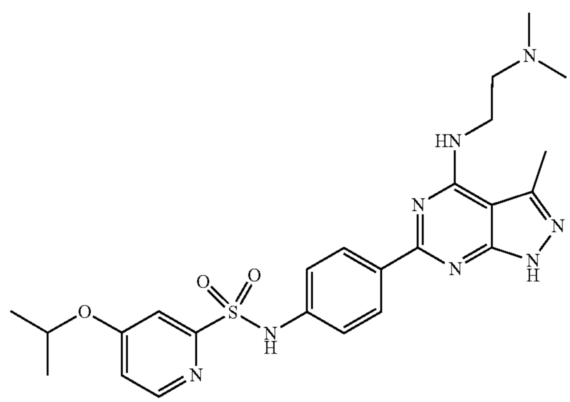 [SMILES: Cc1n[nH]c2nc(-c3ccc(NS(=O)(=O)c4cc(OC(C)C)ccn4)cc3)nc(NCCN(C)C)c12]

(i) 4-isopropoxy-2-methylpyridine

To a stirred mixture of 2-chloropyridin-4-ol (4.5 g, 34.738 mmol, 1.00 equiv.) and $K_2CO_3$ (9.60 g, 69.48 mmol, 2.00 equiv.) in DMF (90 mL, 1163 mmol, 33.5 equiv.) was added 2-iodopropane (8.86 g, 52.11 mmol, 1.50 equiv.) dropwise and stirred at 60° C. for 16 hours. The resulting mixture was extracted with EA (100 ml). The resulting mixture was concentrated under reduced pressure. The residue was purified by reverse flash chromatography with the following conditions: column, silica gel; mobile phase, EA in PE, 0% to 50% gradient in 30 min; detector, UV 254 nm. This resulted in 4-isopropoxy-2-methylpyridine (5 g, 95.19%) as a yellow oil. LCMS (ESI, m/z): 172[M+H]+.

(ii) 2-(benzylsulfanyl)-4-isopropoxypyridine

To a stirred mixture of 4-isopropoxy-2-methylpyridine (5.00 g, 33.1 mmol, 1.00 equiv.) and $Cs_2CO_3$ (18.98 g, 58.27 mmol, 2.00 equiv.) in DMF (100 mL) were added KF (1.69 g, 29.14 mmol, 1.00 equiv.) and benzyl mercaptan (7.24 g, 58.27 mmol, 2.00 equiv.) in portions, and stirred at 60° C. for 16 hours. The resulting mixture was extracted with EA (500 ml). The resulting mixture was concentrated under reduced pressure. The residue was purified by reverse flash chromatography with the following conditions: column, C18 silica gel; mobile phase, ACN in water, 10% to 50% gradient in 30 min; detector, UV 254 nm. This resulted in 2-(benzylsulfanyl)-4-isopropoxypyridine as a yellow oil. LCMS (ESI, m/z): 260[M+H]+

(iii) bis(4-isopropoxypyridine-2-sulfonyl chloride

To a stirred mixture of 2-(benzylsulfanyl)-4-isopropoxypyridine (4 g) in DCM (10 mL) was added HCl (20 mL) and $NaClO_2$ (20 mL) in portions at room temperature. After stirring for 2 hours, the resulting mixture was concentrated under reduced pressure. Desired product could be detected by LCMS. The crude product was used in the next step directly without further purification. LCMS (ESI, m/z): 236[M+H]+.

(iv) 4-isopropoxy-N-[4-(4,4,5,5-tetramethyl-1,3,2-dioxaborolan-2-yl)phenyl]pyridine-2-sulfonamide To a stirred mixture of bis(4-isopropoxypyridine-2-sulfonyl chloride) (3.3 g, 7.001 mmol, 1.00 equiv.) in DCM (10 mL) were added 4-(4,4,5,5-tetramethyl-1,3,2-dioxaborolan-2-yl)aniline (1.53 g, 7.00 mmol, 1.00 equiv.) and pyridine (0.55 g, 7.00 mmol, 1.00 equiv.) in portions at room temperature, and stirred for 4 hours. The resulting mixture was concentrated under reduced pressure. The residue was purified by reverse flash chromatography with the following conditions: column, C18 silica gel; mobile phase, ACN in water, 10% to 90% gradient in 30 min; detector, UV 254 nm. This resulted in 4-isopropoxy-N-[4-(4,4,5,5-tetramethyl-1,3,2-dioxaborolan-2-yl)phenyl]pyridine-2-sulfonamide (4.2 g, 86.05%) as an off-white solid. LCMS (ESI, m/z): 419 [M+H]+.

(v) N-[4-(4-{[2-(dimethylamino)ethyl]amino}-3-methyl-1H-pyrazolo[3,4-d]pyrimidin-6-yl)phenyl]-4-isopropoxypyridine-2-sulfonamide To a solution of 4-isopropoxy-N-[4-(4,4,5,5-tetramethyl-1,3,2-dioxaborolan-2-yl)phenyl]pyridine-2-sulfonamide (180.6 mg, 0.43 mmol, 1.10 equiv.) and 6-chloro-N-[2-(dimethylamino)ethyl]-3-methyl-1H-pyrazolo[3,4-d]pyrimidin-4-amine (100 mg, 0.393 mmol, 1.00 equiv.) in 1,4-dioxane (4 mL, 1.179 mmol) and $H_2O$ (1 mL) were added $CS_2CO_3$ (191.87 mg, 0.590 mmol, 1.5 equiv.) and $Pd(dppf)Cl_2$ (57.45 mg, 0.079 mmol, 0.2 equiv.). After stirring for 16 hours at 100° C. under a nitrogen atmosphere, the resulting mixture was concentrated under reduced pressure. The residue was purified by reverse flash chromatography with the following conditions: column, C18 silica gel; mobile phase, ACN in water, 10% to 90% gradient in 30 min; 40 ml/min, detector, UV 254 nm. The residue was purified by Prep-TLC(Column: YMC-Actus Triart C18, 30*150 mm, 5 um; Mobile Phase A: Water (10 mmol/L NH4HCO3+0.1% NH3·H2O), Mobile Phase B: ACN; Flow rate: 60 mL/min; Gradient: 25% B to 52% B in 7 min, 52% B; Wave Length: 254 nm; RT1 (min): 6.17) to afford N-[4-(4-{[2-(dimethylamino)ethyl]amino}-3-methyl-1H-pyrazolo[3,4-d]pyrimidin-6-yl)phenyl]-4-isopropoxypyridine-2-sulfonamide (23.7 mg, 11.78%) as a white solid. $^1H$ NMR (300 MHZ, DMSO-$d_6$) δ 12.94 (s, 1H), 10.74 (s, 1H), 8.47 (d, J=5.7 Hz, 1H), 8.23-8.20 (m, 2H), 7.43 (d, J=2.4 Hz, 1H), 7.23 (d, J=8.7 Hz, 2H), 7.16 (dd, J=5.7, 2.4 Hz, 1H), 7.01 (t, J=5.6 Hz, 1H), 4.84 (p, J=6.2 Hz, 1H), 3.70 (q, J=6.4 Hz, 2H), 2.56 (t, J=6.9 Hz, 2H), 2.51-2.50 (m, 3H), 2.24 (s, 6H), 1.27 (d, J=6 Hz, 6H). LCMS (ESI, m/z): 511.15[M+H]+.

Compound 74 N-[4-(4-{[3-(dimethylamino)-2,2-difluoropropyl]amino}-3-methyl-1H-pyrazolo[3,4-d]pyrimidin-6-yl)phenyl]-4-(trifluoromethyl)pyridine-2-sulfonamide

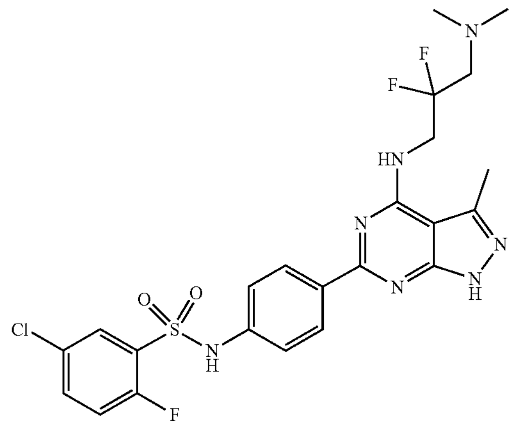 [SMILES: Cc1n[nH]c2nc(-c3ccc(NS(=O)(=O)c4cc(Cl)ccc4F)cc3)nc(NCC(F)(F)CN(C)C)c12]

(i) N1-{6-chloro-3-methyl-1H-pyrazolo[3,4-d]pyrimidin-4-yl}-2,2-difluoropropane-1,3-diamine To a stirred mixture of 4,6-dichloro-3-methyl-1H-pyrazolo[3,4-d]pyrimidine (500 mg, 2.46 mmol, 1.00 equiv.) and DIEA (1910 mg, 14.78 mmol, 6.00 equiv.) in DCM (50 mL) was added 2,2-difluoropropane-1,3-diamine dihydrochloride (450.7 mg, 2.46 mmol, 1.00 equiv.) dropwise at room temperature, and stirred for 48 hours. The resulting mixture was concentrated under reduced pressure. The residue was purified by reverse flash chromatography with the following conditions: column, C18 silica gel; mobile phase, ACN in water, 50 ml/min, 10% to 90% gradient in 30 min; detector, UV 254 nm. This resulted in N1-{6-chloro-3-methyl-1H-pyrazolo[3,4-d]pyrimidin-4-yl}-2,2-difluoropropane-1,3-diamine (400 mg, 58.70%) as a brown yellow solid. LCMS (ESI, m/z): 277[M+H]+.

(ii) 6-chloro-N-[3-(dimethylamino)-2,2-difluoropropyl]-3-methyl-1H-pyrazolo[3,4-d]pyrimidin-4-amine To a stirred mixture of N1-{6-chloro-3-methyl-1H-pyrazolo[3,4-d]pyrimidin-4-yl}-2,2-difluoropropane-1,3-diamine; bis(trifluoroacetic acid) (288 mg, 0.571 mmol, 1.00 equiv.) and DIEA (368.7 mg, 2.85 mmol, 5.00 equiv.) in DMF (30 mL) was added $CH_3I$ (161.98 mg, 1.14 mmol, 2.00 equiv.) dropwise at room temperature, and stirred for 16 hours. The aqueous layer was extracted with EA (300 ml). The resulting mixture was concentrated under reduced pressure. The residue was purified by reverse flash chromatography with the following conditions: column, C18 silica gel; mobile phase, ACN in water, 50 ml/min, 10% to 90% gradient in 30 min; detector, UV 254 nm. This resulted in 6-chloro-N-[3-(dimethylamino)-2,2-difluoropropyl]-3-methyl-1H-pyrazolo[3,4-d]pyrimidin-4-amine (60 mg, 34.51%) as a off-white solid. LCMS (ESI, m/z): 305 [M+H]+.

(iii) N-[4-(4-{[3-(dimethylamino)-2,2-difluoropropyl]amino}-3-methyl-1H-pyrazolo[3,4-d]pyrimidin-6-yl)phenyl]-4-(trifluoromethyl)pyridine-2-sulfonamide To a solution of 6-chloro-N-[3-(dimethylamino)-2,2-difluoropropyl]-3-methyl-1H-pyrazolo[3,4-d]pyrimidin-4-amine (30 mg, 0.098 mmol, 1.00 equiv.) and N-[4-(4,4,5,5-tetramethyl-1,3,2-dioxaborolan-2-yl)phenyl]-4-(trifluoromethyl)pyridine-2-sulfonamide (46.37 mg, 0.108 mmol, 1.10 equiv.) in 1,4-dioxane (1.5 mL) and $H_2O$ (0.37 mL) were added $Cs_2CO_3$ (48.11 mg, 0.147 mmol, 1.50 equiv.) and Pd(dppf)$Cl_2$ (14.41 mg, 0.020 mmol, 0.20 equiv.). After stirring for 16 hours at 100° C. under a nitrogen atmosphere, the resulting mixture was concentrated under reduced pressure. The residue was purified by reverse flash chromatography with the following conditions: column, C18 silica gel; mobile phase, ACN in water, 40 ml/min, 10% to 90% gradient in 10 min; detector, UV 254 nm. The residue was purified by Prep-TLC(Column: XBridge Shield RP18 OBD Column, 30*150 mm, 5 um; Mobile Phase A: Water (10 mmol/L NH4HCO3+0.1% NH3·H2O), Mobile Phase B: ACN; Flow rate: 60 mL/min; Gradient: 22% B to 42% B in 7 min, 42% B; Wave Length: 254 nm; RT1 (min): 5.43) to afford N-[4-(4-{[3-(dimethylamino)-2,2-difluoropropyl]amino}-3-methyl-1H-pyrazolo[3,4-d]pyrimidin-6-yl)phenyl]-4-(trifluoromethyl)pyridine-2-sulfonamide (5.1 mg, 8.94%) as a white solid. 1H NMR (300 MHZ, DMSO-$d_6$) δ 12.95 (s, 1H), 8.92 (s, 1H), 8.25-8.13 (m, 3H), 7.92 (s, 1H), 7.22-7.08 (m, 3H), 4.29-4.17 (m, 2H), 2.82 (t, J=13.5 Hz, 2H), 2.53 (s, 3H), 2.29 (s, 6H). LCMS (ESI, m/z): 571.10 [M+H]+.

Compound 75 5-chloro-N-[4-(4-{[3-(dimethylamino)-2,2-difluoropropyl]amino}-3-methyl-1H-pyrazolo[3,4-d]pyrimidin-6-yl)phenyl]-2-fluorobenzenesulfonamide

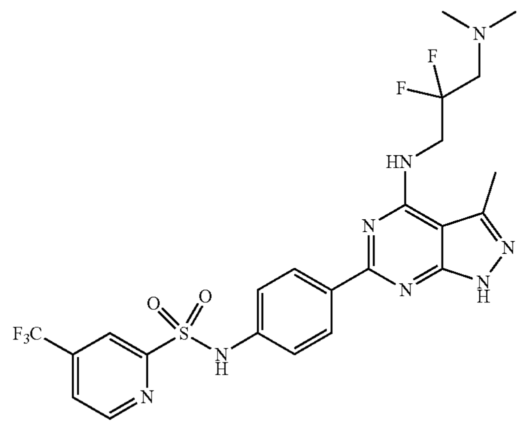 [SMILES: Cc1n[nH]c2nc(-c3ccc(NS(=O)(=O)c4cc(C(F)(F)F)ccn4)cc3)nc(NCC(F)(F)CN(C)C)c12]

This compound was prepared according to the procedure described in example 51. The desired product was obtained (4.5 mg, 8.10%) as an off-white solid. $^1H$ NMR (300 MHZ, Methanol-$d_4$) δ 8.29 (d, J=8.7 Hz, 2H), 7.89 (dd, J=6.0, 2.7 Hz, 1H), 7.65-7.60 (m, 1H), 7.53-7.26 (m, 3H), 4.36-4.32 (m, 2H), 3.96-3.86 (m, 2H), 2.89 (s, 6H), 2.66 (s, 3H), 1.37 (s, 1H). LCMS (ESI, m/z): 554.10[M+H-TFA]+.

Compound 76 5-chloro-2-fluoro-N-{4-[4-({2-[(2-hydroxy-2-methylpropyl)(methyl)amino]ethyl}amino)-3-methyl-1H-pyrazolo[3,4-d]pyrimidin-6-yl]phenyl}benzenesulfonamide

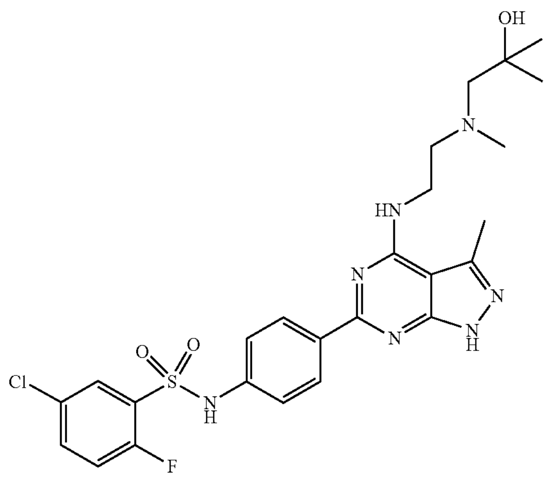 [SMILES: Cc1n[nH]c2nc(-c3ccc(NS(=O)(=O)c4cc(Cl)ccc4F)cc3)nc(NCCN(C)CC(C)(C)O)c12]

(i) tert-butyl N-{2-[(2-hydroxy-2-methylpropyl)(methyl)amino]ethyl}carbamate

To a stirred mixture of tert-butyl N-[2-(methylamino)ethyl]carbamate (1.50 g, 8.61 mmol, 1.00 equiv.) and $K_2CO_3$ (3.57 g, 25.83 mmol, 3.00 equiv.) in ACN (20 mL) was 2,2-dimethyloxirane (0.93 g, 12.91 mmol, 1.50 equiv.) added dropwise at room temperature, and stirred at reflux for 16 hours. The resulting mixture was filtered, the filter cake was washed with ACN (100 ml). The filtrate was concentrated under reduced pressure. Desired product could be detected by LCMS. LCMS (ESI, m/z): 247 [M+H]+.

(ii) 1-[(2-aminoethyl)(methyl)amino]-2-methylpropan-2-ol

To a stirred solution of tert-butyl N-{2-[(2-hydroxy-2-methylpropyl)(methyl)amino]ethyl}carbamate (1.40 g, 1.00 equiv.) in dioxane (10 mL) was added HCl (gas) in 1,4-dioxane (10 mL) dropwise at room temperature, and stirred for 6 hours. The resulting mixture was concentrated under reduced pressure. Desired product could be detected by LCMS. LCMS (ESI, m/z): 147 [M+H]+.

(iii) 1-{[2-({6-chloro-3-methyl-1H-pyrazolo[3,4-d]pyrimidin-4-yl}amino)ethyl](methyl)amino}-2-methylpropan-2-ol To a stirred solution of 1-[(2-aminoethyl)(methyl)amino]-2-methylpropan-2-ol (150 mg, 1.03 mmol, 1.00 equiv.) and DIEA (397.7 mg, 3.08 mmol, 3.00 equiv.) in THF (2 mL) was added 4,6-dichloro-3-methyl-1H-pyrazolo[3,4-d]pyrimidine (208.3 mg, 1.03 mmol, 1.00 equiv.) in portions at room temperature, and stirred for 3 hours. The resulting mixture was concentrated under reduced pressure. Desired product could be detected by LCMS. LCMS (ESI, m/z): 313 [M+H]+

(iv) 5-chloro-2-fluoro-N-{4-[4-({2-[(2-hydroxy-2-methylpropyl)(methyl)amino]ethyl}amino)-3-methyl-1H-pyrazolo[3,4-d]pyrimidin-6-yl]phenyl}benzenesulfonamide To a solution of 1-{[2-({6-chloro-3-methyl-1H-pyrazolo[3,4-d]pyrimidin-4-yl}amino)ethyl](methyl)amino}-2-methylpropan-2-ol (100 mg, 0.320 mmol, 1.00 equiv.) and 5-chloro-2-fluoro-N-[4-(4,4,5,5-tetramethyl-1,3,2-dioxaborolan-2-yl)phenyl]benzenesulfonamide (197.4 mg, 0.48 mmol, 1.50 equiv.) in 1,4-dioxane (4 mL) and $H_2O$ (1.00 mL) were added Pd(dppf)$Cl_2$ (46.78 mg, 0.064 mmol, 0.20 equiv.) and $Cs_2CO_3$ (156.2 mg, 0.480 mmol, 1.50 equiv.). After stirring for 16 hours at 100° C. under a nitrogen atmosphere, the resulting mixture was concentrated under reduced pressure. The residue was purified by reverse flash chromatography with the following conditions: column, C18 silica gel; mobile phase, ACN in water, 10% to 90% gradient in 30 min; detector, UV 254 nm, 40 ml/min. The residue was purified by Prep-TLC(Column: XSelect CSH Prep C18 OBD Column, 19*150 mm, 5 um; Mobile Phase A: Water (10 mmol/L NH4HCO3+0.1% NH3·H2O), Mobile Phase B: ACN; Flow rate: 25 mL/min; Gradient: 23% B to 53% B in 7 min, 53% B; Wave Length: 254 nm; RT1 (min): 6.8) to afford 5-chloro-2-fluoro-N-{4-[4-({2-[(2-hydroxy-2-methylpropyl)(methyl)amino]ethyl}amino)-3-methyl-1H-pyrazolo[3,4-d]pyrimidin-6-yl]phenyl}benzenesulfonamide (3.9 mg, 2.09%) as an off-white solid. $^1H$ NMR (400 MHZ, Methanol-$d_4$) δ 8.28-8.25 (m, 2H), 7.86-7.84 (m, 1H), 7.61-7.57 (m, 1H), 7.29-7.24 (m, 1H), 7.24-7.16 (m, 2H), 3.82 (t, J=6.4 Hz, 2H), 2.85-2.81 (m, 2H), 2.65 (s, 3H), 2.48 (s, 5H), 1.17 (s, 6H). LCMS (ESI, m/z): 562.15 [M+H]+.

Compound 77 2-fluoro-N-{4-[4-({2-[(2-hydroxyethyl)(methyl)amino]ethyl}amino)-3-methyl-1H-pyrazolo[3,4-d]pyrimidin-6-yl]phenyl}-5-methoxybenzenesulfonamide

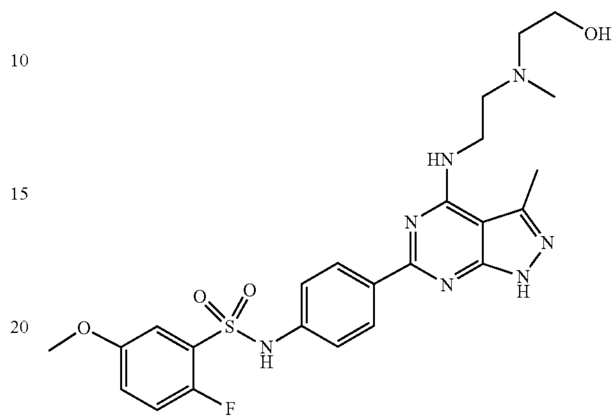

This compound was prepared according to the procedure described in example 51. The desired product was obtained (20.6 mg, 8.96%) as a white solid. $^1H$ NMR (300 MHZ, DMSO-$d_6$) δ 10.93 (s, 1H), 9.34 (s, 1H), 8.27 (d, J=8.7 Hz, 2H), 7.39-7.20 (m, 6H), 4.00 (s, 2H), 3.78-3.69 (m, 5H), 3.53-3.17 (m, 4H), 2.90 (d, J=4.8 Hz, 3H), 2.55 (s, 3H). LCMS (ESI, m/z): 530.20 [M+H]+.

Compound 78 5-chloro-2-fluoro-N-{2-fluoro-4-[4-({2-[(2-hydroxyethyl)(methyl)amino]ethyl}amino)-3-methyl-1H-pyrazolo[3,4-d]pyrimidin-6-yl]phenyl}benzenesulfonamide

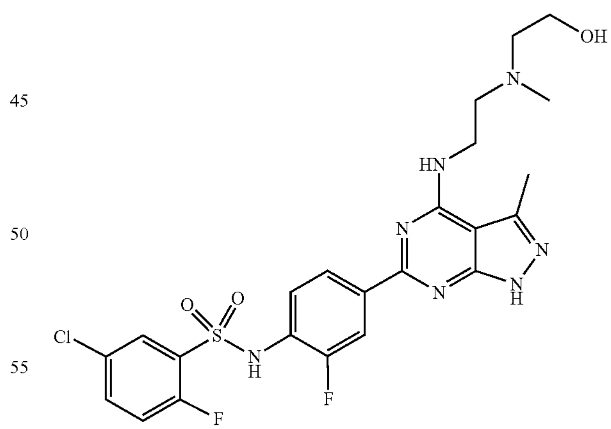

This compound was prepared according to the procedure described in example 51. The desired product was obtained (19.5 mg, 14.80%) as a white solid. $^1H$ NMR (400 MHZ, DMSO-$d_6$) δ 12.96 (s, 1H), 7.95-7.90 (m, 2H), 7.71-7.69 (m, 1H), 7.57 (d, J=8 Hz, 1H), 7.35-7.21 (m, 2H), 7.09 (t, J=5.2 Hz, 1H), 3.86 (d, J=5.6 Hz, 2H), 3.62 (s, 2H), 3.11 (s, 2H), 2.95 (s, 2H), 2.65 (s, 3H), 2.53 (s, 3H). LCMS (ESI, m/z): 552.05 [M+H]+.

Compound 79 5-chloro-2-fluoro-N-(2-fluoro-4-{3-methyl-4-[(1-methylpiperidin-4-yl)oxy]-1H-pyrazolo[3,4-d]pyrimidin-6-yl}phenyl)benzenesulfonamide

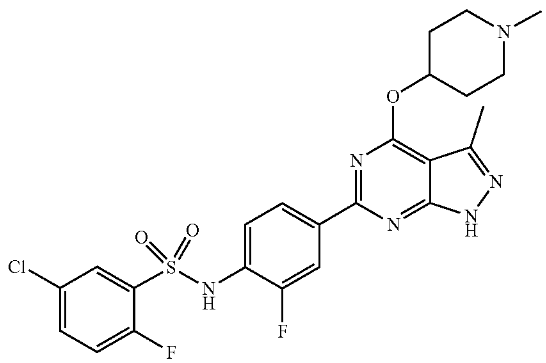 [SMILES: Cc1n[nH]c2nc(-c3ccc(NS(=O)(=O)c4cc(Cl)ccc4F)c(F)c3)nc(OC3CCN(C)CC3)c12]

This compound was prepared according to the procedure described in example 57. The desired product was obtained (10.8 mg, 8.37%) as an off-white solid. $^1$H NMR (300 MHZ, DMSO-$d_6$) δ 13.37 (s, 1H), 7.95-7.88 (m, 2H), 7.73-7.70 (m, 1H), 7.58-7.53 (m, 1H), 7.35-7.25 (m, 2H), 5.63 (s, 1H), 3.12 (s, 4H), 2.69 (s, 3H), 2.53 (s, 3H), 2.20 (s, 2H), 2.07 (s, 3H). LCMS (ESI, m/z): 549.10 [M+H]+.

Compound 80 N-(4-{4-[(1-isopropylpiperidin-4-yl)oxy]-3-methyl-1H-pyrazolo[3,4-d]pyrimidin-6-yl}phenyl)-4-methoxypyridine-2-sulfonamide

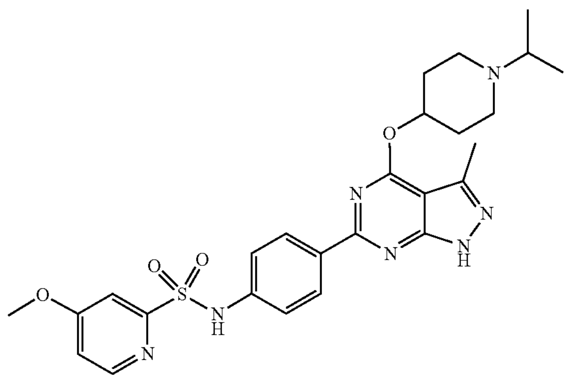 [SMILES: COc1ccnc(S(=O)(=O)Nc2ccc(-c3nc(OC4CCN(C(C)C)CC4)c4c(C)n[nH]c4n3)cc2)c1]

This compound was prepared according to the procedure described in example 57. The desired product was obtained (12.7 mg, 7.30%) as a white solid. $^1$H NMR (400 MHZ, DMSO-$d_6$) δ 13.38 (s, 1H), 8.50 (d, J=5.6 Hz, 1H), 8.23-8.21 (m, 2H), 7.51 (d, J=2.4 Hz, 1H), 7.28-7.24 (m, 2H), 7.19 (dd, J=5.6, 2.5 Hz, 1H), 5.50 (tt, J=7.3, 3.6 Hz, 1H), 3.89 (s, 3H), 2.78-2.67 (m, 3H), 2.08-2.03 (m, 2H), 1.83-1.80 (m, 2H), 1.02 (d, J=6.8 Hz, 6H). LCMS (ESI, m/z): 538.25[M+H]+.

Compound 81

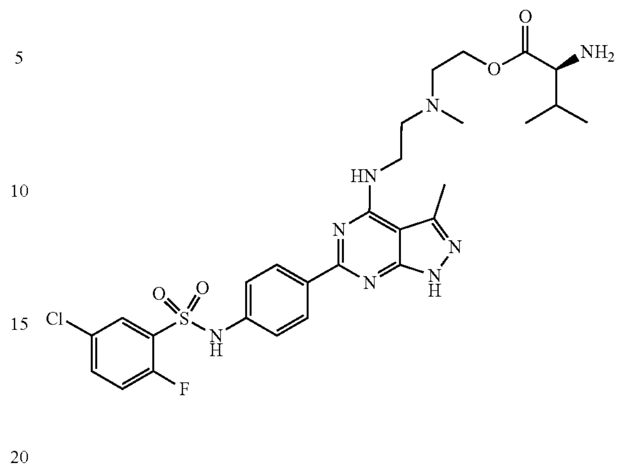

(i) 2-((2-(6-chloro-3-methyl-1-(tetrahydro-2H-pyran-2-yl)-1H-pyrazolo[3,4-d]pyrimidin-4-ylamino)ethyl)(methyl)amino)ethanol Into a 50-mL round-bottom flask, was placed 4,6-dichloro-3-methyl-1-(oxan-2-yl)pyrazolo[3,4-d]pyrimidine (450.00 mg, 1.57 mmol, 1.00 equiv.), 2-[(2-aminoethyl)(methyl)amino]ethanol (277.8 mg, 2.35 mmol, 1.50 equiv.), DCM (10.0 mL), TEA (317.2 mg, 3.13 mmol, 2.00 equiv.). The resulting solution was stirred for 1 overnight at room temperature. The resulting mixture was concentrated. The residue was applied onto a silica gel column with dichloromethane/methanol (100:0 to 85:15). The collected fractions were combined and concentrated. This resulted in 500 mg (77.84%) of 2-[(2-[[6-chloro-3-methyl-1-(oxan-2-yl)pyrazolo[3,4-d]pyrimidin-4-yl]amino]ethyl)(methyl)amino]ethanol as colorless oil. LCMS (ESI, m/z): 369 [M+H]+.

(ii) 4-(N-(5-chloro-2-fluorophenyl)sulfamoyl)phenylboronic acid

Into a 50-mL 3-necked round-bottom flask purged and maintained with an inert atmosphere of nitrogen, was placed 2-[(2-[[6-chloro-3-methyl-1-(oxan-2-yl)pyrazolo[3,4-d]pyrimidin-4-yl]amino]ethyl)(methyl)amino]ethanol (300.00 mg, 0.813 mmol, 1.00 equiv.), 4-(5-chloro-2-fluorobenzenesulfonamido)phenylboronic acid (219.76 mg, 0.667 mmol, 0.82 equiv.), dioxane (8.00 mL), $H_2O$ (2.00 mL, 0.111 mmol, 0.14 equiv.), $Cs_2CO_3$ (529.98 mg, 1.627 mmol, 2.0 equiv.), Pd(dppf)$Cl_2$ (119.02 mg, 0.163 mmol, 0.2 equiv.). The resulting solution was stirred for overnight at 90° C. in an oil bath. The reaction mixture was cooled to room temperature. The resulting mixture was concentrated. The resulting solution was diluted with 50 mL of DCM. The resulting mixture was washed with 2×30 ml of brine and 1×30 ml of water. The mixture was dried over anhydrous sodium sulfate. The residue was applied onto a silica gel column with dichloromethane/methanol (100:0 to 10:90). The collected fractions were combined and concentrated. This resulted in 90 mg (16.11%) of 5-chloro-2-fluoro-N-[4-[4-([2-[(2-hydroxyethyl)(methyl)amino]ethyl]amino)-3-methyl-1-(oxan-2-yl)pyrazolo[3,4-d]pyrimidin-6-yl]phenyl]benzenesulfonamide as colorless oil. LCMS (ESI, m/z): 618 [M+H]+.

(iii) (2S)-2-((2-(6-(4-(5-chloro-2-fluorophenylsulfonamido)phenyl)-3-methyl-1-(tetrahydro-2H-pyran-2-yl)-1H-pyrazolo[3,4-d]pyrimidin-4-ylamino)ethyl)(methyl)amino)ethyl 2-(tert-butoxycarbonylamino)-3-methylbutanoate Into a 50-mL round-bottom flask, was placed 5-chloro-2-fluoro-N-[4-[4-([2-[(2-hydroxyethyl)(methyl)amino]ethyl]amino)-3-methyl-1-(oxan-2-yl)pyrazolo[3,4-d]pyrimidin-6-yl]phenyl]benzenesulfonamide (80.00 mg, 0.129 mmol, 1.00 equiv.), (2S)-2-[(tert-butoxycarbonyl)amino]-3-methylbutanoic acid (30.93 mg, 0.142 mmol, 1.10 equiv.), DCM (8.00 mL), DCC (53.4 mg, 0.258 mmol, 2.00 equiv.), DMAP (15.81 mg, 0.129 mmol, 1.00 equiv.). The resulting solution was stirred for 4 hr at room temperature. The resulting mixture was concentrated. The crude product (150 mg) was purified by Flash-Prep-HPLC with the following conditions (CombiFlash-1): Column, C18 silica gel; mobile phase, water (NH4HCO3 0.05%)/ACN=80:20 increasing to water (NH4HCO3 0.05%)/ACN=30:70 within 45 minutes; Detector, 220 nm. This resulted in 15 mg (12.76%) of 2-[[2-([6-[4-(5-chloro-2-fluorobenzenesulfonamido)phenyl]-3-methyl-1-(oxan-2-yl)pyrazolo[3,4-d]pyrimidin-4-yl]amino)ethyl](methyl)amino]ethyl (2S)-2-[(tert-butoxycarbonyl)amino]-3-methylbutanoate as an off-white solid. LCMS (ESI, m/z): 817 [M+H]+.

(iv) (S)-2-((2-(6-(4-(5-chloro-2-fluorophenylsulfonamido)phenyl)-3-methyl-1H-pyrazolo[3,4-d]pyrimidin-4-ylamino)ethyl)(methyl)amino)ethyl 2-amino-3-methylbutanoate Into a 25-mL round-bottom flask, was placed 2-[[2-([6-[4-(5-chloro-2-fluorobenzenesulfonamido)phenyl]-3-methyl-1-(oxan-2-yl)pyrazolo[3,4-d]pyrimidin-4-yl]amino)ethyl](methyl)amino]ethyl (2S)-2-[(tert-butoxycarbonyl)amino]-3-methylbutanoate (15.00 mg, 0.018 mmol, 1.00 equiv.), HCl (gas) in 1,4-dioxane (2.00 mL). IPA (2.0 ml). The resulting solution was stirred for 4 hr at room temperature. The resulting mixture was concentrated. The crude product (30 mg) was purified with HPLC. Column: XBridge Prep C 18 OBD column, 19*250 mm*5 um, Mobile Phase A: Water (0.05% TFA), Phase B: Mobile ACN; flow rate: 25 ml/min; Gradient: 30% B to 50% B in 7 min; 254/220 nm; Rt: 4.75 min (detected by lcms and collected). 13.6 mg product was obtained as an off-white solid. $^1$H NMR (400 MHZ, DMSO-$d_6$) δ 10.62 (s, 1H), 8.57-8.49 (m, 4H), 7.86 (d, J=8.5 Hz, 2H), 7.49 (s, 1H), 7.40-7.15 (m, 4H), 4.72-4.44 (m, 2H), 4.07 (s, 2H), 3.90 (s, 2H), 3.82-3.30 (m, 3H), 2.98 (s, 3H), 2.59 (d, J=1.5 Hz, 3H), 0.89 (d, J=6.0 Hz, 6H). LCMS (ESI, m/z): 633 [M+H—$CF_3COOH$]+.

Compound 82 2-{[2-({6-[4-(5-chloro-2-fluorobenzenesulfonamido)phenyl]-3-methyl-1H-pyrazolo[3,4-d]pyrimidin-4-yl}amino)ethyl](methyl)amino}ethyl 2,2-dimethylpropanoate

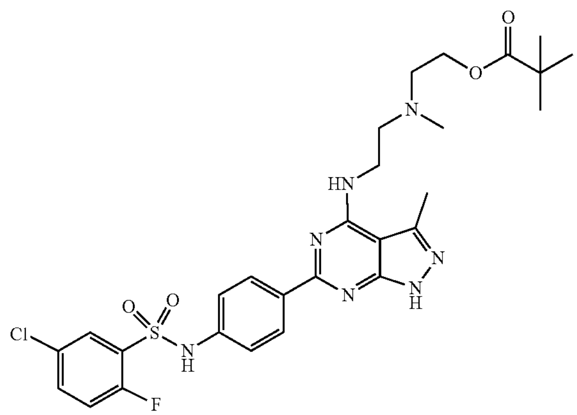 [SMILES: Cc1n[nH]c2nc(-c3ccc(NS(=O)(=O)c4cc(Cl)ccc4F)cc3)nc(NCCN(C)CCOC(=O)C(C)(C)C)c12]

To a stirred mixture of 5-chloro-2-fluoro-N-{4-[4-({2-[(2-hydroxyethyl)(methyl)amino]ethyl}amino)-3-methyl-1H-pyrazolo[3,4-d]pyrimidin-6-yl]phenyl}benzenesulfonamide (100 mg, 0.187 mmol, 1 equiv.) in pivalic acid (3 mL) was added trimethylacetic anhydride (69.76 mg, 0.374 mmol, 2.0 equiv.) dropwise at 40° C., and stirred at 120° C. for 6 hours. The residue was purified by reverse flash chromatography with the following conditions: column, C18 silica gel; mobile phase, can in water, 10% to 50% gradient in 30 min; detector, UV 254 nm, 40 ml/min. The crude product was purified by Prep-HPLC with the following conditions (Column: XBridge Shield RP18 OBD Column, 30*150 mm, 5 um; Mobile Phase A: Water (0.05% TFA), Mobile Phase can ACN; Flow rate: 60 mL/min; Gradient: 27% B to 47% B in 7 min, 47% B; Wave Length: 254 nm; RT1 (min): 4; Number Of Runs: 0) to afford 2-{[2-({6-[4-(5-chloro-2-fluorobenzenesulfonamido)phenyl]-3-methyl-1H-pyrazolo[3,4-d]pyrimidin-4-yl}amino)ethyl](methyl)amino}ethyl 2,2-dimethyl propanoate (21.2 mg, 17.93%) as a white solid. 1H NMR (400 MHZ, Methanol-$d_4$) δ 8.24-8.21 (m, 2H), 7.91-7.89 (m, 1H), 7.65-7.61 (m, 1H), 7.33-7.27 (m, 3H), 4.33 (t, J=4.9 Hz, 2H), 4.22 (d, J=6.1 Hz, 2H), 3.64 (s, 4H), 3.06 (d, J=1.6 Hz, 3H), 2.70-2.65 (m, 3H), 1.10 (s, 9H). LCMS (ESI, m/z): 618.15[M+H]+.

Compound 83 2-{[2-({6-[4-(5-chloro-2-fluorobenzenesulfonamido)phenyl]-3-methyl-1H-pyrazolo[3,4-d]pyrimidin-4-yl}amino)ethyl](methyl)amino}ethyl 3-methylbutanoate

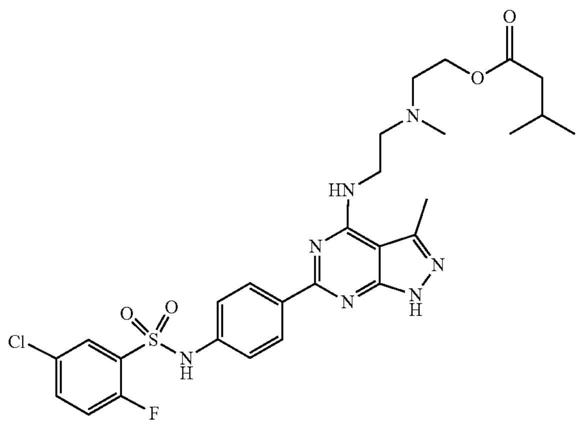 [SMILES: Cc1n[nH]c2nc(-c3ccc(NS(=O)(=O)c4cc(Cl)ccc4F)cc3)nc(NCCN(C)CCOC(=O)CC(C)C)c12]

To a stirred solution 5-chloro-2-fluoro-N-{4-[4-({2-[(2-hydroxyethyl)(methyl)amino]ethyl}amino)-3-methyl-1H-pyrazolo[3,4-d]pyrimidin-6-yl]phenyl}benzenesulfonamide (100 mg, 0.187 mmol, 1.00 equiv.) in DMF (3 mL) and $Et_3N$ (37.90 mg, 0.374 mmol, 2.00 equiv.). pivaloyl chloride (24.84 mg, 0.206 mmol, 1.10 equiv.) dropwise at 0° C. The reaction was stirred for 2 hours at 0° C. The reaction was quenched by the addition of water. The resulted mixture was purified by Prep-HPLC with the following conditions (Column: XBridge Shield RP18 OBD Column 30*150 mm, 5 um; Mobile Phase A: Water (0.05% TFA), Mobile B: ACN; Flow rate: 60 ml/min, Gradient: 25% B to 45% in 7 min, Wave Length 254 nm; RT 4.57 min) to afford 2-{[2-({6-[4-(5-chloro-2-fluorobenzenesulfonamido)phenyl]-3-methyl-1H-pyrazolo[3,4-d]pyrimidin-4-yl}amino)ethyl](methyl)amino}ethyl 3-methylbutanoate TFA salt (21.3 mg) pure: 98.2% as a white solid. 1H NMR (300 MHZ, DMSO-$d_6$) δ 11.09 (s, 1H), 9.71 (s, 1H), 8.42-8.16 (m, 2H), 8.05-7.68 (m, 2H), 7.52 (t, J=9.3 Hz, 1H), 7.39-7.18 (m, 3H), 4.31 (t, J=5.1 Hz, 2H), 4.00 (s, 2H), 3.65-3.51 (m, 2H), 2.95 (s, 3H), 2.57 (s, 3H), 2.06 (d, J=7.1 Hz, 2H), 1.87 (dt, J=13.5, 6.7 Hz, 1H), 0.78 (d, J=6.6 Hz, 5H). LCMS (ESI, m/z): 618 [M+H—$CF_3COOH$]+.

Compound 84 N-[4-(4-[[2-(dimethylamino)ethyl]amino]-3-methyl-1H-pyrazolo[3,4-d]pyrimidin-6-yl)-2-fluorophenyl]-2,5-difluorobenzenesulfonamide

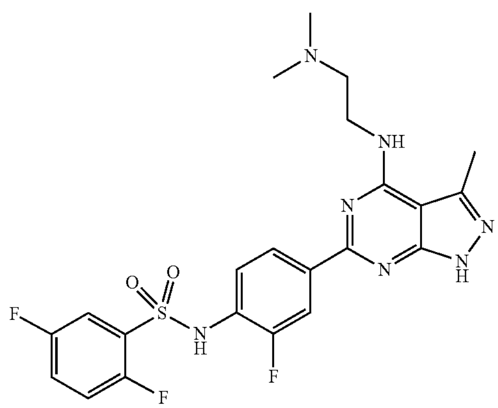

This compound was prepared according to the procedure described in example 38. The desired product as a white solid (23.6 mg, 7.84%). LCMS (ES. m/z): 522 [M-TFA+H]+. $^1$H-NMR ($CD_3OD$, 300 MHZ) δ (ppm): 8.19-8.16 (m, 1H), 8.10-8.06 (dd, J=1.8 &12 Hz, 1H), 7.81-7.78 (m, 1H), 7.68-7.63 (m, 2H), 7.57 (t, J=8.2 Hz, 1H), 7.35-7.29 (t, J=9.3 Hz, 1H), 4.16-4.13 (t, J=5.7 Hz, 2H), 3.56-3.53 (t, J=5.7 Hz, 2H), 2.98 (s, 6H), 2.65 (s, 3H).

Compound 85 N-(2-chloro-4-(4-((2-(dimethylamino)ethyl)amino)-3-methyl-1H-pyrazolo[3,4-d]pyrimidin-6-yl)phenyl)-2,5-difluorobenzenesulfonamide

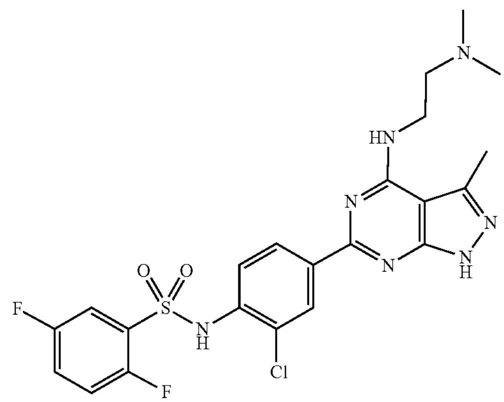 [SMILES: Cc1n[nH]c2nc(-c3ccc(NS(=O)(=O)c4cc(F)ccc4F)c(Cl)c3)nc(NCCN(C)C)c12]

This compound was prepared according to the procedure described in example 38. The desired product as a white solid (4.56 mg, 46%). LCMS: (ES, m/z): [M+H]+=522, $^1$H NMR (300 MHZ, DMSO-$d_6$) δ 12.97 (s, 1H), 9.75 (s, 1H), 8.23 (d, J=2.1 Hz, 1H), 8.94-7.08 (m, 1H), 7.44-7.53 (m, 1H), 7.32 (q, J=8.7, 6.8 Hz, 3H), 7.18 (t, J=5.8 Hz, 1H), 5.76 (s, 2H), 3.94 (d, J=6.2 Hz, 2H), 3.17 (s, 1H), 2.81 (d, J=5.8 Hz, 6H), 2.55 (d, J=7.2 Hz, 3H).

Compound 86 5-chloro-2-fluoro-N-[4-(4-{2-[(2-hydroxyethyl)(methyl)amino]ethoxy}-3-methyl-1H-pyrazolo[3,4-d]pyrimidin-6-yl)phenyl]benzenesulfonamide

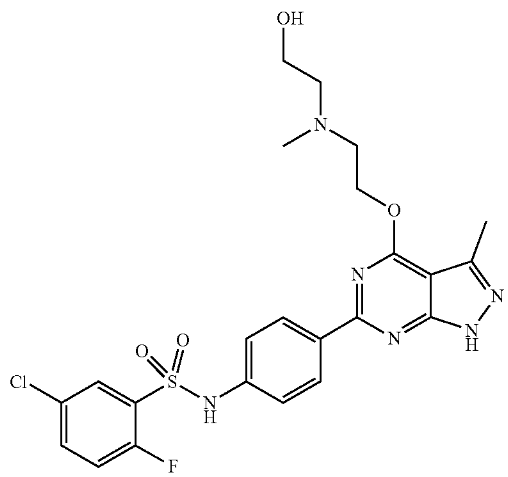 [SMILES: Cc1n[nH]c2nc(-c3ccc(NS(=O)(=O)c4cc(Cl)ccc4F)cc3)nc(OCCN(C)CCO)c12]

This compound was prepared according to the procedure described in example 9. The desired product as an off-white solid (516.3 mg, 30% yield). LCMS (ESI, m/z): 535 [M+H]+. $^1$H NMR (300 MHZ, DMSO-$d_6$) δ 13.43 (s, 1H), 8.33-8.23 (m, 2H), 7.86 (dd, J=6.1, 2.7 Hz, 1H), 7.75 (ddd, J=8.8, 4.1, 2.7 Hz, 1H), 7.48 (t, J=9.3 Hz, 1H), 7.27-7.16 (m, 2H), 4.73 (t, J=5.6 Hz, 2H), 4.46 (s, 1H), 3.51 (t, J=6.2 Hz, 2H), 3.39 (s, 3H), 2.97 (t, J=5.5 Hz, 2H), 2.63 (t, J=6.2 Hz, 2H), 2.49 (s, 3H), 2.39 (s, 3H).

Compound 87 2-[[2-([6-[4-(5-chloro-2-fluorobenzenesulfonamido)phenyl]-3-methyl-1H-pyrazolo[3,4-d]pyrimidin-4-yl]amino)ethyl](methyl)amino]ethyl acetate

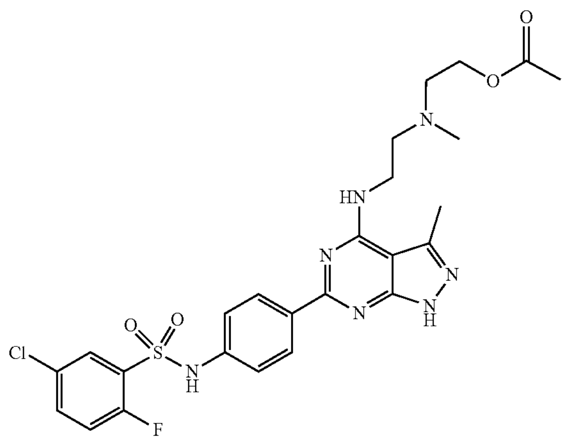 [SMILES: CC(=O)OCCN(C)CCNc1nc(-c2ccc(NS(=O)(=O)c3cc(Cl)ccc3F)cc2)nc2[nH]nc(C)c12]

This compound was prepared according to the procedure described in example 83. The desired product as a white solid (50.3 mg, 95.1% purity). LCMS (ESI, m/z): 576+H]+. $^1$H NMR (300 MHZ, DMSO-$d_6$) δ 12.96 (s, 1H), 10.98 (s, 1H), 8.26 (d, J=8.4 Hz, 2H), 7.89-7.68 (m, 2H), 7.49 (t, J=9.3 Hz, 1H), 7.20 (d, J=8.4 Hz, 2H), 6.98 (t, J=5.6 Hz, 1H), 4.09 (t, J=5.9 Hz, 2H), 3.69 (q, J=6.4 Hz, 2H), 2.69 (dt, J=8.4, 4.6 Hz, 4H), 2.55 (s, 3H), 2.33 (s, 3H), 1.94 (s, 3H).

Compound 88 2-{[2-({6-[4-(5-chloro-2-fluorobenzenesulfonamido)phenyl]-3-methyl-1H-pyrazolo[3,4-d]pyrimidin-4-yl}amino)ethyl](methyl)amino}ethoxyphosphonic acid

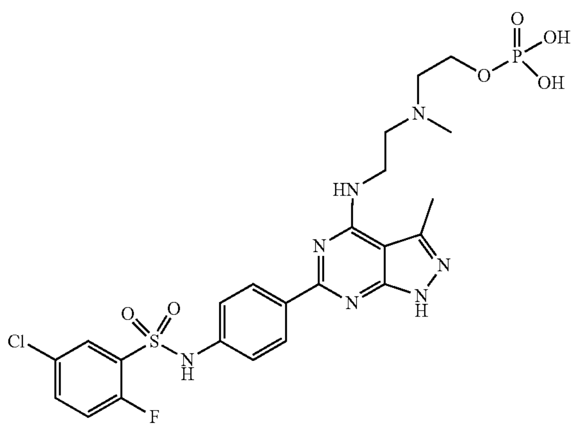 [SMILES: Cc1n[nH]c2nc(-c3ccc(NS(=O)(=O)c4cc(Cl)ccc4F)cc3)nc(NCCN(C)CCOP(=O)(O)O)c12]

Into tetrahydrofuran (3 mL) was added 5-chloro-2-fluoro-N-{4-[4-({2-[(2-hydroxyethyl) (methyl)amino]ethyl}amino)-3-methyl-1H-pyrazolo[3,4-d]pyrimidin-6-yl]phenyl}benzenesulfonamide (200 mg, 0.375 mmol, 1.00 equiv.) at room temperature.

To the above mixture was added (dichlorophosphoryl)oxyphosphonoyl dichloride (0.16 mL, 0.636 mmol, 1.70 equiv.) dropwise at −40° C. The resulting mixture was stirred for additional 1 hour at −40° C. The residue was basified to pH 8 with $NaHCO_3$. The residue was acidified with AcOH. The residue was purified by pre-HPLC: column: XBridge Shield RP18 OBD Column, 19*250 mm, 10 um; Mobile phase A: Water (10 mmol/L NH4HCO3+0.1% NH3·H2O), Mobile phase B: ACN; Flow rate: 25 mL/min; Gradient: 12% B to 28% B in 5 min, 28% B; Wave Length: 220 nm; RT1 (min): 4.58 to afford 2-{[2-({6-[4-(5-chloro-2-fluorobenzenesulfonamido)phenyl]-3-methyl-1H-pyrazolo[3,4-d]pyrimidin-4-yl}amino)ethyl](methyl)amino}ethoxyphosphonic acid (98.3 mg, 41.12%) as a white solid. LCMS (ESI, m/z): 614.1 [M+H]+. $^1$H NMR (300 MHZ, DMSO-$d_6$) δ 13.05 (s, 1H), 11.07 (s, 1H), 8.30-8.27 (m, 2H), 7.87-7.77 (m, 2H), 7.55-7.48 (m, 1H), 7.29-7.22 (m, 3H), 4.15-4.12 (m, 2H), 4.00-3.98 (m, 2H), 3.47 (s, 4H), 2.93 (s, 3H), 2.56 (s, 3H).

Compound 89 2-{[2-({6-[4-(5-chloro-2-fluorobenzenesulfonamido)phenyl]-3-methyl-1H-pyrazolo[3,4-d]pyrimidin-4-yl}amino)ethyl](methyl)amino}ethyl 2-methylpropanoate trifluoroacetic acid

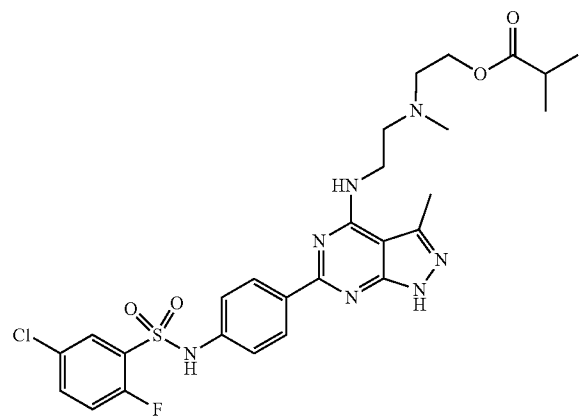 [SMILES: Cc1n[nH]c2nc(-c3ccc(NS(=O)(=O)c4cc(Cl)ccc4F)cc3)nc(NCCN(C)CCOC(=O)C(C)C)c12]

To a stirred solution of 5-chloro-2-fluoro-N-{4-[4-({2-[(2-hydroxyethyl)(methyl)amino]ethyl}amino)-3-methyl-1H-pyrazolo[3,4-d]pyrimidin-6-yl]phenyl}benzenesulfonamide (1.4 g, 2.622 mmol, 1 equiv.) in isobutyric acid (15 mL, 170.249 mmol, 64.94 equiv.) was added isobutyric anhydride (0.62 g, 3.933 mmol, 1.5 equiv.) in portions, and stirred at 120° C. for 16 hours. The residue was purified by reverse flash chromatography with the following conditions: column, C18 silica gel; mobile phase, ACN in water (0.05% TFA), 10% to 50% gradient in 60 min; detector, UV 254 nm, 50 ml/min. This resulted in 2-{[2-({6-[4-(5-chloro-2-fluorobenzenesulfonamido)phenyl]-3-methyl-1H-pyrazolo[3,4-d]pyrimidin-4-yl}amino)ethyl](methyl)amino}ethyl 2-methylpropanoate trifluoroacetic acid (1.0438 g, 54.39%) as a white solid. LCMS (ESI, m/z): 604.15 [M+H]+. $^1$H NMR (400 MHZ, DMSO-$d_6$) δ 11.11 (s, 1H), 9.89 (s, 1H), 8.30-8.28 (m, 2H), 7.87-7.85 (m, 1H), 7.82-7.78 (m, 1H), 7.54-7.50 (m, 1H), 7.37 (s, 1H), 7.25-7.23 (m, 2H), 4.31 (t, J=5.1 Hz, 2H), 4.01 (s, 2H), 3.58-3.44 (m, 4H), 2.96 (s, 3H), 2.57 (s, 3H), 2.48-2.39 (m, 1H), 1.00 (d, J=6.8 Hz, 6H).

Compound 90 2-{[2-({6-[4-(5-chloro-2-fluorobenzenesulfonamido)phenyl]-3-methyl-1H-pyrazolo[3,4-d]pyrimidin-4-yl}amino)ethyl](methyl)amino}ethyl propanoate; bis(trifluoroacetic acid)

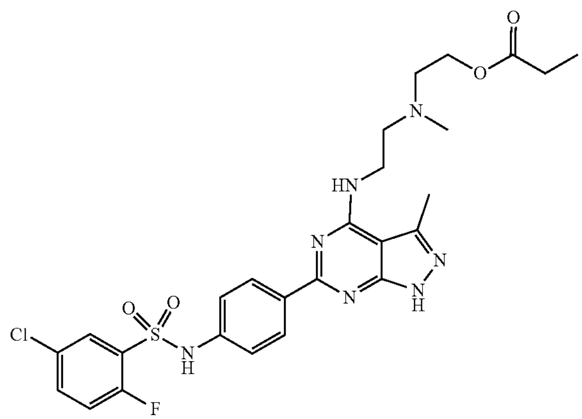 [SMILES: CCC(=O)OCCN(C)CCNc1nc(-c2ccc(NS(=O)(=O)c3cc(Cl)ccc3F)cc2)nc2[nH]nc(C)c12]

bis(5-chloro-2-fluoro-N-{4-[4-({2-[(2-hydroxyethyl)(methyl)amino]ethyl}amino)-3-methyl-1H-pyrazolo[3,4-d]pyrimidin-6-yl]phenyl}benzenesulfonamide) (200 mg, 0.187 mmol, 1.00 equiv.) in propionic acid (3 mL), was added propionic anhydride (97.56 mg, 2.00 equiv.). The mixture was stirred for 4 hours at 100° C. The mixture was allowed to cool down to room temperature. The resulting mixture was concentrated under vacuum. The resulting mixture was diluted with DMF (3 ml). The residue was purified by reverse flash chromatography with the following conditions: column, C18 gel; mobile phase, MeCN water (TFA 0.05%), 10% to 90% gradient in 40 min; detector, UV 254 nm&220 nm. This result to give desired product 2-{[2-({6-[4-(5-chloro-2-fluorobenzenesulfonamido)phenyl]-3-methyl-1H-pyrazolo[3,4-d]pyrimidin-4-yl}amino)ethyl](methyl)amino}ethyl propanoate; bis(trifluoroacetic acid) (114.2 mg, 85.43%) as a white solid. LCMS (ESI, m/z): 590[M+H]+. $^1$H NMR (400 MHZ, DMSO-$d_6$) δ 11.12 (s, 1H), 9.83 (s, 1H), 8.30-8.28 (m, 2H), 7.87 (dd, J=6.1, 2.7 Hz, 1H), 7.80 (m, 1H), 7.52 (t, J=9.3 Hz, 1H), 7.40 (s, 1H), 7.28-7.22 (m, 2H), 4.31 (t, J=5.1 Hz, 2H), 4.01 (m, 2H), 3.58-3.44 (m, 4H), 2.95 (s, 3H), 2.57 (s, 3H), 2.22 (q, J=7.5 Hz, 2H), 0.93 (t, J=7.5 Hz, 3H).

Compound 91 2-{[2-({6-[4-(5-chloro-2-fluorobenzenesulfonamido)phenyl]-3-methyl-1H-pyrazolo[3,4-d]pyrimidin-4-yl}amino)ethyl](methyl)amino}ethyl butanoate trifluoroacetic acid

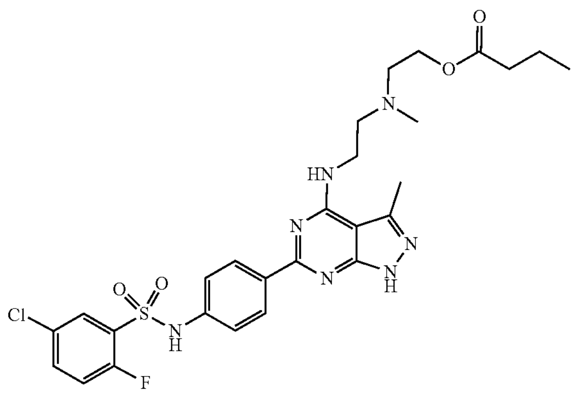 [SMILES: CCCC(=O)OCCN(C)CCNc1nc(-c2ccc(NS(=O)(=O)c3cc(Cl)ccc3F)cc2)nc2[nH]nc(C)c12]

To a stirred solution of 5-chloro-2-fluoro-N-{4-[4-({2-[(2-hydroxyethyl)(methyl)amino]ethyl}amino)-3-methyl-1H-pyrazolo[3,4-d]pyrimidin-6-yl]phenyl}benzenesulfonamide (200 mg, 0.375 mmol, 1.00 equiv.) in butanoic acid (3 mL) was added butyric anhydride (118.50 mg, 0.750 mmol, 2.00 equiv.) dropwise at room temperature, and stirred for 6 hours at 120° C. The residue was purified by reverse flash chromatography with the following conditions: column, C18 silica gel; mobile phase, ACN in water (0.05% TFA), 10% to 50% gradient in 30 min; detector, UV 254 nm. This resulted in 2-{[2-({6-[4-(5-chloro-2-fluorobenzenesulfonamido)phenyl]-3-methyl-1H-pyrazolo[3,4-d]pyrimidin-4-yl}amino)ethyl](methyl)amino}ethyl butanoate trifluoroacetic acid (176.6 mg, 63.04%) as a white solid. LCMS (ESI, m/z): 604.20 [M+H]+. $^1$H NMR (300 MHZ, DMSO-$d_6$) δ 11.09 (s, 1H), 9.75 (s, 1H), 8.30-8.27 (m, 2H), 7.87-7.79 (m, 2H), 7.52 (t, J=9.3 Hz, 1H), 7.36-7.22 (m, 3H), 4.32 (t, J=5.1 Hz, 2H), 3.99 (s, 2H), 2.93-2.85 (m, 3H), 2.73 (s, 1H), 2.57 (s, 3H), 2.15 (t, J=7.4 Hz, 2H), 1.48-1.35 (m, 2H), 0.78 (t, J=7.4 Hz, 3H).

Compound 92 5-chloro-2-fluoro-N-[4-(4-{[(3S,4R)-3-fluoro-1-(2-hydroxy-2-methylpropyl)piperidin-4-yl]oxy}-3-methyl-1H-pyrazolo[3,4-d]pyrimidin-6-yl)phenyl]benzenesulfonamide

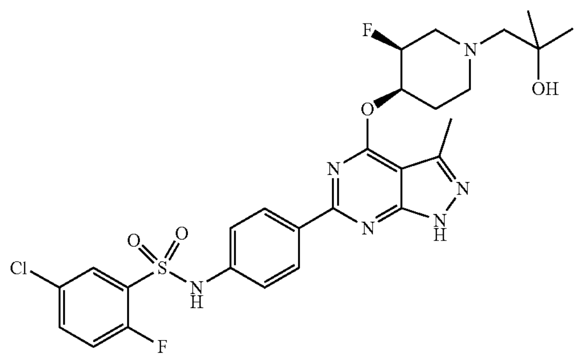 [SMILES: Cc1n[nH]c2nc(-c3ccc(NS(=O)(=O)c4cc(Cl)ccc4F)cc3)nc(O[C@@H]3CCN(CC(C)(C)O)C[C@@H]3F)c12]

(i) 1-[(3S,4R)-4-({6-chloro-3-methyl-1H-pyrazolo[3,4-d]pyrimidin-4-yl}oxy)-3-fluoropiperidin-1-yl]-2-methylpropan-2-ol A solution of (3S,4R)-4-({6-chloro-3-methyl-1H-pyrazolo[3,4-d]pyrimidin-4-yl}oxy)-3-fluoropiperidine hydrochloride (200 mg, 0.621 mmol, 1.00 equiv.), Cs2CO3 (257.39 mg, 1.863 mmol, 3 equiv.) in DMF (10 mL) was stirred for 16 h at 60° C. The solution was collected by filtration. The solid was purified by flash Prep-HPLC with the following conditions (Column, C18 spherical 20-35 um 100 A (120 g); mobile phase A: Water-10 mM NH4HCO3, mobile phase B: Acetonitrile; Flow rate: 50 mL/min; Gradient 41 B to 48 B; 254 nm). This resulted in 1-[(3S,4R)-4-({6-chloro-3-methyl-1H-pyrazolo[3,4-d]pyrimidin-4-yl}oxy)-3-fluoropiperidin-1-yl]-2-methylpropan-2-ol (30 mg, 10.80%) as a yellow oil. LCMS (ES. m/z): 358 [M+H]+.

(ii) 5-chloro-2-fluoro-N-[4-(4-{[(3S,4R)-3-fluoro-1-(2-hydroxy-2-methylpropyl)piperidin-4-yl]oxy}-3-methyl-1H-pyrazolo[3,4-d]pyrimidin-6-yl)phenyl]benzenesulfonamide A solution of 1-[(3S,4R)-4-({6-chloro-3-methyl-1H-pyrazolo[3,4-d]pyrimidin-4-yl}oxy)-3-fluoropiperidin-1-yl]-2- methylpropan-2-ol (30 mg, 0.084 mmol, 1 equiv.), 5-chloro-2-fluoro-N-[4-(4,4,5,5-tetramethyl-1,3,2-dioxaborolan-2-yl)phenyl]benzenesulfonamide (34.52 mg, 0.084 mmol, 1.00 equiv.), $Pd(dppf)Cl_2$ (12.27 mg, 0.017 mmol, 0.20 equiv.), $Cs_2CO_3$ (40.98 mg, 0.126 mmol, 1.50 equiv.) in 1,4-dioxane (3 mL), $H_2O$ (0.75 mL) was stirred for 16 h at 100° C. under nitrogen atmosphere. The resulting mixture was concentrated under reduced pressure. The solid was purified by flash Prep-HPLC with the following conditions (Column, C18 spherical 20-35 um 100 A (800 g); mobile phase A: Water-10 mM $NH_4HCO_3$, mobile phase B: Acetonitrile; Flow rate: 40 mL/min; Gradient 50 B to 58 B; 254 nm). The resulting mixture was concentrated under reduced pressure. The crude product was purified by Prep-HPLC with the following conditions (Column: XBridge Prep OBD C18 Column, 30×150 mm, 5 um; Mobile Phase A: Water (10 mmol/L $NH_4HCO_3$+0.1% $NH_3 \cdot H_2O$), Mobile Phase B: ACN; Flow rate: 60 mL/min; Gradient: 40% B to 50% B in 9 min, 50% B; Wave Length: 254 nm; RT1 (min): 5.85). This resulted in 5-chloro-2-fluoro-N-[4-(4-{[(3S,4R)-3-fluoro-1-(2-hydroxy-2-methylpropyl)piperidin-4-yl]oxy}-3-methyl-1H-pyrazolo[3,4-d]pyrimidin-6-yl)phenyl]benzenesulfonamide (4.5 mg, 8.69%) as a white solid. LCMS (ES. m/z): 607 [M+H]+. $^1$H-NMR (DMSO-$d_6$, 300 MHZ) δ(ppm): 8.28-8.16 (m, 2H), 7.81-7.88 (m, 1H), 7.68-7.65 (m, 1H), 7.43-7.38 (m, 1H), 7.18-7.06 (m, 2H), 5.82-5.74 (m, 1H), 5.09-4.86 (m, 1H), 4.81 (s, 1H), 4.18 (s, 2H), 3.13-2.91 (m, 2H), 2.75 (s, 3H), 2.39 (s, 2H), 2.08-1.91 (m, 2H), 1.16 (s, 6H).

Compound 93 5-chloro-2-fluoro-N-{4-[4-({2-[(2-hydroxyethyl)(isopropyl)amino]ethyl}amino)-3-methyl-1H-pyrazolo[3,4-d]pyrimidin-6-yl]phenyl}benzenesulfonamide

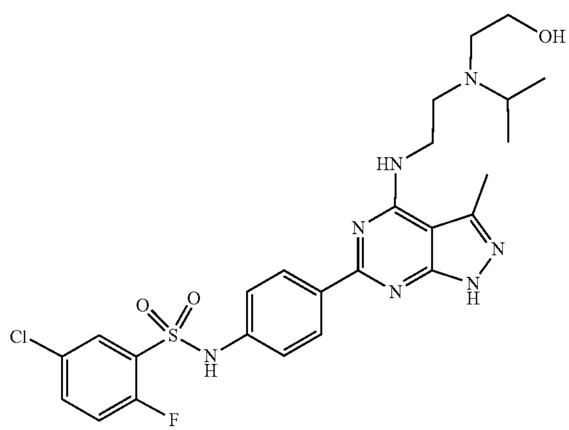 [SMILES: Cc1n[nH]c2nc(-c3ccc(NS(=O)(=O)c4cc(Cl)ccc4F)cc3)nc(NCCN(CCO)C(C)C)c12]

(i) N-{2-[(2-hydroxyethyl)(isopropyl)amino]ethyl}carbamate

To a stirred mixture of tert-butyl N-(2-bromoethyl)carbamate (433 mg, 1.93 mmol, 1.00 equiv.) and 2-(isopropylamino)ethanol (199.3 mg, 1.93 mmol, 1.00 equiv.) in ACN (15 mL) was added $K_2CO_3$ (534.1 mg, 3.86 mmol, 2.00 equiv.) in portions, and stirred at 60° C. for 16 hours. The residue was purified by flash chromatography with the following conditions: column, silica gel; mobile phase, DCM in MeOH 0% to 10% gradient in 30 min; detector, UV 254 nm. This resulted in tert-butyl N-{2-[(2-hydroxyethyl)(isopropyl)amino]ethyl}carbamate (100 mg, 21.01%) as an off-white solid. LCMS (ESI, m/z): 247 [M+H]+.

(ii) 2-[(2-aminoethyl)(isopropyl)amino]ethanol hydrochloride

To a stirred solution of tert-butyl N-{2-[(2-hydroxyethyl)(isopropyl)amino]ethyl}carbamate (100 mg, 0.406 mmol, 1.00 equiv.) in DCM (3 mL) was added HCl (gas) in 1,4-dioxane (3 mL, 98.74 mmol, 243.2 equiv.) dropwise at room temperature, and stirred for 2 hours. The resulting mixture was concentrated under reduced pressure. This resulted in 2-((2-aminoethyl)(isopropyl)amino)ethan-1-ol dihydrochloride (80 mg, 100%) as an off-white solid. LCMS (ESI, m/z): 147 [M−2HCl+H]+.

(iii) 5-chloro-2-fluoro-N-{4-[4-({2-[(2-hydroxyethyl)(isopropyl)amino]ethyl}amino)-3-methyl-1H-pyrazolo[3,4-d]pyrimidin-6-yl]phenyl}benzenesulfonamide This compound was prepared according to the procedure described in example 9. The desired product as a white solid (50.3 mg, 95.1% purity (3.2 mg, 11.78%) as a white solid. LCMS (ESI, m/z): 562.10[M+H]+. $^1$H NMR (300 MHZ, DMSO-$d_6$) δ 12.94 (s, 1H), 8.24 (d, J=8.3 Hz, 2H), 7.83-7.67 (m, 2H), 7.47 (t, J=9.2 Hz, 1H), 7.16 (d, J=8.4 Hz, 2H), 7.02 (m, 1H), 4.45 (s, 1H), 3.63 (q, J=6.7, 6.2 Hz, 2H), 3.45 (m, 2H), 3.07-2.96 (m, 1H), 2.70 (t, J=6.9 Hz, 2H), 2.55 (m, 4H), 0.96 (d, J=6.5 Hz, 6H)

Compound 94 5-chloro-N-{4-[4-({2-[ethyl(2-hydroxyethyl)amino]ethyl}amino)-3-methyl-1H-pyrazolo[3,4-d]pyrimidin-6-yl]phenyl}-2-fluorobenzenesulfonamide

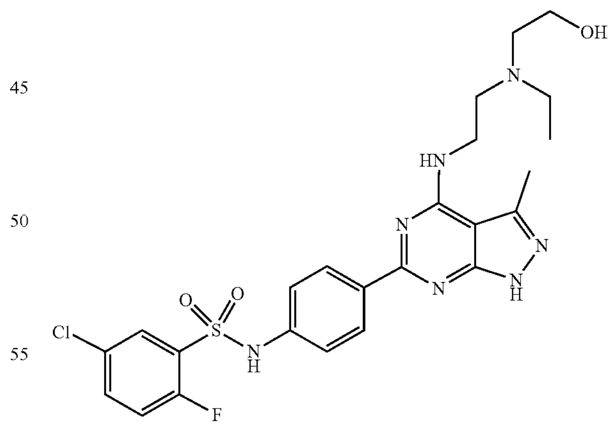

This compound was prepared according to the procedure described in example 93. The desired product as a white solid (22.1 mg, 19.64%). LCMS (ES. m/z): 548 [M+H]+. $^1$H-NMR (DMSO-$d_6$, 300 MHz) δ (ppm): 12.93 (s, 1H), 11.11 (s, 1H), 8.23 (d, J=8.7 Hz, 2H), 7.84-7.70 (m, 2H), 7.49-7.43 (m, 1H), 7.17-6.99 (m, 3H), 4.48 (s, 1H), 3.69-3.61 (m, 2H), 3.51-3.47 (m, 2H), 2.98-2.61 (m, 6H), 2.53 (s, 3H), 1.02-0.97 (m, 3H).

Compound 95 5-chloro-2-fluoro-N-{4-[4-({3-[(2-hydroxyethyl)(methyl)amino]propyl}amino)-3-methyl-1H-pyrazolo[3,4-d]pyrimidin-6-yl]phenyl}benzenesulfonamide

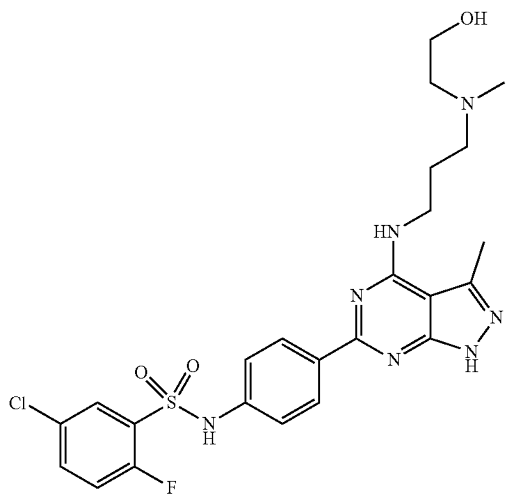 [SMILES: Cc1n[nH]c2nc(-c3ccc(NS(=O)(=O)c4cc(Cl)ccc4F)cc3)nc(NCCCN(C)CCO)c12]

This compound was prepared according to the procedure described in example 9. The desired product as a white solid (3.7 mg, 3.88%). LCMS (ES. m/z): 548 [M+H]+. $^1$H-NMR (DMSO-$d_6$, 300 MHZ) δ (ppm): 12.86 (s, 1H), 8.17 (d, J=8.4 Hz, 2H), 7.81-7.74 (m, 1H), 7.67-7.64 (m, 1H), 7.49-7.29 (m, 2H), 7.07 (d, J=8.4 Hz, 2H), 4.52 (s, 1H), 3.72-3.56 (m, 4H), 2.68-2.59 (m, 4H), 2.48 (s, 3H), 2.25 (s, 3H), 1.92-1.79 (m, 2H).

Compound 96 N-[4-(4-{[2-(dimethylamino)ethyl]amino}-3-methyl-1H-pyrazolo[3,4-d]pyrimidin-6-yl)-2-methoxyphenyl]-2,5-difluorobenzenesulfonamide

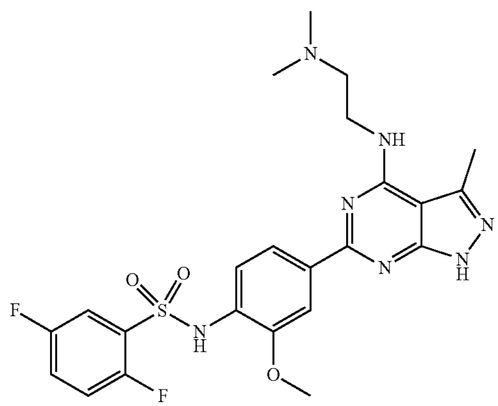 [SMILES: COc1cc(-c2nc(NCCN(C)C)c3c(C)n[nH]c3n2)ccc1NS(=O)(=O)c1cc(F)ccc1F]

This compound was prepared according to the procedure described in example 9. The desired product as an off white solid (120.7 mg, 19.76%). LCMS (ESI, m/z): 518.2 [M+H]+. $^1$H NMR (300 MHZ, DMSO-$d_6$) δ 13.01 (s, 1H), 7.94-7.82 (m, 2H), 7.73-7.51 (m, 3H), 7.29 (d, J=8.2 Hz, 1H), 7.09 (t, J=5.7 Hz, 1H), 3.77-3.71 (m, 2H), 3.62 (s, 3H), 2.65 (t, J=6.8 Hz, 2H), 2.53-2.50 (s, 3H), 2.30-2.14 (m, 6H).

Compound 99 5-chloro-N-{2-chloro-4-[4-({2-[(2-hydroxyethyl)(methyl)amino]ethyl}amino)-3-methyl-1H-pyrazolo[3,4-d]pyrimidin-6-yl]phenyl}-2-fluorobenzenesulfonamide

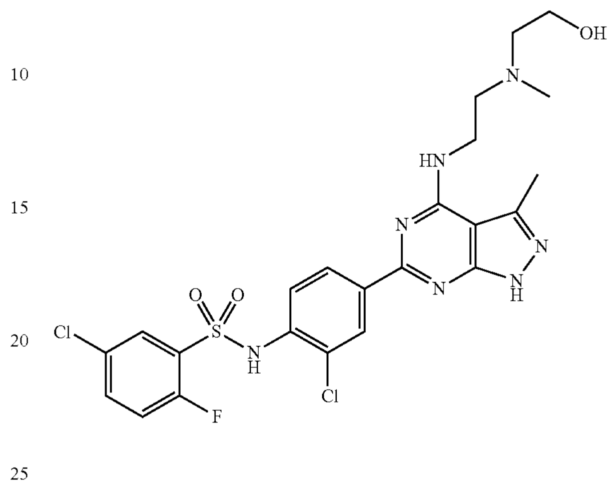

(i) 5-chloro-N-[2-chloro-4-(4,4,5,5-tetramethyl-1,3,2-dioxaborolan-2-yl)phenyl]-2-fluorobenzenesulfonamide Into a 50 mL round-bottom flask were added 2-chloro-4-(4,4,5,5-tetramethyl-1,3,2-dioxaborolan-2-yl)aniline (1 g, 3.944 mmol, 1 equiv), Pyridine (467.99 mg, 5.916 mmol, 1.5 equiv) in DCM (10 mL) at room temperature. The resulting mixture was stirred for 6 h at room temperature. The resulting mixture was concentrated under reduced pressure. The residue was purified by silica gel column chromatography, eluted with PE/EA (10:1) to afford 5-chloro-N-[2-chloro-4-(4,4,5,5-tetramethyl-1,3,2-dioxaborolan-2-yl)phenyl]-2-fluorobenzenesulfonamide (1 g, 56.83%) as an off-white solid. LCMS: (ES, m/z): [M−H]+=446

(ii) 2-[[2-([6-chloro-3-methyl-1H-pyrazolo[3,4-d]pyrimidin-4-yl]amino)ethyl](methyl)amino]ethanol Into a 50-mL round-bottom flask, was placed 4,6-dichloro-3-methyl-1H-pyrazolo[3,4-d]pyrimidine (240.00 mg, 1.182 mmol, 1.00 equiv), DCM (10.00 mL), DIEA (458.33 mg, 3.546 mmol, 3 equiv), 2-[(2-aminoethyl)(methyl)amino]ethanol (209.55 mg, 1.773 mmol, 1.50 equiv). The resulting solution was stirred for 16 hr at room temperature. The resulting mixture was concentrated. The solid was washed with EA and MeOH (10/1). The solids were collected by filtration. This resulted in 220 mg (60.78%) of 2-[[2-([6-chloro-3-methyl-1H-pyrazolo[3,4-d]pyrimidin-4-yl]amino)ethyl](methyl)amino]ethanol as a white solid. LCMS: (ES, m/z): [M+H]+=285

(iii) 5-chloro-N-{2-chloro-4-[4-({2-[(2-hydroxyethyl)(methyl)amino]ethyl}amino)-3-methyl-1H-pyrazolo[3,4-d]pyrimidin-6-yl]phenyl}-2-fluorobenzenesulfonamide A solution of 5-chloro-N-[2-chloro-4-(4,4,5,5-tetramethyl-1,3,2-dioxaborolan-2-yl)phenyl]-2-fluorobenzenesulfonamide (300 mg, 0.672 mmol, 1 equiv), Cs2CO3 (328.65 mg, 1.008 mmol, 1.5 equiv), Pd(dppf)Cl2 (98.41 mg, 0.134 mmol, 0.2 equiv) in $H_2O$ (30.00 mL, 1664.127 mmol, 2476.38 equiv) and dioxane (9.00 mL, 106.163 mmol, 157.98 equiv) was treated for 10 min at room temperature under nitrogen atmosphere. The resulting mixture was stirred for 16 h at 100° C. under nitrogen atmosphere. The mixture was allowed to cool down to room temperature. The residue was purified by silica gel column chromatography, eluted with CH2Cl2/MeOH (10:1) to afford the desired product (138.8 mg, 35.37%) as a off-white solid. LCMS: (ES, m/z): [M+H]+=568 1H NMR (400 MHZ, DMSO-$d_6$) δ 12.95 (s, 1H), 9.59 (s, 1H), 8.23 (s, 1H), 8.02 (d, J=8.6 Hz, 1H), 7.70 (d, J=4.8 Hz, 1H), 7.54 (d, J=8.7 Hz, 1H), 7.35-7.27 (m, 2H), 7.13 (d, J=5.7 Hz, 1H), 5.13 (s, 1H), 3.93 (q, J=6.1 Hz, 2H), 3.68 (s, 6H), 3.15 (d, J=11.7 Hz, 2H), 2.80 (s, 3H), 2.54 (s, 3H).

Compound 100 N-[2-chloro-4-(4-{[2-(dimethylamino)ethyl]amino}-3-methyl-1H-pyrazolo[3,4-d]pyrimidin-6-yl)phenyl]-4-isopropoxypyridine-2-sulfonamide

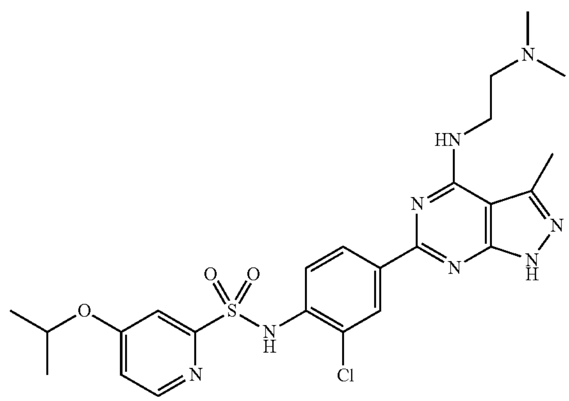 [SMILES: Cc1n[nH]c2nc(-c3ccc(NS(=O)(=O)c4cc(OC(C)C)ccn4)c(Cl)c3)nc(NCCN(C)C)c12]

(i) 4-isopropoxypyridine-2-sulfonyl chloride

Into a 100 mL round-bottom flask were added 2-(benzylsulfanyl)-4-isopropoxypyridine (1 g, 3.855 mmol, 1 equiv.), HCl (5 mL, 164.564 mmol) and NaClO2 (15 mL, 8%) in DCM (20 mL, 314.612 mmol) at room temperature. The resulting mixture was stirred for 4 h at rt. The resulting mixture was extracted with EtOAc (3×20 mL). The combined organic layers were washed with brine (2×15 mL), dried over anhydrous $Na_2SO_4$. After filtration, the filtrate was concentrated under reduced pressure. This resulted in 4-isopropoxypyridine-2-sulfonyl chloride (1 g, 93.54%) as a yellow oil. LCMS: (ES, m/z): [M−H]+=236

(ii) N-[2-chloro-4-(4,4,5,5-tetramethyl-1,3,2-dioxaborolan-2-yl)phenyl]-4-isopropoxypyridine-2-sulfonamide Into a 50 mL round-bottom flask were added 4-({6-chloro-3-methyl-1H-pyrazolo[3,4-d]pyrimidin-4-yl}oxy)-1-methylpiperidine (1 g, 3.549 mmol, 1 equiv), 5-chloro-N-[2-chloro-4-(4,4,5,5-tetramethyl-1,3,2-dioxaborolan-2-yl)phenyl]-2-fluorobenzenesulfonamide (1.58 g, 3.542 mmol, 1.00 equiv.) and Pyridine (0.42 g, 5.324 mmol, 1.5 equiv). in DCM (15 mL, 235.959 mmol, 66.48 equiv.) at room temperature. The resulting mixture was stirred for 4 h at rt. The resulting mixture was concentrated under reduced pressure. The residue was purified by silica gel column chromatography, eluted with PE/EA (10:1) to afford N-[2-chloro-4-(4,4,5,5-tetramethyl-1,3,2-dioxaborolan-2-yl)phenyl]-4-isopropoxypyridine-2-sulfonamide (600 mg, 26.55%) as a yellow solid. CMS: (ES, m/z): [M+H]+=453

(iii) 6-chloro-N-[2-(dimethylamino)ethyl]-3-methyl-1H-pyrazolo[3,4-d]pyrimidin-4-amine Into a 100-mL round-bottom flask, was placed 4,6-dichloro-3-methyl-1H-pyrazolo[3,4-d]pyrimidine (1.00 g, 4.925 mmol, 1.00 equiv.), DCM (30.00 mL), (2-aminoethyl)dimethylamine (521.03 mg, 5.910 mmol, 1.2 equiv.), DIEA (1.90 g, 14.701 mmol, 2.98 equiv.). The resulting solution was stirred for 3 hr at room temperature. The resulting mixture was concentrated. The solids were wished with Ethyl ether. The solids were collected by filtration. This resulted in 1.2 g (86.08%) of 6-chloro-N-[2-(dimethylamino)ethyl]-3-methyl-1H-pyrazolo[3,4-d]pyrimidin-4-amine as a white solid. LCMS: (ES, m/z): [M+H]+=255

(iv) N-[2-chloro-4-(4-{[2-(dimethylamino)ethyl]amino}-3-methyl-1H-pyrazolo[3,4-d]pyrimidin-6-yl)phenyl]-4-isopropoxypyridine-2-sulfonamide A solution of 6-chloro-N-[2-(dimethylamino)ethyl]-3-methyl-1H-pyrazolo[3,4-d]pyrimidin-4-amine (500 mg, 1.963 mmol, 1 equiv.), N-[2-chloro-4-(4,4,5,5-tetramethyl-1,3,2-dioxaborolan-2-yl)phenyl]-4-isopropoxypyridine-2-sulfonamide (888.74 mg, 1.963 mmol, 1 equiv.), Pd(dppf)Cl2 (287.26 mg, 0.393 mmol, 0.2 equiv.), $Cs_2CO_3$ (959.34 mg, 2.945 mmol, 1.5 equiv.) in dioxane (10 mL) and $H_2O$ (3 mL) was treated for 10 min at room temperature under nitrogen atmosphere. The resulting mixture was stirred for 16 h at 100° C. under nitrogen atmosphere. The mixture was allowed to cool down to room temperature. The resulting mixture was concentrated under reduced pressure. The residue was purified by silica gel column chromatography, eluted with CH2Cl2/MeOH (10:1) to afford the desired product (129.9 mg, 11.44%) as a brown solid. LCMS: (ES, m/z): [M+H]+=5451H NMR (400 MHZ, DMSO-$d_6$) δ 13.04 (s, 1H), 11.18 (s, 1H), 8.13-8.43 (d, J=5.6 Hz, 3H), 7.25-7.47 (d, J=8.6 Hz, 3H), 7.11 (dd, J=5.7, 2.5 Hz, 1H), 4.79 (p, J=6.0 Hz, 1H), 3.91 (q, J=6.1 Hz, 2H), 3.18 (t, J=6.4 Hz, 2H), 2.70 (s, 4H), 2.57 (s, 2H), 1.92 (s, 4H), 1.26 (dd, J=14.0, 6.5 Hz, 6H), 0.90 (t, J=7.0 Hz, 1H).

Compound 101 5-chloro-N-(2-chloro-4-{3-methyl-4-[(1-methylpiperidin-4-yl)oxy]-1H-pyrazolo[3,4-d]pyrimidin-6-yl}phenyl)-2-fluorobenzenesulfonamide

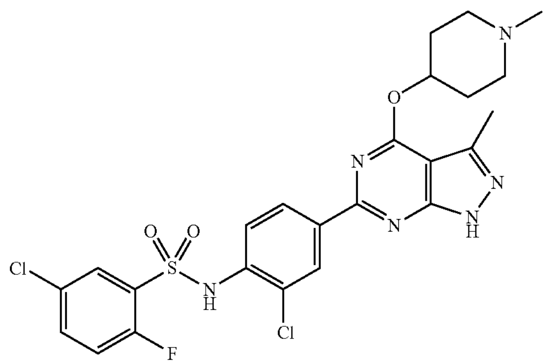 [SMILES: Cc1n[nH]c2nc(-c3ccc(NS(=O)(=O)c4cc(Cl)ccc4F)c(Cl)c3)nc(OC3CCN(C)CC3)c12]

(i) 4-({6-chloro-3-methyl-1H-pyrazolo[3,4-d]pyrimidin-4-yl}oxy)-1-methylpiperidine Into a 50 mL round-bottom flask were added 4,6-dichloro-3-methyl-1H-pyrazolo[3,4-d]pyrimidine (500 mg, 2.463 mmol, 1 equiv.), 4-piperidinol, 1-methyl-(0.28 g, 2.463 mmol, 1 equiv.) in THF (10 mL) and added NaH (0.09 g, 3.695 mmol, 1.5 equiv.) at 0° C. The resulting mixture was stirred for 4 h at room temperature. The reaction was quenched by the addition of Water (10 mL) at room temperature. The aqueous layer was extracted with EtOAc (3×50 mL). The resulting mixture was concentrated under reduced pressure. The residue was purified by silica gel column chromatography, eluted with PE/EA (5:1) to afford 4-({6-chloro-3-methyl-1H-pyrazolo[3,4-d]pyrimidin-4-yl}oxy)-1-methylpiperidine (300 mg, 43.24%) as a white solid. LCMS: (ES, m/z): [M−H]+=282

(ii) 5-chloro-N-(2-chloro-4-{3-methyl-4-[(1-methylpiperidin-4-yl)oxy]-1H-pyrazolo[3,4-d]pyrimidin-6-yl}phenyl)-2-fluorobenzenesulfonamide A solution of 4-({6-chloro-3-methyl-1H-pyrazolo[3,4-d]pyrimidin-4-yl}oxy)-1-methylpiperidine (400 mg, 1.420 mmol, 1 equiv), 5-chloro-N-[2-chloro-4-(4,4,5,5-tetramethyl-1,3,2-dioxaborolan-2-yl)phenyl]-2-fluorobenzenesulfonamide (633.38 mg, 1.420 mmol, 1 equiv.), Pd(dppf)Cl2 (207.77 mg, 0.284 mmol, 0.2 equiv.), Cs2CO3 (693.87 mg, 2.130 mmol, 1.5 equiv.) in $H_2O$ (3 mL) and dioxane (12 ml) was treated for 10 min at room temperature under nitrogen atmosphere. The resulting mixture was stirred for 16 h at 100° C. under nitrogen atmosphere. The mixture was allowed to cool down to room temperature. The resulting mixture was concentrated under reduced pressure. The residue was purified by silica gel column chromatography, eluted with CH2C12/MeOH (10:1) to afford the desired product (113.4 mg, 14.05%) as a white solid. LCMS: (ES, m/z): [M+H]+=565, 1H NMR (300 MHZ, DMSO-$d_6$) δ 13.33 (s, 1H), 9.56 (s, 1H), 8.21 (d, J=2.1 Hz, 1H), 8.01 (dd, J=8.7, 2.2 Hz, 1H), 7.71 (dd, J=6.0, 2.8 Hz, 1H), 7.52 (dt, J=8.7, 3.4 Hz, 1H), 7.23-7.35 (m, 2H), 5.64 (s, 1H), 3.39 (s, 4H), 3.17 (d, J=4.0 Hz, 3H), 2.79 (s, 3H), 2.53 (s, 3H), 2.26 (s, 2H), 2.12 (s, 2H).

Compound 102 N-(2-chloro-4-{3-methyl-4-[(1-methylpiperidin-4-yl)oxy]-1H-pyrazolo[3,4-d]pyrimidin-6-yl}phenyl)-2,5-difluorobenzenesulfonamide

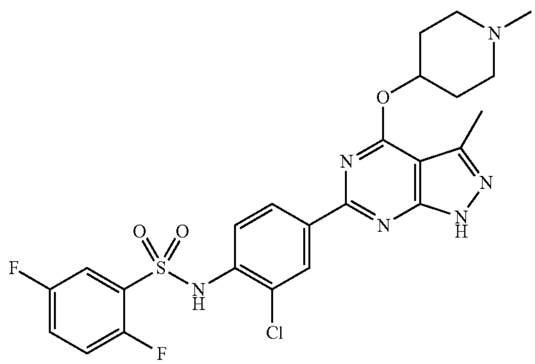 [SMILES: Cc1n[nH]c2nc(-c3ccc(NS(=O)(=O)c4cc(F)ccc4F)c(Cl)c3)nc(OC3CCN(C)CC3)c12]

To a stirred mixture of 4-({6-chloro-3-methyl-1H-pyrazolo[3,4-d]pyrimidin-4-yl}oxy)-1-methylpiperidine (0.5 g, 1.775 mmol, 1 equiv) and N-[2-chloro-4-(4,4,5,5-tetramethyl-1,3,2-dioxaborolan-2-yl)phenyl]-2,5-difluorobenzenesulfonamide (0.84 g, 1.953 mmol, 1.1 equiv) in 1,4-dioxane (8 mL) and $H_2O$ (2 mL), was added $Cs_2CO_3$ (0.87 g, 2.662 mmol, 1.5 equiv) and Pd(dppf)cl2 (0.26 g, 0.355 mmol, 0.2 equiv) in portions at 100° C. under N2 atmosphere for 16 h. The resulting mixture was concentrated under reduced pressure. The residue was purified by reverse flash chromatography with the following conditions: column, silica gel; mobile phase, MeOH in DCM, 0% to 15% gradient in 30 min; detector, UV 254 nm. This resulted in N-(2-chloro-4-{3-methyl-4-[(1-methylpiperidin-4-yl)oxy]-1H-pyrazolo[3,4-d]pyrimidin-6-yl}phenyl)-2,5-difluorobenzenesulfonamide (0.2104 g, 21.23%) as an off-white solid. LCMS (ESI, m/z): 549[M+H]+. 1H NMR (300 MHZ, DMSO-d6) δ 13.33 (s, 1H), 9.60 (s, 1H), 8.21 (d, J=2.2 Hz, 1H), 8.00 (dd, J=8.7, 2.2 Hz, 1H), 7.49 (ddd, J=8.1, 5.4, 2.9 Hz, 1H), 7.29 (dq, J=8.1, 2.9, 1.7 Hz, 3H), 5.63 (s, 1H), 3.21 (s, 4H), 2.76 (s, 3H), 2.53 (s, 3H), 2.16 (d, J=48.7 Hz, 4H).

Compound 103 N-[2-chloro-4-(4-{[2-(dimethylamino)ethyl]amino}-3-methyl-1H-pyrazolo[3,4-d]pyrimidin-6-yl)phenyl]pyridine-2-sulfonamide

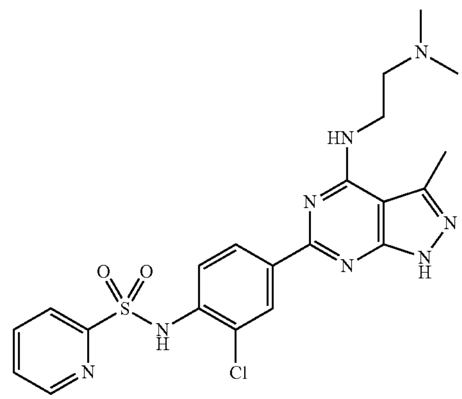 [SMILES: Cc1n[nH]c2nc(-c3ccc(NS(=O)(=O)c4ccccn4)c(Cl)c3)nc(NCCN(C)C)c12]

(i) Pyridine-2-sulfonyl chloride

To a stirred mixture of 2-pyridinethiol (0.5 g, 4.498 mmol, 1 equiv) in DCM (5 mL, 78.653 mmol, 17.49 equiv.) was added HCl (10 mL, 329.128 mmol, 73.17 equiv.) and NaOCl (10 mL, 147.770 mmol, 32.85 equiv.) in portions at 0° C. The aqueous layer was extracted with $H_2O$ (10 ml×3) and DCM (10 ml×3). The resulting mixture was concentrated under reduced pressure. This resulted in pyridine-2-sulfonyl chloride (0.4 g, 30.04%) as a yellow oil. LCMS (ESI, m/z): 178 [M+H]+.

(ii) N-[2-chloro-4-(4,4,5,5-tetramethyl-1,3,2-dioxaborolan-2-yl)phenyl]pyridine-2-sulfonamide To a stirred mixture of pyridine-2-sulfonyl chloride (0.4 g, 2.252 mmol, 1 equiv.) and 2-chloro-4-(4,4,5,5-tetramethyl-1,3,2-dioxaborolan-2-yl)aniline (0.57 g, 2.252 mmol, 1 equiv.) in DCM (4 mL, 62.922 mmol, 27.94 equiv.) was added Pyridine (0.53 g, 6.756 mmol, 3 equiv.) in portions at RT. The resulting mixture was concentrated under reduced pressure. The residue was purified by reverse flash chromatography with the following conditions: column, silica gel; mobile phase, PE in EA, 0% to 50% gradient in 30 min; detector, UV 254 nm. This resulted in N-[2-chloro-4-(4,4,5,5-tetramethyl-1,3,2-dioxaborolan-2-yl)phenyl]pyridine-2-sulfonamide (0.2 g, 15.34%) as an off-white solid. LCMS (ESI, m/z): 395 [M+H]+.

(iii) N-[2-chloro-4-(4-{[2-(dimethylamino)ethyl]amino}-3-methyl-1H-pyrazolo[3,4-d]pyrimidin-6-yl)phenyl]pyridine-2-sulfonamide To a stirred mixture of 6-chloro-N-[2-(dimethylamino)ethyl]-3-methyl-1H-pyrazolo[3,4-d]pyrimidin-4-amine (0.15 g, 0.589 mmol, 1 equiv.) and N-[2-chloro-4-(4,4,5,5-tetramethyl-1,3,2-dioxaborolan-2-yl)phenyl]pyridine-2-sulfonamide (0.26 g, 0.648 mmol, 1.1 equiv.) in 1,4-dioxane (8 mL) and $H_2O$ (2 mL), was added $Cs_2CO_3$ (0.29 g, 0.883 mmol, 1.5 equiv.) and Pd(dppf)Cl2 (0.09 g, 0.118 mmol, 0.2 equiv.) in portions at 100° C. under $N_2$ atmosphere for overnight. The resulting mixture was concentrated under reduced pressure. The residue was purified by reverse flash chromatography with the following conditions: column, silica gel; mobile phase, MeOH in DCM, 0% to 15% gradient in 30 min; detector, UV 254 nm. This resulted in the desired product (0.0389 g, 13.28%) as a off-white solid. LCMS (ESI, m/z): 553 [M+H]+1H NMR (300 MHZ, DMSO-$d_6$) δ 12.98 (s, 1H), 9.86 (s, 1H), 8.63 (d, J=4.4 Hz, 1H), 8.25 (d, J=2.0 Hz, 1H), 8.10-7.77 (m, 3H), 7.59-7.40 (m, 2H), 7.14 (t, J=5.7 Hz, 1H), 3.84 (q, J=6.2 Hz, 2H), 3.02 (t, J=6.5 Hz, 2H), 2.57 (d, J=15.7 Hz, 9H).

Compound 107 N-[2-chloro-4-(4-{[2-(dimethylamino)ethyl]amino}-3-methyl-1H-pyrazolo[3,4-d]pyrimidin-6-yl)phenyl]-4-methoxypyridine-2-sulfonamide; trifluoroacetic acid

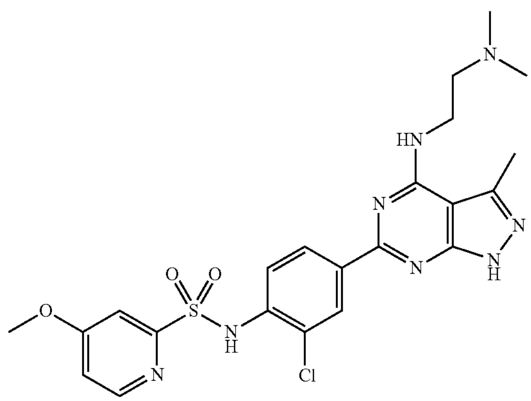

This compound was prepared according to a procedure similar to the synthesis of Compound 84. The desired product was obtained as an off-white solid (51.4 mg, 16.59%). LCMS: (ES, m/z): [M+H]+=517.1H NMR (400 MHz, DMSO-$d_6$) δ 13.20 (s, 1H), 10.34 (s, 1H), 9.56 (s, 1H), 8.56 (d, J=5.6 Hz, 1H), 8.35 (d, J=1.9 Hz, 1H), 8.28 (dd, J=8.5, 2.0 Hz, 1H), 7.51 (d, J=8.5 Hz, 1H), 7.44 (d, J=2.4 Hz, 1H), 7.38 (q, J=5.7 Hz, 1H), 7.27 (dd, J=5.6, 2.5 Hz, 1H), 3.99 (q, J=5.9 Hz, 2H), 3.91 (s, 2H), 2.89 (d, J=4.4 Hz, 6H), 2.58 (s, 3H).

Compound 111 5-chloro-N-[2-chloro-4-(4-{[2-(dimethylamino)ethyl]amino}-3-methyl-1H-pyrazolo[3,4-d]pyrimidin-6-yl)phenyl]-2-fluorobenzenesulfonamide

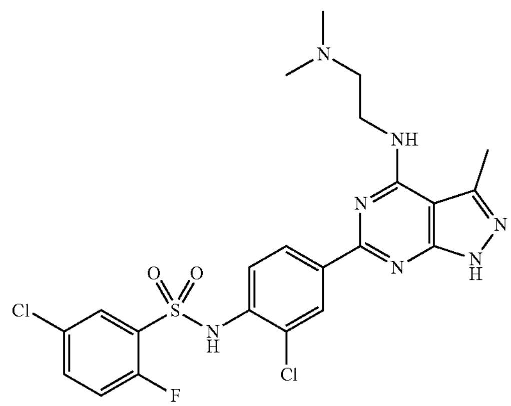 [SMILES: Cc1n[nH]c2nc(-c3ccc(NS(=O)(=O)c4cc(Cl)ccc4F)c(Cl)c3)nc(NCCN(C)C)c12]

This compound was prepared according to a procedure similar to the synthesis of Compound 84. The desired product was obtained as a white solid (0.0328 g, 12.83%). LCMS (ESI, m/z): 538 [M+H]+. 1H NMR (300 MHZ, DMSO-$d_6$) δ 12.94 (s, 1H), 8.21 (d, J=2.1 Hz, 1H), 7.98 (d, J=8.7 Hz, 1H), 7.76-7.45 (m, 2H), 7.32-7.02 (m, 3H), 3.91 (d, J=5.9 Hz, 2H), 2.85-2.67 (m, 6H), 2.54 (s, 5H).

Compound 112 N-[2-chloro-4-(4-{[2-(dimethylamino)ethyl]amino}-3-methyl-1H-pyrazolo[3,4-d]pyrimidin-6-yl)phenyl]-4-methylpyridine-2-sulfonamide; trifluoroacetic acid

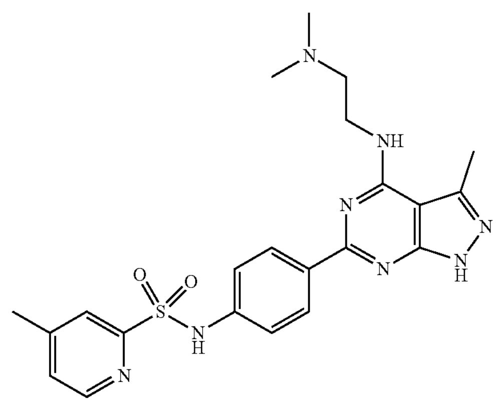 [SMILES: Cc1ccnc(S(=O)(=O)Nc2ccc(-c3nc(NCCN(C)C)c4c(C)n[nH]c4n3)cc2)c1]

This compound was prepared according to a procedure similar to the synthesis of Compound 84. The desired product was obtained as a (32.2 mg, 10.62%) as an off-white solid. LCMS: (ES, m/z): [M+H]+=5011H NMR (400 MHZ, DMSO-$d_6$) δ 13.17 (s, 1H), 10.28 (s, 1H), 9.47 (s, 1H), 8.58 (d, J=2.1 Hz, 1H), 8.33 (d, J=2.0 Hz, 1H), 8.27 (dd, J=8.4, 2.0 Hz, 1H), 7.90 (dd, J=8.2, 2.2 Hz, 1H), 7.84 (d, J=8.0 Hz, 1H), 7.50 (d, J=8.5 Hz, 1H), 7.36 (p, J=5.5, 4.9 Hz, 1H), 3.98 (q, J=5.9 Hz, 2H), 3.42 (q, J=5.7 Hz, 2H), 2.89 (d, J=4.2 Hz, 6H), 2.58 (s, 3H), 2.41 (s, 3H).

Compound 126 2,5-difluoro-N-(2-fluoro-4-{3-methyl-4-[(1-methylpiperidin-4-yl)oxy]-1H-pyrazolo[3,4-d]pyrimidin-6-yl}phenyl)benzenesulfonamide

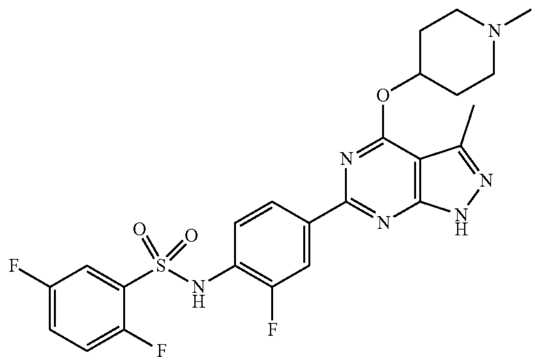 [SMILES: Cc1n[nH]c2nc(-c3ccc(NS(=O)(=O)c4cc(F)ccc4F)c(F)c3)nc(OC3CCN(C)CC3)c12]

This compound was prepared according to a procedure similar to the synthesis of Compound 102. The desired product was obtained as a yellow solid (0.4049 g, 42.11%). LCMS (ESI, m/z): 533 [M+H]+. $^1$H NMR (300 MHz, DMSO-$d_6$) δ13.41 (s, 1H), 9.95 (s, 1H), 8.10-7.61 (m, 2H), 7.65-7.04 (m, 5H), 5.71 (d, J=36.7 Hz, 1H), 3.21-3.09 (m, 4H), 2.73 (s, 3H), 2.42 (s, 3H), 2.16 (d, J=44.1 Hz, 4H).

Compound 154 5-chloro-N-(4-(4-((2-(dimethylamino)ethyl)(methyl)amino)-3-methyl-1H-pyrazolo[3,4-d]pyrimidin-6-yl)phenyl)-2-fluorobenzenesulfonamide

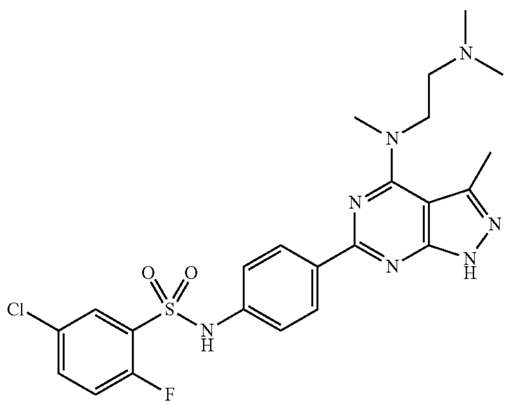 [SMILES: Cc1n[nH]c2nc(-c3ccc(NS(=O)(=O)c4cc(Cl)ccc4F)cc3)nc(N(C)CCN(C)C)c12]

This compound was prepared according to the procedure described in example 9. The desired product was obtained as an off-solid (5 mg, 4.9%). LCMS (ESI, m/z): 519.8 [M+H]+. $^1$H NMR (400 MHZ, DMSO-$d_6$): δ 11.05 (s, 1H), 8.26 (d, J=8.60, 2H), 7.87-7.73 (m, 2H), 7.50 (s, 1H), 7.23 (d J=8.79 Hz, 2H), 4.19 (m, 2H), 3.46-3.40 (m, 2H), 3.38 (s, 3H), 2.85 (d, J=4.49 Hz, 6H), 2.59 (s, 3H).

Compound 156 N-[2-chloro-4-(4-{[(3S,4R)-3-fluoropiperidin-4-yl]oxy}-3-methyl-1H-pyrazolo[3,4-d]pyrimidin-6-yl)phenyl]-2,5-difluorobenzenesulfonamide hydrochloride

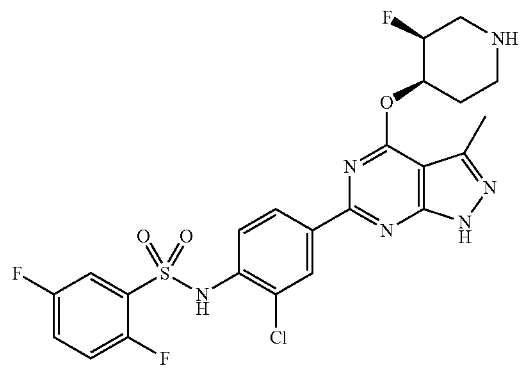

This compound was prepared according to a procedure similar to the synthesis of Compound 29. The desired product was obtained as an off-white solid (0.2211 g, 77.66%) LCMS (ESI, m/z): 553 [M+H]+, $^1$H NMR (300 MHZ, DMSO-$d_6$) δ 13.67 (s, 1H), 10.81 (s, 1H), 9.30 (s, 1H), 8.78 (s, 1H), 8.46-8.27 (m, 2H), 7.72-7.44 (m, 4H), 5.90 (dd, J=26.8, 9.3 Hz, 1H), 5.46 (s, 1H), 3.67 (s, 4H), 2.56 (s, 3H) 2.21 (s, 2H).

Compounds 127-155 and 157 to 174 are prepared according to procedures similar to other procedures described herein.

TABLE A

| Listing of compounds<br>Compound Number and Chemical Formula |
|---|
| 1 |
| 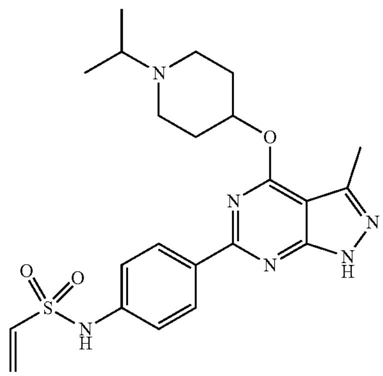 [SMILES: C=CS(=O)(=O)Nc1ccc(-c2nc(OC3CCN(C(C)C)CC3)c3c(C)n[nH]c3n2)cc1] |

TABLE A-continued
| Listing of compounds<br>Compound Number and Chemical Formula |
|---|
| 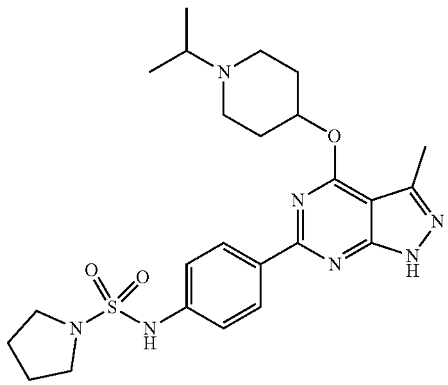 [SMILES: Cc1n[nH]c2nc(-c3ccc(NS(=O)(=O)N4CCCC4)cc3)nc(OC3CCN(C(C)C)CC3)c12] 2 |
| 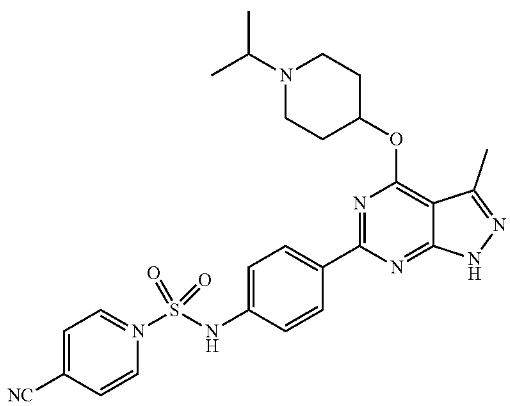 3 |
| 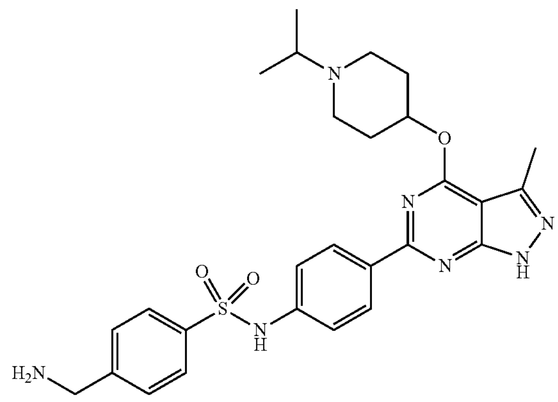 [SMILES: Cc1n[nH]c2nc(-c3ccc(NS(=O)(=O)c4ccc(CN)cc4)cc3)nc(OC3CCN(C(C)C)CC3)c12] 4 |
| 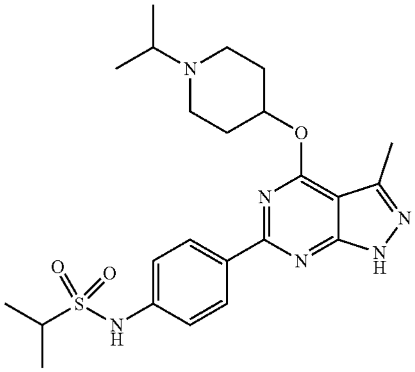 [SMILES: Cc1n[nH]c2nc(-c3ccc(NS(=O)(=O)C(C)C)cc3)nc(OC3CCN(C(C)C)CC3)c12] 5 |

TABLE A-continued
| Listing of compounds<br>Compound Number and Chemical Formula |
|---|
| 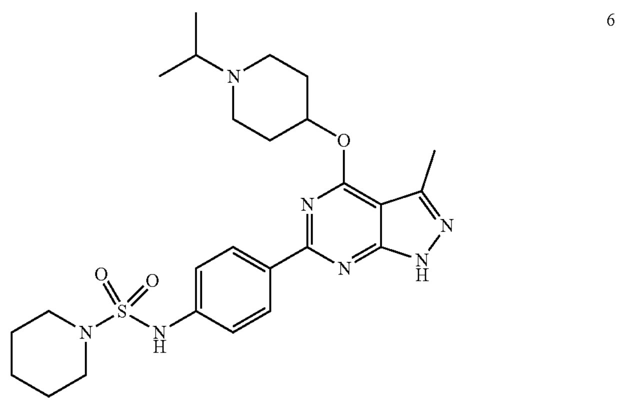 6 |
| 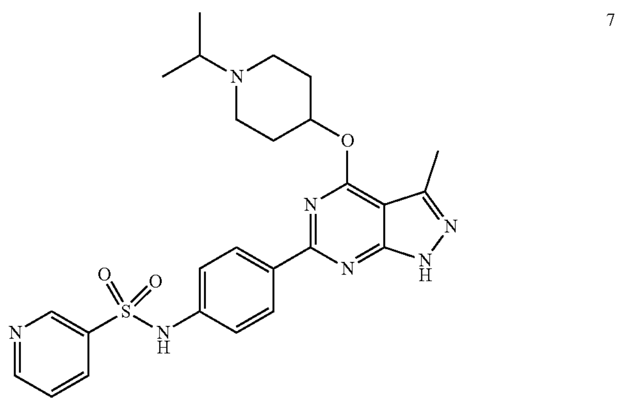 7 |
| 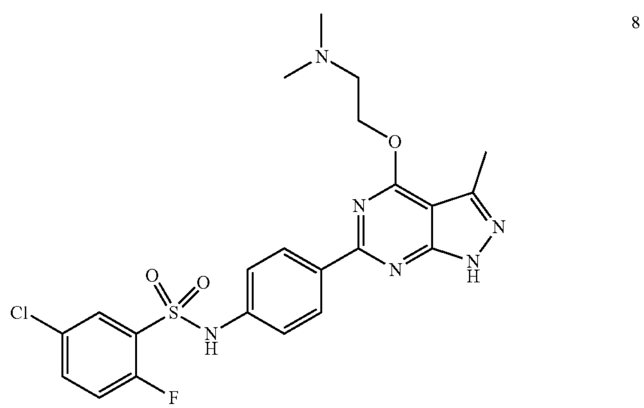 8 |

TABLE A-continued
| Listing of compounds<br>Compound Number and Chemical Formula |
|---|
| 9<br>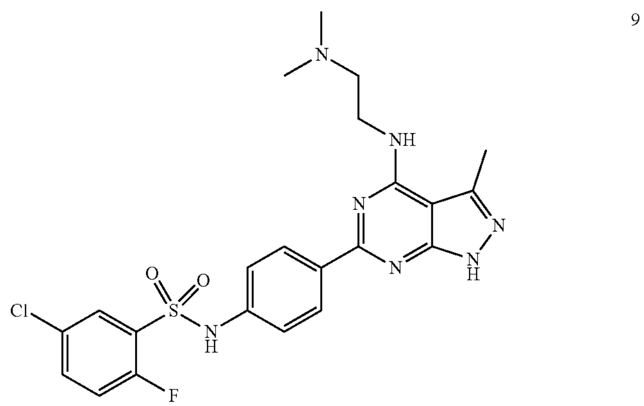 |
| 10<br>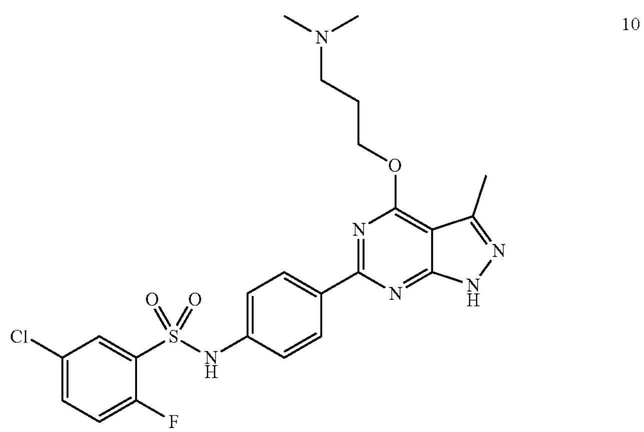 |
| 11<br>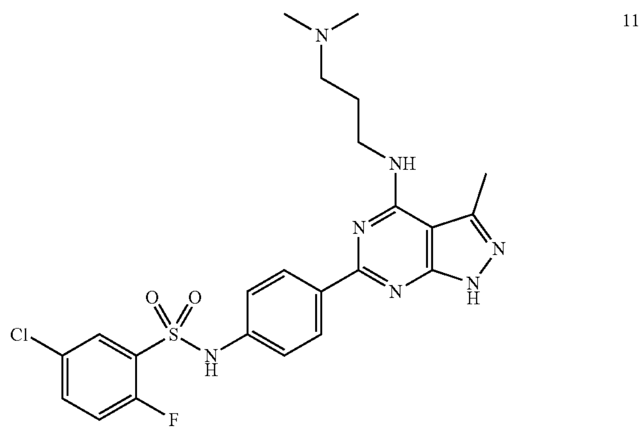 |

TABLE A-continued
| Listing of compounds<br>Compound Number and Chemical Formula | |
|---|---|
| 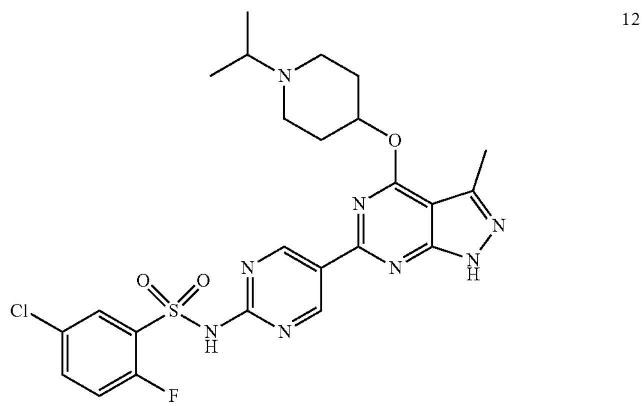 | 12 |
| 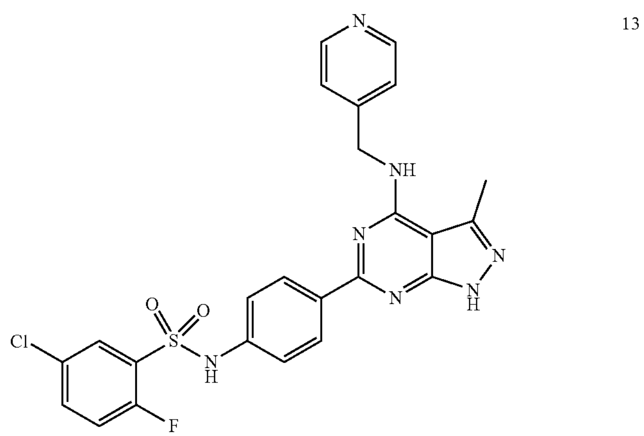 | 13 |
| 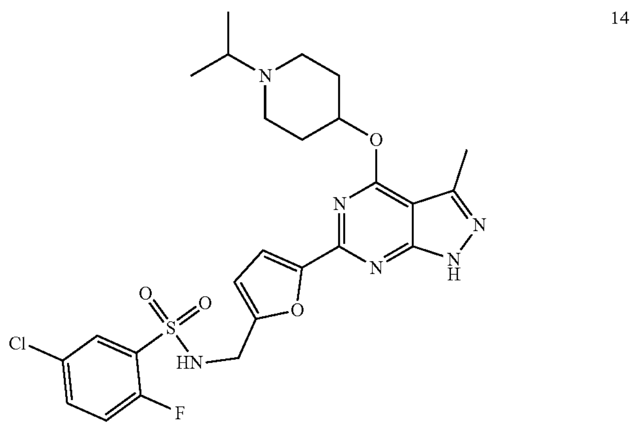 | 14 |

TABLE A-continued
| Listing of compounds Compound Number and Chemical Formula |
|---|
| 15 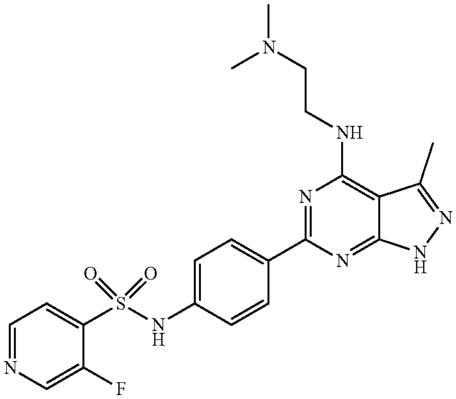 [SMILES: Cc1n[nH]c2nc(-c3ccc(NS(=O)(=O)c4ccncc4F)cc3)nc(NCCN(C)C)c12] |
| 16 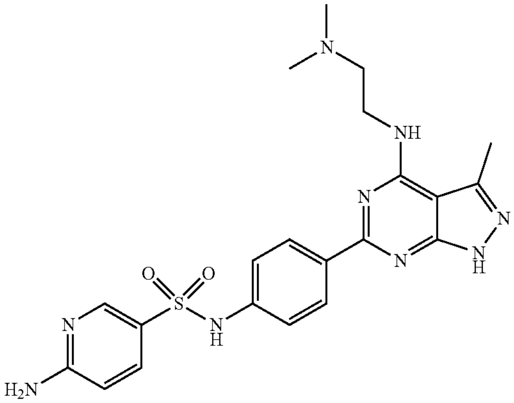 [SMILES: Cc1n[nH]c2nc(-c3ccc(NS(=O)(=O)c4ccc(N)nc4)cc3)nc(NCCN(C)C)c12] |
| 17 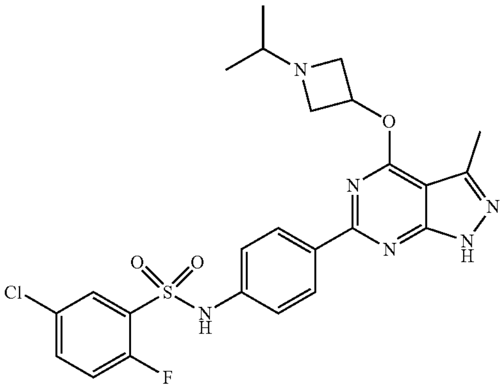 [SMILES: Cc1n[nH]c2nc(-c3ccc(NS(=O)(=O)c4cc(Cl)ccc4F)cc3)nc(OC3CN(C(C)C)C3)c12] |
| 18 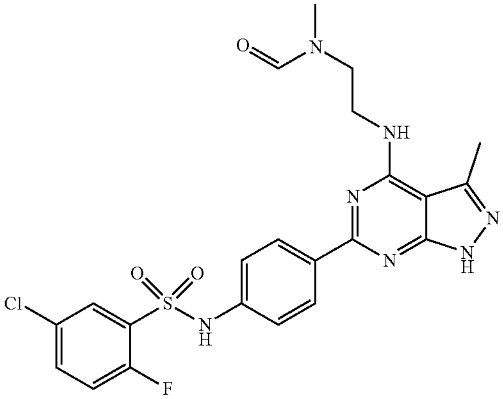 [SMILES: Cc1n[nH]c2nc(-c3ccc(NS(=O)(=O)c4cc(Cl)ccc4F)cc3)nc(NCCN(C)C=O)c12] |

TABLE A-continued
| Listing of compounds<br>Compound Number and Chemical Formula |
|---|
19
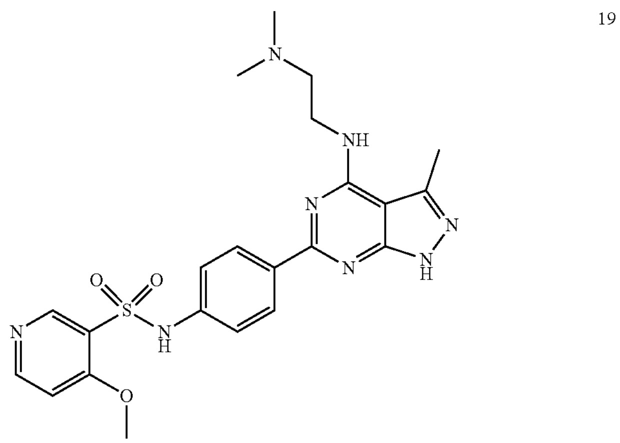
20
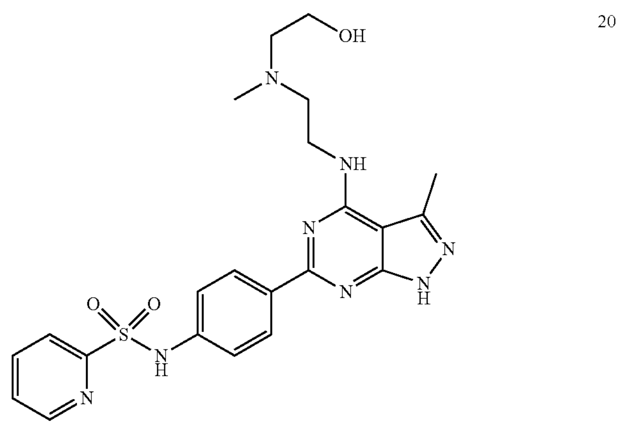
21
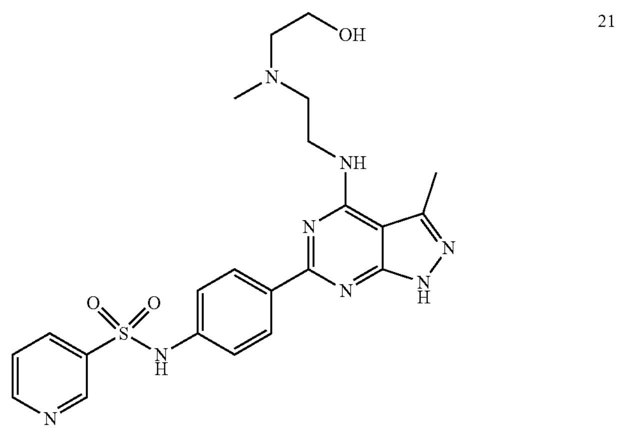

TABLE A-continued
Listing of compounds
Compound Number and Chemical Formula
22
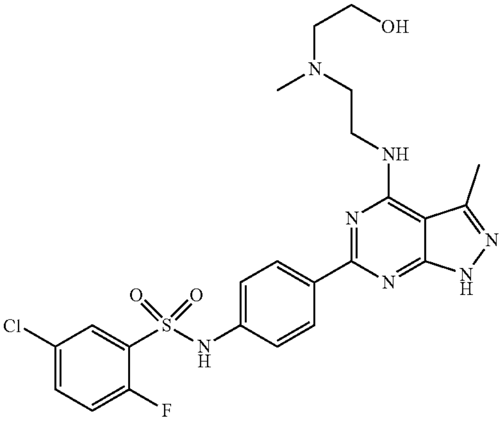 [SMILES: Cc1n[nH]c2nc(-c3ccc(NS(=O)(=O)c4cc(Cl)ccc4F)cc3)nc(NCCN(C)CCO)c12]
23
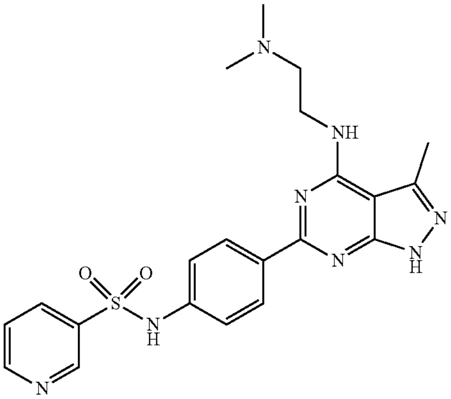 [SMILES: Cc1n[nH]c2nc(-c3ccc(NS(=O)(=O)c4cccnc4)cc3)nc(NCCN(C)C)c12]
24
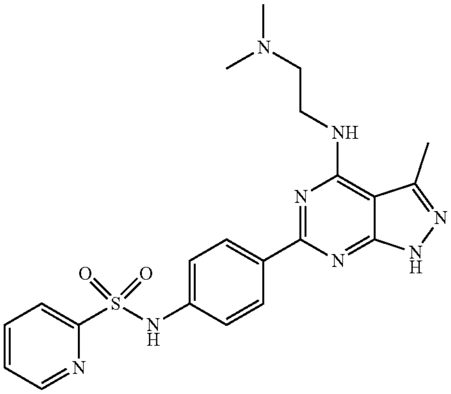 [SMILES: Cc1n[nH]c2nc(-c3ccc(NS(=O)(=O)c4ccccn4)cc3)nc(NCCN(C)C)c12]
25
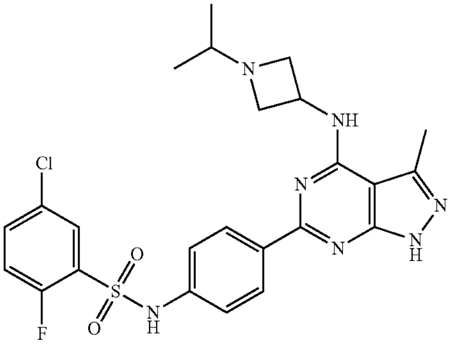 [SMILES: Cc1n[nH]c2nc(-c3ccc(NS(=O)(=O)c4cc(Cl)ccc4F)cc3)nc(NC3CN(C(C)C)C3)c12]

TABLE A-continued
| Listing of compounds<br>Compound Number and Chemical Formula |
|---|
| 26<br>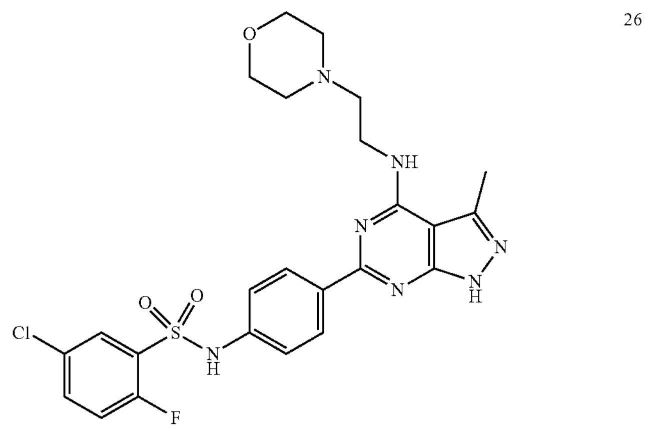 |
| 27<br>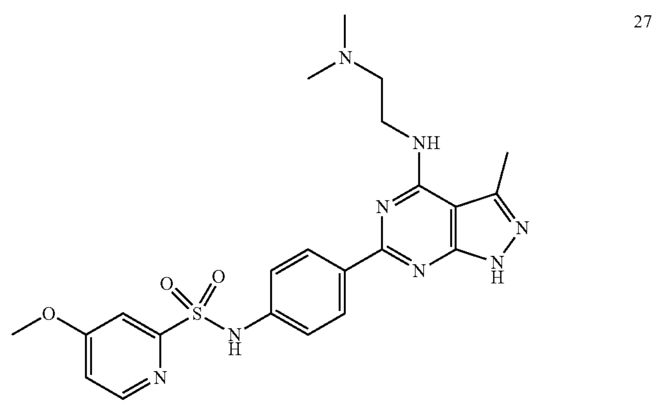 |
| 28<br>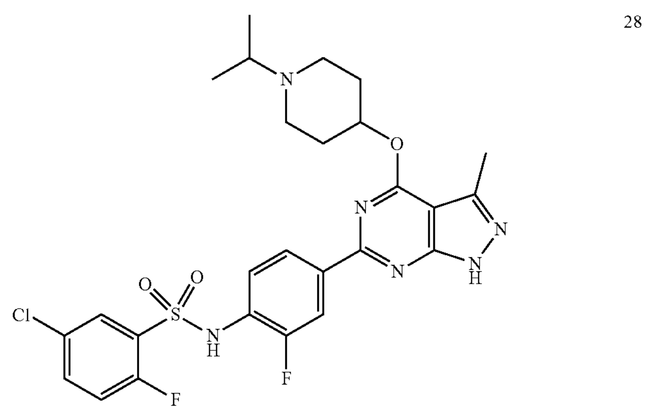 |
| 29<br>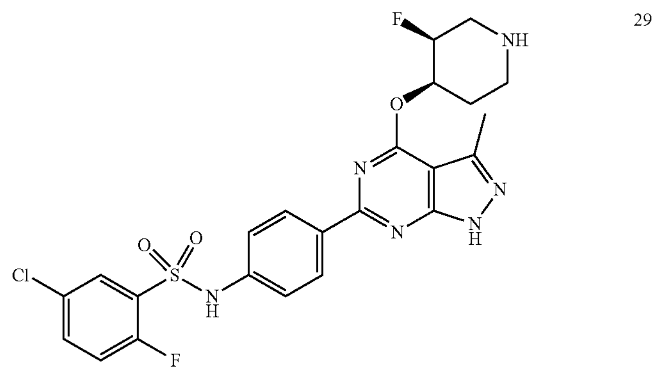 |

TABLE A-continued
| Listing of compounds<br>Compound Number and Chemical Formula |
|---|
30
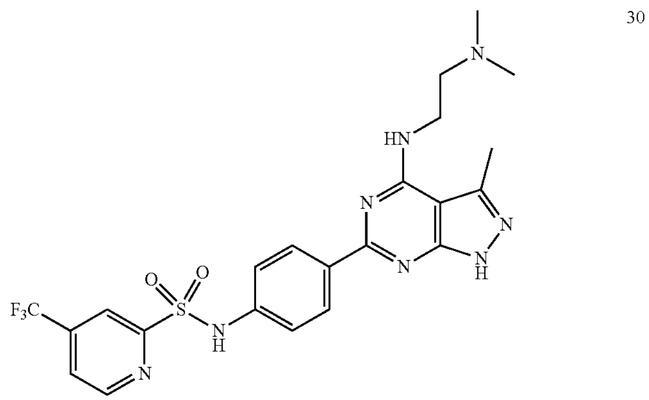
31
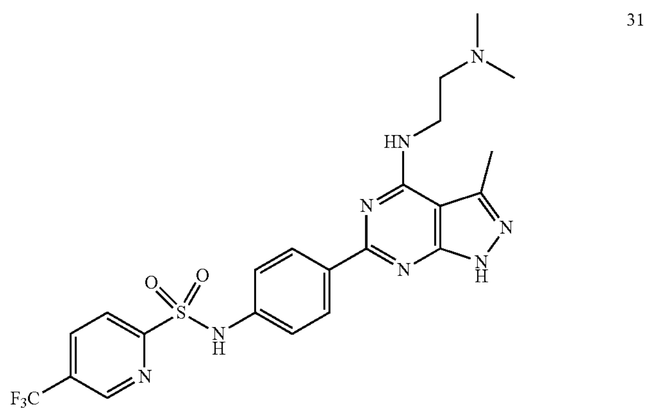
32
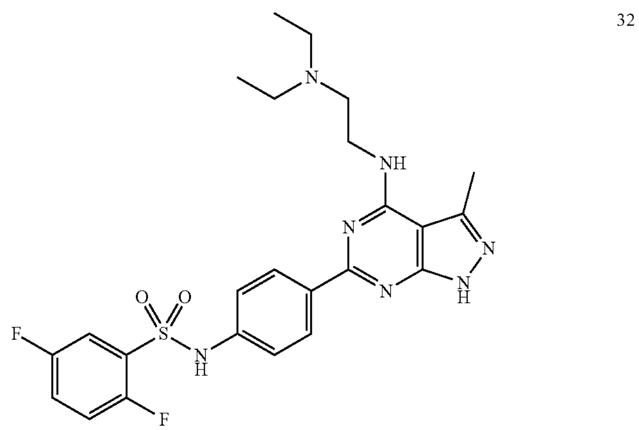

TABLE A-continued
| Listing of compounds<br>Compound Number and Chemical Formula |
|---|
| 33<br>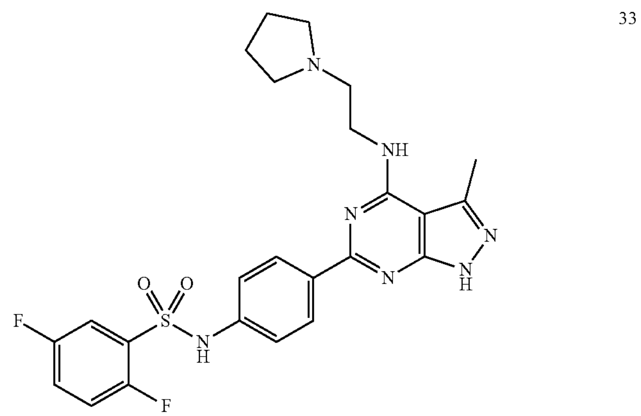 |
| 34<br>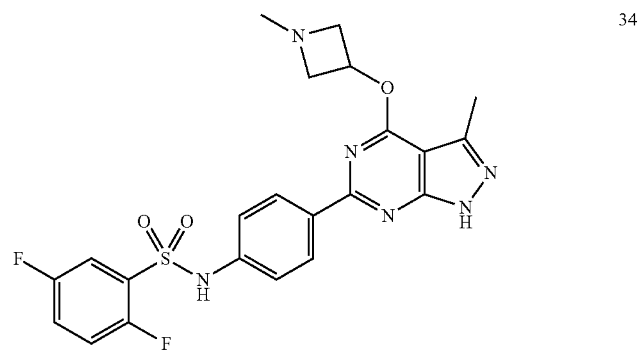 |
| 35<br>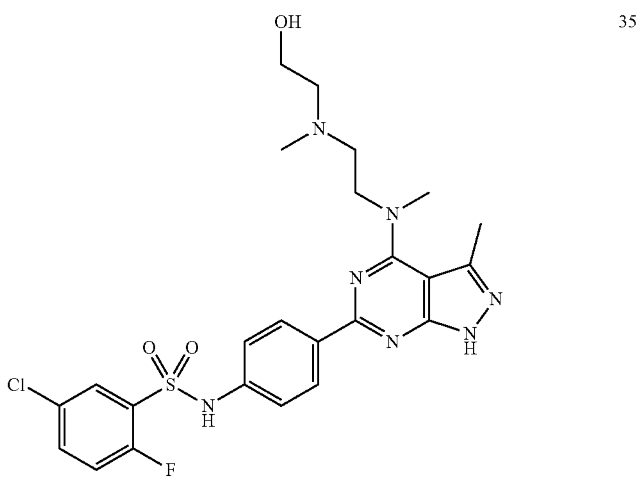 |

TABLE A-continued
| Listing of compounds<br>Compound Number and Chemical Formula |
|---|
| 36 |
| 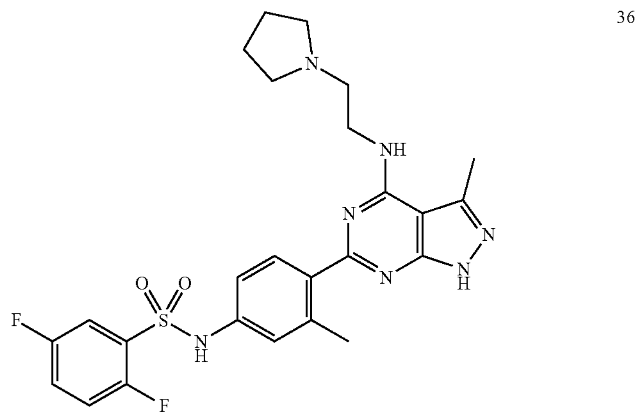 |
| 37 |
| 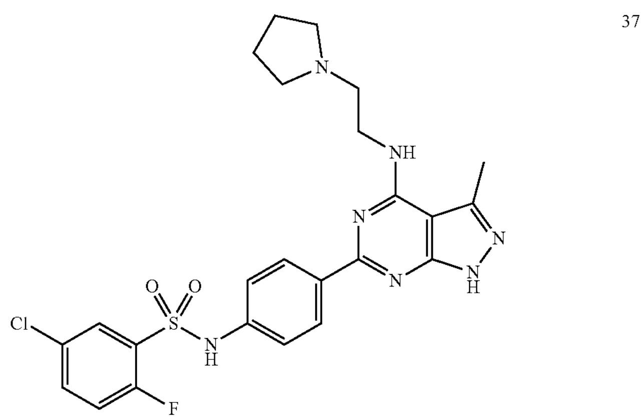 |
| 38 |
| 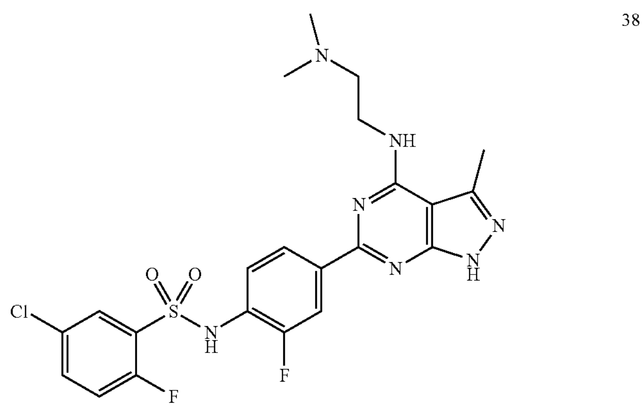 |

TABLE A-continued
Listing of compounds
Compound Number and Chemical Formula
39
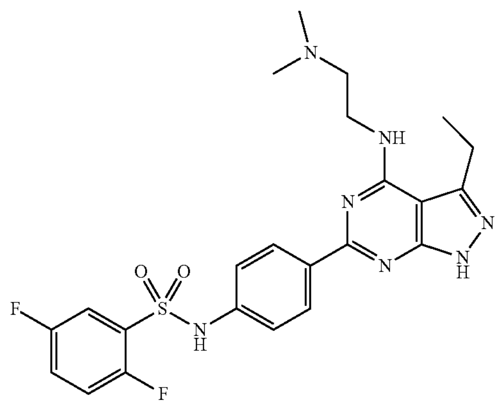 [SMILES: CCc1n[nH]c2nc(-c3ccc(NS(=O)(=O)c4cc(F)ccc4F)cc3)nc(NCCN(C)C)c12]
40
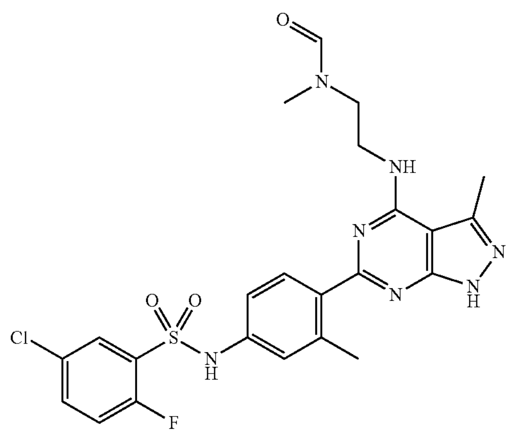 [SMILES: Cc1cc(NS(=O)(=O)c2cc(Cl)ccc2F)ccc1-c1nc(NCCN(C)C=O)c2c(C)n[nH]c2n1]
41
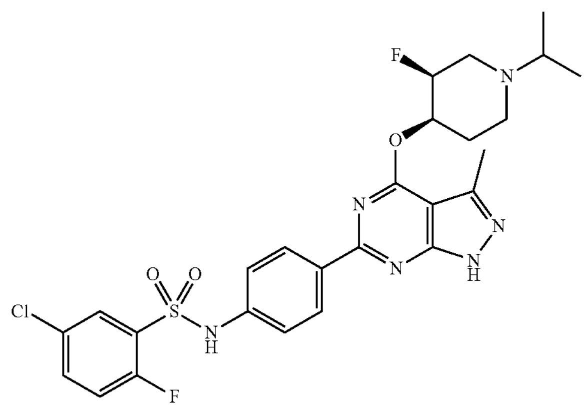 [SMILES: Cc1n[nH]c2nc(-c3ccc(NS(=O)(=O)c4cc(Cl)ccc4F)cc3)nc(O[C@@H]3CCN(C(C)C)C[C@@H]3F)c12]

TABLE A-continued
| Listing of compounds<br>Compound Number and Chemical Formula |
|---|
| 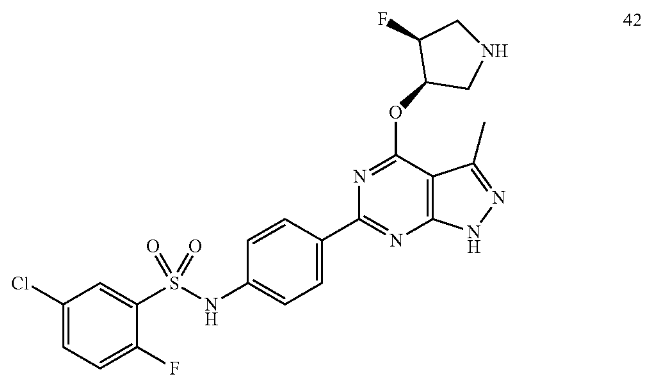 42 |
| 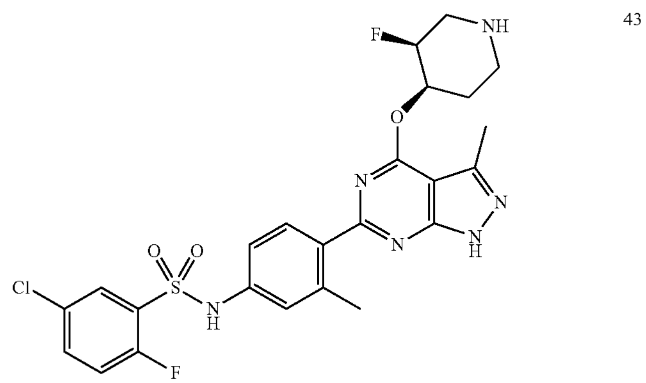 43 |
| 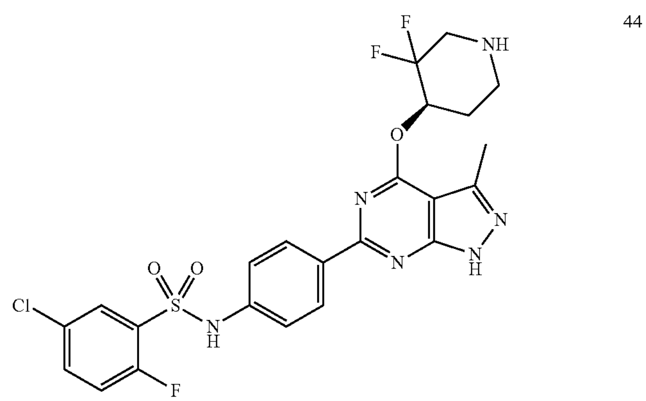 44 |
| 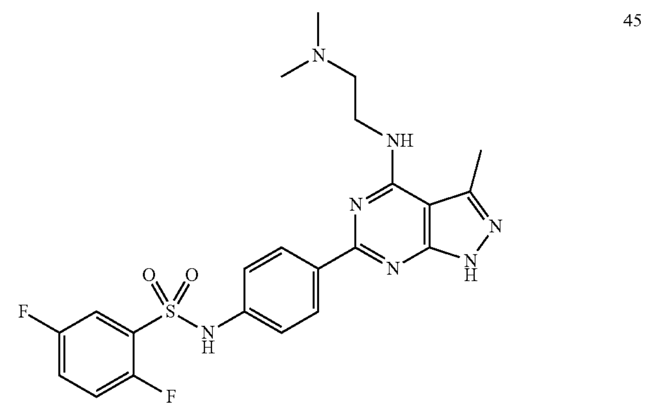 45 |

TABLE A-continued
| Listing of compounds<br>Compound Number and Chemical Formula |
|---|
| 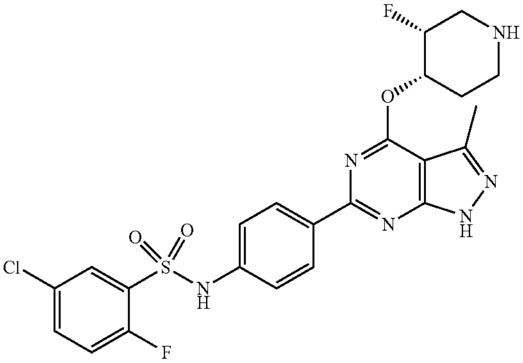 [SMILES: Cc1n[nH]c2nc(-c3ccc(NS(=O)(=O)c4cc(Cl)ccc4F)cc3)nc(O[C@H]3CCNC[C@H]3F)c12] 46 |
| 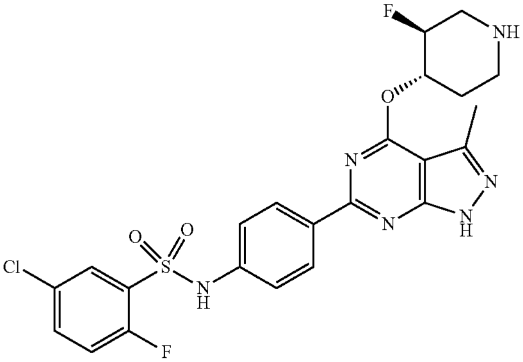 [SMILES: Cc1n[nH]c2nc(-c3ccc(NS(=O)(=O)c4cc(Cl)ccc4F)cc3)nc(O[C@H]3CCNC[C@@H]3F)c12] 47 |
| 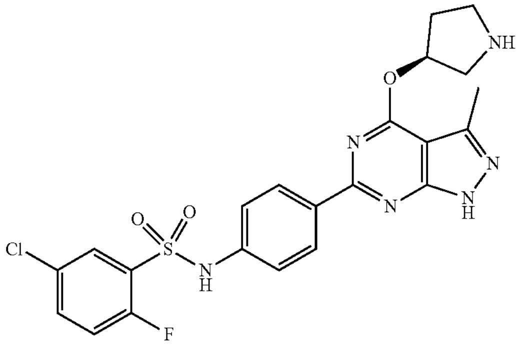 [SMILES: Cc1n[nH]c2nc(-c3ccc(NS(=O)(=O)c4cc(Cl)ccc4F)cc3)nc(O[C@H]3CCNC3)c12] 48 |
| 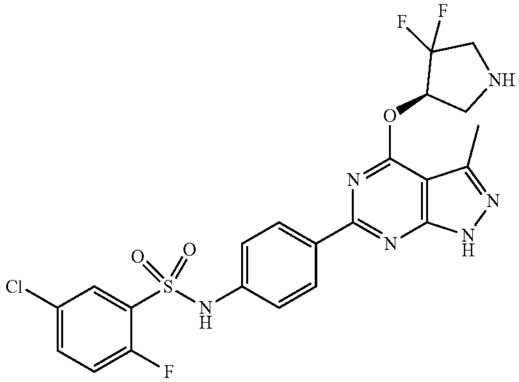 [SMILES: Cc1n[nH]c2nc(-c3ccc(NS(=O)(=O)c4cc(Cl)ccc4F)cc3)nc(O[C@@H]3CNCC3(F)F)c12] 49 |

TABLE A-continued
| Listing of compounds<br>Compound Number and Chemical Formula |
| --- |
| 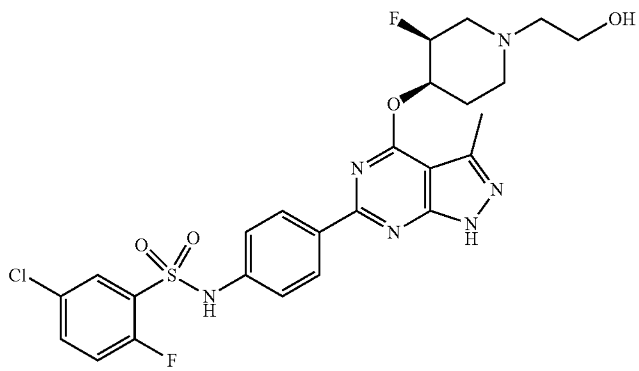 [SMILES: Cc1n[nH]c2nc(-c3ccc(NS(=O)(=O)c4cc(Cl)ccc4F)cc3)nc(O[C@@H]3CCN(CCO)C[C@@H]3F)c12] 50 |
| 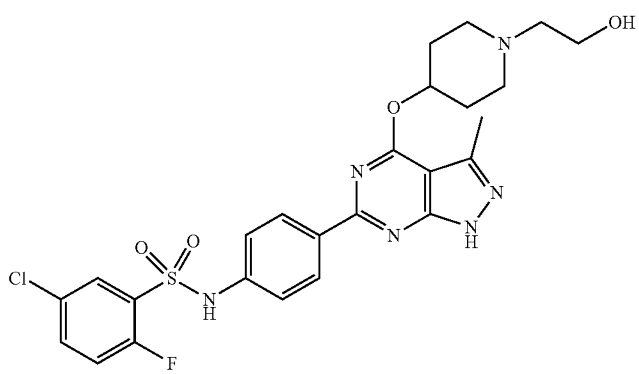 [SMILES: Cc1n[nH]c2nc(-c3ccc(NS(=O)(=O)c4cc(Cl)ccc4F)cc3)nc(OC3CCN(CCO)CC3)c12] 51 |
| 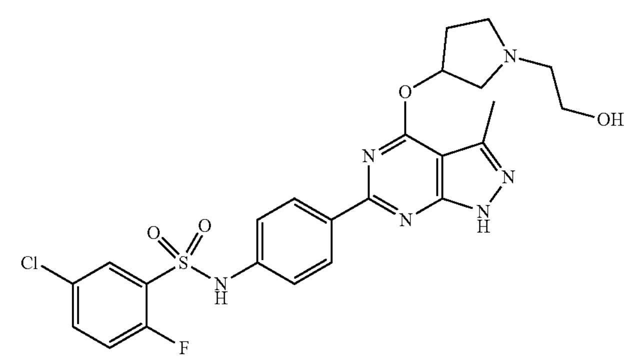 [SMILES: Cc1n[nH]c2nc(-c3ccc(NS(=O)(=O)c4cc(Cl)ccc4F)cc3)nc(OC3CCN(CCO)C3)c12] 52 |
| 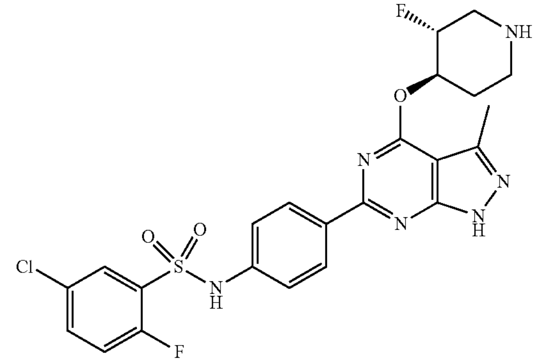 [SMILES: Cc1n[nH]c2nc(-c3ccc(NS(=O)(=O)c4cc(Cl)ccc4F)cc3)nc(O[C@@H]3CCNC[C@H]3F)c12] 53 |

TABLE A-continued
| Listing of compounds<br>Compound Number and Chemical Formula |
|---|
| 54<br>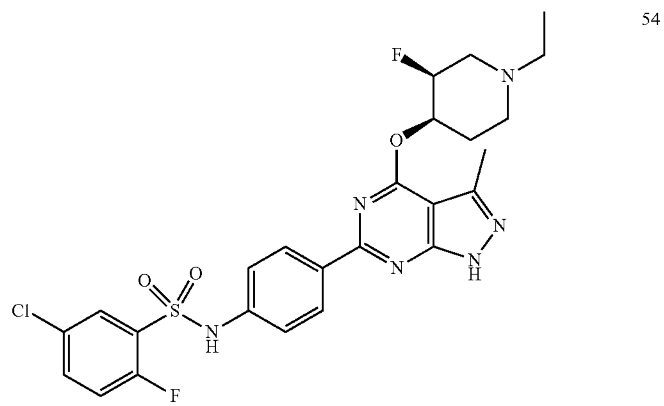 |
| 55<br>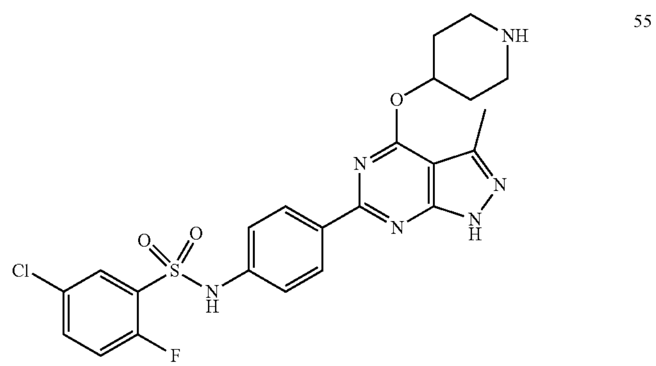 |
| 56<br>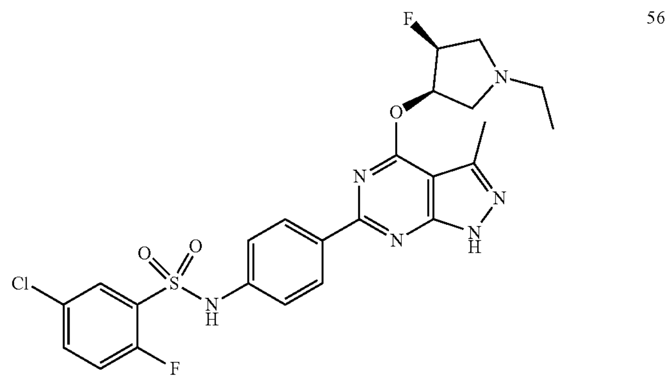 |
| 57<br>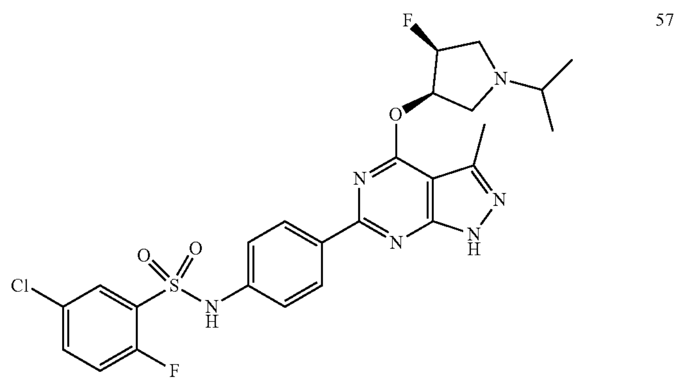 |

TABLE A-continued
| Listing of compounds<br>Compound Number and Chemical Formula |
| --- |
| 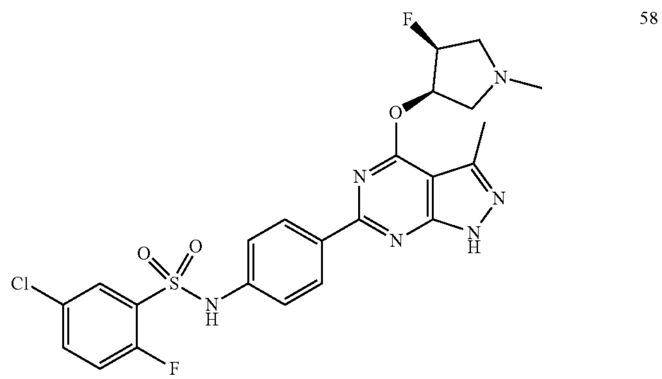 58 |
| 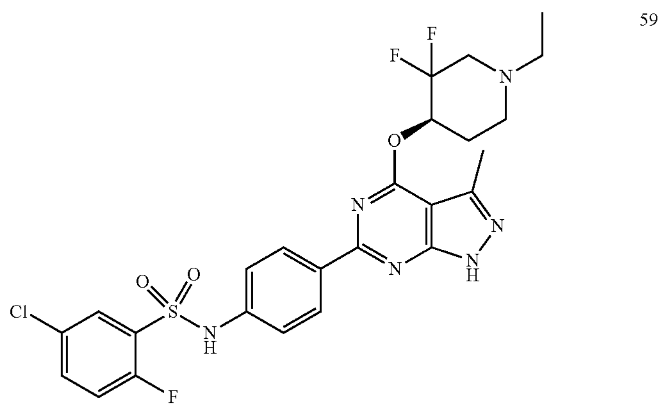 59 |
| 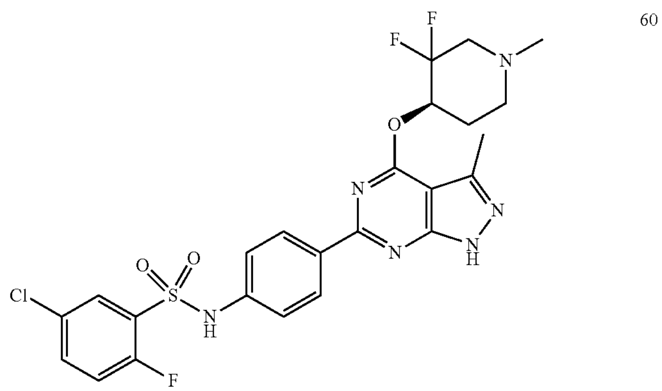 60 |
| 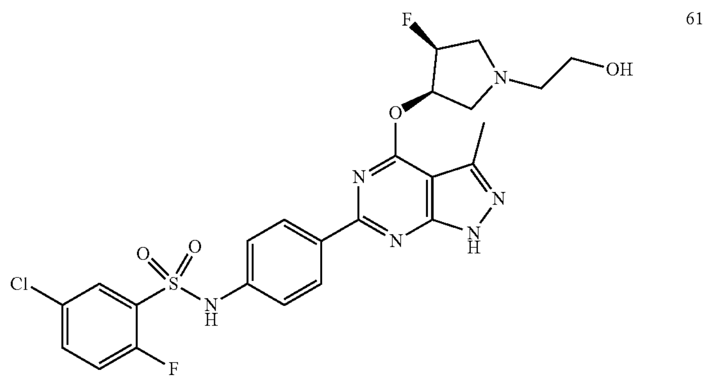 61 |

TABLE A-continued
| Listing of compounds<br>Compound Number and Chemical Formula | |
|---|---|
| 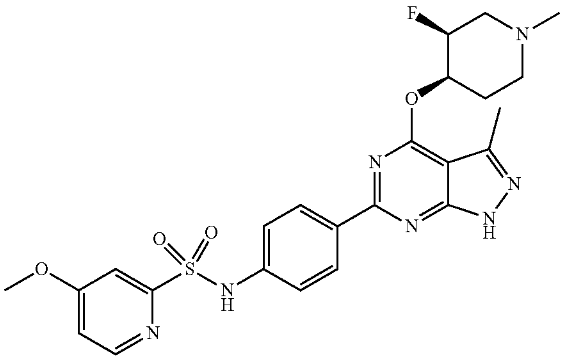 | 62 |
| 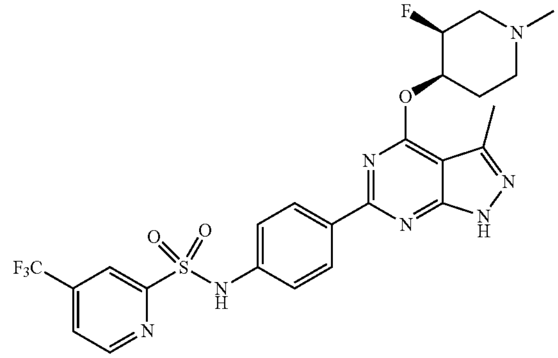 [SMILES: Cc1n[nH]c2nc(-c3ccc(NS(=O)(=O)c4cc(C(F)(F)F)ccn4)cc3)nc(O[C@@H]3CCN(C)C[C@@H]3F)c12] | 63 |
| 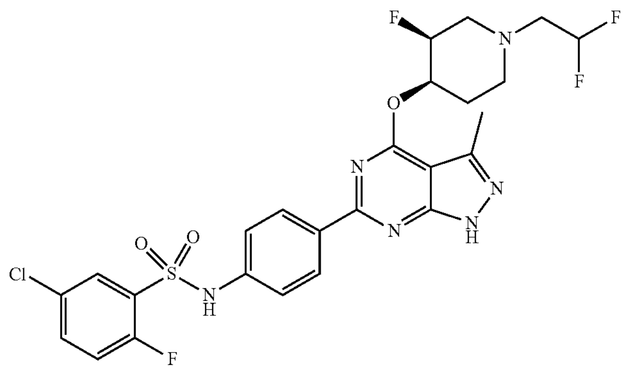 [SMILES: Cc1n[nH]c2nc(-c3ccc(NS(=O)(=O)c4cc(Cl)ccc4F)cc3)nc(O[C@@H]3CCN(CC(F)F)C[C@@H]3F)c12] | 64 |
| 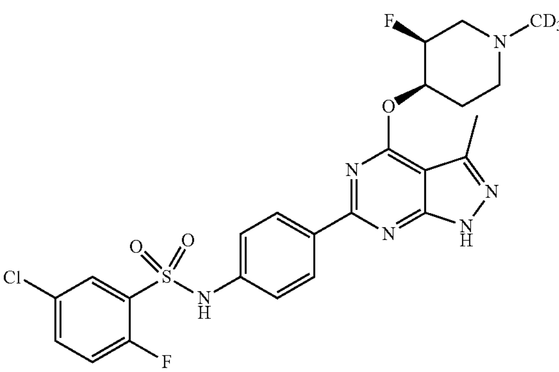 | 65 |

TABLE A-continued
| Listing of compounds<br>Compound Number and Chemical Formula | |
|---|---|
| 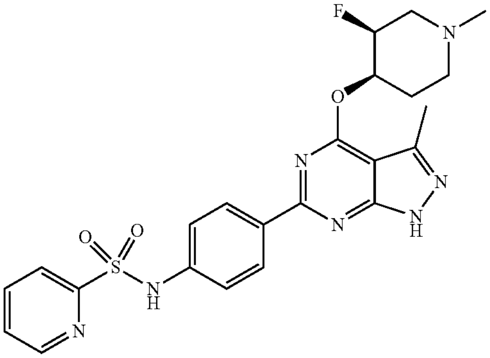 [SMILES: Cc1n[nH]c2nc(-c3ccc(NS(=O)(=O)c4ccccn4)cc3)nc(O[C@@H]3CCN(C)C[C@@H]3F)c12] | 66 |
| 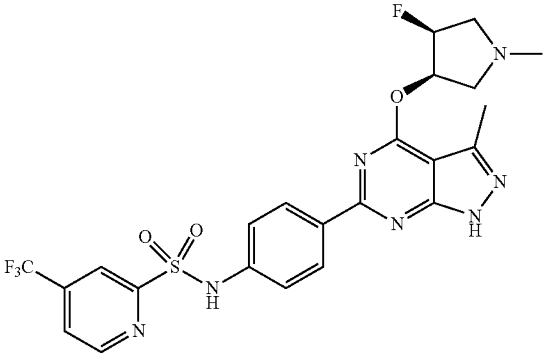 [SMILES: Cc1n[nH]c2nc(-c3ccc(NS(=O)(=O)c4cc(C(F)(F)F)ccn4)cc3)nc(O[C@@H]3CN(C)C[C@@H]3F)c12] | 67 |
| 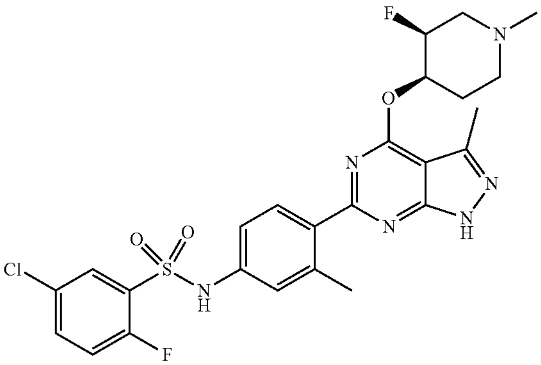 [SMILES: Cc1cc(NS(=O)(=O)c2cc(Cl)ccc2F)ccc1-c1nc(O[C@@H]2CCN(C)C[C@@H]2F)c2c(C)n[nH]c2n1] | 68 |
| 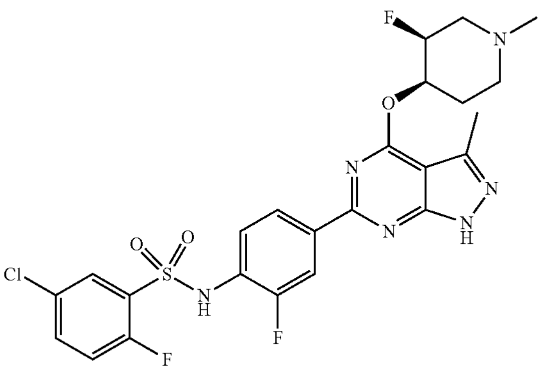 [SMILES: Cc1n[nH]c2nc(-c3ccc(NS(=O)(=O)c4cc(Cl)ccc4F)c(F)c3)nc(O[C@@H]3CCN(C)C[C@@H]3F)c12] | 69 |

TABLE A-continued
| Listing of compounds Compound Number and Chemical Formula |
| --- |
| 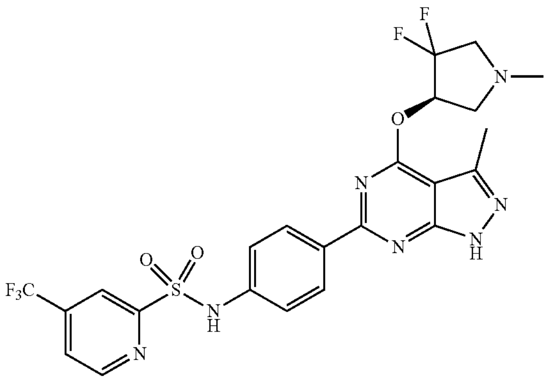 [SMILES: Cc1n[nH]c2nc(-c3ccc(NS(=O)(=O)c4cc(C(F)(F)F)ccn4)cc3)nc(O[C@@H]3CN(C)CC3(F)F)c12] 70 |
| 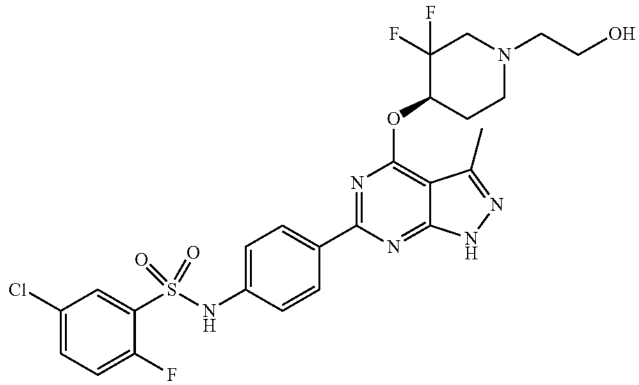 [SMILES: Cc1n[nH]c2nc(-c3ccc(NS(=O)(=O)c4cc(Cl)ccc4F)cc3)nc(O[C@@H]3CCN(CCO)CC3(F)F)c12] 71 |
| 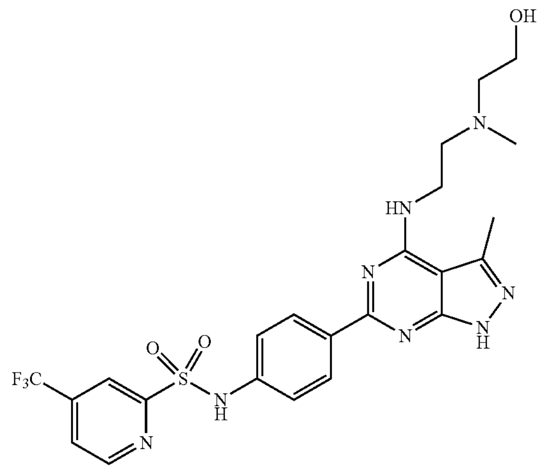 [SMILES: Cc1n[nH]c2nc(-c3ccc(NS(=O)(=O)c4cc(C(F)(F)F)ccn4)cc3)nc(NCCN(C)CCO)c12] 72 |

TABLE A-continued
| Listing of compounds<br>Compound Number and Chemical Formula |
|---|
| 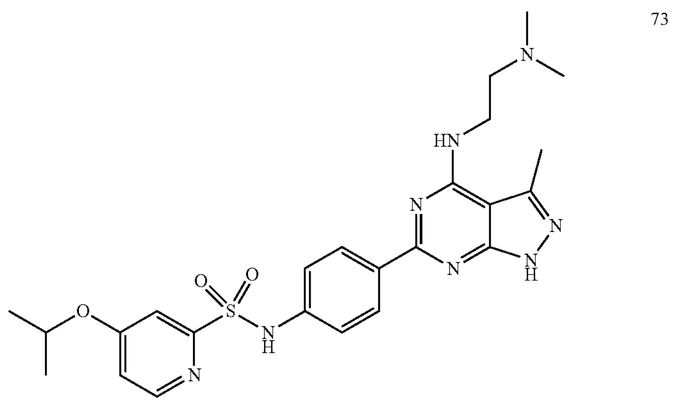 73 |
| 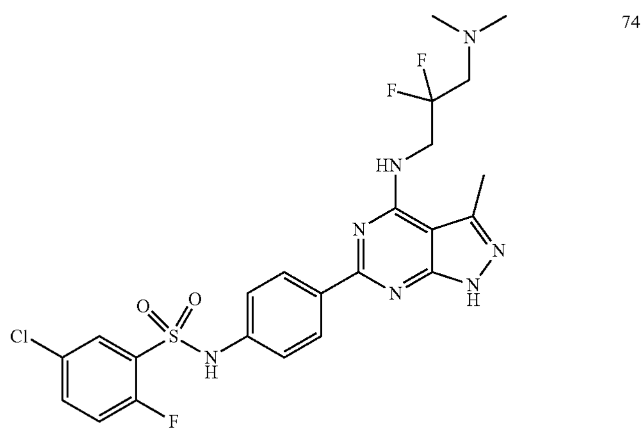 74 |
| 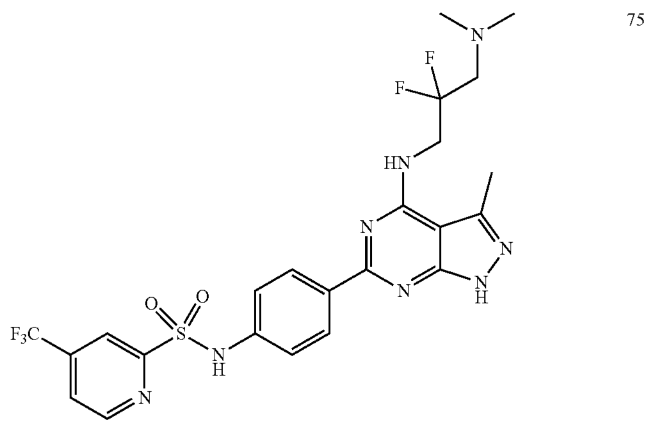 75 |

TABLE A-continued
| Listing of compounds<br>Compound Number and Chemical Formula |
|---|
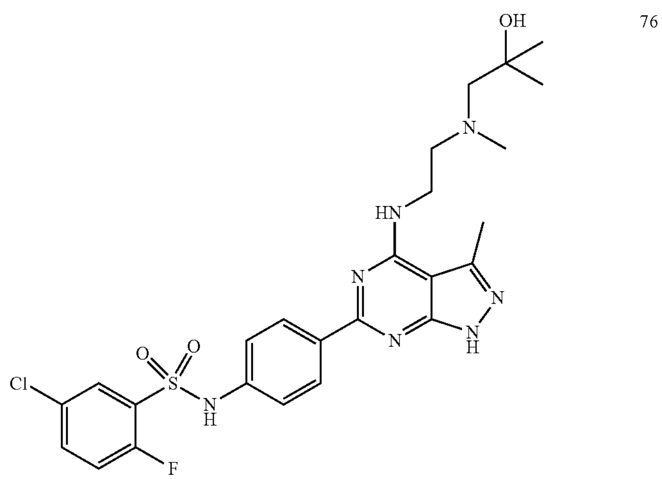
76
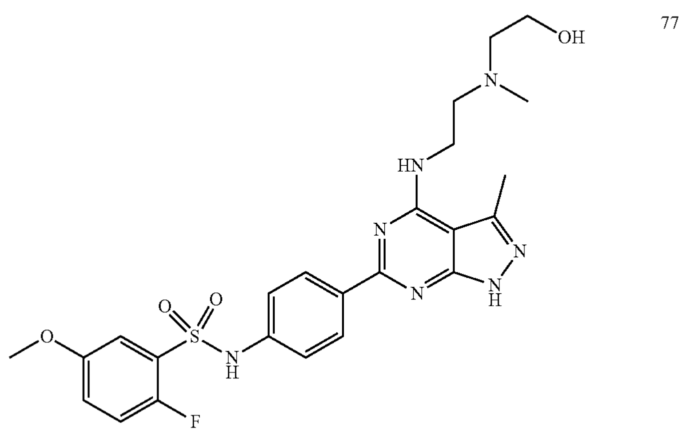
77
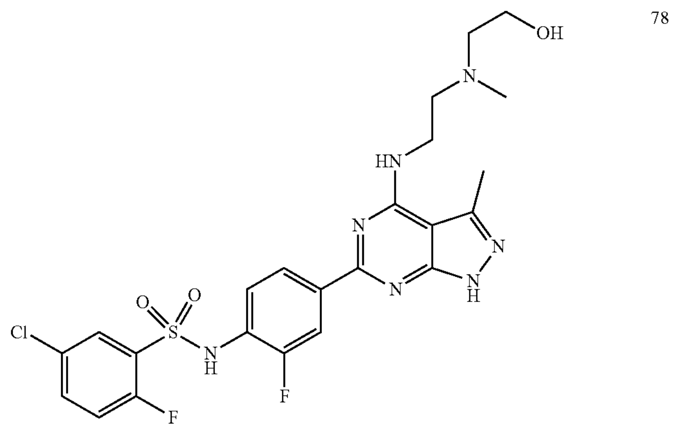
78

TABLE A-continued
| Listing of compounds Compound Number and Chemical Formula |
|---|
| 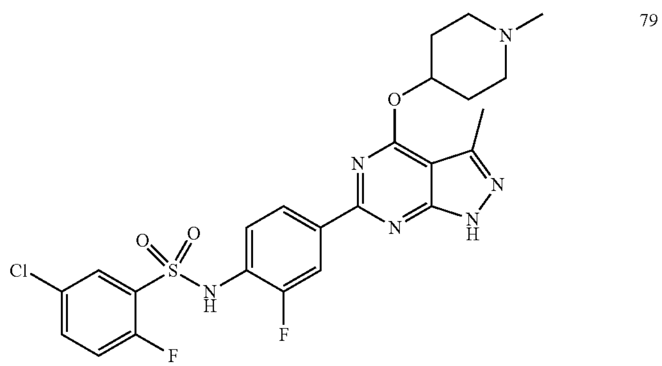 79 |
| 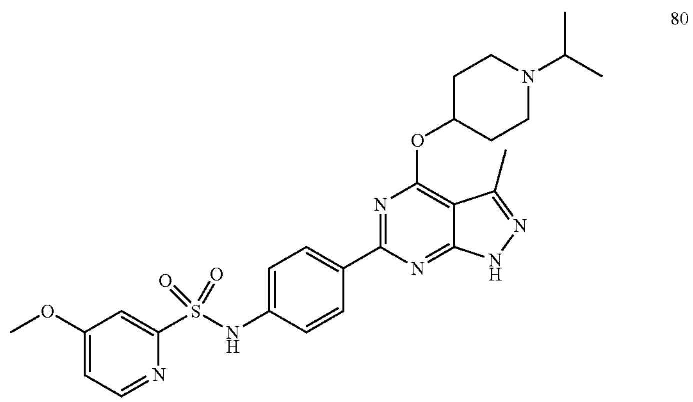 80 |
| 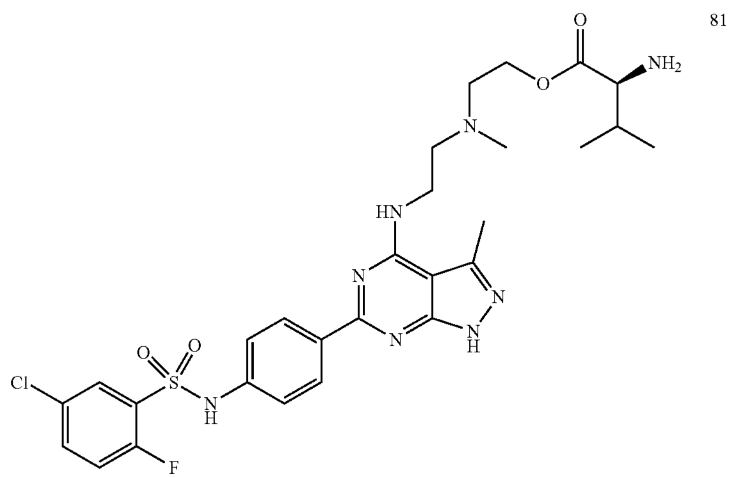 81 |

TABLE A-continued
| Listing of compounds<br>Compound Number and Chemical Formula |
|---|
| 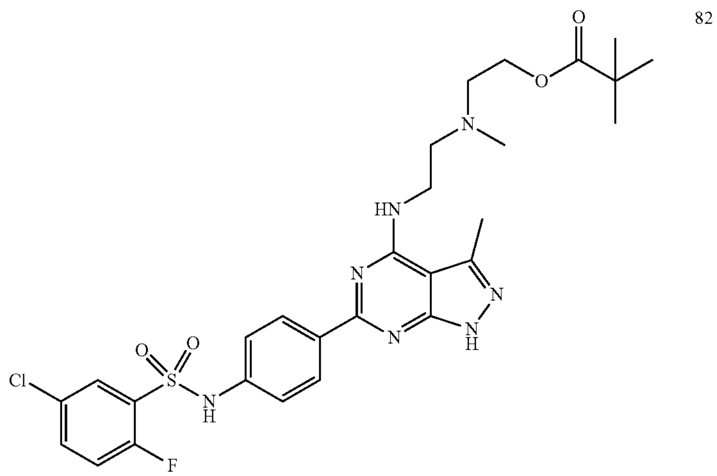 82 |
| 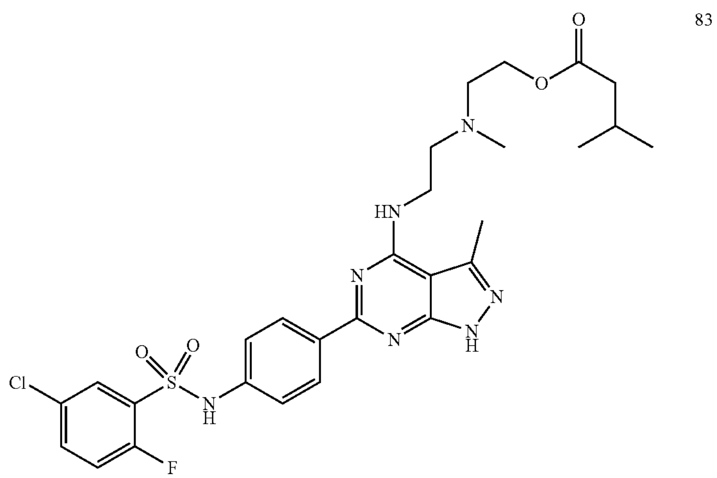 83 |
| 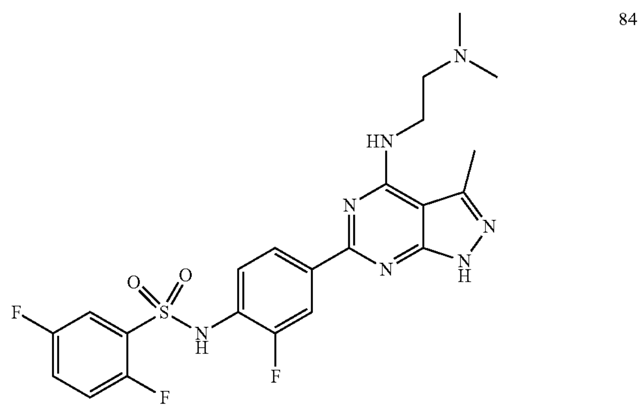 84 |

TABLE A-continued
| Listing of compounds<br>Compound Number and Chemical Formula |
|---|
| 85<br>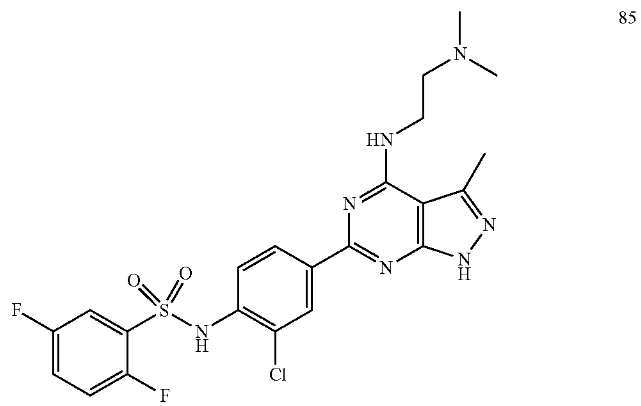 |
| 86<br>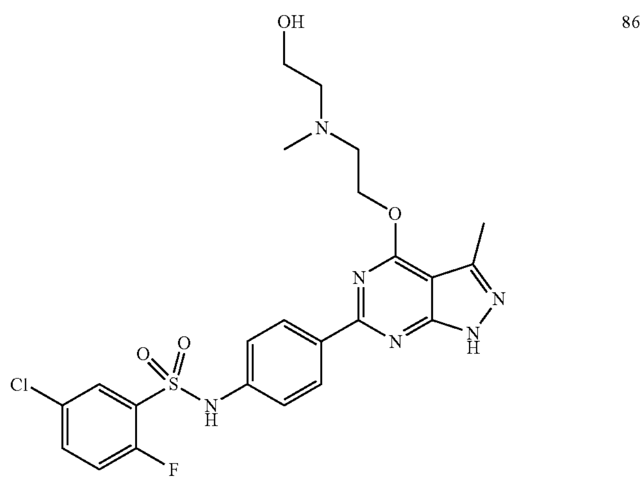 |
| 87<br>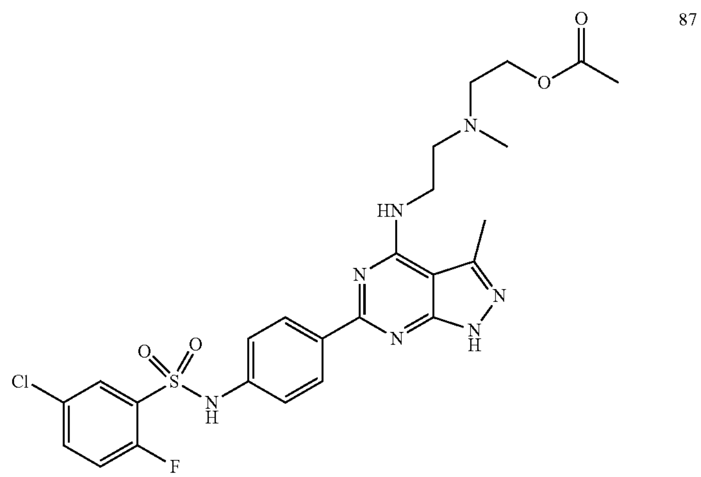 [SMILES: CCCC(=O)OCCN(C)CCNc1nc(-c2ccc(NS(=O)(=O)c3cc(Cl)ccc3F)cc2)nc2[nH]nc(C)c12] |

TABLE A-continued
| Listing of compounds Compound Number and Chemical Formula |
|---|
| 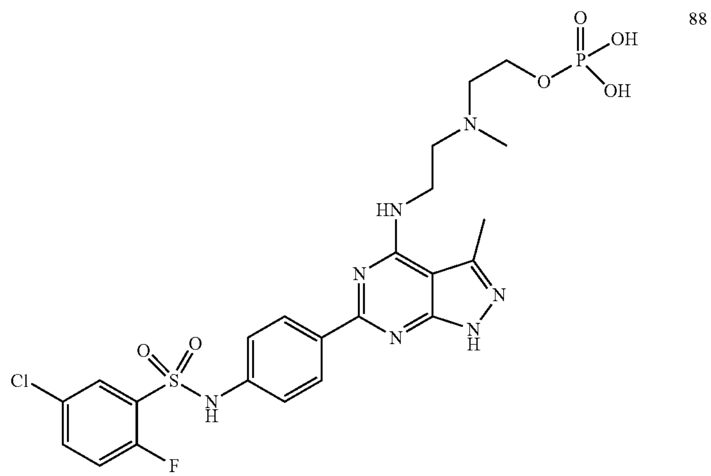 88 |
| 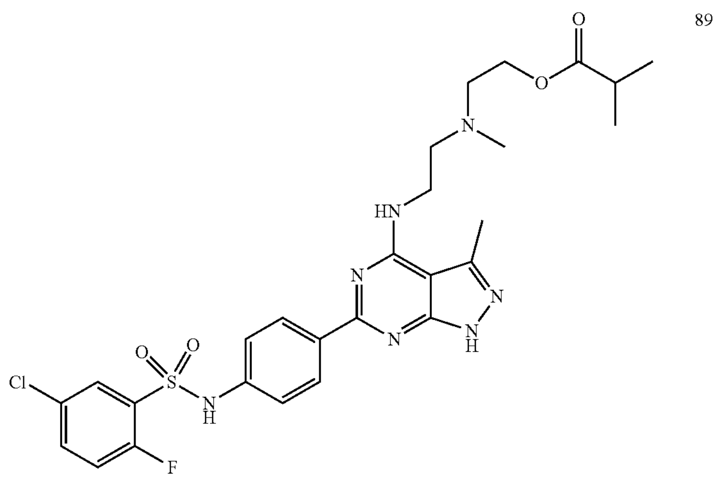 89 |
| 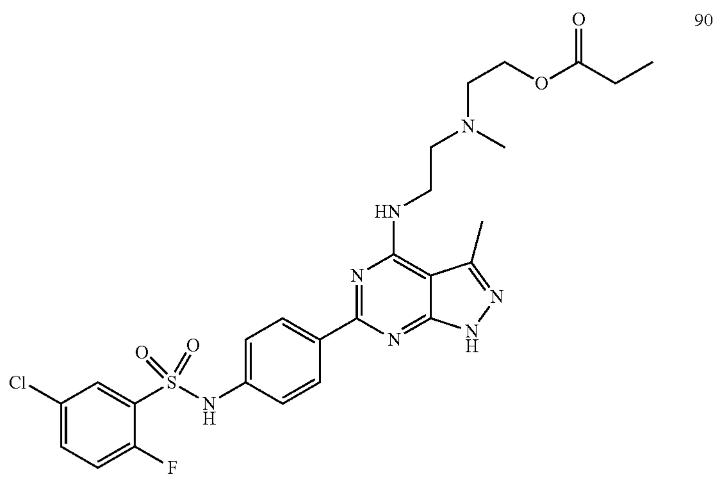 90 |

TABLE A-continued
| Listing of compounds<br>Compound Number and Chemical Formula |
|---|
| 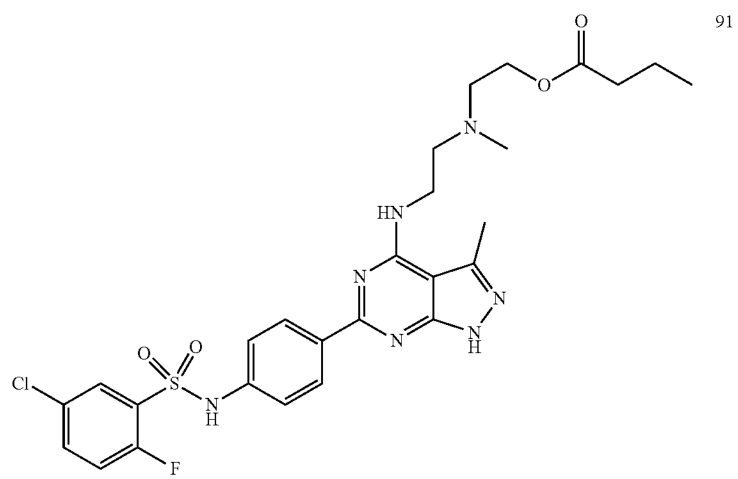 91 |
| 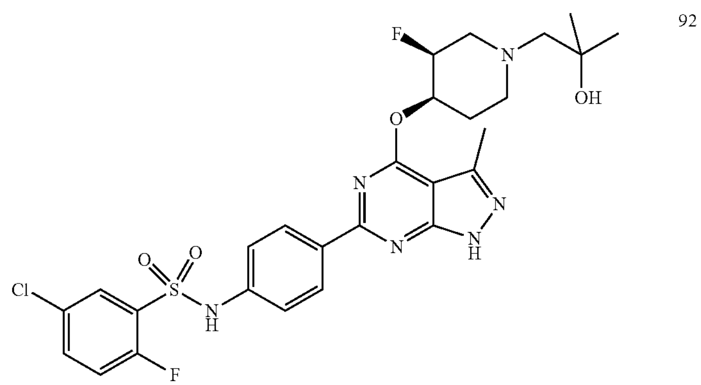 92 |
| 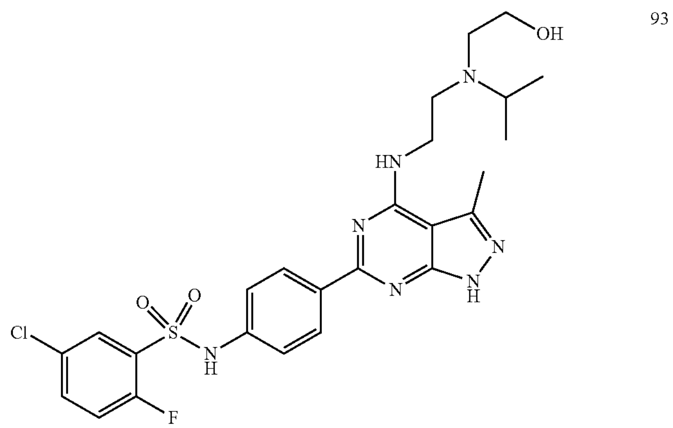 93 |

TABLE A-continued
| Listing of compounds<br>Compound Number and Chemical Formula |
|---|
| 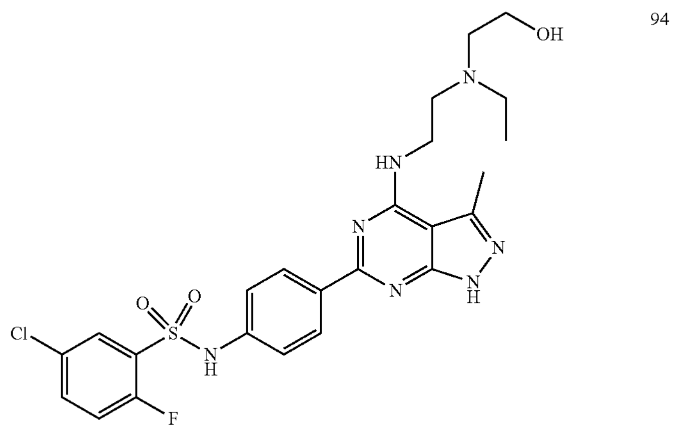 94 |
| 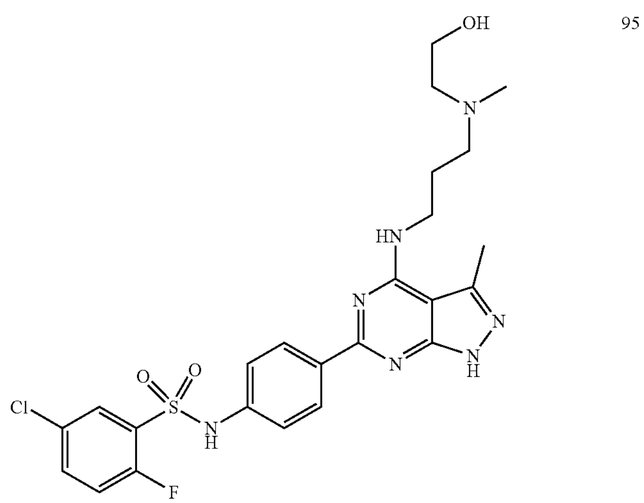 95 |
| 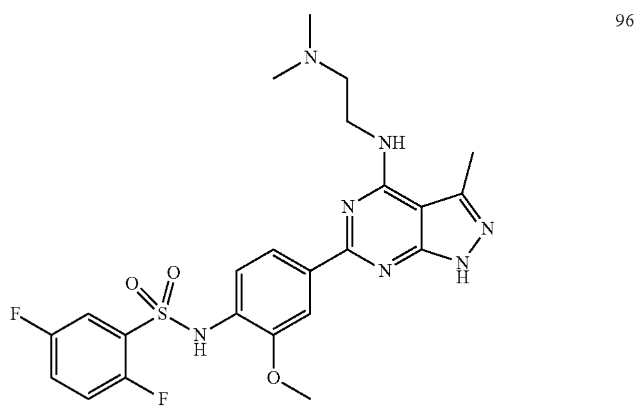 96 |

TABLE A-continued
| Listing of compounds<br>Compound Number and Chemical Formula |
|---|
| 97<br>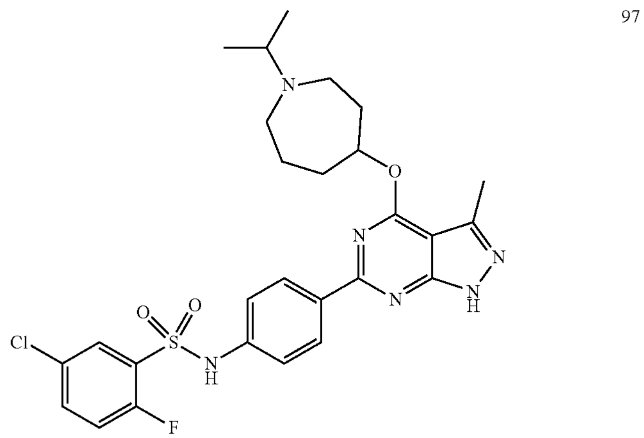 |
| 98<br>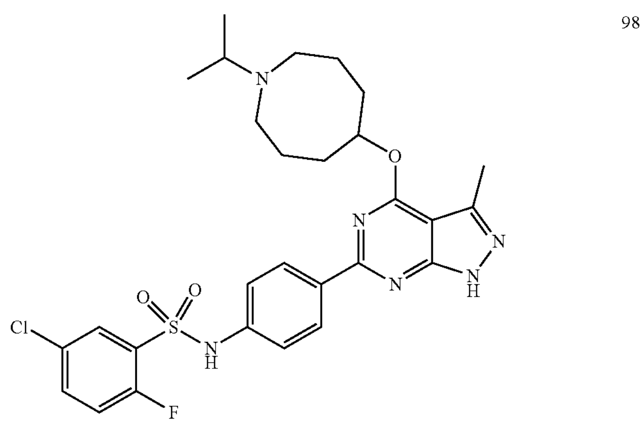 |
| 99<br>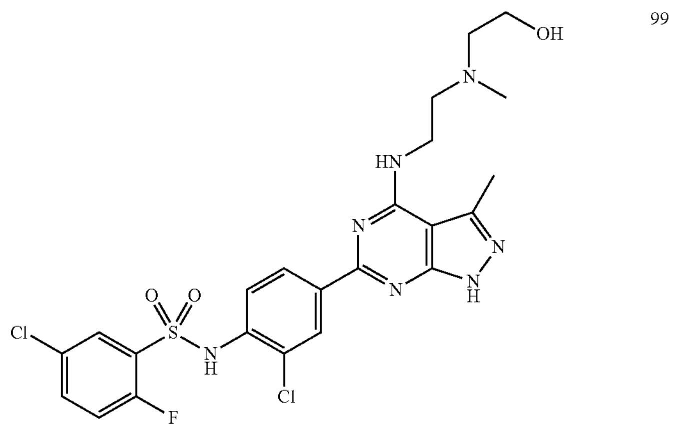 |

TABLE A-continued
| Listing of compounds<br>Compound Number and Chemical Formula |
|---|
| 100 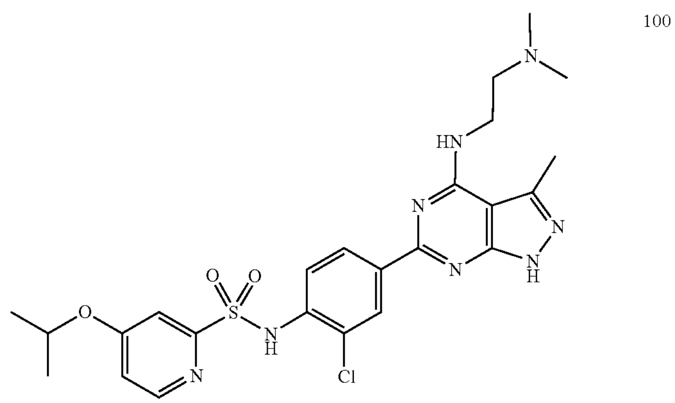 |
| 101 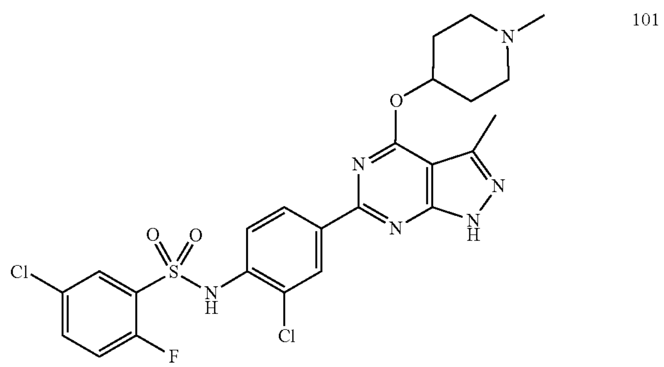 |
| 102 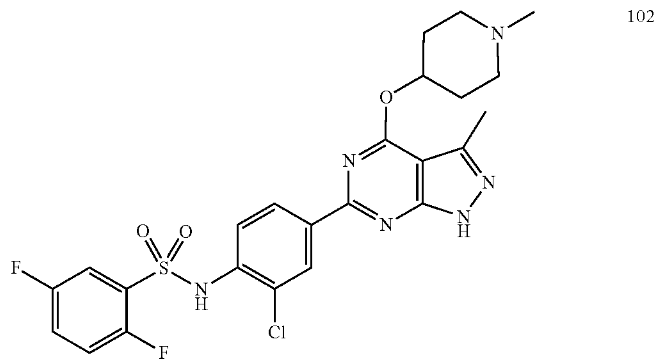 |
| 103 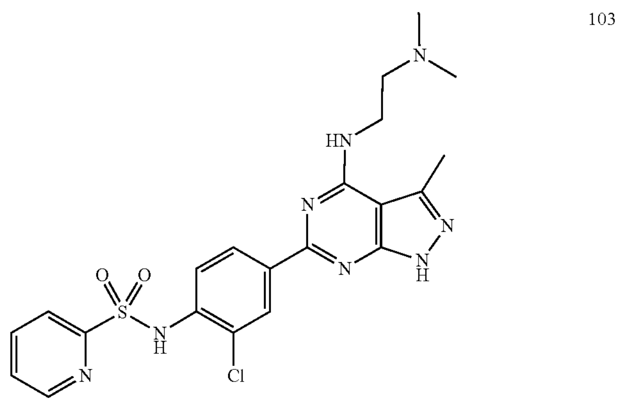 |

TABLE A-continued
| Listing of compounds<br>Compound Number and Chemical Formula |
|---|
| 104<br>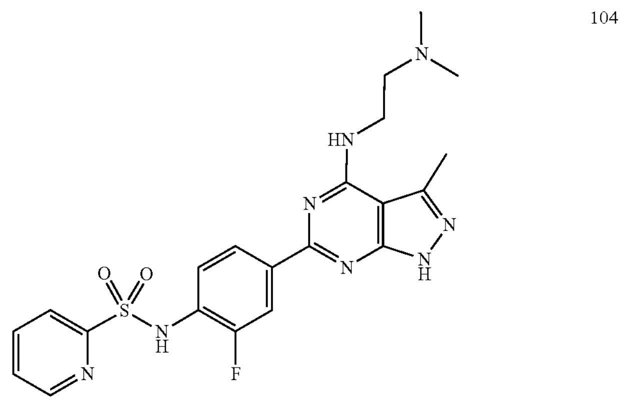 |
| 105<br>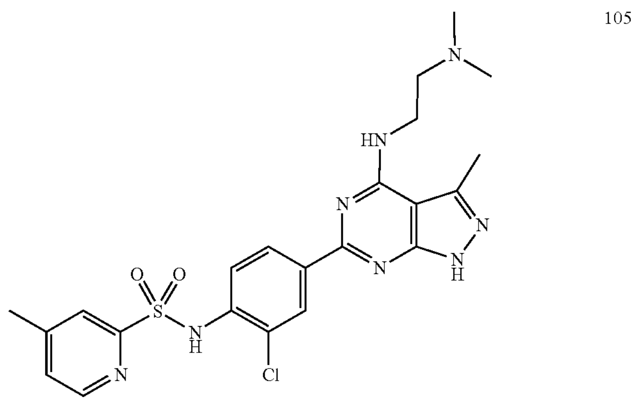 |
| 106<br>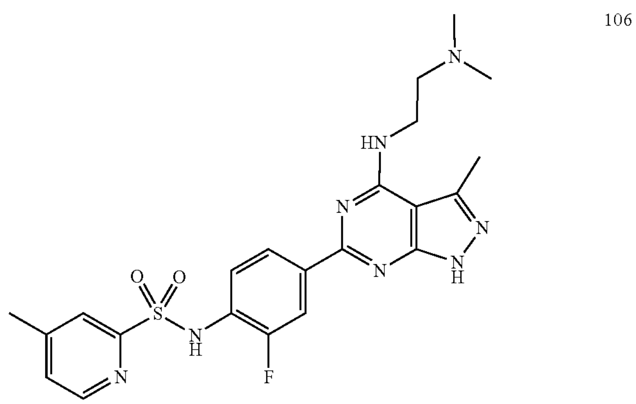 |
| 107<br>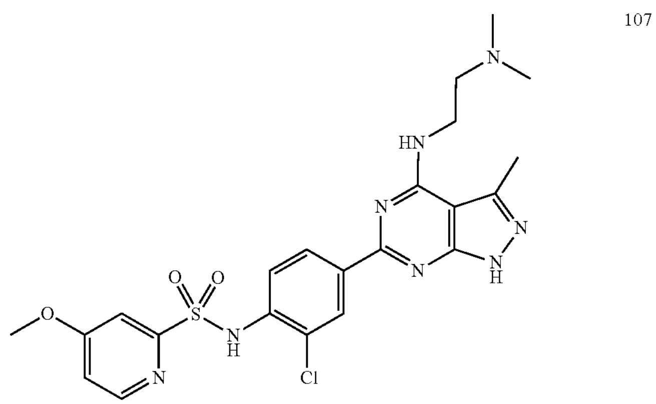 |

TABLE A-continued
| Listing of compounds<br>Compound Number and Chemical Formula |
|---|
108
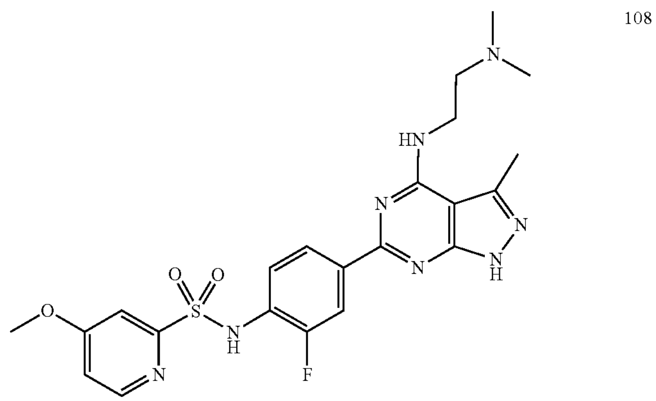
109
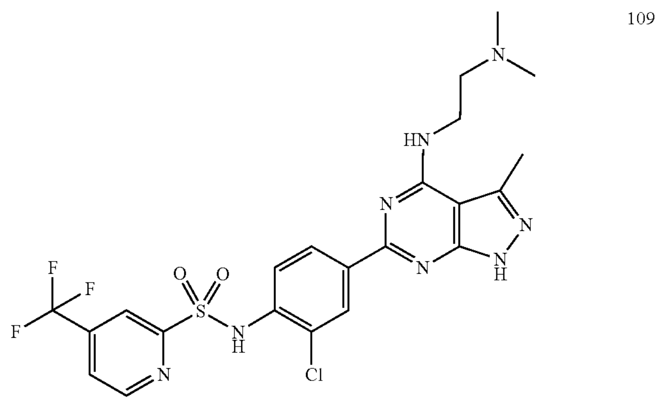
110
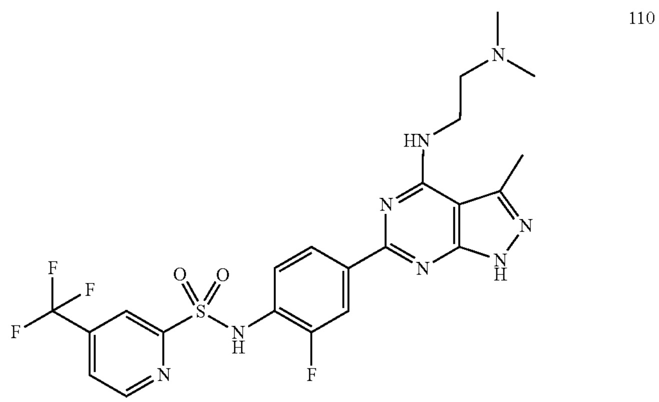

TABLE A-continued
| Listing of compounds<br>Compound Number and Chemical Formula |
|---|
| 111<br>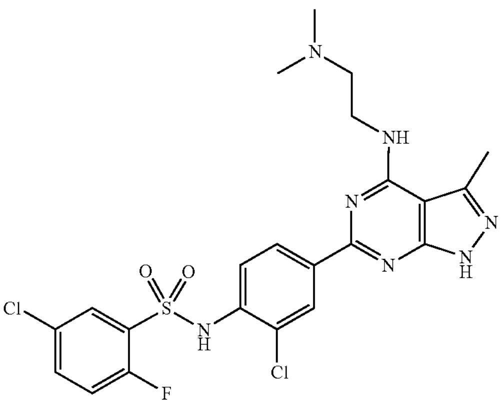 [SMILES: Cc1n[nH]c2nc(-c3ccc(NS(=O)(=O)c4cc(Cl)ccc4F)c(Cl)c3)nc(NCCN(C)C)c12] |
| 112<br>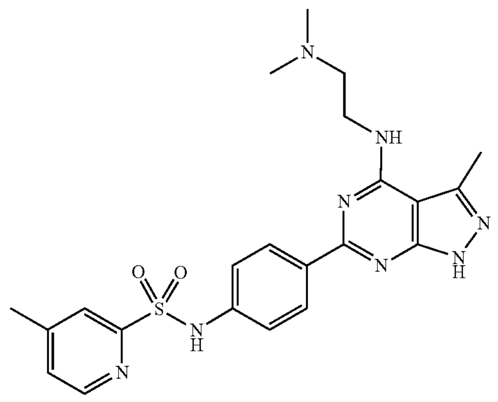 [SMILES: Cc1ccnc(S(=O)(=O)Nc2ccc(-c3nc(NCCN(C)C)c4c(C)n[nH]c4n3)cc2)c1] |
| 113<br>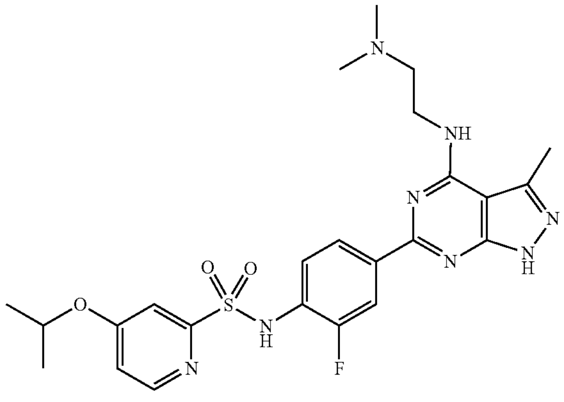 [SMILES: Cc1n[nH]c2nc(-c3ccc(NS(=O)(=O)c4cc(OC(C)C)ccn4)c(F)c3)nc(NCCN(C)C)c12] |

TABLE A-continued
| Listing of compounds<br>Compound Number and Chemical Formula |
|---|
| 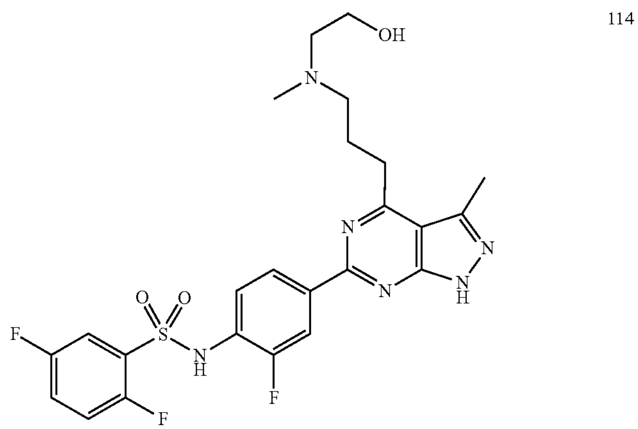 114 |
| 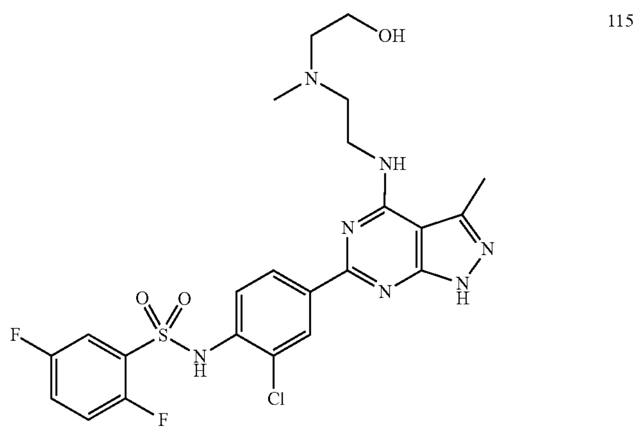 115 |
| 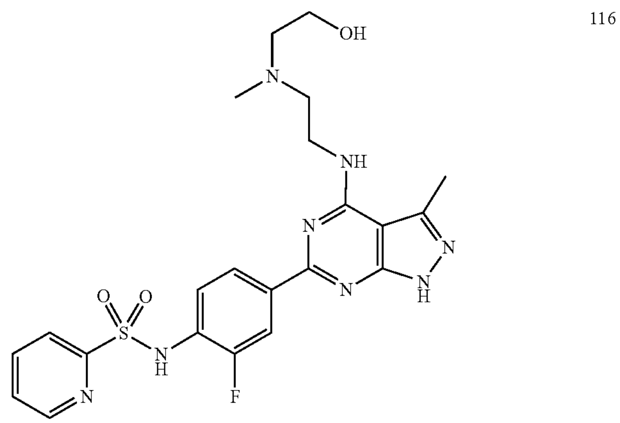 116 |

TABLE A-continued
| Listing of compounds<br>Compound Number and Chemical Formula |
|---|
| 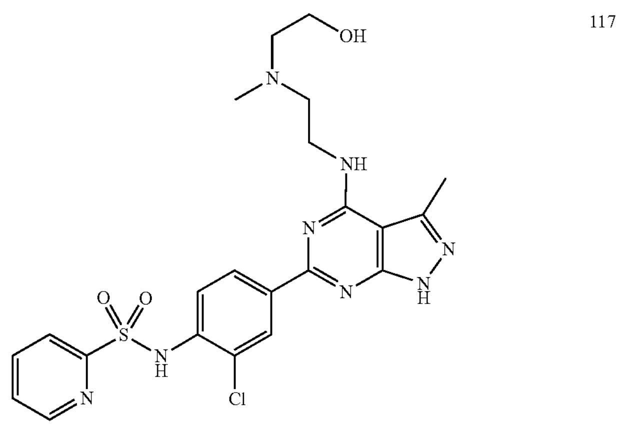 117 |
| 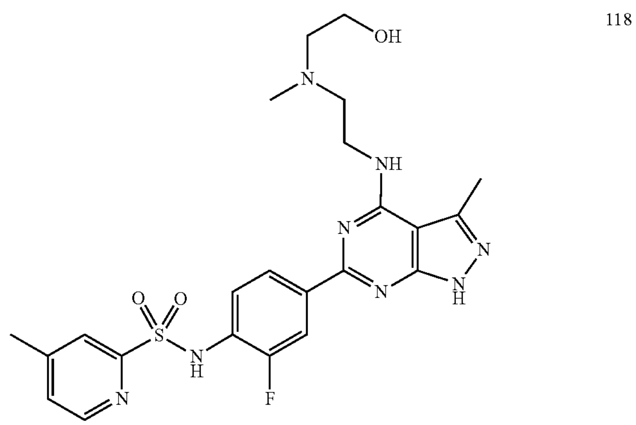 118 |
| 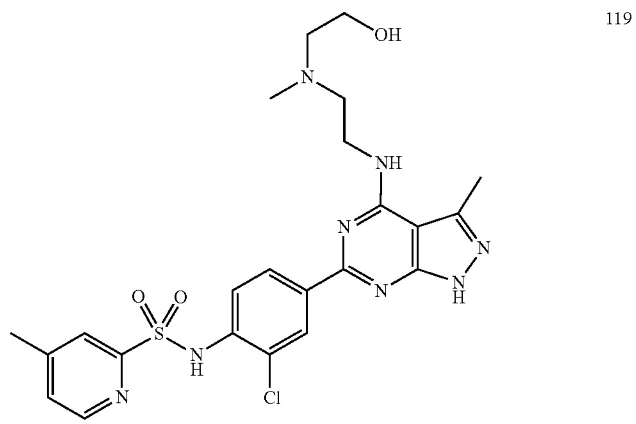 119 |

TABLE A-continued
| Listing of compounds<br>Compound Number and Chemical Formula |
|---|
| 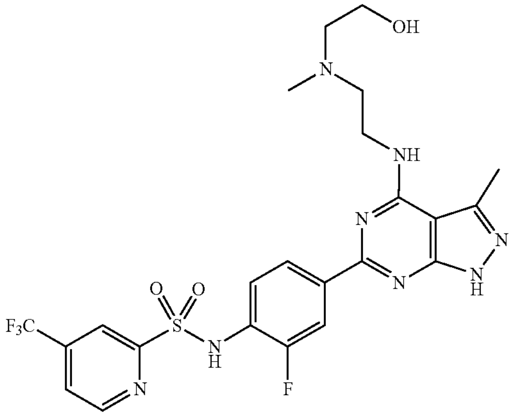 120 |
| 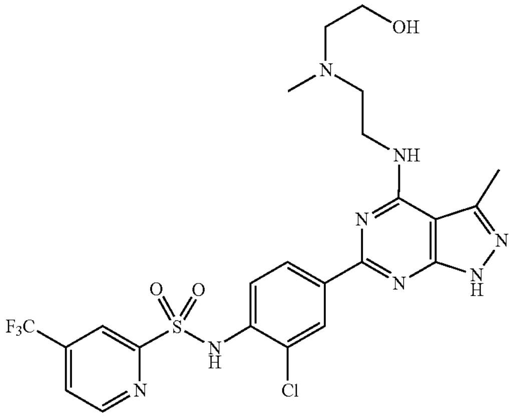 [SMILES: Cc1n[nH]c2nc(-c3ccc(NS(=O)(=O)c4cc(C(F)(F)F)ccn4)c(F)c3)nc(NCCN(C)CCO)c12] 121 |
| 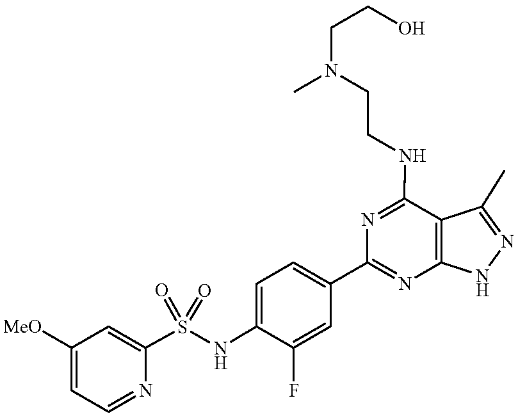 [SMILES: COc1ccnc(S(=O)(=O)Nc2ccc(-c3nc(NCCN(C)CCO)c4c(C)n[nH]c4n3)cc2F)c1] 122 |

TABLE A-continued
Listing of compounds
Compound Number and Chemical Formula
123
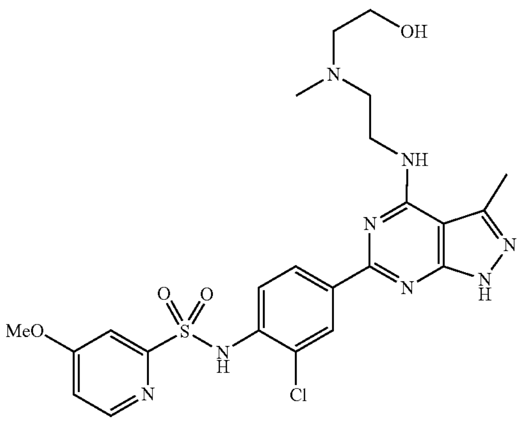 [SMILES: COc1ccnc(S(=O)(=O)Nc2ccc(-c3nc(NCCN(C)CCO)c4c(C)n[nH]c4n3)cc2Cl)c1]
124
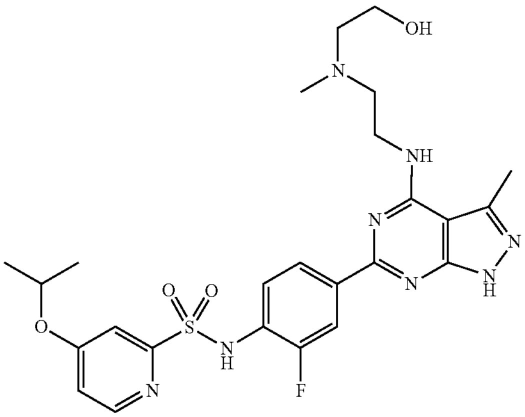 [SMILES: Cc1n[nH]c2nc(-c3ccc(NS(=O)(=O)c4cc(OC(C)C)ccn4)c(F)c3)nc(NCCN(C)CCO)c12]
125
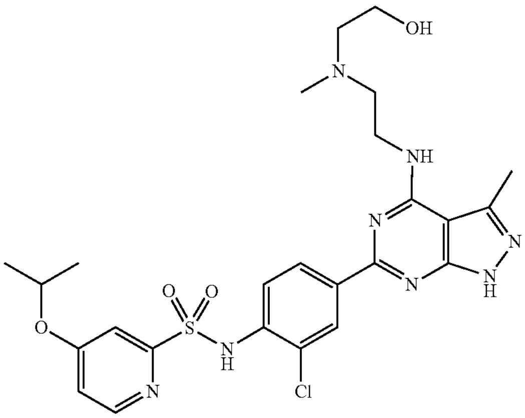 [SMILES: Cc1n[nH]c2nc(-c3ccc(NS(=O)(=O)c4cc(OC(C)C)ccn4)c(Cl)c3)nc(NCCN(C)CCO)c12]

TABLE A-continued
| Listing of compounds<br>Compound Number and Chemical Formula |
|---|
| 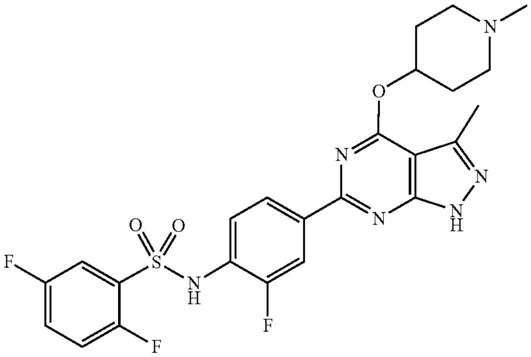 [SMILES: Cc1n[nH]c2nc(-c3ccc(NS(=O)(=O)c4cc(F)ccc4F)c(F)c3)nc(OC3CCN(C)CC3)c12] 126 |
| 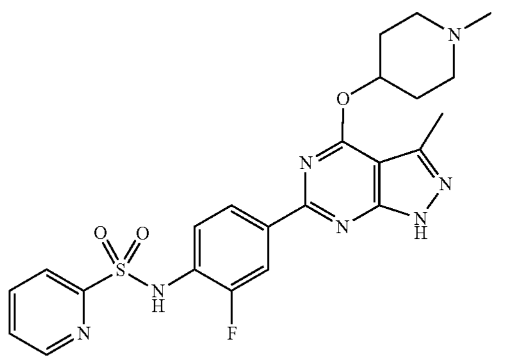 127 |
| 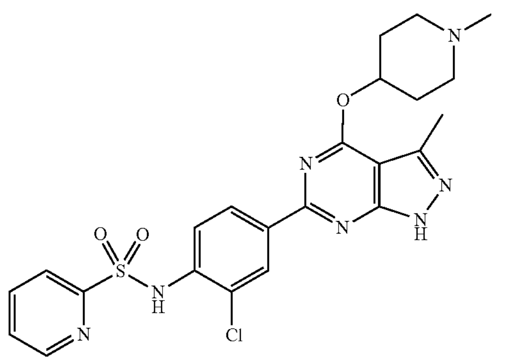 [SMILES: Cc1n[nH]c2nc(-c3ccc(NS(=O)(=O)c4ccccn4)c(F)c3)nc(OC3CCN(C)CC3)c12] 128 |
| 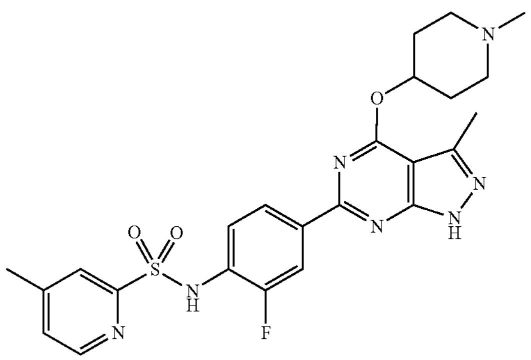 129 |

TABLE A-continued
| Listing of compounds |
| --- |
| Compound Number and Chemical Formula |
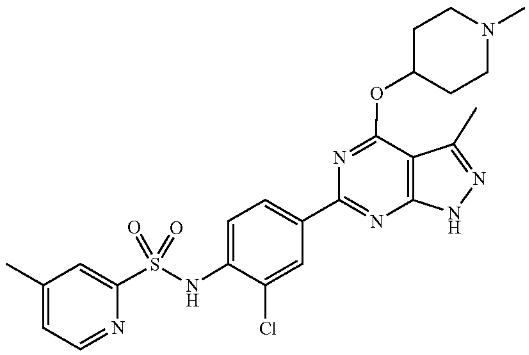
130
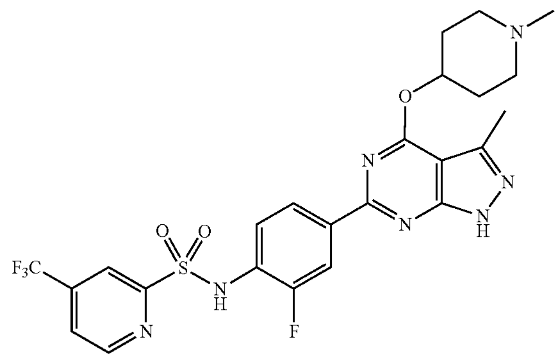 [SMILES: Cc1n[nH]c2nc(-c3ccc(NS(=O)(=O)c4cc(C(F)(F)F)ccn4)c(F)c3)nc(OC3CCN(C)CC3)c12]
131
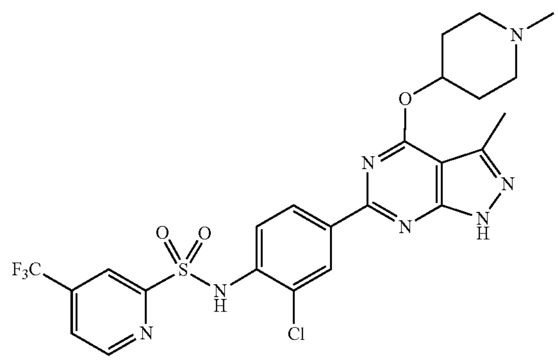
132
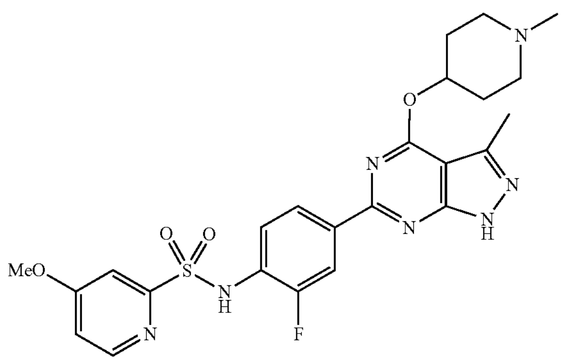 [SMILES: COc1ccnc(S(=O)(=O)Nc2ccc(-c3nc(OC4CCN(C)CC4)c4c(C)n[nH]c4n3)cc2F)c1]
133

TABLE A-continued
| Listing of compounds<br>Compound Number and Chemical Formula |
|---|
| 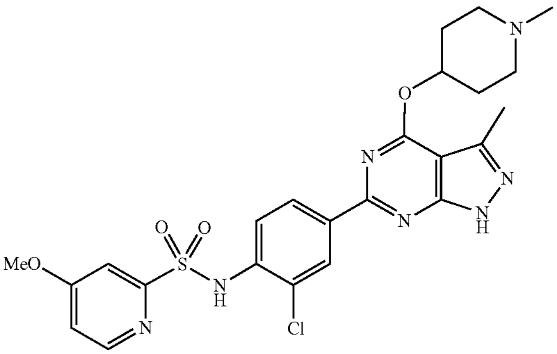 [SMILES: COc1ccnc(S(=O)(=O)Nc2ccc(-c3nc(OC4CCN(C)CC4)c4c(C)n[nH]c4n3)cc2Cl)c1] 134 |
| 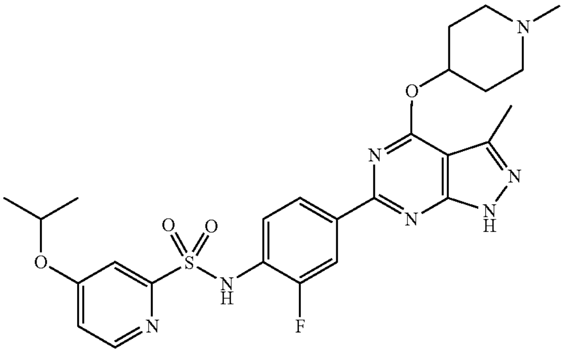 [SMILES: Cc1n[nH]c2nc(-c3ccc(NS(=O)(=O)c4cc(OC(C)C)ccn4)c(F)c3)nc(OC3CCN(C)CC3)c12] 135 |
| 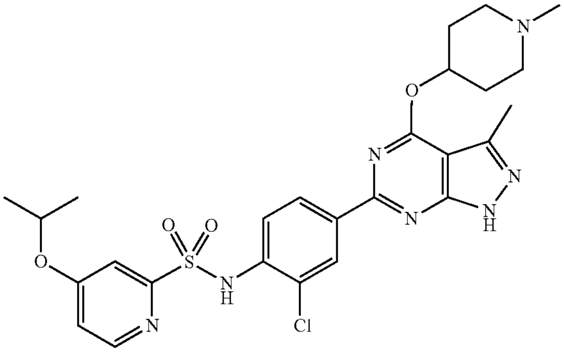 [SMILES: Cc1n[nH]c2nc(-c3ccc(NS(=O)(=O)c4cc(OC(C)C)ccn4)c(Cl)c3)nc(OC3CCN(C)CC3)c12] 136 |
| 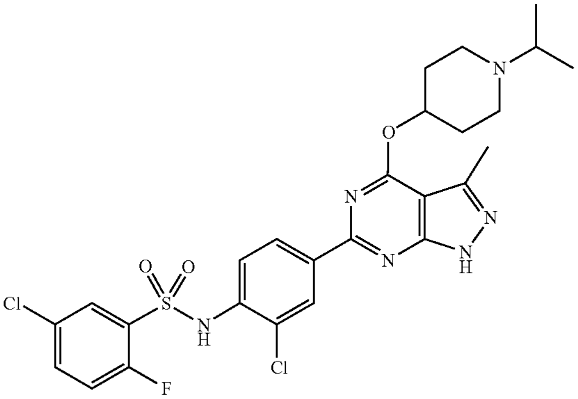 [SMILES: Cc1n[nH]c2nc(-c3ccc(NS(=O)(=O)c4cc(Cl)ccc4F)c(Cl)c3)nc(OC3CCN(C(C)C)CC3)c12] 137 |

TABLE A-continued
| Listing of compounds<br>Compound Number and Chemical Formula |
|---|
| 138 |
| 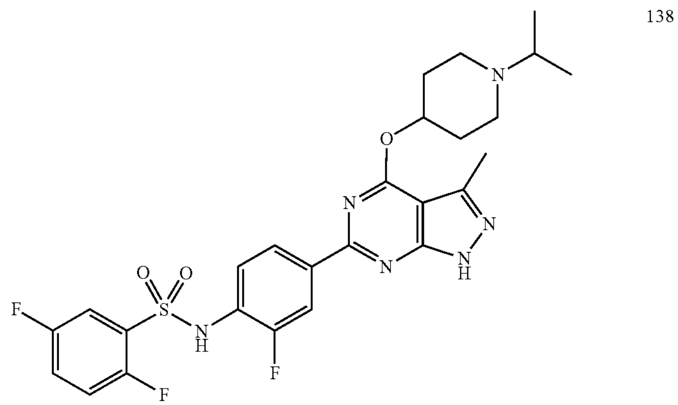 |
| 139 |
| 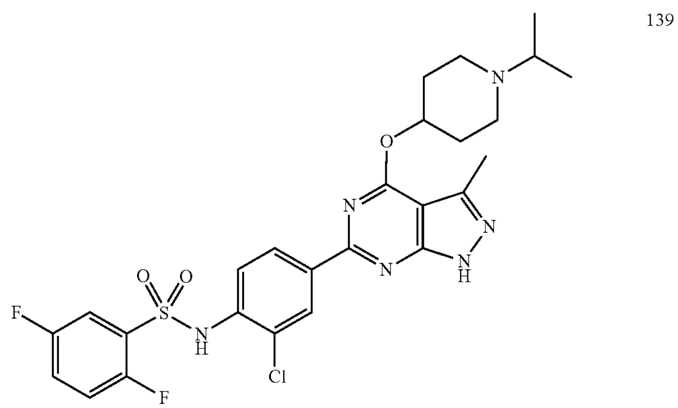 |
| 140 |
| 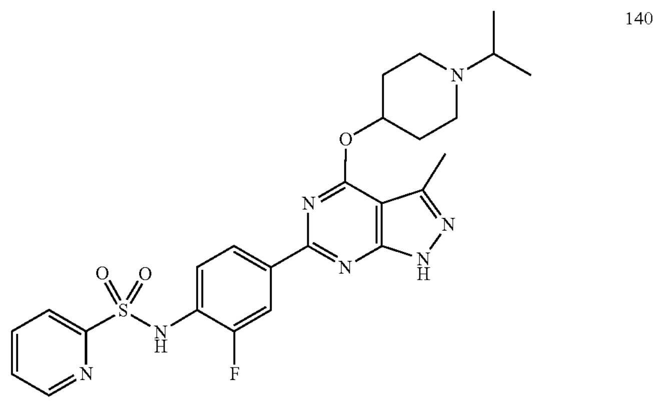 |

TABLE A-continued
Listing of compounds
Compound Number and Chemical Formula
141
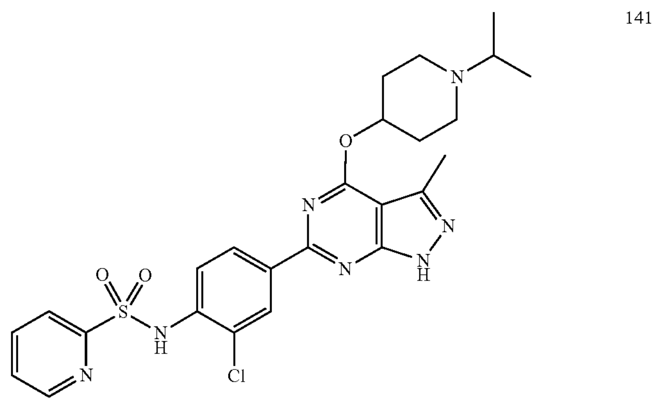
142
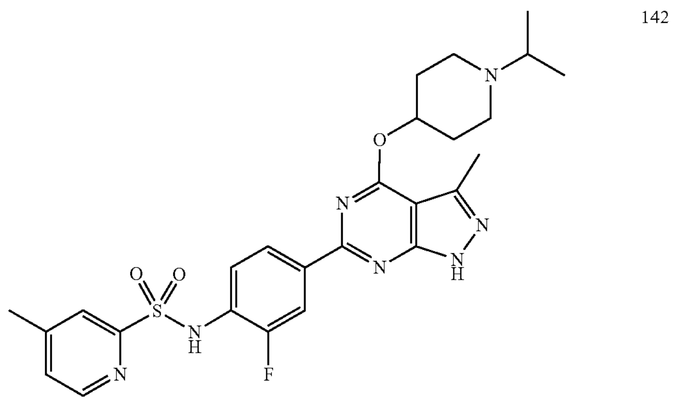
143
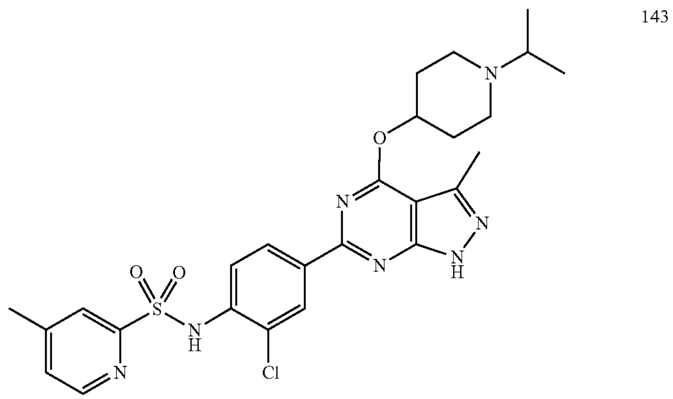
144
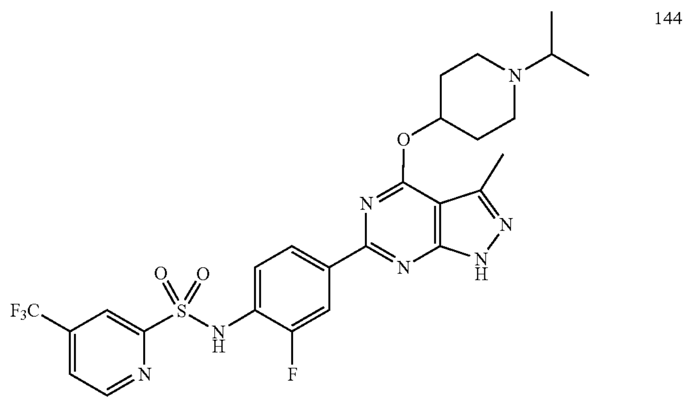

TABLE A-continued
| Listing of compounds<br>Compound Number and Chemical Formula |
|---|
| 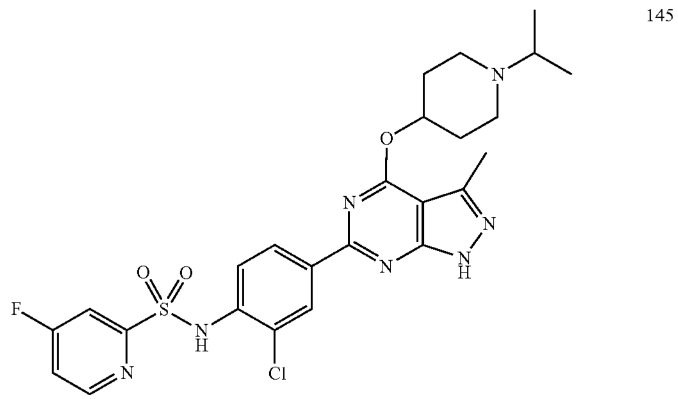 145 |
| 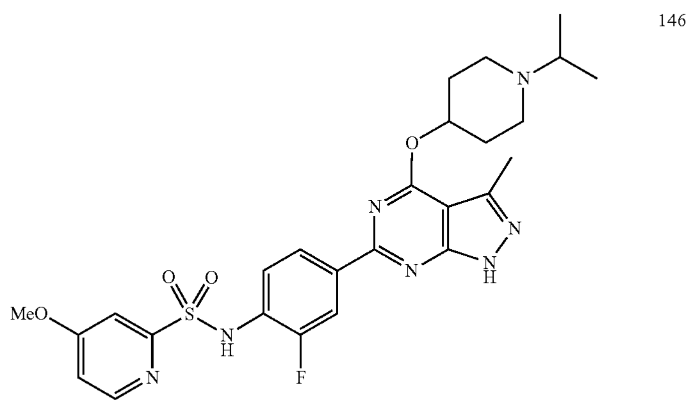 146 |
| 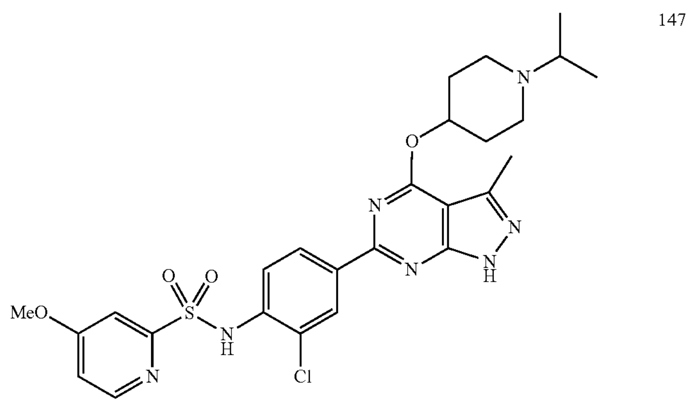 147 |

TABLE A-continued
| Listing of compounds<br>Compound Number and Chemical Formula |
| --- |
| 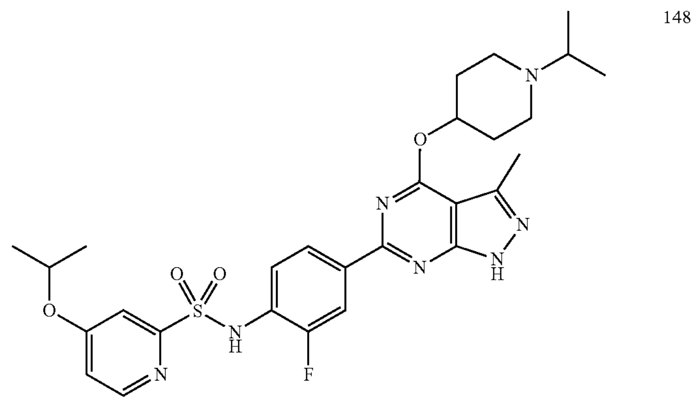 148 |
| 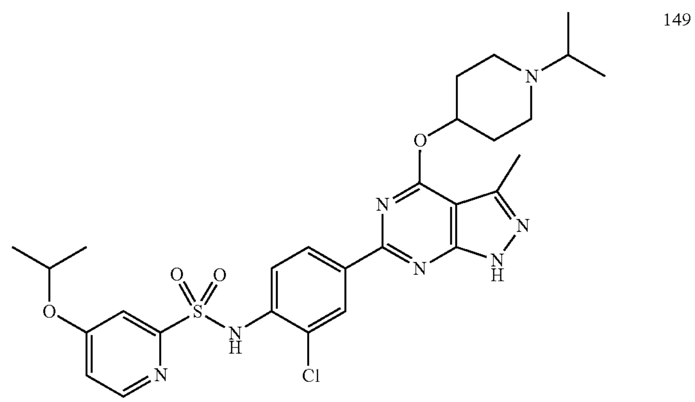 149 |
| 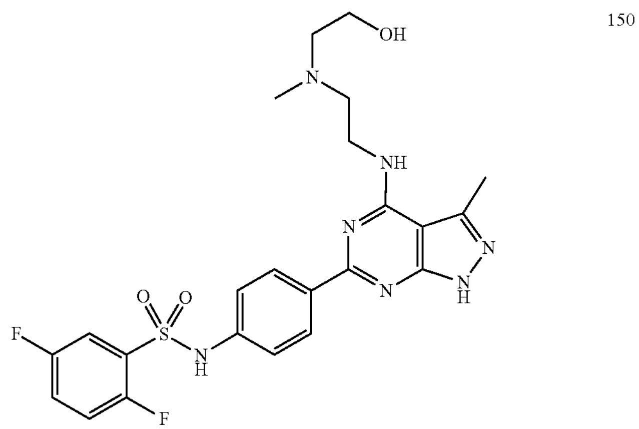 150 |

TABLE A-continued
| Listing of compounds<br>Compound Number and Chemical Formula |
|---|
| 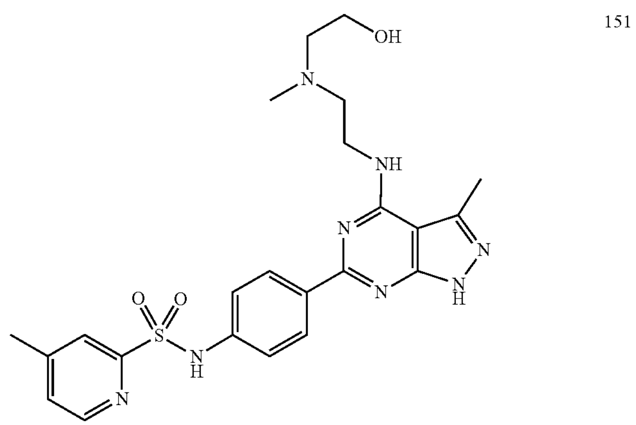 151 |
| 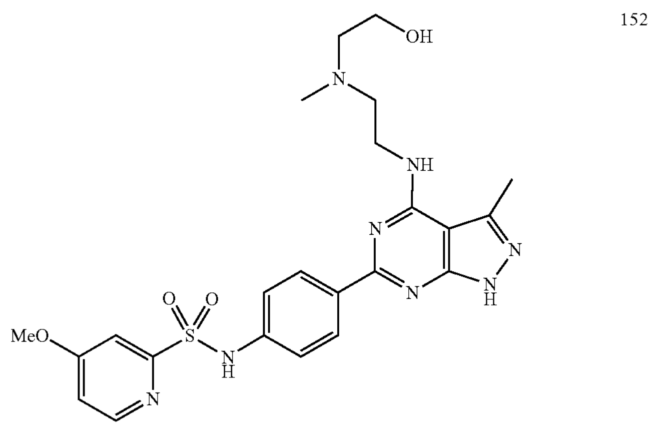 152 |
| 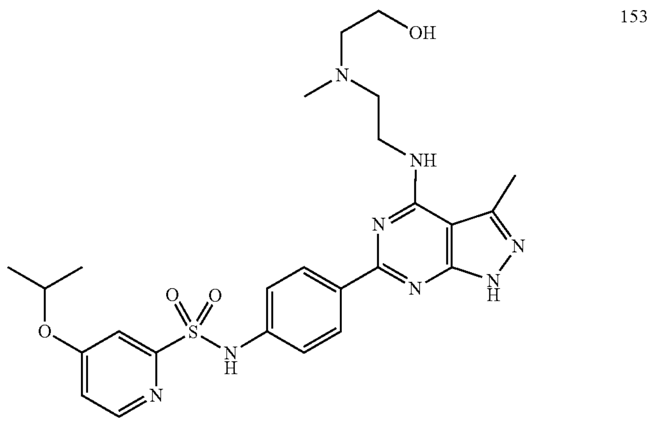 153 |

TABLE A-continued
| Listing of compounds<br>Compound Number and Chemical Formula |
|---|
| 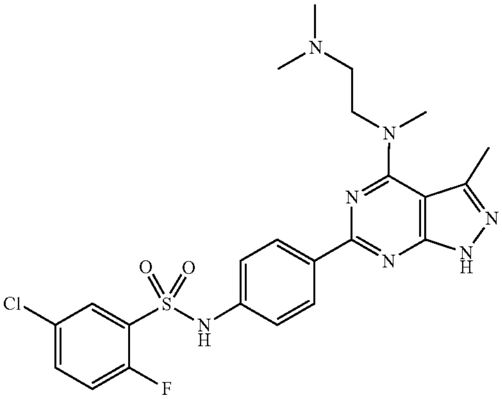 [SMILES: Cc1n[nH]c2nc(-c3ccc(NS(=O)(=O)c4cc(Cl)ccc4F)cc3)nc(N(C)CCN(C)C)c12] 154 |
| 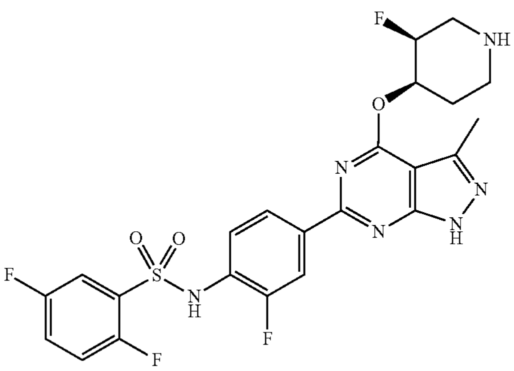 [SMILES: Cc1n[nH]c2nc(-c3ccc(NS(=O)(=O)c4cc(F)ccc4F)c(F)c3)nc(O[C@@H]3CCNC[C@@H]3F)c12] 155 |
| 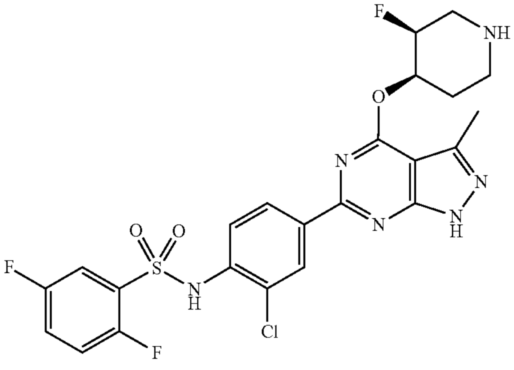 156 |
| 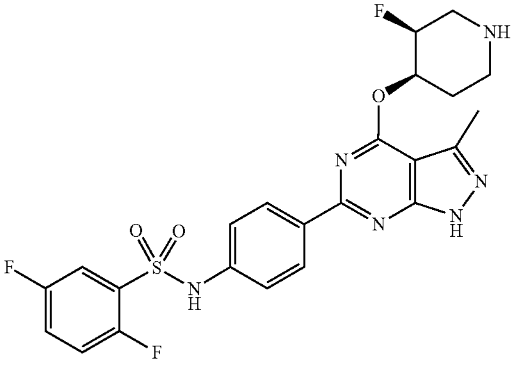 [SMILES: Cc1n[nH]c2nc(-c3ccc(NS(=O)(=O)c4cc(F)ccc4F)cc3)nc(O[C@@H]3CCNC[C@@H]3F)c12] 157 |

TABLE A-continued
| Listing of compounds<br>Compound Number and Chemical Formula |
| --- |
| 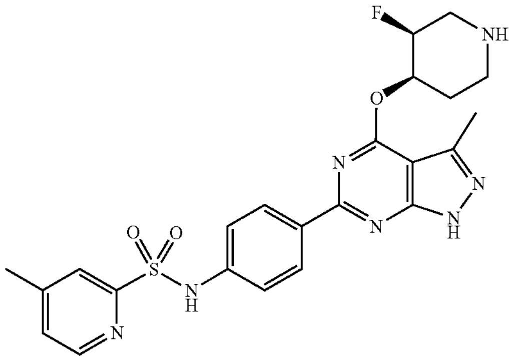 [SMILES: Cc1ccnc(S(=O)(=O)Nc2ccc(-c3nc(O[C@@H]4CCNC[C@@H]4F)c4c(C)n[nH]c4n3)cc2)c1] 159 |
| 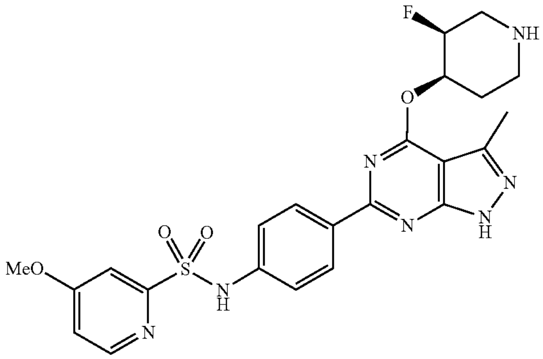 [SMILES: COc1ccnc(S(=O)(=O)Nc2ccc(-c3nc(O[C@@H]4CCNC[C@@H]4F)c4c(C)n[nH]c4n3)cc2)c1] 161 |
| 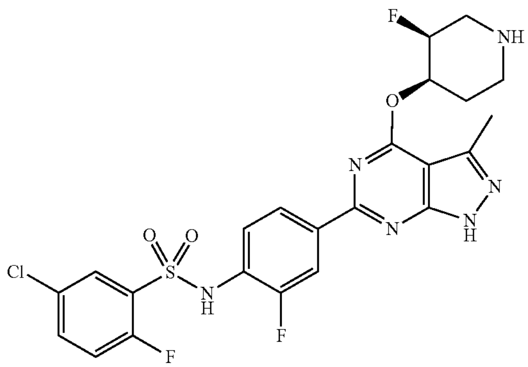 [SMILES: Cc1n[nH]c2nc(-c3ccc(NS(=O)(=O)c4cc(Cl)ccc4F)c(F)c3)nc(O[C@@H]3CCNC[C@@H]3F)c12] 163 |
| 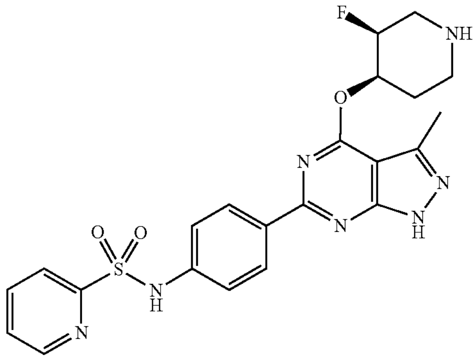 [SMILES: Cc1n[nH]c2nc(-c3ccc(NS(=O)(=O)c4ccccn4)cc3)nc(O[C@@H]3CCNC[C@@H]3F)c12] 158 |

TABLE A-continued
| Listing of compounds<br>Compound Number and Chemical Formula |
| --- |
| 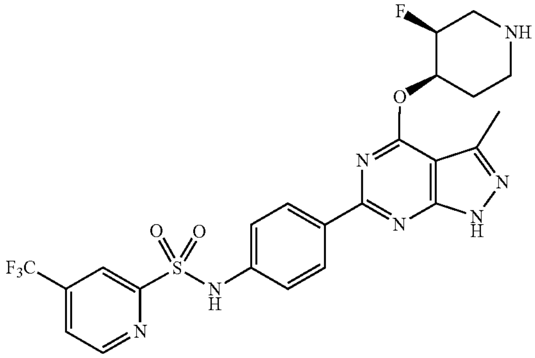 [SMILES: Cc1n[nH]c2nc(-c3ccc(NS(=O)(=O)c4cc(C(F)(F)F)ccn4)cc3)nc(O[C@@H]3CCNC[C@@H]3F)c12] 160 |
| 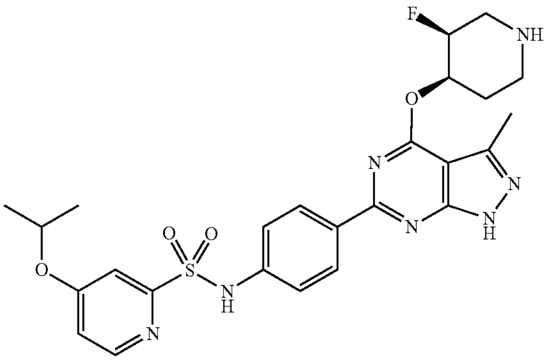 [SMILES: Cc1n[nH]c2nc(-c3ccc(NS(=O)(=O)c4cc(OC(C)C)ccn4)cc3)nc(O[C@@H]3CCNC[C@@H]3F)c12] 162 |
| 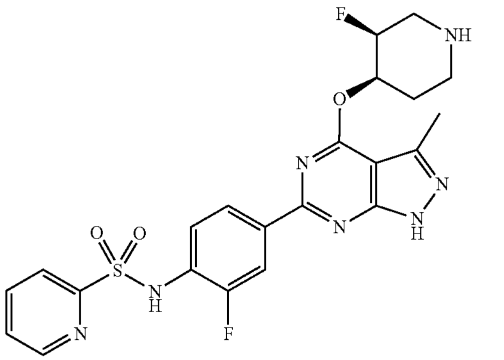 [SMILES: Cc1n[nH]c2nc(-c3ccc(NS(=O)(=O)c4ccccn4)c(F)c3)nc(O[C@@H]3CCNC[C@@H]3F)c12] 164 |
| 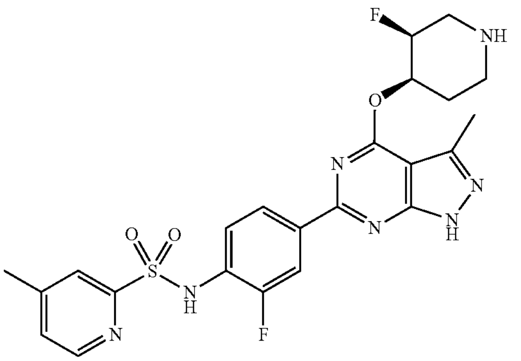 [SMILES: Cc1ccnc(S(=O)(=O)Nc2ccc(-c3nc(O[C@@H]4CCNC[C@@H]4F)c4c(C)n[nH]c4n3)cc2F)c1] 165 |

TABLE A-continued
| Listing of compounds<br>Compound Number and Chemical Formula |
|---|
| 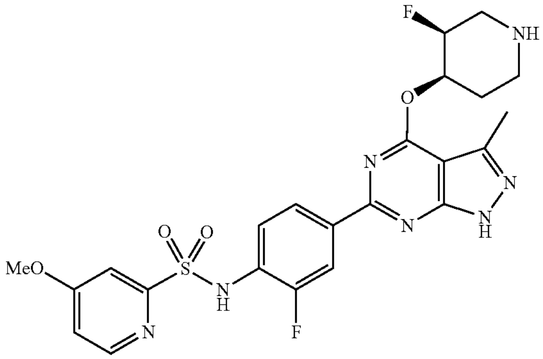 167 |
| 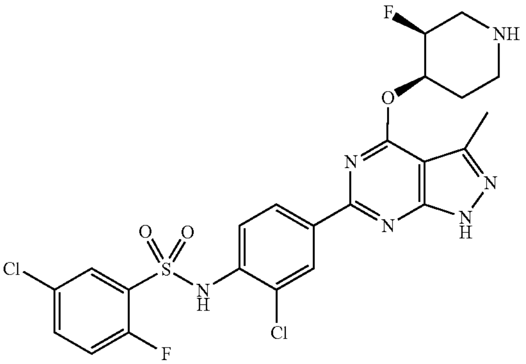 [SMILES: Cc1n[nH]c2nc(-c3ccc(NS(=O)(=O)c4cc(Cl)ccc4F)c(Cl)c3)nc(O[C@@H]3CCNC[C@@H]3F)c12] 169 |
| 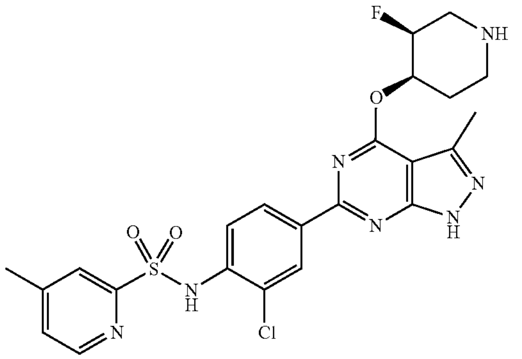 [SMILES: Cc1ccnc(S(=O)(=O)Nc2ccc(-c3nc(O[C@@H]4CCNC[C@@H]4F)c4c(C)n[nH]c4n3)cc2Cl)c1] 171 |
| 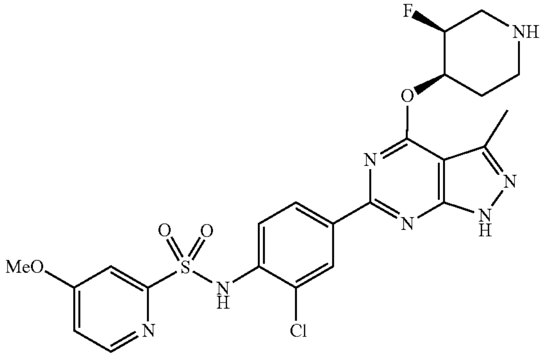 [SMILES: COc1ccnc(S(=O)(=O)Nc2ccc(-c3nc(O[C@@H]4CCNC[C@@H]4F)c4c(C)n[nH]c4n3)cc2Cl)c1] 173 |

TABLE A-continued
| Listing of compounds<br>Compound Number and Chemical Formula |
|---|
| 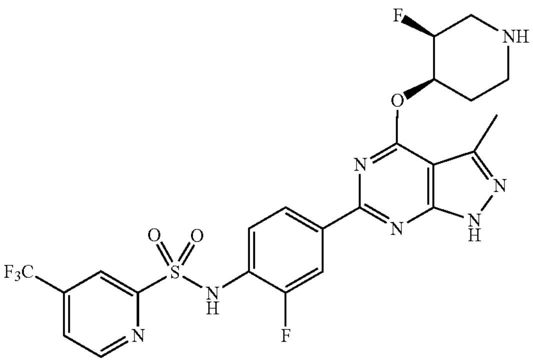 [SMILES: Cc1n[nH]c2nc(-c3ccc(NS(=O)(=O)c4cc(C(F)(F)F)ccn4)c(F)c3)nc(O[C@@H]3CCNC[C@@H]3F)c12] 166 |
| 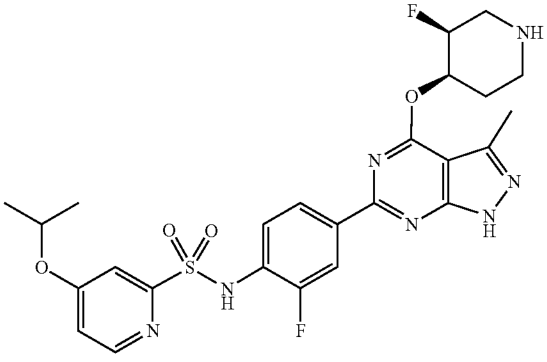 [SMILES: Cc1n[nH]c2nc(-c3ccc(NS(=O)(=O)c4cc(OC(C)C)ccn4)c(F)c3)nc(O[C@@H]3CCNC[C@@H]3F)c12] 168 |
| 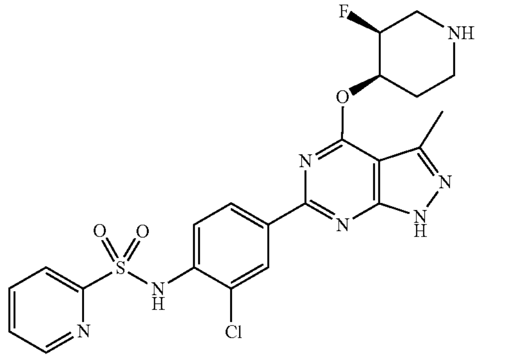 170 |
| 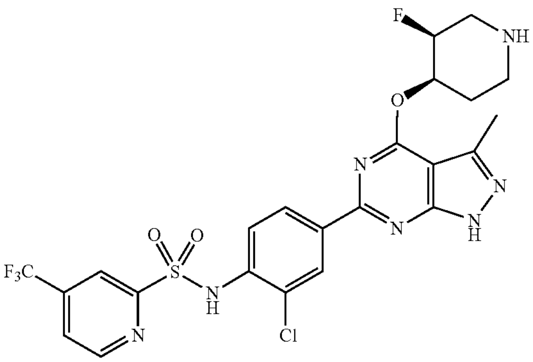 [SMILES: Cc1n[nH]c2nc(-c3ccc(NS(=O)(=O)c4cc(C(F)(F)F)ccn4)c(Cl)c3)nc(O[C@@H]3CCNC[C@@H]3F)c12] 172 |

TABLE A-continued

| Listing of compounds Compound Number and Chemical Formula |
|---|
| 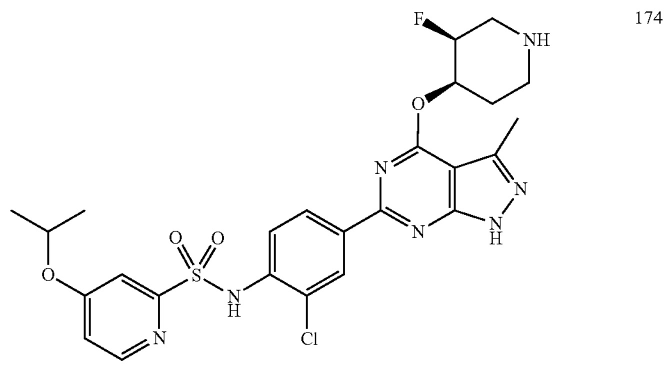 174 |

Biological Activity

SGK1 Assay

The ability of the synthesized compounds to inhibit SGK-1 was assessed in an enzymatic assay by determining their effect on the ability of the isolated SGK1 enzyme to catalyze the transfer of the phosphate from ATP to serine/threonine residues in a labeled substrate peptide and in cellular assay by using the NanoBRET target engagement assay kit.

Enzymatic activity assay. The compounds were tested for SGK-1 activity by measuring the ability of the compound to inhibit the transfer of phosphate from ATP by the isolated enzyme to serine/threonine residues in a fluorescein labeled substrate peptide, FLPeptide 6 (PerkinElmer, Waltham, USA, Cat. No: 760350). The enzymatic reaction was initiated by addition of 15 μL of solution 1 containing (in mM) 10 MgCl2, 0.010% Brij-35, 2 DTT, 0.05% BSA, 1 EGTA, 50 HEPE (pH7.5) and 0.665 nM SGK to 5 μL of solution 2 containing 10 MgCl2, 0.010% of Brij-35, 2 DTT, 0.05% BSA, 1 EGTA, 50 HEPES (pH7.5), 6 UM of FLPeptide and 80 UM of ATP. After incubating the plate at room temperature for 90 min, 75 μL of stopping buffer (containing 0.5 M EDTA) is added to terminate the reaction. The samples were analyzed using an EZ reader. For the determination of the compound dose response, stock solution of compound prepared in DMSO was diluted and tested in a 10 point, three-fold dilution series run in duplicate beginning at 10 μM final concentration.

Cellular enzymatic activity assay. The cellular SGK1-kinase activity is determined using SGK1 NanoBRET™ target engagement (TE) intracellular kinase assay kit. The BRET methodology relies on the emission of an optical signal dependent on the spatial proximity of the luciferase-conjugated target protein and a fluorescent-labelled tracer molecule. The displacement of the tracer by a competitive inhibitor therefore diminishes the apparent BRET signal. HEK293 cells that were cultured in Dulbecco modified Eagle medium (DMEM), was transfected with 9 ug/mL Carrier DNA and 1 ug/mL SGK1-NanoLuc fusion vector and mix lipid:DNA complex with 1:20 (v:v) cell suspension. Transfected cells were seeded at 2000 cells/100 μL/well in 96-well plate and incubated overnight. After overnight incubation, 5 μL 20× NanoBRET tracer was added per well (final 0.5 uM), followed by 10 μL 10× cpd solution per well, incubated for 2 hours at 37° C., 5% $CO_2$. 50 μL 3× complete substrate solution was then added per well and the luminescence signal was read after 15-30 min equilibration at room temperature using Synergy 4 plate reader.

TABLE B

IC$_{50}$ values for inhibition of SGK-1 activity

| Compound No. | SGK1 (IC50 nM) [20 μM ATP] | Whole cell SGK1 (IC50 nM) |
|---|---|---|
| 1 | 1042 | |
| 2 | 376 | |
| 3 | 511 | |
| 4 | 3050 | |
| 5 | 2071 | |
| 6 | 689 | |
| 7 | 67.4 | |
| 8 | 1.64 | |
| 9 | 0.73 | 7 |
| 10 | 1.61 | |
| 11 | 2.41 | |
| 12 | 16.9 | |
| 13 | 11.7 | |
| 14 | 4065 | |
| 15 | 8.66 | |
| 16 | 398 | |
| 17 | 1.80 | 195 |
| 18 | 1.35 | 193.9 |
| 19 | 17.5 | 6792 |
| 20 | 52.7 | >10000 |
| 21 | 68.8 | >10000 |
| 22 | 0.272 | 113.5 |
| 23 | 21.7 | 7290 |
| 24 | 3.7 | 1446 |
| 25 | 1.7 | 108 |
| 26 | 3.9 | 185 |
| 27 | 1.2 | 88 |
| 28 | 1.32 | 5.15 |
| 29 | 0.595 | 3 |
| 30 | 2.05 | 278 |
| 31 | | 4015 |
| 32 | 9.46 | 629 |
| 33 | 5.75 | 255 |
| 34 | 2.47 | 44 |
| 35 | | 151 |
| 36 | | >10000 |
| 37 | | 119 |
| 38 | <0.508 | 20.5 |
| 39 | | 279 |
| 40 | | 2275 |
| 41 | | 50 |
| 42 | 1.08 | 16 |
| 43 | | 19 |
| 44 | | 11 |

TABLE B-continued

| IC$_{50}$ values for inhibition of SGK-1 activity | | |
|---|---|---|
| Compound No. | SGK1 (IC50 nM) [20 μM ATP] | Whole cell SGK1 (IC50 nM) |
| 45 | 1.47 | 90.2 |
| 46 | 2.44 | 31 |
| 47 | 5.97 | 31 |
| 48 | 1.82 | 75 |
| 49 | 8.68 | 76 |
| 50 | 3.04 | 5 |
| 51 | | 15 |
| 52 | | 58 |
| 53 | 2.96 | 11 |
| 54 | | 62 |
| 55 | | 76 |
| 56 | 5.43 | 25 |
| 57 | | 71 |
| 58 | 6.12 | 42 |
| 59 | | 233 |
| 60 | | 55 |
| 61 | | 47 |
| 62 | | 36 |
| 63 | 5.97 | 141 |
| 64 | | 233 |
| 65 | | 22 |
| 66 | 3.830 | 239 |
| 67 | | 116 |
| 68 | 1.268 | 52 |
| 69 | 1.391 | 11 |
| 70 | | 585 |
| 71 | 1556 | |
| 72 | >10000 | |
| 73 | 0.631 | 92 |
| 74 | 349 | |
| 75 | 5890 | |
| 77 | | 256 |
| 78 | 1.044 | 181 |
| 79 | 3.061 | 15 |
| 80 | 1.232 | 34 |
| 84 | <0.508 | 89 |
| 85 | 0.6 | 52 |
| 86 | 1.600 | 86 |
| 92 | | 238 |
| 93 | | 387 |
| 94 | | 250 |
| 95 | | 627 |
| 96 | 1.087 | 85 |
| 154 | 0.98 | 65 |
| 155 | | 34 |
| 156 | | 21 |

Solubility

Buffer for preparing FeSSIF buffer was prepared by dissolving 4.040 g of NaOH, 8.650 g of glacial acetic acid and 11.874 g of NaCl in about 900 mL ultrapure water and the pH of the solution was adjusted to 5.0 with 1 N NaOH or 1 N HCl. Then the solution was diluted with ultrapure water to 1000 mL at room temperature. 11.200 g of FaSSIF, FeSSIF & FaSSGF Powder was added to about 500 mL of buffer. Stir until the powder was completely dissolved. Then the solution was diluted with the buffer to 1000 mL at room temperature. Ready to use within 48 hours at room temperature and 24 hours at 37° C.

Preparation of stock solutions the stock solutions of test compounds and control compound progesterone were prepared in DMSO at the concentration of 10 mM.

Procedure for solubility determination 30 μL of stock solution (10 mM) of each sample was placed in order into its proper 96-well rack, 970 μL of FeSSIF or PBS pH 7.4 was added into each vial of the cap-less Solubility Sample plate. The assay was performed in duplicate. Add one stir stick to each vial and seal using a molded PTFE/Silicone plug. Then the Solubility Sample plate was transferred to the Eppendorf Thermomixer Comfort plate shaker and shaken at 25° C. at 1100 RPM for 2 hours. After completion of the 2 hours, plugs were removed and the stir sticks were removed using a big magnet, the samples from the Solubility Sample plate were transferred into the filter plate. Using the Vacuum Manifold, all the samples were filtered. Aliquot of 5 μL was taken from the filtrate followed by addition of 5 μL DMSO and 490 μL of a mixture of H2O and acetonitrile. The dilution factor was changed according to the solubility values and the LC-MS signal response.

Preparation of 3 μM standards (STD) From the 10 mM DMSO STD plate, 15 μL was transferred into the remaining empty plate, and then 485 μL of DMSO was added to that plate to have a STD concentration of 300 M. From the 300 μM DMSO STD plate, 5 μL DMSO STD was transferred into the remaining empty plate, and then 5 μL FeSSIF or PBS pH 7.4 and 490 μL of a mixture of H2O and acetonitrile was added to that plate to have a final STD concentration of 3 μM. The concentration of the standard samples was changed according to the LC-MS signal response.

Procedure for sample analysis the plate was placed into the well plate autosampler. The samples were evaluated by LC-MS/MS analysis (LC system: Shimadzu, MS analysis: Triple Quad™ 5500 instrument from AB Inc (Canada) with an ESI interface, method: temperature 40° C., Injection volume: 1 μL or 2 μL, Column: XSelect Hss T3 2.5 μm (2.1×50 mm) Column XP, Mobile phase: 0.1% formic acid in water (A) and 0.1% formic acid in acetonitrile (B) and Elution rate: 1.0 mL/min)

Data analysis All calculations were carried out using Microsoft Excel. The filtrate was analyzed and quantified against a standard of known concentration using LC coupled with mass spectral peak identification and quantitation. Solubility values of the test compound and control compound were calculated as follows:

$$[\text{Sample}] = \frac{\text{AREA}_{Sample} \times INJVOL_{Std} \times DF_{Sample} \times [STD]}{\text{AREA}_{Std} \times INJVOL_{Sample}}$$

Any value of the compounds that was not within the specified limits was rejected and the experiment was repeated.

TABLE C

| Solubility of the compound | | |
|---|---|---|
| Compound No. | Solubility PBS pH 7.4 (μM) | Solubility FeSSiF (μM) |
| 1 | 290 | 279 |
| 2 | 59.1 | 291 |
| 3 | 19 | 325 |
| 4 | 293 | 17.6 |
| 5 | 40 | 315 |
| 6 | 299 | 258 |
| 7 | 23 | 324 |
| 8 | 0.23 | 91 |
| 9 | 8.5 | 289 |
| 12 | 2.5 | 33 |
| 13 | <0.12 | 5.81 |
| 15 | 282 | 289 |
| 17 | 1.12 | 202 |
| 18 | 52 | 268 |
| 19 | 37 | 297 |
| 20 | 82 | 277 |
| 21 | 2.26 | 302 |

TABLE C-continued

| Solubility of the compound | | |
|---|---|---|
| Compound No. | Solubility PBS pH 7.4 (μM) | Solubility FeSSiF (μM) |
| 22 | 8.37 | 289 |
| 23 | 13.7 | 274 |
| 24 | 278 | 300 |
| 25 | 15.6 | 301 |
| 26 | 5.10 | 285 |
| 27 | 36.5 | 256 |
| 28 | 1.7 | 293 |
| 29 | 3 | 245 |
| 30 | 295 | 276 |
| 33 | 3.8 | 298 |
| 38 | 15.9 | 298 |
| 45 | 7.98 | 277 |
| 46 | 0.70 | 174 |
| 47 | 16.8 | 211 |
| 48 | 63.6 | 178 |
| 49 | 0.27 | 265 |
| 53 | 11.3 | 283 |
| 55 | 1.37 | 244 |
| 56 | 0.48 | 73.7 |
| 58 | 0.92 | 262 |
| 62 | 0.36 | 16.2 |
| 63 | 1.9 | 205 |
| 64 | <0.24 | 6.43 |
| 65 | 0.73 | 210 |
| 66 | 1.51 | 32.9 |
| 73 | 265 | 311 |
| 78 | 16 | 275 |
| 79 | 2.6 | 321 |
| 84 | 3.38 | 297 |
| 85 | 4.5 | 315 |
| 86 | 0.66 | 75 |
| 87 | 0.60 | 290 |
| 154 | 1.61 | 136 |

Kinase Selectivity

The following compounds were profiled against a 50-kinase Mixed panel at 10 UM using the KinaseSeeker™ assay. Mixed Kinase Panel:

AKT1, AKT2, AKT3, PDK1/PDPK1, PKA/PRKACA, PKC-ε/PRKCE, PKG1/PRKG1, PKX/PRKX, RPS6KA3/RSK2, RPS6KA4/MSK2, YANK2, AMPK-α1/AMPK, CAMK1D, CAMK2D, DAPK3, MARK1, MARK2, PIM1, SNF1LK/SIK1, SNF1LK2/SIK2/QIK, CLK2, CDK5, p38-α/MAPK14, AAK1, AURKA, AURKB, AURKC, PLK4, SLK, TAOK1, YSK1, ABL1, DDR1, EPHA5, EPHB2, FLT1/VEGFR1, FLT3, HCK, IGF1R, ITK, KIT, MUSK, PDGFRB, PTK2B/PYK2, SRC, TNK1, VEGFR2/KDR/FLK1, ACVR2A/ACVR2, MLK2/MAP3K10, MLK3/MAP3K11.

Assay Design KinaseSeeker is a homogeneous competition binding assay where the displacement of an active site dependent probe by an inhibitor is measured by a change in luminescence signal. Luminescence readout translates into a highly sensitive and robust assay with low background and minimal interference from test compounds.

Assay Method 10 mM stock of the compound was diluted in DMSO to a concentration of 250 μM. Prior to initiating a profiling campaign, the compound was evaluated for false positive against split-luciferase. The compound was then screened in duplicate against each of the kinases. For kinase assays, each Cfluc-Kinase was translated along with Fos-Nfluc using a cell-free system (cell lysate) at 30° C. for 90 min. 24 μL aliquot of this lysate containing either 1 μL of DMSO (for no inhibitor control) or compound solution in DMSO (10 μM final concentration) was incubated for 2 hours at room temperature in presence of a kinase specific probe. 80 μL of luciferin assay reagent was added to each solution and luminescence was immediately measured on a luminometer.

$$\% \text{ Inhibition} = \frac{ALU_{Control} - ALU_{Sample}}{ALU_{Control}} \times 100$$

Profiling data for all kinases was plotted as % inhibition vs. kinases profiled. A heat map representing the effect of compounds on kinases was also generated.

TABLE D

| Kinase Selectivity of the compounds | |
|---|---|
| Compound No. | Kinase-Select. >50% at 10 μM |
| 7 | 0 |
| 8 | 10 |
| 9 | 11 |
| 12 | 2 |
| 18 | 9 |
| 21 | 0 |
| 22 | 10 |
| 23 | 0 |
| 24 | 0 |
| 28 | 12 |
| 38 | 13 |
| 45 | 2 |
| 50 | 14 |
| 58 | 14 |
| 63 | 12 |
| 69 | 15 |
| 73 | 1 |
| 78 | 13 |
| 79 | 15 |
| 84 | 4 |
| 85 | 13 |
| 86 | 9 |

hERG

Cell lines and cell culture hERG stably expressed HEK 293 cell line (Cat #K1236) was purchased from Invitrogen. The cells are cultured in 85% DMEM, 10% dialyzed FBS, 0.1 mM NEAA, 25 mM HEPES, 100 U/mL Penicillin-Streptomycin and 5 μg/mL Blasticidin and 400 μg/mL Geneticin. Cells are split using TrypLE™ Express about three times a week, and maintained between ~40% to ~80% confluence. Before the assay, the cells were transferred onto the coverslips at 5×105 cells/per 6 cm cell culture dish and induced with doxycycline at 1 μg/mL for 48 hours.

Solution preparations Extracellular solution (in mM): 132 NaCl, 4 KCl, 3 $CaCl_2$, 0.5 $MgCl_2$, 11.1 glucose, and 10 HEPES (pH adjusted to 7.35 with NaOH). Intercellular solution (in mM): 140 KCl, 2 $MgCl_2$, 10 EGTA, 10 HEPES and 5 MgATP (pH adjusted to 7.35 with KOH)

Working solution preparation for test compound Test compounds were initially prepared in DMSO with final concentration of 10 mM as stock solution according to SOP-ADMET-MAN-007. Then stock solution of each compound was serial-diluted by ratio of 1:3 with DMSO to prepare additional 3 intermediate solutions including 3.33, 1.11 and 0.37 mM. Before hERG assay, the working solutions were prepared by dilution of 10, 3.33, 1.11- and 0.37-mM intermediate solutions in 1000 folds using extracellular solution, so that the final concentration of working solution was 10, 3.33, 1.11 and 0.37 mM, while 30 μM working solution was prepared by 333.333-folds dilution of 10 mM DMSO stock. The final DMSO concentration in working solutions was maintained in range of 0.1-0.3% (v/v). hERG current in presence of 5 doses including 30, 10, 3.33, 1.11 and 0.37 UM, was measured for IC50 determination.

Data analysis Percent current inhibition was calculated using the following equation.

$$\text{Peak current inhibition} = \left(1 - \frac{\text{Peak tail curent}_{compound} - \text{Peak tail current}_{positive\ control}}{\text{Peak tail curent}_{Blank\ vehicle} - \text{Peak tail current}_{positive\ control}}\right) \times 100$$

The dose response curve of test compounds was plotted with % inhibition against the concentration of test compounds using Graphpad Prism 8.0, and fit the data to a sigmoid dose-response curve with a variable slope.

TABLE E hERG values of the compounds

| Compound No. | hERG (IC50, nM) |
|---|---|
| 7 | 5402 |
| 9 | 1539 |
| 12 | >30000 (34%) |
| 15 | >30000 (17%) |
| 17 | 1857 |
| 18 | >10000 (19%) |
| 19 | >10000 (9%) |
| 20 | >30000 (10%) |
| 21 | >10000 (17%) |
| 22 | 22847 |
| 23 | >30000 (20%) |
| 24 | >30000 (18%) |
| 25 | 7780 |
| 26 | 3115 |
| 27 | >30000 (37%) |
| 28 | 1599 |
| 29 | 7429 |
| 30 | 7665 |
| 32 | 2882 |
| 33 | 4774 |
| 34 | 1918 |
| 35 | 3564 |
| 37 | 3541 |
| 38 | 5241 |
| 41 | 982 |
| 42 | 10743 |
| 43 | 2015 |
| 44 | 6165 |
| 45 | 6075 |
| 46 | 3744 |
| 47 | 4683 |
| 48 | 12692 |
| 49 | 31449 |
| 50 | 5255 |
| 51 | 1040 |
| 52 | 8946 |
| 53 | 4664 |
| 54 | 2664 |
| 55 | 20713 |
| 56 | 4727 |
| 57 | 4652 |
| 58 | 4970 |
| 59 | >30000 (43%) |
| 60 | 16436 |
| 61 | 14541 |
| 62 | >30000 (26%) |
| 63 | 5903 |
| 64 | >30000 (43%) |
| 65 | 1730 |
| 66 | >30000 (43%) |
| 67 | 4778 |
| 68 | 725 |
| 69 | 3575 |

TABLE E-continued hERG values of the compounds

| Compound No. | hERG (IC50, nM) |
|---|---|
| 70 | >10000 (18%) |
| 72 | >30000 (7%) |
| 73 | 5874 |
| 76 | 8503 |
| 77 | >30000 (40%) |
| 78 | 14912 |
| 79 | 1883 |
| 80 | 5117 |
| 84 | 15734 |
| 85 | 4243 |
| 86 | 10267 |
| 93 | 4061 |
| 94 | 5178 |
| 95 | >30000 |
| 96 | 918 |
| 99 | 4184 |
| 154 | 370 |
| 155 | >30000 (42%) |
| 156 | 5707 |

Determination of the Efficacy of SGK1 Inhibitors on LQT3 by Studying its Effect on the Action Potential Duration (APD) of LQT-Patient Derived Cardiomyocytes (iPSC-CMs)

SGK1 inhibition is suggested to decrease the APD of cardiomyocytes that exhibits the phenotype of LQT3 patients. Incubation with SGK1 inhibitors reduces the APD of the cardiomyocytes which can be investigated by imaging of cells using FluoVolt dye.

Material and methods for differentiation of cardiomyocytes: Stem cells derived from LQT-3 patients (iPSCs) were cultured in mTeSR™1 media (STEMCELL Tech., 85851) in 6-cm dishes pre-coated with Geltrex (Life Technology, A1413302) and incubated at 37° C. and 5% $CO_2$. At 85% confluence, iPSCs were disaggregated with ReLeSR™ (STEMCELL Tech., 05872), passaged into 24-well plates, and allowed to grow for 3-4 days to create a monolayer. The differentiation strategy used has been reported previously. For differentiation, the culture medium was changed to RPMI 1640 GlutaMAX™ plus 25 mM HEPES supplemented with B27-minus Insulin (Gibco, A18956-01) containing CHIR99021 (TOCRIS, 4423, 6 μM as working concentration) from days 0 to 2. On day 2, medium was changed to RPMI-B27-minus insulin containing IWP2 (TOCRIS, 3533, 5 μM as working concentration) and incubated until day 4. On day 4, the medium was changed back to normal RPMI GlutaMAX™-B27-minus insulin and cells were maintained in this media until beating cardiomyocytes appeared, typically around day 10 or day 12. After beating was seen, iPSC-CMs were maintained in cardiomyocyte maintenance medium (DMEM, No phenol red, 2% charcoal stripped FBS). Cardiomyocyte differentiation and maintenance are done in a 24 well format. Prior to each experiment iPSC-CMs need to be re-plated onto a 35 mm dish and allowed to stabilize for 1 week. Following stabilization of iPSC-CMs in a glass bottom 35 mm dish for 1 week, compounds are applied.

Experiment design of APD measurement: iPSC-CMs are maintained in DMEM plus 2% FBS until replating. $3\times10^5$ cells are plated into each 35 mm glass dish in DMEM plus 20% FBS and maintained in DMEM plus 2% for 1 week for CM stabilization. Either DMSO, Mex (10 uM), SGK1 Inhibitor Compound (3 uM), or SGK1 Inhibitor Compound (30 uM) in DMEM plus 2% FBS are added to the plated cells. At 4 hours post drug administration, the media with the drug is washed out of the first set of 4 plates and replaced with a Tyrode solution containing the FluoVolt dye. Live imaging is taken of approximately 10-12 randomly selected "flashing" cells (see live imaging methods section). Cells are paced at 1 Hz. The raw data from live cell imaging is exported to Excel software (Microsoft, Redmond, WA) and then analyzed with an "in-lab" developed Excel-based program. The loading of the FluoVolt dye in the experiments is performed as follows: Before starting, pre-warm 6.5 mL Tyrode's solution to 37° C. Aspirate medium and rinse cells with 1 mL Tyrode. Add 1.25 µL PowerLoad and 0.125 µL FluoVolt to 0.5 mL Tyrode's and add to the center of the 35 mm dish glass inset. Incubate 20 min at 37° C. Rinse cells 3 times with 1 mL Tyrode's. Add 2 mL Tyrode's. Image cells within 2 h, using GFP filter.

Live cell imaging for action potential duration (APD) measurement: iPSC-CMs were cultured on 35 mm glass bottom dishes (MatTek, P35G-1.5-10-C) that was pre-coated with fibronectin solution at 10 µg/ml (Thermofisher, 3016015) at 37° C., 5% $CO_2$. For imaging, cells were incubated at 37° C., 5% CO2 for 20 minutes in Tyrode solution containing a fluorescent voltage sensitive dye, FluoVolt (ThermoFisher, Cat #F10488, working concentration of 5 uM) and Pluronic® F-127 (Thremofisher, P3000MP, working concentration of 0.05%). They were then washed three times in fresh Tyrode solution. During imaging, the dishes were kept in a heated 37° C. stage-top environment chamber supplied with 5% $CO_2$. Imaging of voltage-indicated cellular action potential duration (APD) was taken under a 40×-water objective using a Nikon Eclipse Ti light microscope. Time-lapse videos of multiple, individual beating iPSC-CMs, paced at 1 Hz were recorded at a speed of 20 milliseconds per frame for 20 seconds at 5% LED power. Single regions of interest were selected for every beating iPSC-CM captured in the recordings. The raw data was exported to Excel software (Microsoft, Redmond, WA) and then analyzed with an "in-lab" developed Excel-based program.

TABLE F

Effects of compounds on APD90 of 4-week-old P1332L-SCN5A iPSC-CMs (4-hour treatment) APD shortening and concentration

| Compound No. | APD shortening | Concentration |
|---|---|---|
| Mexiletine | 700 vs 550 ms | 10 µM |
| EMD638683 | 700 vs 580 ms | 5 µM |
| 45 | 620 vs 620 ms | 30 nM |
| 24 | 580 vs 430 ms | 3 µM |
| 29 | 673 vs 514 ms | 3 nM |
| 22 | 620 vs 500 ms | 30 nM |
| 38 | 568 vs 451 ms | 300 nM |
| 84 | 606 vs 486 ms | 100 nM |
| 85 | 593 vs 464 ms | 10 nM |

Pharmacokinetic Data

Protocol for PK study in CD1 mouse via oral/IV administration

All experimental procedures have been conducted in accordance to German Animal Protection Law, as well as according to international animal welfare legislation and rules.

PO (30 mg/kg, 10 mL/Kg) Dosing:

Three male CD1 mice (6-8 weeks, 20-30 g) were used for this study. Each mouse was given 30 mg/kg of the tested drug by oral route PO. The test compound was dissolved in 0.5% HEC, 0.4% Tween 80 in saline for oral PK. Following the administration of the test compound, 30 uL of blood was collected from each mouse at 0.25, 0.5, 1, 2, 4, 8, 24 h post dosing to measure the concentration of test samples in the plasma. For the processing of collected blood samples, the collected blood sample is dissolved in heparin to prevent the coagulation of blood, following which it is centrifuged at 4000 g for 5 minutes. After centrifugation, the separated plasma will be stored in freezer at 75±15° C. A LC-MS/MS system is used to measure the concentration of the test sample in plasma. WinNonlin (Phoenix™, version 6.1) will be used for the pharmacokinetic calculations and from the plasma concentration versus time data C max, T max, T 1/2, AUC inf, AUC last, the number of points for regression are calculated.

IV (2 mg/kg, 5 mL/Kg) Dosing

Three male CD1 mice (6-8 weeks, 20-30 g) were used for this study. Each mouse was given 2 mg/kg of the tested drug by IV route PO. The test compound was dissolved 5% DMSO in "20% SBE in PBS (pH 7.4)". Following the administration of the test compound, 30 uL of blood was collected from each mouse at 0.25, 0.5, 1, 2, 4, 8, 24 h post dosing to measure the concentration of test samples in the plasma. For the processing of collected blood samples, the collected blood sample is dissolved in heparin to prevent the coagulation of blood, following which it is centrifuged at 4000 g for 5 minutes. After centrifugation, the separated plasma will be stored in freezer at 75±15° C. A LC-MS/MS system is used to measure the concentration of the test sample in plasma. WinNonlin (Phoenix™, version 6.1) will be used for the pharmacokinetic calculations and from the plasma concentration versus time data C max, T max, T 1/2, AUC inf, AUC last, the number of points for regression are calculated.

TABLE G

Mouse Pharmacokinetic data

| Compound No. | Cmax (ng/ml) | T1/2 (h) | Bioavailability F % |
|---|---|---|---|
| 18 | 2.3 | N/A | 0.5 |
| 19 | 9.3 | N/A | 0.31 |
| 22 | 37.9 | 2.3 | 2.5 |
| 24 | 45.1 | 2.3 | 1.55 |
| 27 | 40.3 | 2.7 | N/A |
| 28 | 4015 | 3.4 | 51 |
| 29 | 115 | 1.04 | 8 |
| 30 | 548 | 4.4 | 18.8 |
| 38 | 2340 | 2.2 | 41 |
| 63 | 1116 | 12* | N/A |
| 50 | 54.9 | 3.2 | N/A |
| 73 | 143 | 1.5 | N/A |
| 77 | 16.8 | 2.2 | 0.75 |
| 78 | 111 | 2.5 | 4.9 |
| 79 | 3717 | 3 | 128 |
| 82 | 607 | 1.7 | 4.5 |
| 83 | 788 | 2.4 | 4.9 |
| 84 | 621 | 2.3 | 22 |
| 86 | 40.9 | 26 h* | 3.1 |
| 87 | 1019 | 2 | 7.5 |
| 88 | 14.5 | 4.3 | 1.6 |
| 89 | 1737 | 1.2 | 11 |
| 90 | 523 | 2.4 | 5.5 |
| 91 | 319 | 4.5 | 2.2 |

Protocol for PK Study in SD Rat Via Oral/IV Administration

All experimental procedures have been conducted in accordance to German Animal Protection Law, as well as according to international animal welfare legislation and rules.

PO (30 mg/kg, 10 ml/kg) Dosing:

Three male SD rat (6-8 weeks, 200-300 g) were used for this study. Each mouse was given 30 mg/kg of the tested drug by oral route PO. The test compound was dissolved in 0.5% HEC, 0.4% Tween 80 in saline for oral PK. Following the administration of the test compound, 200 uL of blood was collected from each rat at 0.25, 0.5, 1, 2, 4, 8, 24 h post dosing to measure the concentration of test samples in the plasma. For the processing of collected blood samples, the collected blood sample is dissolved in heparin to prevent the coagulation of blood, following which it is centrifuged at 4000 g for 5 minutes. After centrifugation, the separated plasma will be stored in freezer at 75±15° C. A LC-MS/MS system is used to measure the concentration of the test sample in plasma. WinNonlin (Phoenix™, version 6.1) will be used for the pharmacokinetic calculations and from the plasma concentration versus time data C max, T max, T 1/2, AUC inf, AUC last, the number of points for regression are calculated.

IV (2 mg/kg, 5 ml/kg) Dosing

Six male SD rat (6-8 weeks, 200-300 g) were used for this study. Each mouse was given 2 mg/kg of the tested drug by IV route PO. The test compound was dissolved 5% NMP, 5% solutol in "20% SBE in PBS (pH 7.4)". Following the administration of the test compound, 200 uL of blood was collected from each rat at 0.25, 0.5, 1, 2, 4, 8, 24 h post dosing to measure the concentration of test samples in the plasma. For the processing of collected blood samples, the collected blood sample is dissolved in heparin to prevent the coagulation of blood, following which it is centrifuged at 4000 g for 5 minutes. After centrifugation, the separated plasma will be stored in freezer at 75±15° C. A LC-MS/MS system is used to measure the concentration of the test sample in plasma. WinNonlin (Phoenix™, version 6.1) will be used for the pharmacokinetic calculations and from the plasma concentration versus time data C max, T max, T 1/2, AUC inf, AUC last, the number of points for regression are calculated.

TABLE H

| Rat Pharmacokinetic data | | | |
|---|---|---|---|
| Compound No. | Cmax (ng/ml) | T1/2 (h) | Bioavailability F % |
| 22 | 41.9 | 5.14 | 2.79 |
| 29 | 16 | 9.7 | 0.45 |
| 45 | 131 | 3.63 | 4.68 |
| 79 | 3397 | 5.06 | 40.5 |
| 84 | 2470 | 3.15 | 17.9 |
| 85 | 2747 | 3.6 | 92 |
| 86 | 354 | 4.9 | 6.7 |
| 96 | 267 | 3.3 | 24 |
| 99 | 141 | 10 | 5.6 |
| 100 | 2480 | 3.8 | 39.5 |
| 101 | 8117 | 3.8 | 75 |
| 155 | 283 | 7.5 | 5.3 |
| 156 | 548 | 5.2 | 12 |

CYP Inhibition

The master solution was prepared according to Table I, and then 1 μL of 2 mM of compound solution or 1 μL of DMSO was added to the above master solution. The final concentration of test compound and control compounds was 10 μM.

TABLE I

| Preparation of master solution | | | |
|---|---|---|---|
| Reagent | Stock Concentration | Volume | Final Concentration |
| $MgCl_2$ solution | 50 mM | 20 μL | 5 mM |
| Phosphate buffer | 200 mM | 100 μL | 100 mM |
| Ultra-pure $H_2O$ | — | 56 μL | — |
| Human liver microsomes | 20 mg/mL | 2 μL | 0.2 mg/mL |

For CYP1A2 inhibition, 1 μL of specific drug substrate (Phenacetin: 8 mM) was added at the final concentration of 40 UM to the above solution.

For CYP2B6 inhibition, 1 μL of specific drug substrate (Bupropion: 10 mM) was added at the final concentration of 50 μM to the above solution.

For CYP2$C_9$ inhibition, 1 μL of specific drug substrate (Tolbutamide: 40 mM) was added at the final concentration of 200 UM to the above solution.

For CYP2D6 inhibition, 1 μL of specific drug substrate (Dextromethorphan: 2 mM) was added at the final concentration of 10 μM to the above solution.

For CYP3A4/5 inhibition, 1 μL of specific drug substrate (Midazolam: 1 mM) was added at the final concentration of 5 μM to the above solution.

For CYP3A4/5 inhibition, 1 μL of specific drug substrate (Testosterone: 10 mM) was added at the final concentration of 50 M to the above solution.

The mixture was pre-warmed at 37° C. for 5 min. The reaction was started by the addition of 20 μL of 10 mM NADPH solution at the final concentration of 1 mM and carried out at 37° C.

The reaction was stopped by addition of 400 μL of cold quench solution (methanol containing internal standards (IS: 100 nM alprazolam, 500 nM labetalol and 2 μM ketoprofen)) at the designated time points (Phenacetin: 20 min; Bupropion: 20 min; Tolbutamide: 20 min; Dextromethorphan: 20 min; Midazolam: 5 min; Testosterone: 10 min). Samples were vortexed for 5 minutes and centrifuged at 3220 g for 40 minutes at 4° C. And then 100 UL of the supernatant was transferred to a new 96-well plate with 100 L water for LC-MS/MS analysis. All experiments were performed in duplicate. The formation of metabolites was analyzed by using LC-MS/MS. A decrease in the formation of the metabolites in peak area ratios to vehicle control was used to calculate % inhibition values.

$$\% \text{ Remaining activity} = (\text{average ratio of test compounds or inhibitor})/(\text{average ratio of vehicle control}) * 100$$

$$\% \text{ Inhibition} = 100 - \% \text{ Remaining activity}$$

TABLE J

| Inhibition percentages for test compound and known inhibitors against CYP1A2, CYP2B6, CYP2C9, CYP2D6 and CYP3A4 | | | | | | |
|---|---|---|---|---|---|---|
| | % Inhibition @ 10 μM | | | | | |
| Compound | CYP1A2 (Phenacetin) | CYP2B6 (Bupropion) | CYP2C9 (Tolbutamide) | CYP2D6 (Dextro-methorphan) | CYP3A4 (Midazolam) | CYP3A4 (Testosterone) |
| Furafylline | 78 | — | — | — | — | — |
| Sulfaphenazole | — | — | 89 | — | — | — |
| Quinidine | — | — | — | 95 | — | — |
| Ketoconazole | — | 82 | — | — | 100 | 99 |
| 2 | 5.9 | −5.0 | 13 | 7.3 | 7.0 | 13 |
| 29 | 8.8 | 26 | 75 | 26 | 54 | 77 |
| 44 | 11 | 39 | 92 | 44 | 93 | 91 |
| 84 | −0.9 | 1.2 | 2.2 | 0 | 0.5 | 3.0 |
| 63 | 2.4 | 12 | 65 | 7.5 | −24 | −2 |
| 85 | −0.7 | 7.7 | 9.4 | 1.8 | 19 | −2.9 |

Safety Margin

A safety margin can be obtained by calculating hERG/$IC_{50}$, using the values $IC_{50}$ (Whole cell) and hERG ($IC_{50}$, nM) from tables B and E, respectively. A higher safety margin is desired. The safety margins of several compounds of the present application were compared with each other and with the safety margin of example compounds disclosed in patent application Pub No. WO 2014/140065, which is hereby incorporated by reference in its entirety. Some safety margin values are shown at Table K.

The safety margin of several compounds of the following Formula is shown at Table K, to evaluate the effect of the Z—$R_3$ group on the safety margin.

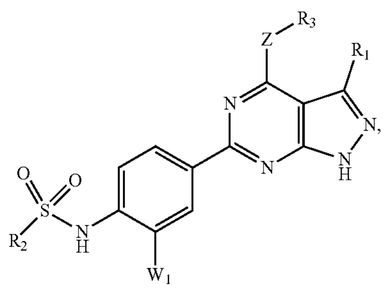

where

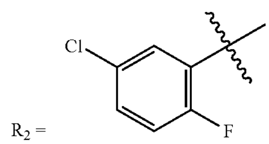

$R_1$=methyl, $W_1$=H, and Z—$R_3$ variable.

TABLE K

| Effect of Z—$R_3$ on safety margin hERG/$IC_{50}$ | | |
|---|---|---|
| Compound No. | Formula | hERG/$IC_{50}$ |
| From WO 2014/140065 | 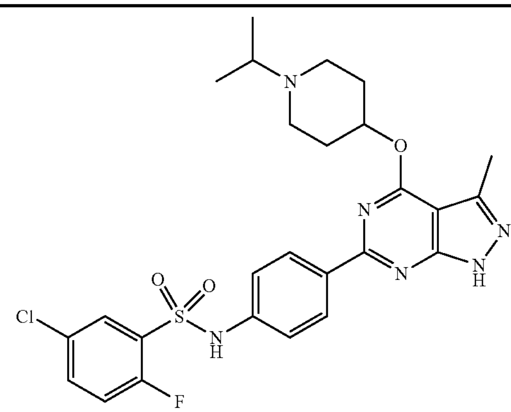 | 33 |

TABLE K-continued
| Effect of Z—$R_3$ on safety margin hERG/$IC_{50}$ | | |
|---|---|---|
| Compound No. | Formula | hERG/$IC_{50}$ |
| From WO 2014/140065 | 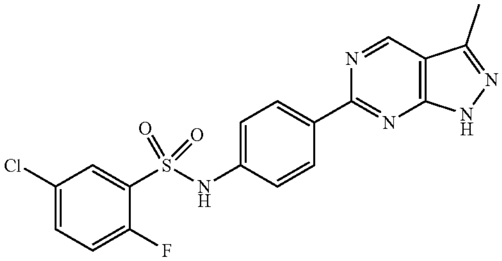 [SMILES: Cc1n[nH]c2nc(-c3ccc(NS(=O)(=O)c4cc(Cl)ccc4F)cc3)ncc12] | 1.7 |
| 154 | 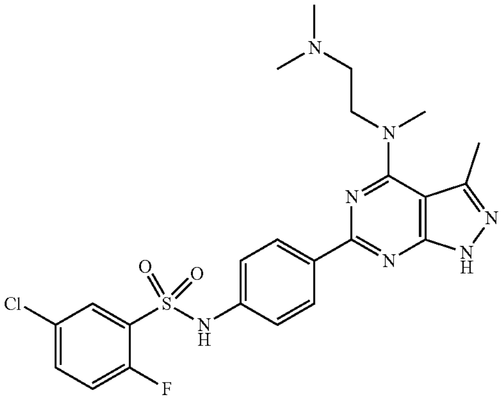 [SMILES: Cc1n[nH]c2nc(-c3ccc(NS(=O)(=O)c4cc(Cl)ccc4F)cc3)nc(N(C)CCN(C)C)c12] | 5.7 |
| 29 | 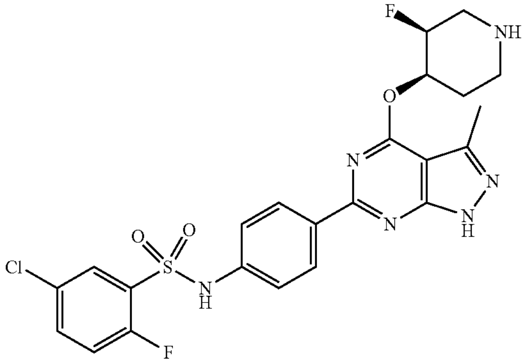 [SMILES: Cc1n[nH]c2nc(-c3ccc(NS(=O)(=O)c4cc(Cl)ccc4F)cc3)nc(O[C@@H]3CCNC[C@@H]3F)c12] | 2476 |

TABLE K-continued
| Effect of Z—$R_3$ on safety margin hERG/$IC_{50}$ | | |
|---|---|---|
| Compound No. | Formula | hERG/$IC_{50}$ |
| 26 | 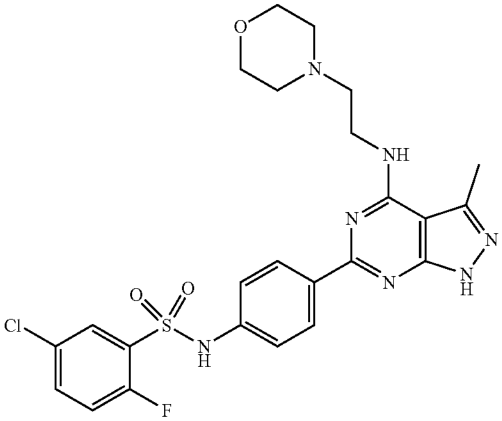 [SMILES: Cc1n[nH]c2nc(-c3ccc(NS(=O)(=O)c4cc(Cl)ccc4F)cc3)nc(NCCN3CCOCC3)c12] | 17 |
| 25 | 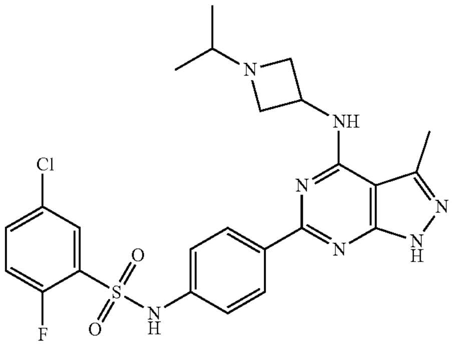 [SMILES: Cc1n[nH]c2nc(-c3ccc(NS(=O)(=O)c4cc(Cl)ccc4F)cc3)nc(NC3CN(C(C)C)C3)c12] | 72 |
| 22 | 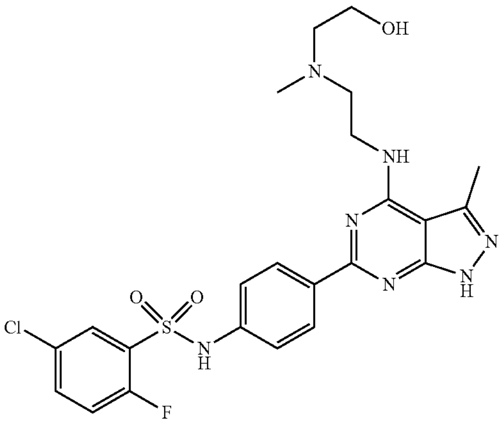 [SMILES: Cc1n[nH]c2nc(-c3ccc(NS(=O)(=O)c4cc(Cl)ccc4F)cc3)nc(NCCN(C)CCO)c12] | 201 |

TABLE K-continued

| Effect of Z—$R_3$ on safety margin hERG/$IC_{50}$ | | |
|---|---|---|
| Compound No. | Formula | hERG/$IC_{50}$ |
| 9 | 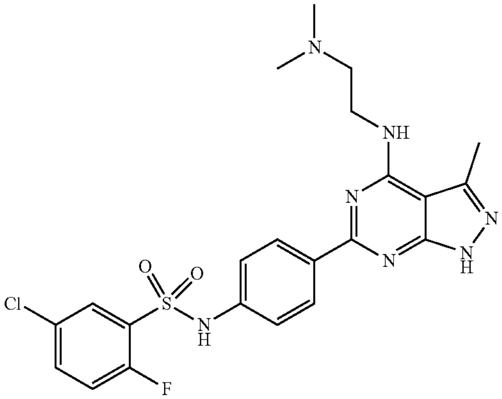 [SMILES: Cc1n[nH]c2nc(-c3ccc(NS(=O)(=O)c4cc(Cl)ccc4F)cc3)nc(NCCN(C)C)c12] | 220 |

It was also found that when $W_1$ is F or Cl, bioavailability is generally improved compared to when $W_1$ is H, while generally maintaining an acceptable safety margin. This can be seen, for example, when comparing several compounds, as shown in Table L:

TABLE L

| Effect of $W_1$ on Bioavailability and hERG/$IC_{50}$ | | | |
|---|---|---|---|
| Compound No. | Formula | hERG/ $IC_{50}$ | pK Data in Rat |
| 45 | 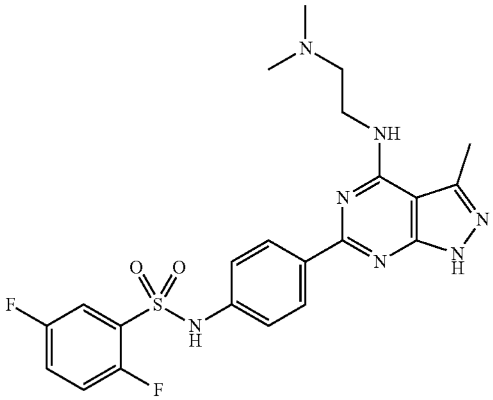 [SMILES: Cc1n[nH]c2nc(-c3ccc(NS(=O)(=O)c4cc(F)ccc4F)cc3)nc(NCCN(C)C)c12] | 68 | Cmax = 131 ng/mL F = 4.7% |
| 84 | 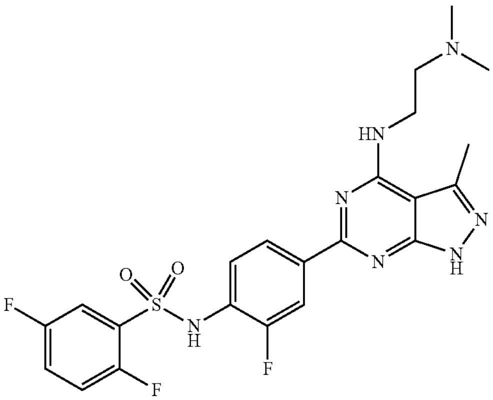 [SMILES: Cc1n[nH]c2nc(-c3ccc(NS(=O)(=O)c4cc(F)ccc4F)c(F)c3)nc(NCCN(C)C)c12] | 177 | Cmax = 2470 ng/mL F = 17.9% |

TABLE L-continued
| Effect of $W_1$ on Bioavailability and hERG/$IC_{50}$ | | | |
|---|---|---|---|
| Compound No. | Formula | hERG/ $IC_{50}$ | pK Data in Rat |
| 85 | 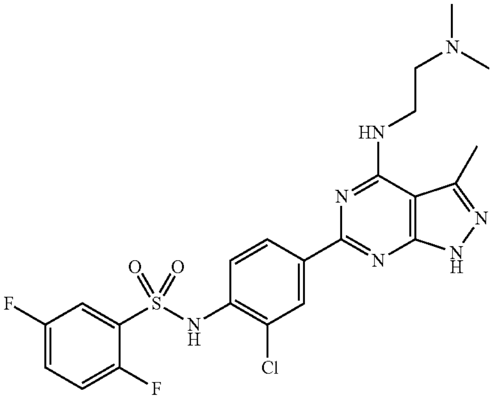 [SMILES: Cc1n[nH]c2nc(-c3ccc(NS(=O)(=O)c4cc(F)ccc4F)c(Cl)c3)nc(NCCN(C)C)c12] | 82 | Cmax = 2747 ng/mL F = 92% |
| 22 | 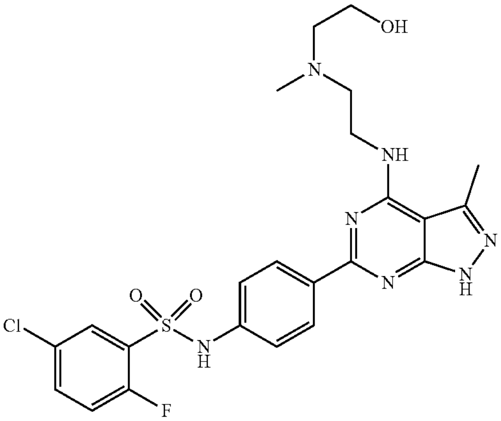 [SMILES: Cc1n[nH]c2nc(-c3ccc(NS(=O)(=O)c4cc(Cl)ccc4F)cc3)nc(NCCN(C)CCO)c12] | 201 | Cmax = 42 ng/mL F = 2.8% |
| 78 | 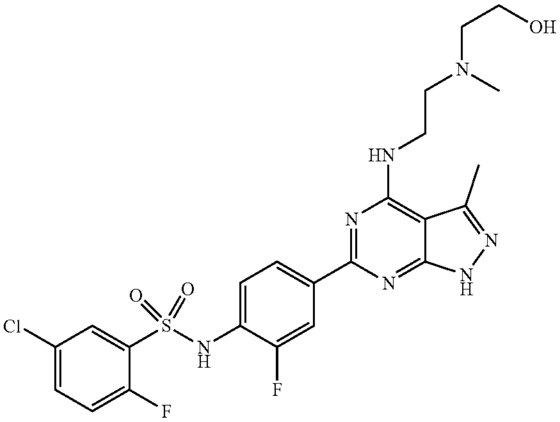 [SMILES: Cc1n[nH]c2nc(-c3ccc(NS(=O)(=O)c4cc(Cl)ccc4F)c(F)c3)nc(NCCN(C)CCO)c12] | 82 | Cmax = 69 ng/mL F = 4.9% |

TABLE L-continued
| Effect of $W_1$ on Bioavailability and hERG/$IC_{50}$ | | | |
|---|---|---|---|
| Compound No. | Formula | hERG/ $IC_{50}$ | pK Data in Rat |
| 99 | 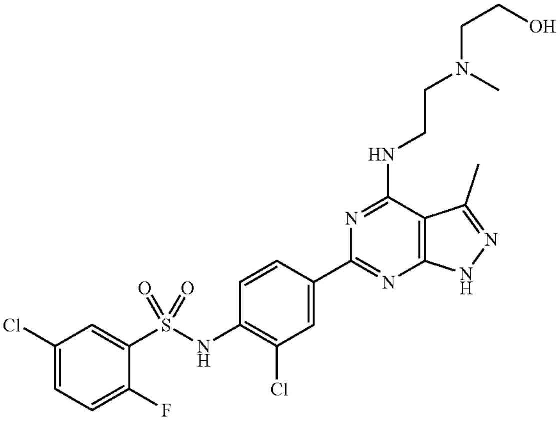 [SMILES: Cc1n[nH]c2nc(-c3ccc(NS(=O)(=O)c4cc(Cl)ccc4F)c(Cl)c3)nc(NCCN(C)CCO)c12] | 91 | Cmax = 141 ng/mL F = 5.6% |
| From WO 2014/140065 | 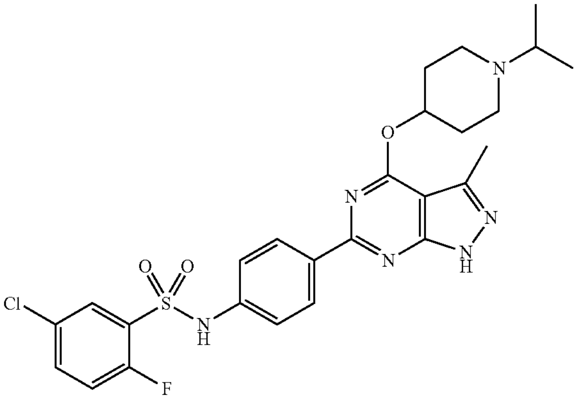 [SMILES: Cc1n[nH]c2nc(-c3ccc(NS(=O)(=O)c4cc(Cl)ccc4F)cc3)nc(OC3CCN(C(C)C)CC3)c12] | 33 | Cmax = 981 ng/mL F = 28.5% |
| 28 | 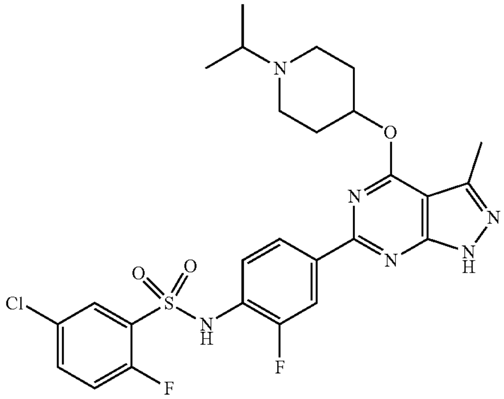 [SMILES: Cc1n[nH]c2nc(-c3ccc(NS(=O)(=O)c4cc(Cl)ccc4F)c(F)c3)nc(OC3CCN(C(C)C)CC3)c12] | 310 | Cmax = 4017 ng/mL F = 51% |

It was also found that the $R_2$ group generally has an effect on activity and kinase selectivity. Several examples are shown at Table M:
TABLE M
| Effect of $R_2$ on hERG/IC50 and kinase selectivity | | | |
|---|---|---|---|
| Compound Structure | Cpd No. | hERG/$IC_{50}$ | Kinase-Select. >50%@10 μM |
| 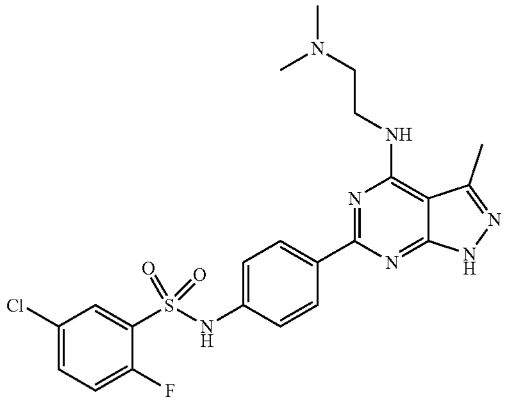 [SMILES: Cc1n[nH]c2nc(-c3ccc(NS(=O)(=O)c4cc(Cl)ccc4F)cc3)nc(NCCN(C)C)c12] | 9 | 220 | 11 |
| 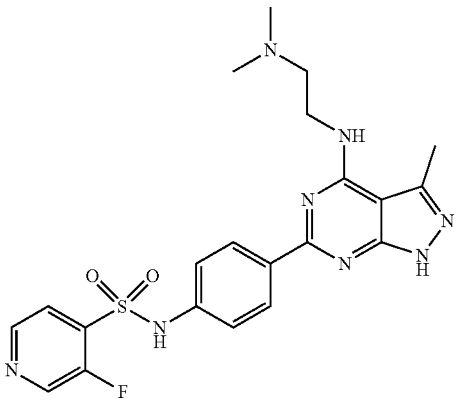 [SMILES: Cc1n[nH]c2nc(-c3ccc(NS(=O)(=O)c4ccncc4F)cc3)nc(NCCN(C)C)c12] | 15 | 4.7 | |
| 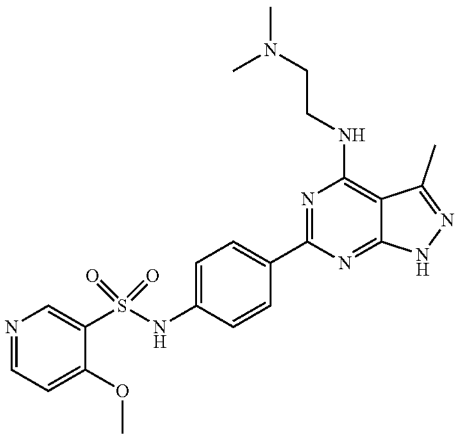 [SMILES: COc1ccncc1S(=O)(=O)Nc1ccc(-c2nc(NCCN(C)C)c3c(C)n[nH]c3n2)cc1] | 19 | 1.5 | |

TABLE M-continued
| Effect of $R_2$ on hERG/IC50 and kinase selectivity | | | |
|---|---|---|---|
| Compound Structure | Cpd No. | hERG/$IC_{50}$ | Kinase-Select. >50%@10 μM |
| 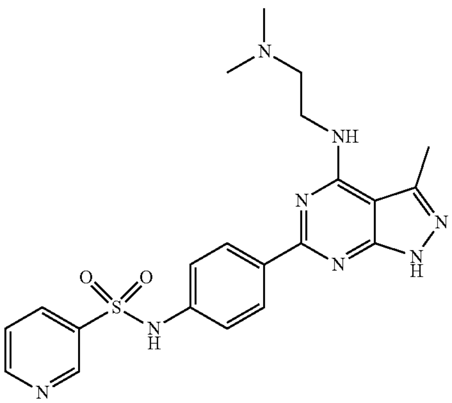 [SMILES: Cc1n[nH]c2nc(-c3ccc(NS(=O)(=O)c4cccnc4)cc3)nc(NCCN(C)C)c12] | 23 | 4.1 | 0 |
| 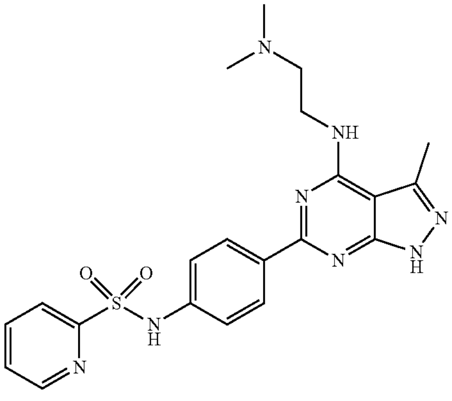 [SMILES: Cc1n[nH]c2nc(-c3ccc(NS(=O)(=O)c4ccccn4)cc3)nc(NCCN(C)C)c12] | 24 | 20.7 | 0 |
| 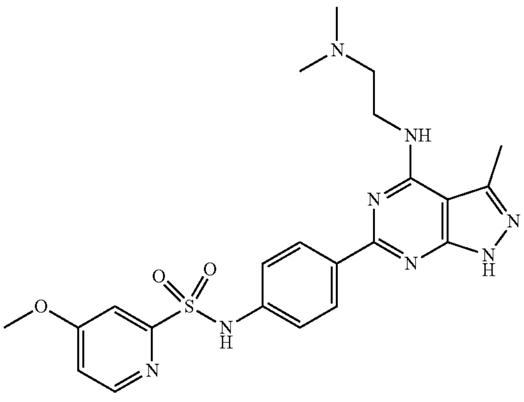 [SMILES: COc1ccnc(S(=O)(=O)Nc2ccc(-c3nc(NCCN(C)C)c4c(C)n[nH]c4n3)cc2)c1] | 27 | 341 | |

TABLE M-continued
| Effect of $R_2$ on hERG/IC50 and kinase selectivity | | | |
|---|---|---|---|
| Compound Structure | Cpd No. | hERG/$IC_{50}$ | Kinase-Select. >50%@10 μM |
| 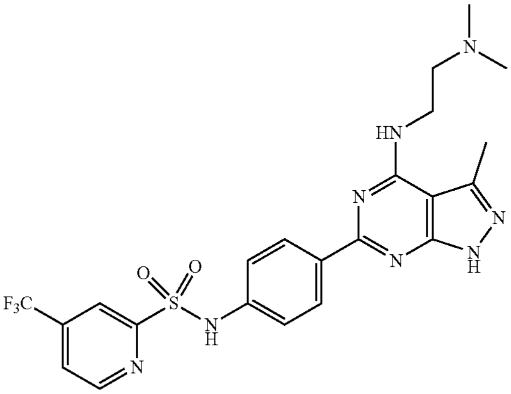 [SMILES: Cc1n[nH]c2nc(-c3ccc(NS(=O)(=O)c4cc(C(F)(F)F)ccn4)cc3)nc(NCCN(C)C)c12] | 30 | 28 | 4 |
| 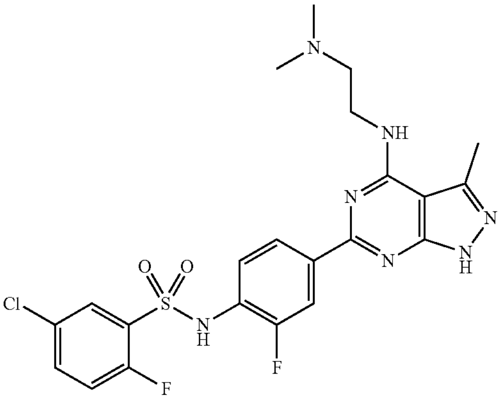 [SMILES: Cc1n[nH]c2nc(-c3ccc(NS(=O)(=O)c4cc(Cl)ccc4F)c(F)c3)nc(NCCN(C)C)c12] | 38 | 256 | 13 |
| 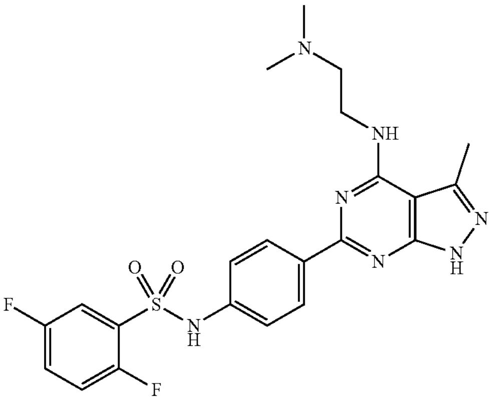 [SMILES: Cc1n[nH]c2nc(-c3ccc(NS(=O)(=O)c4cc(F)ccc4F)cc3)nc(NCCN(C)C)c12] | 45 | 67 | 2 |

TABLE M-continued
| Effect of $R_2$ on hERG/IC50 and kinase selectivity | | | |
|---|---|---|---|
| Compound Structure | Cpd No. | hERG/$IC_{50}$ | Kinase-Select. >50%@10 μM |
| 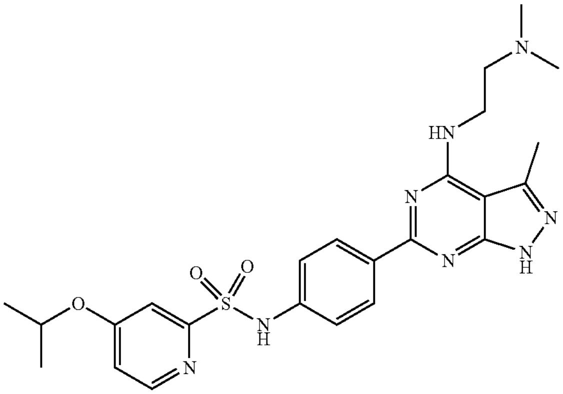 [SMILES: Cc1n[nH]c2nc(-c3ccc(NS(=O)(=O)c4cc(OC(C)C)ccn4)cc3)nc(NCCN(C)C)c12] | 73 | 64 | |
| 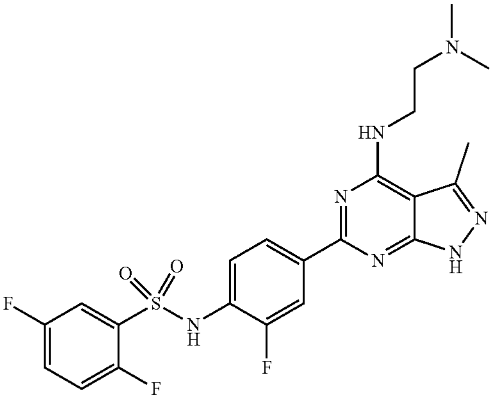 [SMILES: Cc1n[nH]c2nc(-c3ccc(NS(=O)(=O)c4cc(F)ccc4F)c(F)c3)nc(NCCN(C)C)c12] | 84 | 177 | 4 |
| 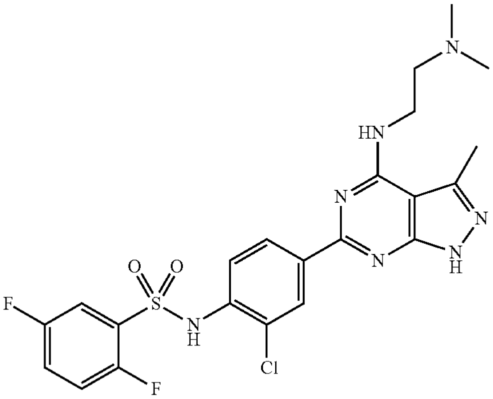 [SMILES: Cc1n[nH]c2nc(-c3ccc(NS(=O)(=O)c4cc(F)ccc4F)c(Cl)c3)nc(NCCN(C)C)c12] | 85 | 82 | 13 |

TABLE M-continued

| Effect of $R_2$ on hERG/IC50 and kinase selectivity | | | |
|---|---|---|---|
| Compound Structure | Cpd No. | hERG/$IC_{50}$ | Kinase-Select. >50%@10 μM |
| 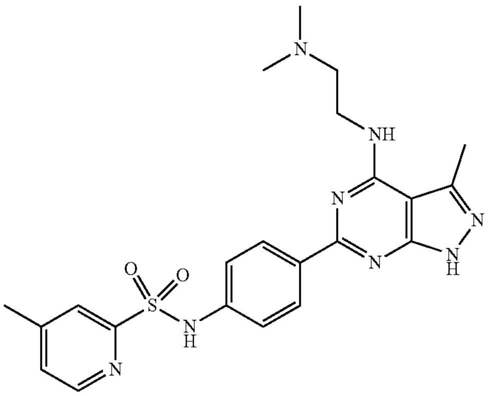 [SMILES: Cc1ccnc(S(=O)(=O)Nc2ccc(-c3nc(NCCN(C)C)c4c(C)n[nH]c4n3)cc2)c1] | 112 | 49 | |

All publications, patents and patent applications are incorporated by reference in their entirety, as though individually incorporated by reference. The invention has been described with reference to various specific and preferred embodiments and techniques. However, it should be understood that many variations and modifications may be made while remaining within the spirit and scope of the invention.

The invention claimed is:

1. A compound of Formula Vb:

Formula Vb

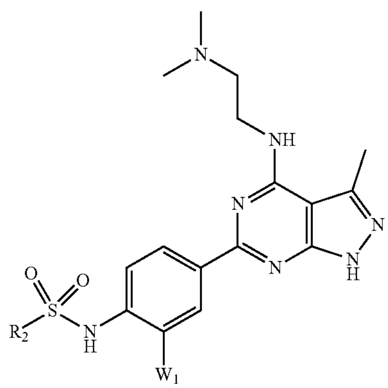

or a pharmaceutically acceptable salt thereof, wherein:

$R_2$ is

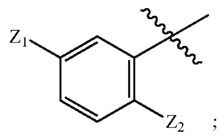

$Z_1$ and $Z_2$ are independently from one another a halogen; and $W_1$ is a halogen.

2. The compound of claim 1, wherein $W_1$ is selected from the group consisting of Cl and F.

3. The compound of claim 1, wherein $Z_1$ and $Z_2$ are independently from one another selected from the group consisting of Cl and F.

4. The compound of claim 1, wherein $R_2$ is

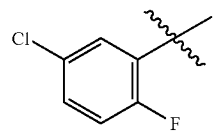

5. The compound of claim 1, wherein $R_2$ is

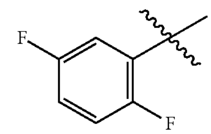

6. The compound of claim 1, which is:

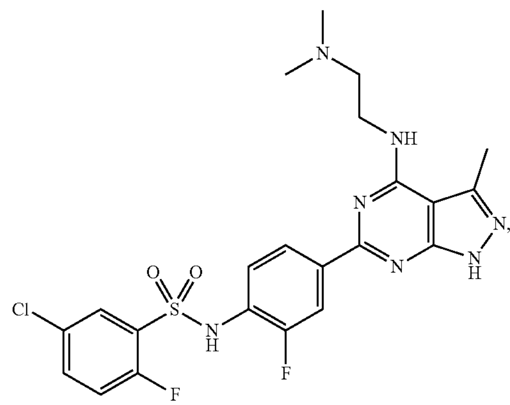

-continued

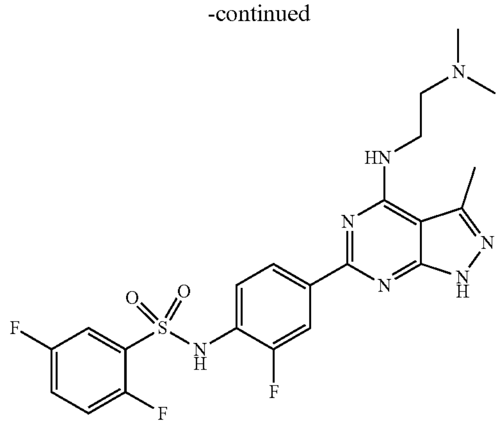

,

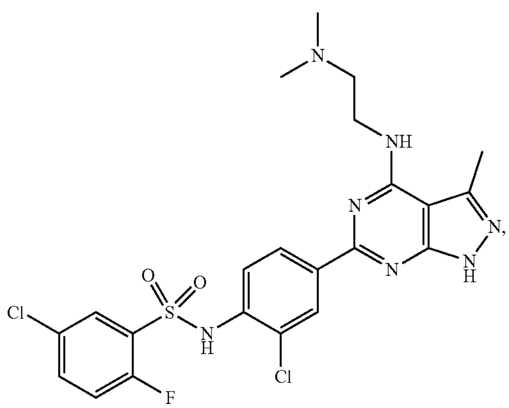

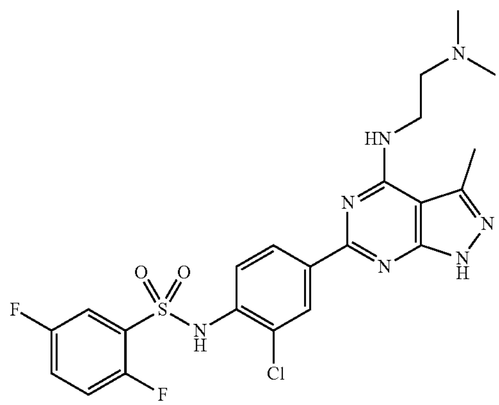

, or a pharmaceutically acceptable salt thereof.

7. A compound of Formula V:

Formula V

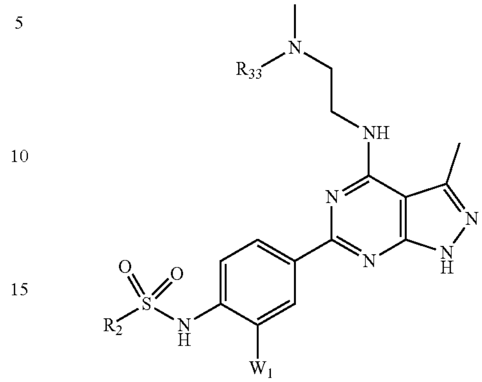

or a pharmaceutically acceptable salt thereof, wherein:

$R_2$ is

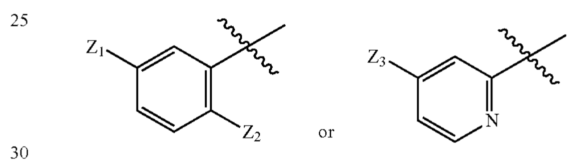

or

;

$Z_1$ and $Z_2$ are independently from one another selected from the group consisting of halogen, $(C_1-C_4)$alkyl, —OH, —O—$(C_1-C_4)$alkyl, —$CF_3$, and —CN;

$Z_3$ is selected from the group consisting of H, halogen, $(C_1-C_4)$alkyl, —OH, —O—$(C_1-C_4)$alkyl, —$CF_3$ and —CN;

$W_1$ is selected from the group consisting of H and halogen;

$R_{33}$ is —$CH_3$ or —$(CH_2)$—$(CH_2)$—$OR_{27}$; and $R_{27}$ is selected from the group consisting of H, —C(═O)—$(C_1-C_4)$alkyl, a natural amino acid bound by the α-carboxyl group, and —P(═O)$(OH)_2$.

8. The compound of claim 7, wherein $W_1$ is selected from the group consisting of Cl and F.

9. The compound of claim 7, wherein $R_2$ is

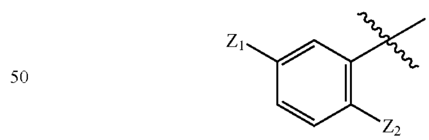

.

10. The compound of claim 9, wherein $Z_1$ and $Z_2$ are independently from one another selected from the group consisting of Cl, F, —$CH_3$, —CN, —$OCH(CH_3)_2$ and —OMe.

11. The compound of claim 9, wherein $R_2$ is

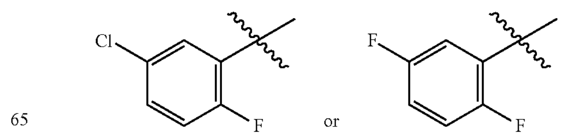

or

.

12. The compound of claim 7, wherein $R_2$ is

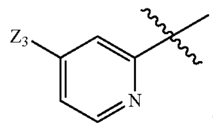

13. The compound of claim 12, wherein $Z_3$ is selected from the group consisting of H, Cl, F, —$CH_3$, —CN, —$OCH(CH_3)_2$ and —OMe.

14. The compound of claim 7, wherein $R_{33}$ is —$(CH_2)$—$(CH_2)$—$OR_{27}$.

15. The compound of claim 14, wherein $R_{27}$ is selected from the group consisting of H and —C(═O)—($C_1$-$C_4$) alkyl.

16. The compound of claim 7, which is:

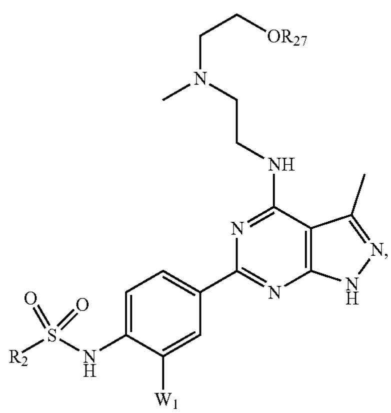

or a pharmaceutically acceptable salt thereof, wherein:

$R_2$ is selected from the group consisting of:

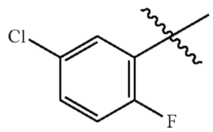,
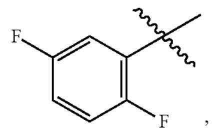 [SMILES: *c1cc(F)ccc1F],
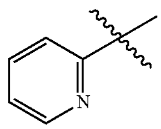,
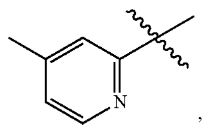,
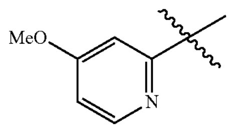,
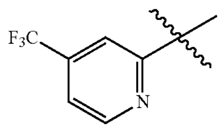
and -continued

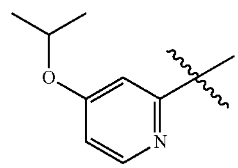;

$W_1$ is selected from the group consisting of H, Cl and F; and $R_{27}$ is selected from the group consisting of: H,

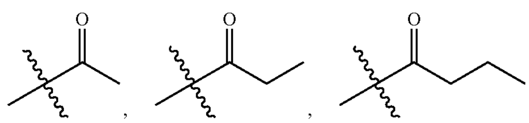

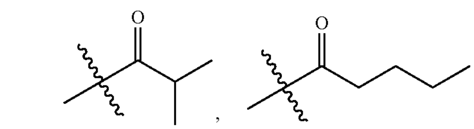

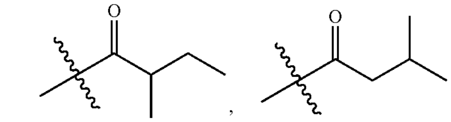
and

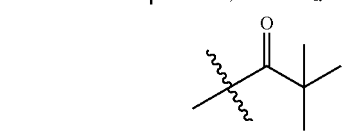

17. The compound of claim 16, wherein $R_{27}$ is H.

18. The compound of claim 7, which is:

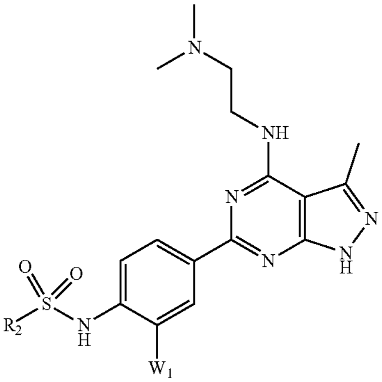

or a pharmaceutically acceptable salt thereof, wherein:

$R_2$ is selected from the group consisting of:

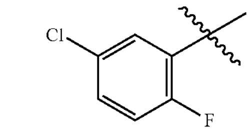,
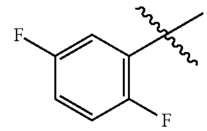,

-continued
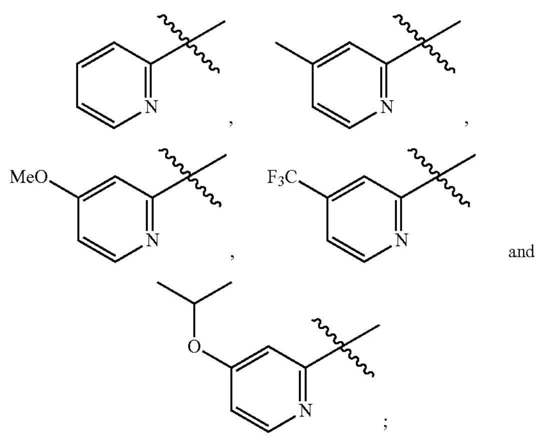
and
$W_1$ is selected from the group consisting of H, Cl and F.
19. The compound of claim 7, which is:
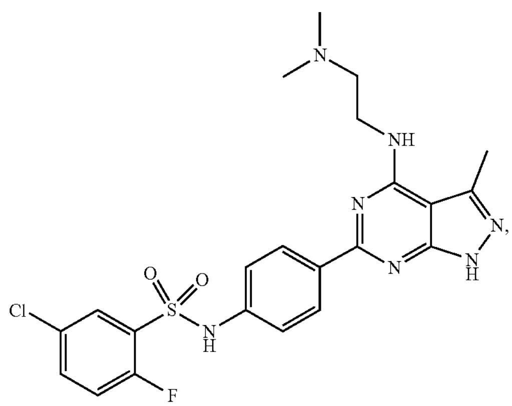
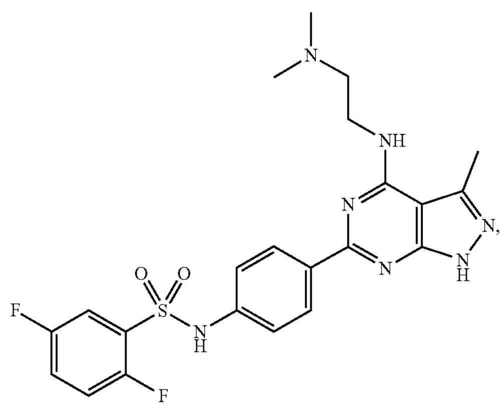
-continued
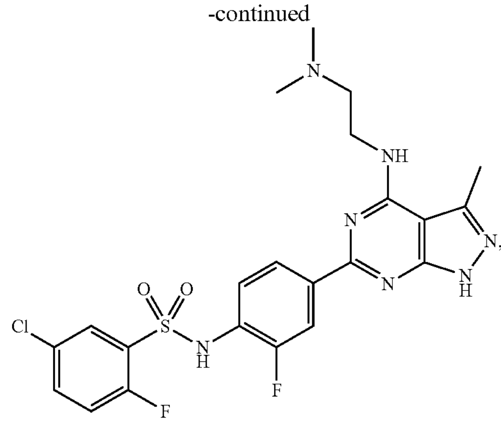
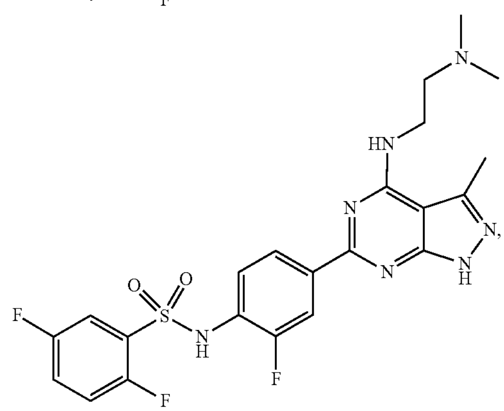
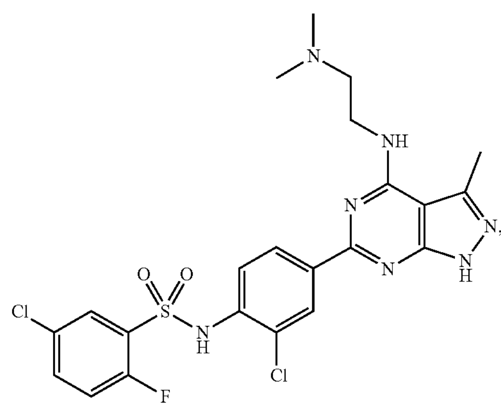
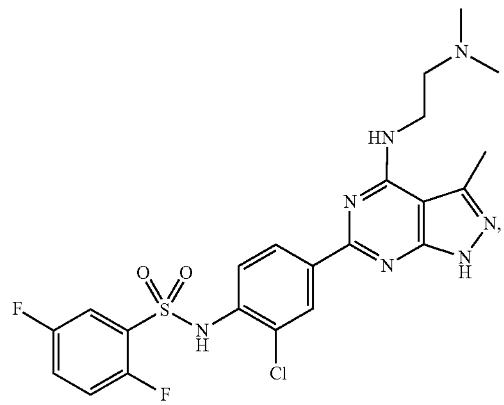

-continued
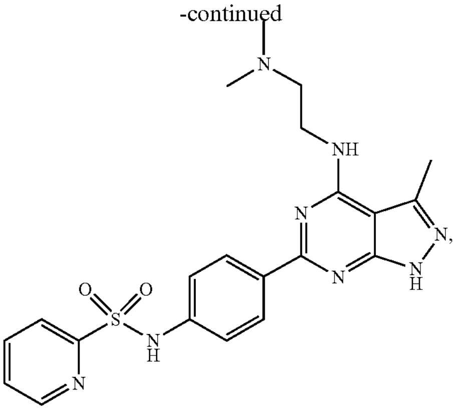
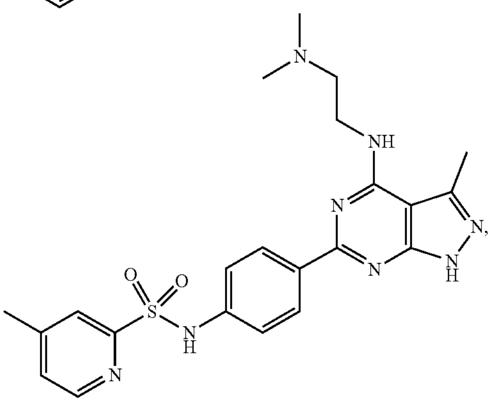
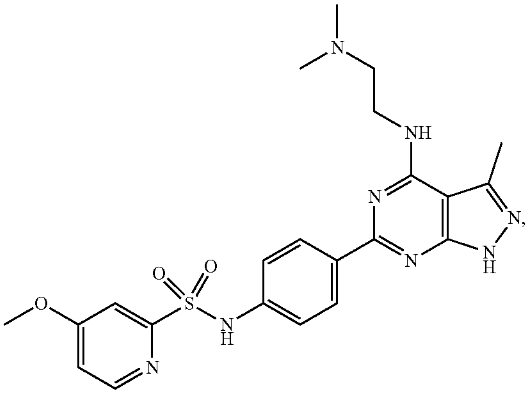
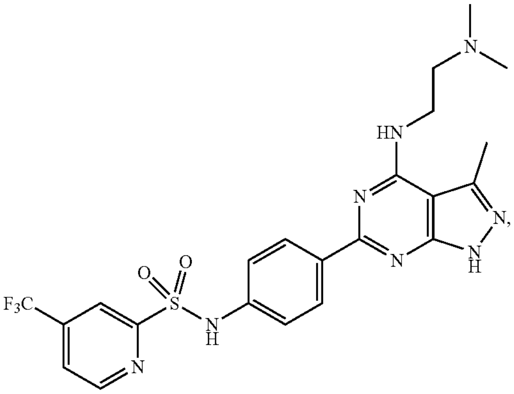
-continued
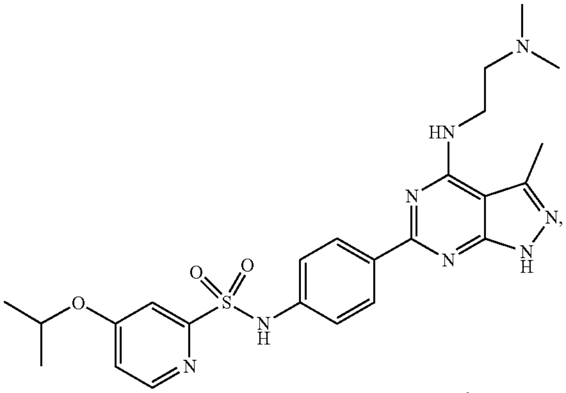
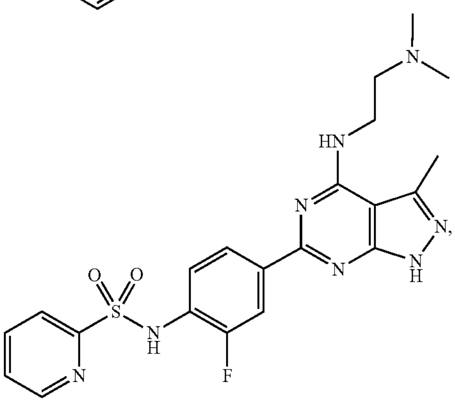
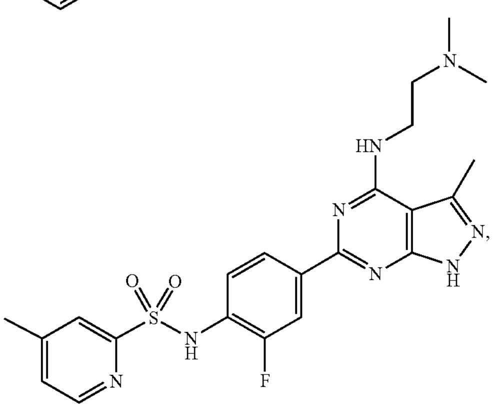
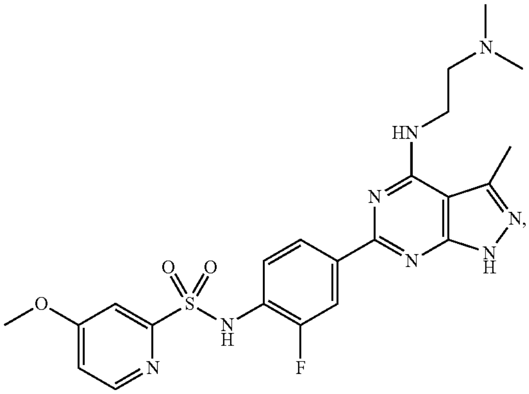

-continued
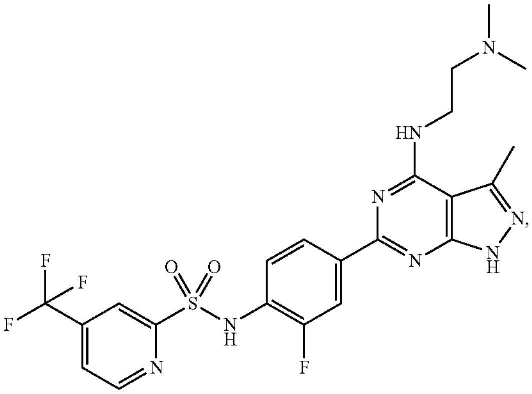
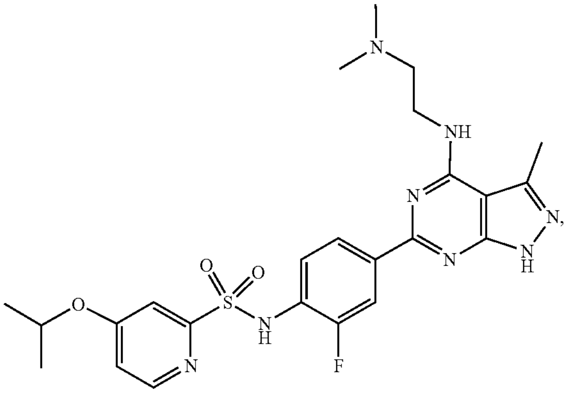
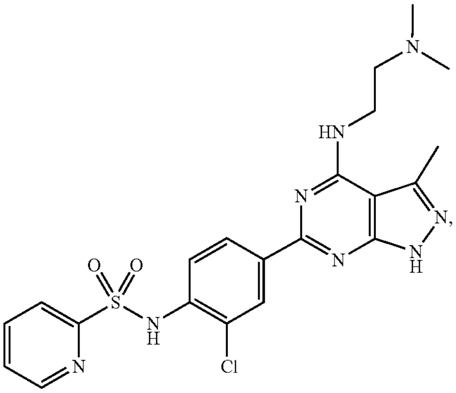
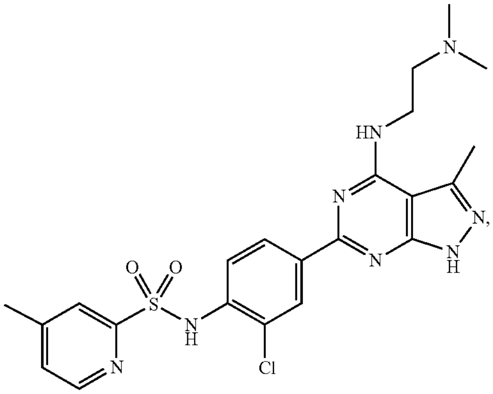
-continued
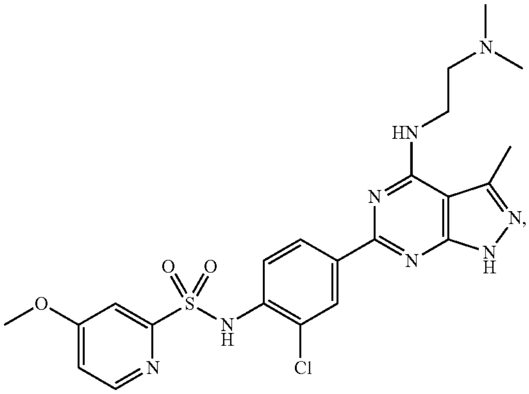
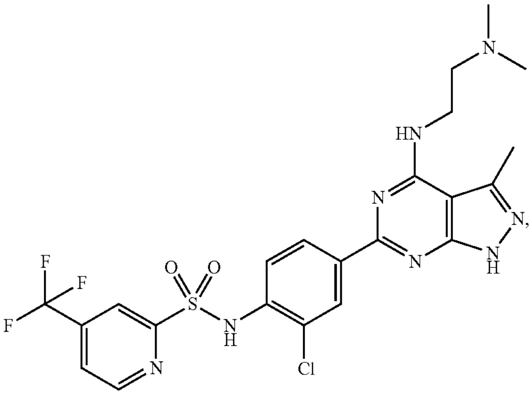
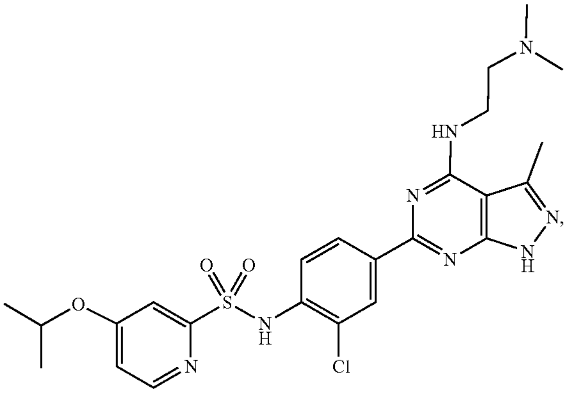
or a pharmaceutically acceptable salt thereof.

20. The compound of claim 7, which is:
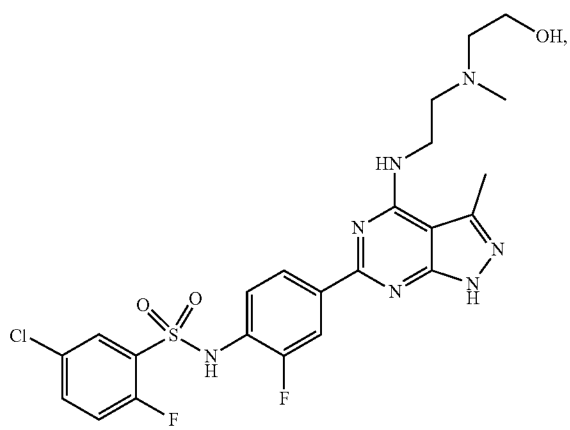
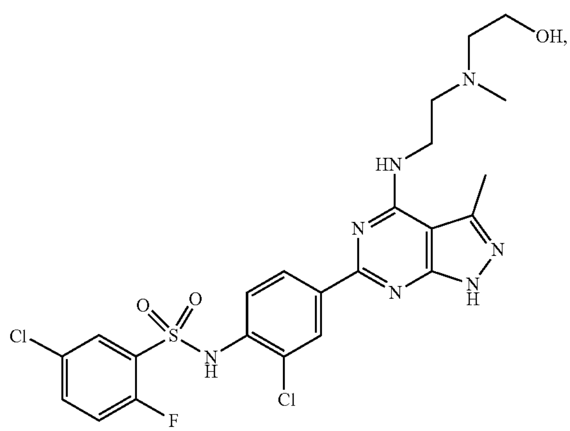
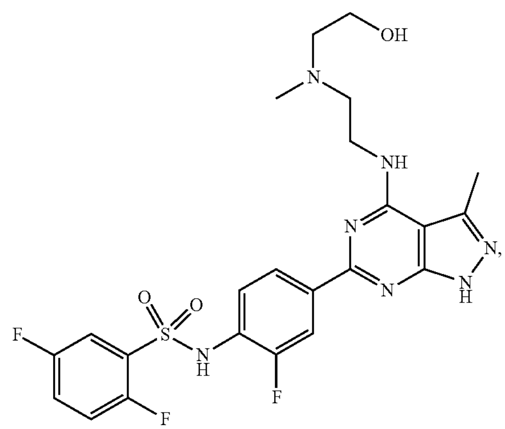
-continued
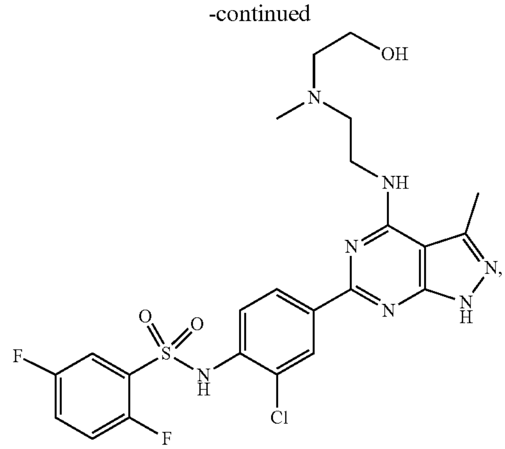
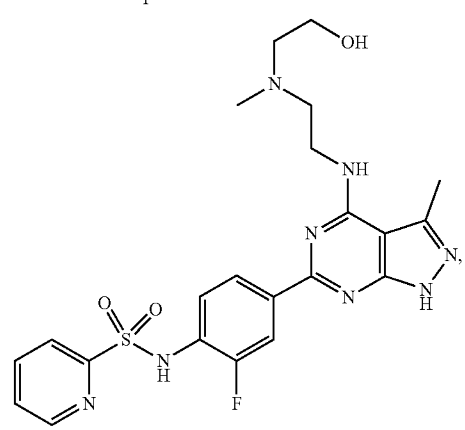
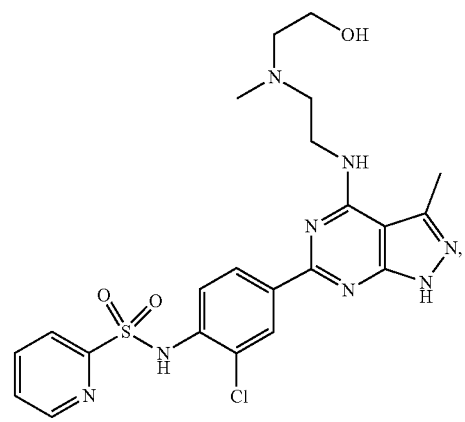
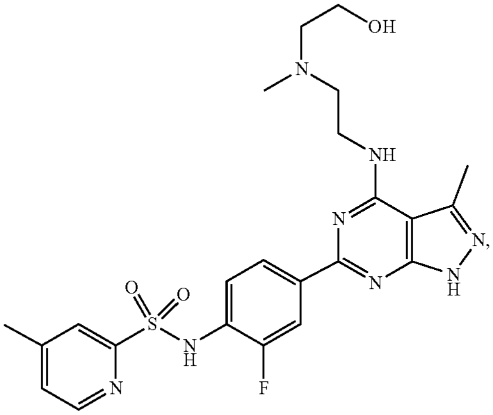

-continued
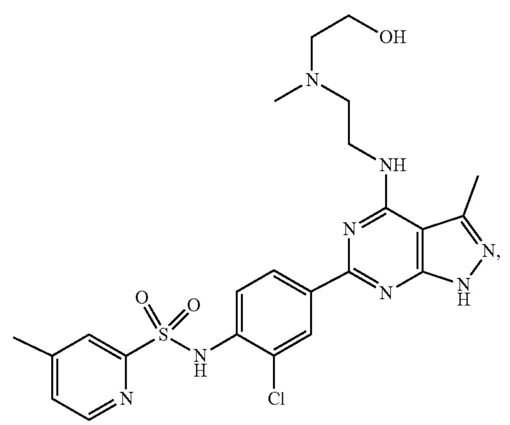
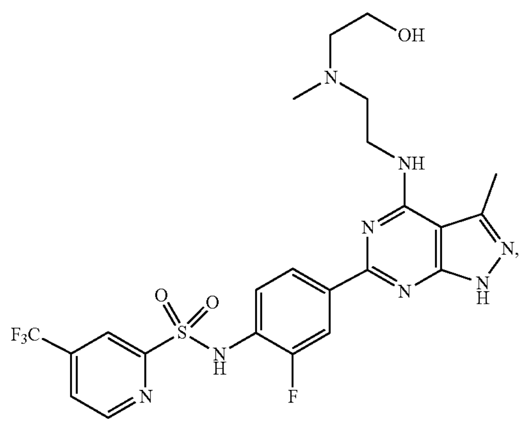
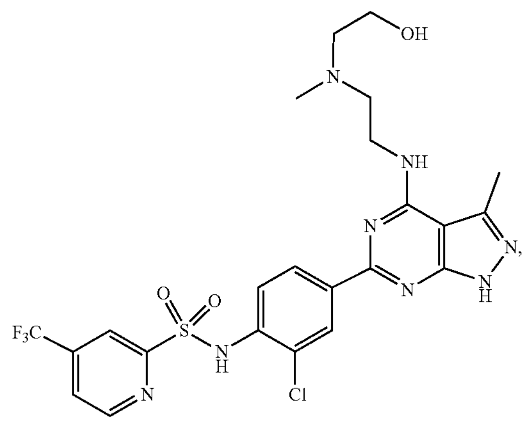
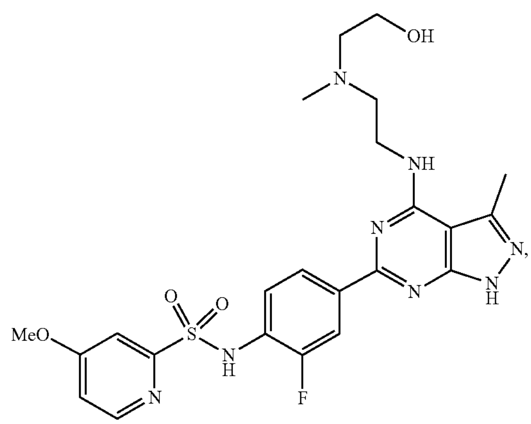
-continued
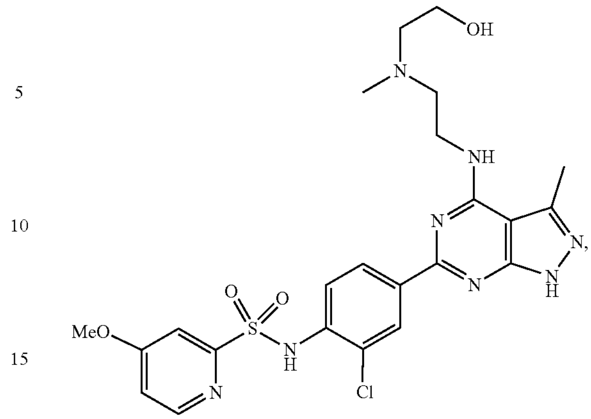
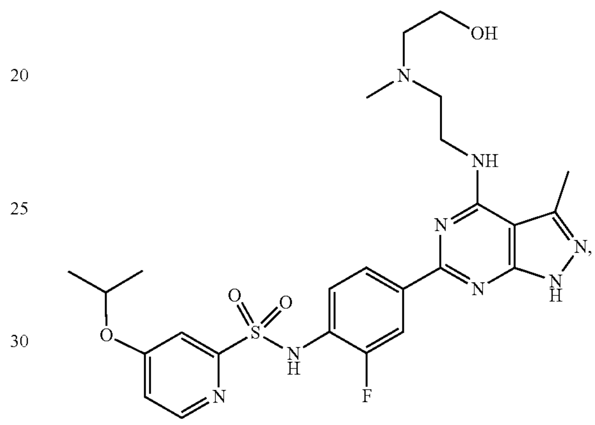
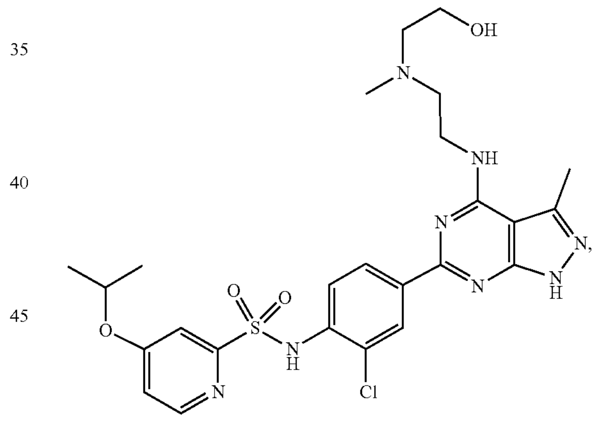
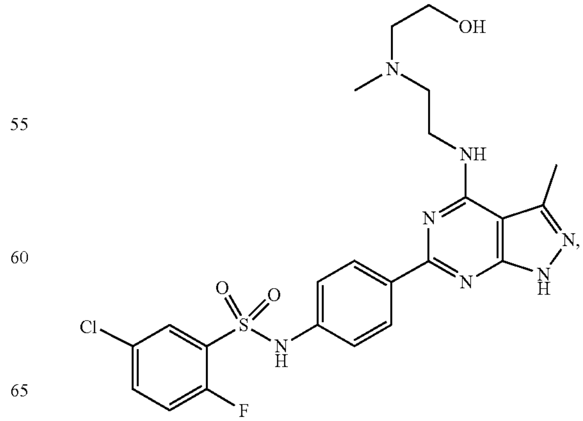

-continued
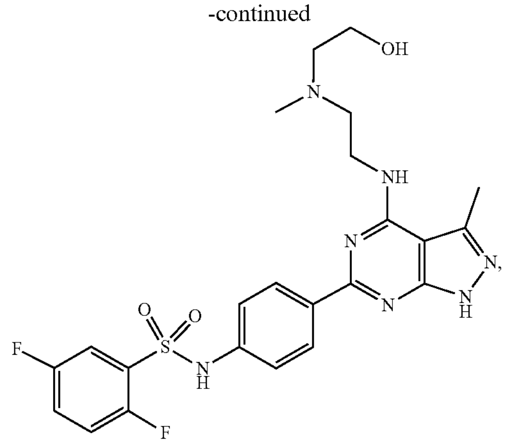
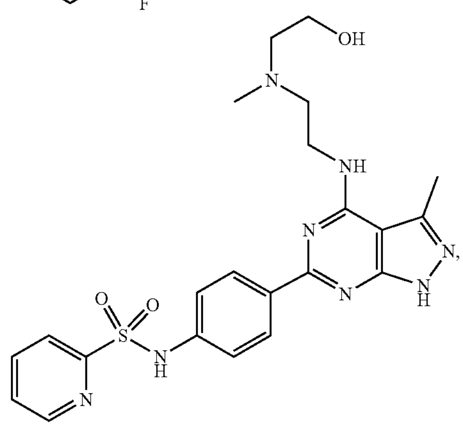
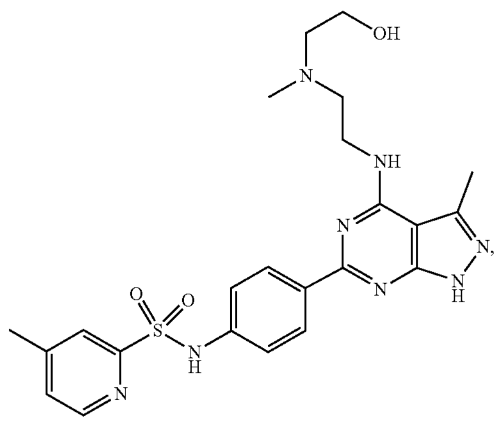
-continued
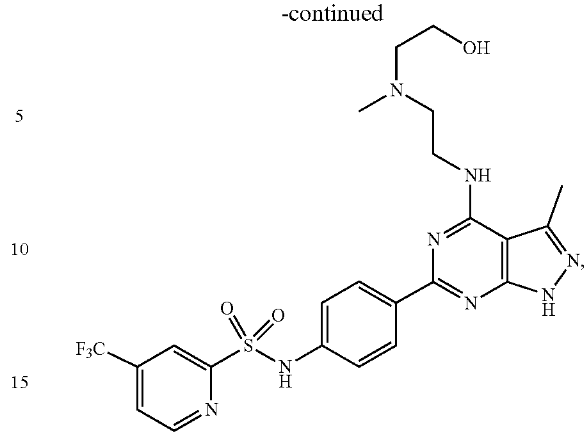
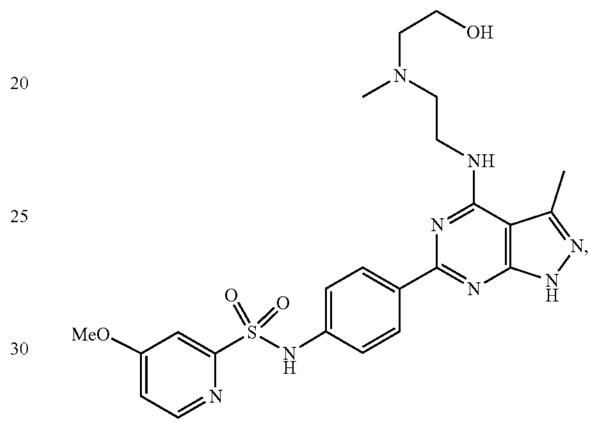
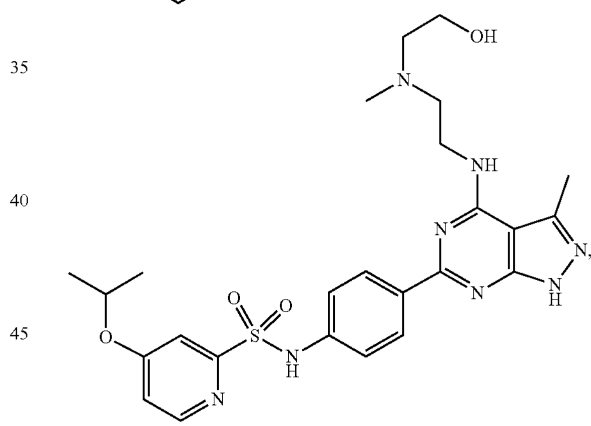
or a pharmaceutically acceptable salt thereof.
* * * * *